US010669562B2

(12) United States Patent
Mermod et al.

(10) Patent No.: US 10,669,562 B2
(45) Date of Patent: Jun. 2, 2020

(54) HIGH EFFICIENCY GENE TRANSFER AND EXPRESSION IN MAMMALIAN CELLS BY A MULTIPLE TRANSFECTION PROCEDURE OF MAR SEQUENCES

(71) Applicant: SELEXIS S.A., Plan les Ouates (CH)

(72) Inventors: Nicolas Mermod, Buchillion (CH); Pierre Alain Girod, Lausanne (CH); Philipp Bucher, Lausanne (CH); Duc-Quang Nguyen, Saint Prex (CH); David Calabrese, Plan-les-Ouates (CH); Damien Saugy, Lausanne (CH); Stefania Puttini, Lausanne (CH)

(73) Assignee: SELEXIS S.A., Plan les Ouates (CH)

( * ) Notice: Subject to any disclaimer, the term of this patent is extended or adjusted under 35 U.S.C. 154(b) by 0 days.

(21) Appl. No.: 15/846,279

(22) Filed: Dec. 19, 2017

(65) Prior Publication Data
US 2018/0187229 A1 Jul. 5, 2018

Related U.S. Application Data

(60) Division of application No. 13/536,383, filed on Jun. 28, 2012, now Pat. No. 9,879,297, which is a continuation of application No. 10/595,495, filed as application No. PCT/EP2004/011974 on Oct. 22, 2004, now Pat. No. 8,252,917.

(60) Provisional application No. 60/513,574, filed on Oct. 24, 2003.

(30) Foreign Application Priority Data

Jun. 2, 2004 (EP) .................... 04002722

(51) Int. Cl.
C12P 21/00 (2006.01)
C12N 15/63 (2006.01)
C12N 15/79 (2006.01)
C12N 15/62 (2006.01)
G16B 5/00 (2019.01)
C12N 15/10 (2006.01)
C12N 15/11 (2006.01)
G16B 15/00 (2019.01)
G16B 30/00 (2019.01)

(52) U.S. Cl.
CPC .......... C12P 21/00 (2013.01); C12N 15/1089 (2013.01); C12N 15/11 (2013.01); C12N 15/63 (2013.01); G16B 5/00 (2019.02); G16B 15/00 (2019.02); G16B 30/00 (2019.02)

(58) Field of Classification Search
None
See application file for complete search history.

(56) References Cited

U.S. PATENT DOCUMENTS

| 3,532,560 A | 10/1970 | Tomioka et al. |
| 4,094,640 A | 6/1978 | Iwantscheff et al. |
| 4,873,316 A | 10/1989 | Meade et al. |
| 5,464,758 A | 11/1995 | Gossen et al. |
| 5,610,053 A | 3/1997 | Chung et al. |
| 5,773,695 A | 6/1998 | Thompson et al. |
| 5,831,063 A | 11/1998 | Hughes-Jones |
| 5,907,078 A | 5/1999 | Greenberg et al. |
| 6,043,077 A | 3/2000 | Barber et al. |
| 6,245,974 B1 | 6/2001 | Michalowski et al. |
| 6,252,058 B1 | 6/2001 | Thompson |
| 6,338,066 B1 | 1/2002 | Martin et al. |
| 6,410,314 B1 | 6/2002 | Balker et al. |
| 6,426,446 B1 | 7/2002 | McElroy et al. |
| 6,429,357 B1 | 8/2002 | McElroy et al. |
| 6,437,217 B1 | 8/2002 | McElroy et al. |
| 6,521,449 B1 | 2/2003 | Polack et al. |
| 6,537,542 B1 | 3/2003 | Treco et al. |
| 6,565,844 B1 | 5/2003 | Treco et al. |
| 6,569,681 B1 | 5/2003 | Ivanov |
| 6,573,429 B1 | 6/2003 | Shinmyo et al. |
| 6,583,338 B2 | 6/2003 | McElroy et al. |
| 6,596,514 B2 | 7/2003 | Morris et al. |
| 6,635,806 B1 | 10/2003 | Kriz et al. |
| 6,649,373 B2 | 11/2003 | Brough et al. |
| 6,660,521 B2 | 12/2003 | Brough et al. |
| 6,706,470 B2 | 3/2004 | Choo et al. |
| 6,730,826 B2 | 5/2004 | Wagner et al. |
| 6,747,189 B1 | 6/2004 | McElroy et al. |

(Continued)

FOREIGN PATENT DOCUMENTS

| EP | 0663921 B1 | 9/1993 |
| EP | 0264166 B1 | 8/1996 |

(Continued)

OTHER PUBLICATIONS

Sequence Alignment of Instant SEQ ID No. 26 with SEQ ID No. 1509 of US Patent Application Publication No. 2009/0018031, Search conducted on Jan. 17, 2020, 5 pages. (Year: 2020).*

(Continued)

Primary Examiner — Channing S Mahatan
(74) Attorney, Agent, or Firm — Agris & Von Natzmer, LLP; Joyce Von Natzmer

(57) ABSTRACT

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

46 Claims, 15 Drawing Sheets
Specification includes a Sequence Listing.

(56) References Cited

U.S. PATENT DOCUMENTS

| | | |
|---|---|---|
| 6,752,880 B2 | 6/2004 | Ahn et al. |
| 6,783,756 B2 | 8/2004 | Bujard et al. |
| 6,821,775 B1 | 11/2004 | Kovesdi et al. |
| 6,897,066 B1 | 5/2005 | Harrington |
| 8,252,917 B2 | 8/2012 | Mermod et al. |
| 2002/0001579 A1 | 1/2002 | Hillenberg et al. |
| 2002/0068362 A1 | 6/2002 | Murray et al. |
| 2002/0073448 A1 | 6/2002 | Michalowski et al. |
| 2002/0094967 A1 | 7/2002 | Antoniou et al. |
| 2002/0098475 A1 | 7/2002 | Luo et al. |
| 2002/0103148 A1 | 8/2002 | Agarwal et al. |
| 2003/0018997 A1 | 1/2003 | Conkling et al. |
| 2003/0032597 A1 | 2/2003 | Sebestyen |
| 2003/0054548 A1 | 3/2003 | Kaleko et al. |
| 2003/0082552 A1 | 5/2003 | Wolffe et al. |
| 2003/0087342 A1 | 5/2003 | Mermod et al. |
| 2003/0100077 A1 | 5/2003 | Korte et al. |
| 2003/0140363 A1 | 7/2003 | Rapp |
| 2003/0140364 A1 | 7/2003 | Hichney et al. |
| 2003/0157715 A1 | 8/2003 | Laemmli |
| 2003/0224477 A1 | 12/2003 | Heartlein et al. |
| 2003/0228612 A1 | 12/2003 | Kenward et al. |
| 2003/0232414 A1 | 12/2003 | Moore |
| 2004/0016015 A1 | 1/2004 | Nguyen et al. |
| 2004/0038394 A1 | 2/2004 | Kim et al. |
| 2004/0072352 A1 | 4/2004 | Kim et al. |
| 2004/0076954 A1 | 4/2004 | Caldwell et al. |
| 2004/0077842 A1 | 4/2004 | Himawan |
| 2004/0088764 A1 | 5/2004 | Gleba et al. |
| 2004/0103454 A1 | 5/2004 | Conkling et al. |
| 2004/0115776 A1 | 6/2004 | Simesen et al. |
| 2004/0126883 A1 | 7/2004 | Liu |
| 2004/0216189 A1 | 10/2004 | Houmard et al. |
| 2004/0221330 A1 | 11/2004 | Klimyuk et al. |
| 2004/0242512 A1 | 12/2004 | Misawa et al. |
| 2005/0022262 A1 | 1/2005 | Vance |
| 2005/0034187 A1 | 2/2005 | Golovko et al. |
| 2005/0050581 A1 | 3/2005 | Harvey et al. |
| 2005/0064467 A1 | 3/2005 | Ivanova et al. |
| 2005/0129669 A1 | 6/2005 | Treco et al. |
| 2005/0130267 A1 | 6/2005 | Wolffe et al. |
| 2009/0018031 A1* | 1/2009 | Trinklein .......... C12N 15/1051 506/10 |

FOREIGN PATENT DOCUMENTS

| | | |
|---|---|---|
| EP | 1135512 A1 | 9/2001 |
| EP | 1471144 B1 | 10/2004 |
| FR | 2832423 A1 | 5/2003 |
| JP | 2002531097 A | 9/2002 |
| WO | 9639488 A1 | 12/1996 |
| WO | 1997027207 A1 | 7/1997 |
| WO | 1997046687 A1 | 12/1997 |
| WO | 2000005393 A2 | 2/2000 |
| WO | 2000020950 A1 | 4/2000 |
| WO | 2000032800 A1 | 6/2000 |
| WO | 2002009507 A1 | 2/2002 |
| WO | 2002068669 A2 | 9/2002 |
| WO | 2002072138 A1 | 9/2002 |
| WO | 2002074969 A2 | 9/2002 |
| WO | 2002000262 A3 | 10/2002 |
| WO | 2002077180 A2 | 10/2002 |
| WO | 2002079447 A9 | 11/2002 |
| WO | 2003043415 A1 | 5/2003 |
| WO | 2004053137 A2 | 6/2004 |
| WO | 2003024199 A3 | 7/2004 |
| WO | 2004055182 A1 | 7/2004 |
| WO | 2004094640 A1 | 11/2004 |
| WO | 2005040377 A2 | 5/2005 |
| WO | 2005040384 A1 | 5/2005 |
| WO | 2005021765 A3 | 6/2005 |
| WO | 2004053106 A3 | 9/2006 |
| WO | 2008023247 A3 | 2/2008 |

OTHER PUBLICATIONS

Adam C. Bell and Gary Felsenfeld, Stopped at the border: boundries and insulators, Current Opinion in Genetics & Development, 1999, p. 191-198, vol. 9, Elsevier Science Ltd., US.

AL389920, *Homo sapiens* chromosome 1 clone RP5-852H15. Jul. 10, 2001. McLay, K.

Aribert Stief, et al. A nuclear DNA attachment element mediates elevated and position-independent gene activity, Nature, Sep. 28, 1989, pp. 343-345, vol. 341, Nature Publishing Group, US.

Bejamin Ortiz, et al., Adjacent DNA elements dominantly restrict the ubiquitous activity of a novel chromatin-opening region to specific tissues, The EMBO Journal, 1997, pp. 5037-5045, vol. 16, No. 16, Oxford University Press, UK.

Benham, C., et al., Stress-induced Duplex DNA Destabilization in Scaffold/Matrix Attachment Regions, J. Mol. Biol., 1997, 274, pp. 181-196.

Bode J et al: "Scaffold/matrix-attached regions: Structural properties creating transcriptionally active loci" in International Review of Cytology, Academic Press, 1995, pp. 389-454.

Bode Juergen et al: "Transcriptional augmentation: Modulation of gene expression by scaffold/matrix-attached regions (S/MAR elements)" in Critical Reviews in Eukaryotic Gene Expression, vol. 10, No. 1, 2000,pp. 73-90.

Bode, J. et al., Scaffold/Matrix-Attached Regions: Structural Properties Creating Transcriptionally Active Loci, International Review of Cytology, vol. 162A; p. 389-444 (1995).

Boulikas Teni: "Nature of DNA sequences at the attachment regions of genes to the nuclear matrix" in Journal of Cellular Biochemistry, vol. 52, No. 1, 1993, pp. 14-22.

Bucher, P., et al., A Flexible Motif Search Technique Based on Generalized Profiles, Swiss Institute for Experimental Cancer Research, Jan. 24, 1996, pp. 0-27.

C. Piechaczek, et al., A vector based on the SV40 origin of replication and chromosomal S/MARs replicates episomally in CHO cells, Nucleic Acids Research, 1999, pp. 426-428, vol. 27, No. 2, Oxford University Press, UK.

Cai, S., et al., Tissue-specific nuclear architecture and gene expression regulated by SATB1, Nat. Genet., 2003, vol. 34, No. 1, pp. 42-51.

Chao Chen and Lawrence A. Chasin, Cointegration of DNA Molecules Introduced into Mammalian Cells by Electroporation, Somatic Cell and Molecular Genetics, Jul. 1998, pp. 249-256, vol. 24, No. 4, Springer Netherlands, US.

Cornelia M. Gorman and Bruce H. Howard, Expression of recombinant plasmids in mammalian cells is enhanced by sodium butyrate, Nucleic Acids Research, 1983, pp. 7631-7648, vol. 11, No. 21, IRL Press Limited, UK.

Cox et al., "Molecular Cloning and Characterization of a Novel Mouse Macrophage Gene that Encodes a Nuclear Protein Comprising Polyglutamine Repeats and Interspersing Histidines," in the Journal of Biological Chemistry, vol. 271(41), Oct. 11, 1996, pp. 25515-25523.

Craig Hart and Ulrich Laemmli, Facilitation of chromatin dynamics by SARs, Current Opinion in Genetics & Development, 1998, pp. 519-525, vol. 8, Current Biology Limited, US.

Dagmar Klehr, et al., Scaffold-Attached Regions from the Human Interferon ,i3 Domain Can Be Used to Enhance the Stable Expression of Genes under the Control of Various Promoters, Biochemistry, 1991, pp. 1264-1270, vol. 30, American Chemical Society, US.

Dale Talbot, et al., The 5' flanking region of the rat LAP (C/EBPf) gene can direct high-level, position-independent, copy numberdependent expression in multiple tissues in transgenic mice, Nucleic Acids Research, 1994, pp. 756-766, vol. 22, No. 5, Oxford University Press, US.

Database EMBL [Online] Feb. 11, 1995, "G. gallus lysozyme gene promoter" X84223 retrieved from EBI accession No. EM.sub.—VRT:X84223 Database accession No. X84223.

Database EMBL [Online] Jan. 4, 2002, "Human DNA sequence from clone RP4-743D20 on chromosome 1 Contains novel gene and a CpG island." XP002322943 retrieved from EBI accession No. EM.sub.-HUM:AL663105.

(56) References Cited

OTHER PUBLICATIONS

Database EMBL [Online] Jul. 16, 1990, "Chicken Lysozyme gene intrinsically curved segment of DNA" X52989 retrieved from EBI accession No. EM.sub.—VRT:X52989 Database accession No. X52989.
Database EMBL [Online] Jun. 14, 1996, G. gallus lysozyme gene 5' matrix attachment region (MAR) subfragment B-1-H1 X98408 retrieved from EBI accession No. EM.sub.—VRT:X98408 Database accession No. X98408.
Database EMBL [Online] May 17, 2000, "Cloning vector pMAR luciferase reporter vector containing MAR insulator sequence". AJ277960 retrieved from EBI accession No. EM.sub.—SYN:AJ277960 Database accession No. AJ277960.
Database EMBL [online], "Human DNA Sequence from Clone RP11-329A14 on Chromosome 1 Contains the 5' end of the SPATA6 Gene for Spermatogenesis Associated 6, an Amyotrophic Lateral Sclerosis 2 (Juvenile) Chromosome Region, Candidate 2 (ALS2CR2) Pseudogene, a Ribosomal Protein L21 (RPL21) Pseudogene and a CpG Island," XP002488536, May 26, 2000.
Database EMBL, Jan. 12, 2006, Birren B. Nusbaum C. Lander E.: "Mus musculus chromosome 1, clone RP23-444A8" Database accession No. AC102666.
Database EMBL, May 16, 2004, Kruchowski S et al.: "The sequence of Mus musculus BAC clone RP23-388E14" Database accession No. AC134595.
Eliette Bonnefoy, et al., Specific Binding of High-Mobility-Group I (HMGI) Protein and Histone H1 to the Upstream AT-Rich Region of the Murine Beta Interferon Promoter: HMGI Protein Acts as a Potential Antirepressor of the Promoter, Molecular and Cellular Biology, Apr. 1999, pp. 2803-2816, vol. 19, No. 4, American Society for Microbiology, US.
Evans et al., "A comparative study of S/MAR prediction tools," BMC Bioinformatics, vol. 8 (71), Mar. 2, 2007, pp. 1-29.
Frank Grosveld, Activation by locus control regions?, Current Opinion in Gentles & Development, 1999, pp. 152-157, vol. 9, Elsevier Science Ltd., US.
Frisch et al., "In Silico Prediction of Scaffold/Matrix Attachment Regions in Large Genomic Sequences," in Genome Research, Cold Spring Harbor Laboratory Press, Woodbury, NY, vol. 12(2), Feb. 1, 2002, pp. 349-354.
Frisch M et al: "In silico prediction of scaffold/matrix attachment regions in large genomic sequences" in Genome Research, Cold Spring Harbor Laboratory Press, Woodbury, NY, US, vol. 12, No. 2, Feb. 2002, pp. 349-354.
Gail Urlaub, et al., Deletion of the diploid dihydrofolate reductase locus from cultured mammalian cells, Cell, Jun. 1983, pp. 405-412, vol. 33, MIT, US.
Gautam Singh, et al., Mathematical model to predict regions of chromatin attachment to the nuclear matrix, Nucleic Acids Research, 1997, pp. 1419-1425, vol. 25, No. 7, Oxford University Press, UK.
GenBank Accession AL445164, Jan. 26, 2001.
GenBank Accession No. AL121984, Jul. 29, 2000.
GenBank Accession No. AL592166, Mar. 23, 2003.
George C. Allen, et al., High-Level Transgene Expression in Plant Cells: Effects of a Strong Scaffold Attachment Region from Tobacco, The Plant Cell, May 1996, pp. 899-913, vol. 8, American Society of Plant Physiologists, US.
George W. Cox, et al., Molecular Cloning and Characterization of a Novel MouseMacrophage Gene That Encodes a Nuclear Protein ComprisingPolyglutamine Repeats and Interspersing Histidines, The Journal of Biological Chemistry, Oct. 11, 1996, pp. 25515-25523, vol. 271, No. 41, The American Society for Biochemistry and Molecular Biology, US.
Girod Pierre-Alain et al: "Genome-wide prediction of matrix attachment regions that increase gene expression in mammalian cells" in Nature Methods, vol. 4, No. 9, Aug. 5, 2007, pp. 747-753.
Girod Pierre-Alain et al: "Use of the chicken lysozyme 5' matrix attachment region to generate high producer CHO cell lines" in Biotechnology and Bioengineering, vol. 91, No. 1, Jul. 2005, pp. 1-11.
Glazko, G., et al., Comparative study and prediction of DNA fragments associated with various elements of the nuclear matrix, Biochimica et Biophysica Acta, 1517, 2001, pp. 351-364.
Goetze, S., et al., Computational and in Vitro Analysis of Destabilized DNA Regions in the interferon Gene Cluster: Potential of Predicting Functional Gene Domains, Biochemistry, 2003, 42, pp. 154-166.
Grant MacGregor and C. Thomas Caskey, Construction of plasmids that express E. coli b-galactosidase in mammalian cells, Nucleic Acids Research, 1989, p. 2365, vol. 17, No. 6, IRL Press, US.
Gutierrez-Adan A et al: "Effect of Flanking Matrix Attachment Regions on the Expression of Microinjected Transgenes During Preimplantation Development of Mouse Embryos" in Transgenic Research, London, GB, vol. 9, No. 2, Apr. 2000, pp. 81-89.
J. Patrick Condreay, et al., Transient and stable gene expression in mammalian cells transduced with a recombinant baculovirus vector, Cell Biology, Jan. 1999, pp. 127-132, vol. 96, Proc. Natl. Acad. Sci. USA, US.
Joaquin Castilla, et al., Engineering passive immunity in transgenic mice secreting virus-neutralizing antibodies in milk, Nature Biotechnology, Apr. 1998, pp. 349-354, vol. 16, Nature Publishing Group, US.
Jurgen Bode, et al., Transcriptional Augmentation: Modulation of Gene Expression by Scaffold/Matrix-Attached Regions (S/MAR Elements), Critical ReviewsTM in Eukaryotic Gene Expression, 2000, pp. 73-90, vol. 10(1), Begell House, Inc., US.
Kevin Wells, et al., Codon optimization, genetic insulation, and an rtTA reporter improve performance of the tetracycline switch, Transgenic Research, 1999, pp. 371-381, vol. 8, Kluwer Academic Publishers, NL.
Kiehr et al., "Scaffold-Attached Regions from the Human Interferon B Domain Can Be Used to Enhance the Stable Expression of Genes Under the Control of Various Promoters," Biochemistry, vol. 30, 1991, pp. 1264-1270.
Kim Jong-Mook et al: "Improved recombinant gene expression in CHO cells using matrix attachment regions" in Journal of Biotechnology, Elsevier Science Publishers, Amsterdam, NL, vol. 107, No. 2, Jan. 22, 2004, pp. 95-105.
Kries et al. A non-curved chicken lysozyme 5' matrix attachment site is 3' followed by a strongly curved DNA sequence. Nucleic Acids Research, vol. 18, No. 13, pp. 3881-3885, 1990.
Kries et al: "A non-curved chicken lysyzyme matrix attachment site is 3' followed by a strongly curved DNA sequence" in Nucleic Acids Research, Oxford University Press, Surrey, GB, vol. 18, No. 13, Jul. 11, 1990, pp. 3881-3885.
Kwaks et al., "Identification of Anti-Repressor Elements that Confer High and Stable Protein Production in Mammalian Cells," in Nature Biotechnology, Nature Publishing Group, New York, NY, vol. 21(5), May 20, 2003, pp. 553-558.
Kwaks et al: "Employing epigenetics to augment the expression of therapeutic proteins in mammalian cells" in Trends in Biotechnology, Elsevier Publications, Cambridge, GB, vol. 24, No. 3, Mar. 2006, pp. 137-142.
Lad, H., Human DNA sequence from clone RP11-329A14 on chromosome 1, GenBank Accession No. AL356968, May 26, 2000.
Leonora Poljak, et al., SARs stimulate but do not confer position independent gene expression, Nucleic Acids Research, 1994, pp. 4386-4394, vol. 22, No. 21, Oxford University Press, UK.
Levitsky et al., "Nucleosomal DNA Property Database," in Bioinformatics, vol. 15(7/8), 1999, pp. 582-592.
Liebich I et al: "Evaluation of sequence motifs found in scaffold/matrix-attached regions (S/MARs)" in Nucleic Acids Research, Oxford University Press, Surrey, GB, vol. 30, No. 15, Aug. 1, 2002, pp. 3433-3442.
Liebich Ines et al: "S/MARt DB: A database on scaffold/matrix attached regions" Nucleic Acids Research, vol. 30, No. 1, Jan. 1, 2002, pp. 372-374.
Loc Phi-Van, et al., The Chicken Lysozyme 5' Matrix Attachment Region Increases Transcription from a Heterologous Promoter in Heterologous Cells and Dampens Position Effects on the Expression of Transfected Genes, Molecular and Cellular Biology, May 1990, pp. 2302-2307, vol. 10, No. 5, American Society for Microbiology, US.

(56) References Cited

OTHER PUBLICATIONS

MacGregor, et al., "Construction of Plasmids that Express *E. coli* B-Galactosidase in Mammalian Cells," Nucleic Acids Research, vol. 17, No. 6, IRL Press, US, 1989 p. 2365.

Manju Agarwal, et al., Scaffold Attachment Region-Mediated Enhancement of Retroviral Vector Expression in Primary T Cells, Journal of Virology, May 1998, pp. 3720-3728, vol. 72, No. 5, American Society for Microbiology, US.

Marini, J., et al., Bent Helical structure in kinetoplast DNA, Proc. Natl. Acad. Sci. USA, vol. 79, 1982, pp. 7664-7668.

Mark Walters, et al., The Chicken b-Globin 59HS4 Boundary Element Blocks Enhancer-Mediated Suppression of Silencing,Mark Walters, et al., The Chicken b-Globin 59HS4 Boundary Element Blocks Enhancer-Mediated Suppression of Silencing, Molecular and Cellular Biology, May 1999, pp. 3714-3726, vol. 19, No. 5, American Society for Microbiology, US Molecular and Cellular Biology, May 1999, pp. 3714-3726, vol. 19, No. 5, American Society for Microbiology, US.

Markus O. Imhof, et al., A regulatory network for the efficient control of transgene expression, The Journal of Gene Medicine, 2000, pp. 107-116, vol. 2, John Wiley & Sons, Ltd., US.

Martin Fussenegger, et al., Genetic optimization of recombinant glycoprotein production by mammalian cells, TIBTECH, Jan. 1999, pp. 35-42, vol. 17, Elsevier Science Ltd., US.

Martin Jordan, 'et al., Transfecting mammalian cells: optimization of critical parameters affecting calcium-phosphate precipitate formation, Nucleic Acids Research, 1996, pp. 596-601, vol. 24, No. 4, Oxford University Press, UK.

Masaaki Tatsuka, et al., Experimental Cell Research, 1988, pp. 154-162, vol. 178, Academic Press, Inc., SE.

Matthias Frisch, et al., In Silico Prediction of Scaffold/Matrix Attachment Regions in Large Genomic Sequences, Genome Research, 2001, pp. 349-354, vol. 12, Cold Harbor Laboratory Press, US.

Michael Kalos and R. E. K. Fournier, Molecular and Cellular Biology, Jan. 1995, pp. 198-207, vol. 15, No. 1, American Society for Microbiology, US.

Monique Zahn-Zabal, et al., Development of stable cell lines for production or regulated expression using matrix attachment regions, Journal of Biotechnology, 2001, pp. 29-42, vol. 87, Elsiver Science Ltd., US.

Moore, M., et al., Human DNA sequence from clone RP11-277C14 on chromosome 1 Contains part of the DNM3 gene for dynamin 3, EMBL.

N. M. Greenberg, et al., The rat probasin gene promoter directs hormonally and developmentally regulated expression of a heterologous gene specifically to the prostate in transgenic mice, Molecular Endocrinology, 1994, pp. 230-239, vol. 8, No. 2, The Endocrine Society, US.

Olivier Cuvier, et al., Identification of a Class of Chromatin Boundary Elements, Molecular and Cellular Biology, Dec. 1998, pp. 7478-7486, vol. 18, No. 12, American Society for Microbiology, US.

Otmane Boussif, et al., A versatile vector for gene and oligonucleotide transfer into cellsin culture and in vivo: Polyethylenimine, Biochemistry, Aug. 1995, pp. 7297-7301, vol. 92, Proc. Natl. Acad. Sci. USA, US.

Phi-Van & Staetling; The matrix attachment regions of the chicken lysozyme gene co-map with the boundaries of the chromatin domain, EMBO J. 7, No. 3: 655-664 (1988).

Pierre Rollini, et al. Identification and characterization of nuclear matrix-attach,emt regions in the human serpin gene cluster at 14q32.1, Nucleic Acids Research, 1999, pp. 3779-3791, vol. 27, No. 19, Oxford University Press, UK.

Quandt, K, et al., MatInd and MatInspector: new fast and versatile tools for detection of consensus matches in nucleotide sequence data, Nucleic Acids Research, 1995, vol. 23, No. 23, pp. 4878-4884.

Randal Kaufman and Phillip Sharp, Amplification and Expression of Sequences Cotransfected with a Modular Dihydrofolate Reductase Complementary DNA Gene, Journal of Molecular Biology, 1982, pp. 601-621, vol. 159, Academic Press Inc. (London) Ltd., UK.

Robert McKnight, et al., Martrix-attachment regions can impart position-independent regulation of a tissue-specific gene in transgenic mice, Genetics, Aug. 1992, pp. 6943-6947, vol. 89, Proc. Natl. Acad. Sci. USA, US.

Robert Pawliuk, et al., Retroviral vectors aimed at the gene therapy of human beta-golbin gene disorder, Annals New York Academy of Sciences, 1998, pp. 151-162 , vol. 850, New York Academy of Sciences, US.

Roulet et al., "Evaluation of computer tools for the prediction of transcription factor binding sites on genomic DNA," Bioinformation Systems, e.V., available at http://www.bioinfo.de/isb/1998010004/main.html, accessed Sep. 7, 2010.

Sequence Alignment of SEQ ID 24 with SEQ ID No. 2 of U.S. Appl. No. 13/1496,517, 6 pages, search conducted by examiner of U.S. Appl. No. 13/536,383, filed Dec. 16, 2014.

Sequence Alignment of SEQ ID 27 with SEQ ID No. 3 of U.S. Appl. No. 13/1496,517, 5 pages, search conducted by examiner of U.S. Appl. No. 13/536,383, filed Dec. 16, 2014.

Singh et al., "Mathematical Model to Predict Regions of Chromatin Attachment to the Nuclear Matrix," in Nucleic Acid Research, vol. 25(7), 1997, pp. 1419-1425.

Singh G B et al: "Mathematical model to predict regions of chromatin attachment to the nuclear matrix" in Nucleic Acids Research, Oxford University Press, Surrey, GB, vol. 25, No. 7, 1997, pp. 1419-1425.

Southgate et al, Transcriptional Targeting to Anterior Pituitary Lactotrophic Cells Using Recombinant Adenovirus Vectors in Vitro and in Vivo in Normal and Estrogen/Sulpiride-Induced Hyperplasic Anterios Pituitaries, Endocr, 2000, vol. 141 pp. 3493-3505.

Sylvia Miescher, et al., CHO expression of a novel human recombinant IgG1 anti-RhD antibody isolated by ohage display, British Journal of Haematology, 2000, pp. 157-166, vol. 111, Blackwell Science Ltd., UK.

T. D. Southgate, et al., Transcriptional Targeting to Anterior Pituitary Lactotrophic Cells Using Recombinant Adenovirus Vectors in Vitro and in Vivo in Normal and Estrogen/Sulpiride-Induced Hyperplasic Anterior Pituitaries, Endocrinology, 2000, pp. 3493-3505, vol. 141, No. 9, The Endocrine Society, US.

Tatsuka et al, An Improved Method of Electroporation for Introducing Biologically Active Foreign Genes into Cultured Mammalian Cells, Exp Cell Res, 1988, vol. 178 pp. 154-162.

Ted H.J. Kwaks, et al., Identification of anti-repressor elements that confer high and stable protein production in mammalian cells, Nature Biotechnology, May 2003, pp. 553-558, vol. 21, Nature Publishing Group, US.

Thomas Jenuwein, et al., Extension of chromatin accessibility by nuclear matrix attachment regions, Nature, Jan. 16, 1997, pp. 269-272, vol. 385, Nature Publishing Group, US.

Tianyun Wang et al: "Increased expression of transgene in stably transformed cells of Dunaliella salina by matrix attachment regions" in Applied Microbiology and Biotechnology, Springer-Verlag, BE, vol. 76, No. 3, Jul. 5, 2007, pp. 651-657.

Tobias Neff, et al., Stem Cell Gene Therapy, Position Effects and Chromatin Insulators, Hematopoietic Stem Cells, Stem Cells, 1997, pp. 265-271, vol. 15(suppl 1), AlphaMed Press, US.

Vain P et al: "Matrix Attachment Regions Increase Transgene Expression Levels and Stability in Transgenic Rice Plants and Their Progeny" in Plant Journal, Blackwell Scientific Publications, Oxford, GB, vol. 18, No. 3, 1999, pp. 233-242.

Van Durnen, C., et al., A bipartite sequence element associated with matrix/scaffold attachment regions, Nucleic Acids Research, 1999, vol. 27, No. 14, pp. 2924-2930.

Victor Levitsky, et al., Nucleosomal DNA property database, Bioinformatics, 1999, pp. 582-592, vol. 15, Nos. 7/8, Oxford University Press, UK.

Wallis, J., et al., Human DNA sequence from clone RP11-269F19 on chromosome 1 Contains the KIF2C gene for kinesin family member 2C, a novel gene, the RPS8 gene for ribosomal protein S8, a ribosomal protein S15a (RPS15A) pseudogene, the VMD2L2 gene for vitelliform macular dystrophy-like 2, the CNK gene for cytokine-indu, EMBL.

(56) References Cited

OTHER PUBLICATIONS

Whitehead S., A Human DNA sequence from clone RP4-736G20 on chromosome Xq23-24 contains part of a novel gene (KIAA1495); GenBank Accession AL 445164, Jan. 26, 2001.
Whitelaw C B A et al: "Matrix attachment region regulates basal beta-lactoglobulin transgene expression" in Gene, Elsevier, Amsterdam, NL, vol. 244, No. 1-2, Feb. 2000, pp. 73-80.
Xin Bi and James R. Broach, UASrpg can function as a heterochromatin boundary element in yeast, Genes & Development, 1999, pp. 1089-1101, vol. 13, Cold Spring Harbor Laboratory Press, US.
Yamamoto, et al., High efficiency gene transfer by multiple transfection protocol, Histochem. J., 1999, vol. 31, No. 4, pp. 241-243.
Yamamura J et al: "Analysis of sequence-dependent curvature in matrix attachment regions" in FEBS Letters, Elsevier Amsterdam, NL, vol. 489, No. 2-3, Feb. 2, 2001, pp. 166-170.
Yaolin Wang, et al., Ligand-inducible and liver-specific target gene expression in transgenic mice, Nature Biotechnology, Mar. 1997, pp. 239-243, vol. 15, Nature Publishing Group, US.
Zahn-Zabal et al., "Development of Stable Cell Lines for Production or Regulated Expression Using Matrix Attachment Regions," in Journal of Biotechnology, vol. 87, 2001, pp. 29-42.

\* cited by examiner

HIGH EFFICIENCY GENE TRANSFER AND EXPRESSION IN MAMMALIAN CELLS BY A MULTIPLE TRANSFECTION PROCEDURE OF MAR SEQUENCES

This is a divisional application of U.S. application Ser. No. 13/536,383, filed Jun. 28, 2012, which is incorporated herein by reference in its entirety and which is a divisional application of U.S. application Ser. No. 10/595,495 filed Apr. 24, 2006, now U.S. Pat. No. 8,252,917, which is the U.S. national stage of International application no. PCT/EP2004/011974, filed Oct. 22, 2004 designating the United States and claiming the benefit of U.S. provisional application no. 60/513,574, filed Oct. 24, 2003 and priority to European application no. 04002722.9, filed Feb. 6, 2004.

FIELD OF THE INVENTION

The present invention relates to purified and isolated DNA sequences having protein production increasing activity and more specifically to the use of matrix attachment regions (MARs) for increasing protein production activity in a eukaryotic cell. Also disclosed is a method for the identification of said active regions, in particular MAR nucleotide sequences, and the use of these characterized active MAR sequences in a new multiple transfection method.

BACKGROUND OF THE INVENTION

Nowadays, the model of loop domain organization of eukaryotic chromosomes is well accepted (Boulikas T, "Nature of DNA sequences at the attachment regions of genes to the nuclear matrix", *J. Cell Biochem.*, 52:14-22, 1993). According to this model chromatin is organized in loops that span 50-100 kb attached to the nuclear matrix, a proteinaceous network made up of RNPs and other nonhistone proteins (Bode J, Stengert-Iber M, Kay V, Schalke T and Dietz-Pfeilstetter A, *Crit. Rev. Euk. Gene Exp.*, 6:115-138, 1996).

The DNA regions attached to the nuclear matrix are termed SAR or MAR for respectively scaffold (during metaphase) or matrix (interphase) attachment regions (Hart C and Laemmli U (1998), "Facilitation of chromatin dynamics by SARs" *Curr Opin Genet Dev* 8, 519-525.)

As such, these regions may define boundaries of independent chromatin domains, such that only the encompassing cis-regulatory elements control the expression of the genes within the domain.

However, their ability to fully shield a chromosomal locus from nearby chromatin elements, and thus confer position-independent gene expression, has not been seen in stably transfected cells (Poljak L, Seum C, Mattioni T and Laemmli U. (1994) "SARs stimulate but do not confer position independent gene expression", *Nucleic Acids Res* 22, 4386-4394). On the other hand, MAR (or S/MAR) sequences have been shown to interact with enhancers to increase local chromatin accessibility (Jenuwein T, Forrester W, Fernandez-Herrero L, Laible G, Dull M, and Grosschedl R. (1997) "Extension of chromatin accessibility by nuclear matrix attachment regions" *Nature* 385, 269-272). Specifically, MAR elements can enhance expression of heterologous genes in cell culture lines (Kalos M and Fournier R (1995) "Position-independent transgene expression mediated by boundary elements from the apolipoprotein B chromatin domain" *Mol Cell Biol* 15, 198-207), transgenic mice (Castilla J, Pintado B, Sola, I, Sanchez-Morgado J, and Enjuanes L (1998) "Engineering passive immunity in transgenic mice secreting virus-neutralizing antibodies in milk" *Nat Biotechnol* 16, 349-354) and plants (Allen G, Hall GJ, Michalowski S, Newman W, Spiker S, Weissinger A, and Thompson W (1996), "High-level transgene expression in plant cells: effects of a strong scaffold attachment region from tobacco" *Plant Cell* 8, 899-913). The utility of MAR sequences for developing improved vectors for gene therapy is also recognized (Agarwal M, Austin T, Morel F, Chen J, Bohnlein E, and Plavec I (1998), "Scaffold attachment region-mediated enhancement of retroviral vector expression in primary T cells" *J Virol* 72, 3720-3728).

Recently, it has been shown thatchromatin-structure modifying sequences including MARs, as exemplified by the chicken lysozyme 5' MAR is able to significantly enhance reporter expression in pools of stable Chinese Hamster Ovary (CHO) cells (Zahn-Zabal M, et al., "Development of stable cell lines for production or regulated expression using matrix attachment regions" *J Biotechnol*, 2001, 87(1): p. 29-42). This property was used to increase the proportion of high-producing clones, thus reducing the number of clones that need to be screened. These benefits have been observed both for constructs with MARs flanking the transgene expression cassette, as well as when constructs are co-transfected with the MAR on a separate plasmid. However, expression levels upon co-transfection with MARs were not as high as those observed for a construct in which two MARs delimit the transgene expression unit. A third and preferable process was shown to be the transfection of transgenes with MARs both linked to the transgene and on a separate plasmid (Girod et al., submitted for publication). However, one persisting limitation of this technique is the quantity of DNA that can be transfected per cell. Many multiples transfection protocols have been developed in order to achieve a high transfection efficiency to characterize the function of genes of interest. The protocol applied by Yamamoto et al, 1999 ("High efficiency gene transfer by multiple transfection protocol", *Histochem. J.* 31(4), 241-243) leads to a transfection efficiency of about 80% after 5 transfections events, whereas the conventional transfection protocol only achieved a rate of <40%. While this technique may be useful when one wishes to increase the proportion of expressing cells, it does not lead to cells with a higher intrinsic productivity. Therefore, it cannot be used to generate high producer monoclonal cell lines. Hence, the previously described technique has two major drawbacks:

i) this technique does not generate a homogenous population of transfected cells, since it cannot favor the integration of further gene copy, nor does it direct the transgenes to favorable chromosomal loci, ii) the use of the same selectable marker in multiple transfection events does not permit the selection of doubly or triply transfected cells.

In patent application WO02/074969, the utility of MARs for the development of stable eukaryotic cell lines has also been demonstrated. However, this application does not disclose neither any conserved homology for MAR DNA element nor any technique for predicting the ability for a DNA sequence to be a MAR sequence.

In fact no clear-cut MAR consensus sequence has been found (Boulikas T, "Nature of DNA sequences at the attachment regions of genes to the nuclear matrix", *J. Cell Biochem.*, 52:14-22, 1993) but evolutionarily, the structure of these sequences seem to be functionally conserved in eukaryotic genomes, since animal MARs can bind to plant nuclear scaffolds and vice versa (Mielke C, Kohwi Y, Kohwi-Shigematsu T and Bode J, "Hierarchical binding of DNA fragments derived from scaffold-attached regions: correlation of properties in vitro and function in vivo", *Biochemistry*, 29:7475-7485, 1990).

The identification of MARs by biochemical studies is a long and unpredictable process; various results can be obtained depending on the assay (Razin S V, "Functional architecture of chromosomal DNA domains", *Crit Rev Eukaryot Gene Expr.*, 6:247-269, 1996). Considering the huge number of expected MARs in a eukaryotic genome and the amount of sequences issued from genome projects, a tool able to filter potential MARS in order to perform targeted experiments would be greatly useful.

Currently two different predictive tools for MARs are available via the Internet. The first one, MAR-Finder (Singh G B, Kramer J A and Krawetz S A, "Mathematical model to predict regions of chromatin attachment to the nuclear matrix", Nucleic Acid Research, 25:1419-1425, 1997) is based on set of patterns identified within several MARs and a statistical analysis of the co-occurrence of these patterns. MAR-Finder predictions are dependent of the sequence context, meaning that predicted MARs depend on the context of the submitted sequence. The other predictive software, SMARTest (Frisch M, Frech K, Klingenhoff A, Cartharius K, Liebich I and Werner T, "In silico prediction of scaffold/matrix attachment regions in large genomic sequences", Genome Research, 12:349-354, 2001), use weight-matrices derived from experimentally identified MARs. SMARTest is said to be suitable to perform large-scale analyses. But actually aside its relative poor specificity, the amount of hypothetical MARs rapidly gets huge when doing large scale analyses with it, and in having no way to increase its specificity to restrain the number of hypothetical MARs, SMARTest becomes almost useless to screen for potent MARs form large DNA sequences.

Some other softwares, not available via the Internet, also exists; they are based as well on the frequency of MAR motifs (MRS criterion; Van Drunen C M et al., "A bipartite sequence element associated with matrix/scaffold attachment regions", *Nucleic Acids Res*, 27:2924-2930, 1999), (ChrClass; Glazko G V et al., "Comparative study and prediction of DNA fragments associated with various elements of the nuclear matrix", *Biochim. Biophys. Acta,* 1517: 351-356, 2001) or based on the identification of sites of stress-induced DNA duplex (SIDD; Benham C and al., "Stress-induced duplex DNA destabilization in scaffold/matrix attachment regions", *J. Mol. Biol.*, 274:181-196, 1997). However, their suitability to analyze complete genome sequences remains unknown, and whether these tools may allow the identification of protein production-increasing sequences has not been reported.

Furthermore, due to the relatively poor specificity of these softwares (Frisch M, Frech K, Klingenhoff A, Cartharius K, Liebich I and Werner T, "In silico prediction of scaffold/matrix attachment regions in large genomic sequences", *Genome Research,* 12:349-354, 2001), the amount of hypothetical MARs identified in genomes rapidly gets unmanageable when doing large scale analyses, especially if most of these have no or poor activity in practice. Thus, having no way to increase prediction specificity to restrain the number of hypothetical MARs, many of the available programs become almost useless to identify potent genetic elements in view of efficiently increasing recombinant protein production.

Since all the above available predictive methods have some drawbacks that prevent large-scale analyses of genomes to identify reliably novel and potent MARs, the object of this invention is to 1) understand the functional features of MARs that allow improved recombinant protein expression; 2) get a new Bioinformatic tool compiling MAR structural features as a prediction of function, in order to 3) perform large scale analyses of genomes to identify novel and more potent MARs, and, finally 4) to demonstrate improved efficiency to increase the production of recombinant proteins from eukaryotic cells or organisms when using the newly identified MAR sequences.

SUMMARY OF THE INVENTION

This object has been achieved by providing an improved and reliable method for the identification of DNA sequences having protein production increasing activity, in particular MAR nucleotide sequences, and the use of these characterized active MAR sequences in a new multiple transfection method to increase the production of recombinant proteins in eukaryotic cells.

BRIEF DESCRIPTION OF THE FIGURES

FIG. 8 (B) represents a Map of locations for various DNA sequence motifs within the cLysMAR. Vertical lines represent the position of the computer-predicted sites or sequence motifs along the 3034 base pairs of the cLysMAR and its active regions, as presented in FIG. 5. The putative transcription factor sites, (MEF2 05, Oct-1, USF-02, GATA, NFAT) for activators and (CDP, SATB1, CTCF, ARBP/MeCP2) for repressors of transcription, were identified using MatInspector (Genomatix), and CpG islands were identified with CPGPLOT. Motifs previously associated with MAR elements are labeled in black and include CpG dinucleotides and CpG islands, unwinding motifs (AATATATT and MTATT), poly As and Ts, poly Gs and Cs, Drosophila topoisomerase II binding sites (GTNWAYATTNATTNATNNR (SEQ ID NO: 242)) which had identity to the 6 bp core and High mobility group I (HMG-I/Y) protein binding sites. Other structural motifs include nucleosome-binding and nucleosome disfavoring sites and a motif thought to relieve the superhelical strand of DNA. FIG. 8(A) represents the comparison of the ability of portions of the cLysMAR to activate transcription with MAR prediction score profiles with MarFinder. The top diagram shows the MAR fragment activity as in FIG. 5, while the middle and bottom curves show MARFinder-predicted potential for MAR activity and for bent DNA structures respectively.

FIG. 9(A), represents the DNA melting temperature, double helix bending, major groove depth and minor groove width profiles of the 5'-MAR and were determined using the algorithms of Levitsky et al (Levitsky V G, Ponomarenko M P, Ponomarenko J V, Frolov A S, Kolchanov N A "Nucleosomal DNA property database", *Bioinformatics*, 15; 582592, 1999). The most active B, K and F fragments depicted at the top are as shown as in FIG. 1. FIG. 9(B), represents the enlargement of the data presented in panel A to display the F fragment map aligned with the tracings corresponding to the melting temperature (top curve) and DNA bending (bottom curve). The position of the most active FIB fragment and protein binding site for specific transcription factors are as indicated.

DETAILED DESCRIPTION OF THE INVENTION

Figure 1:
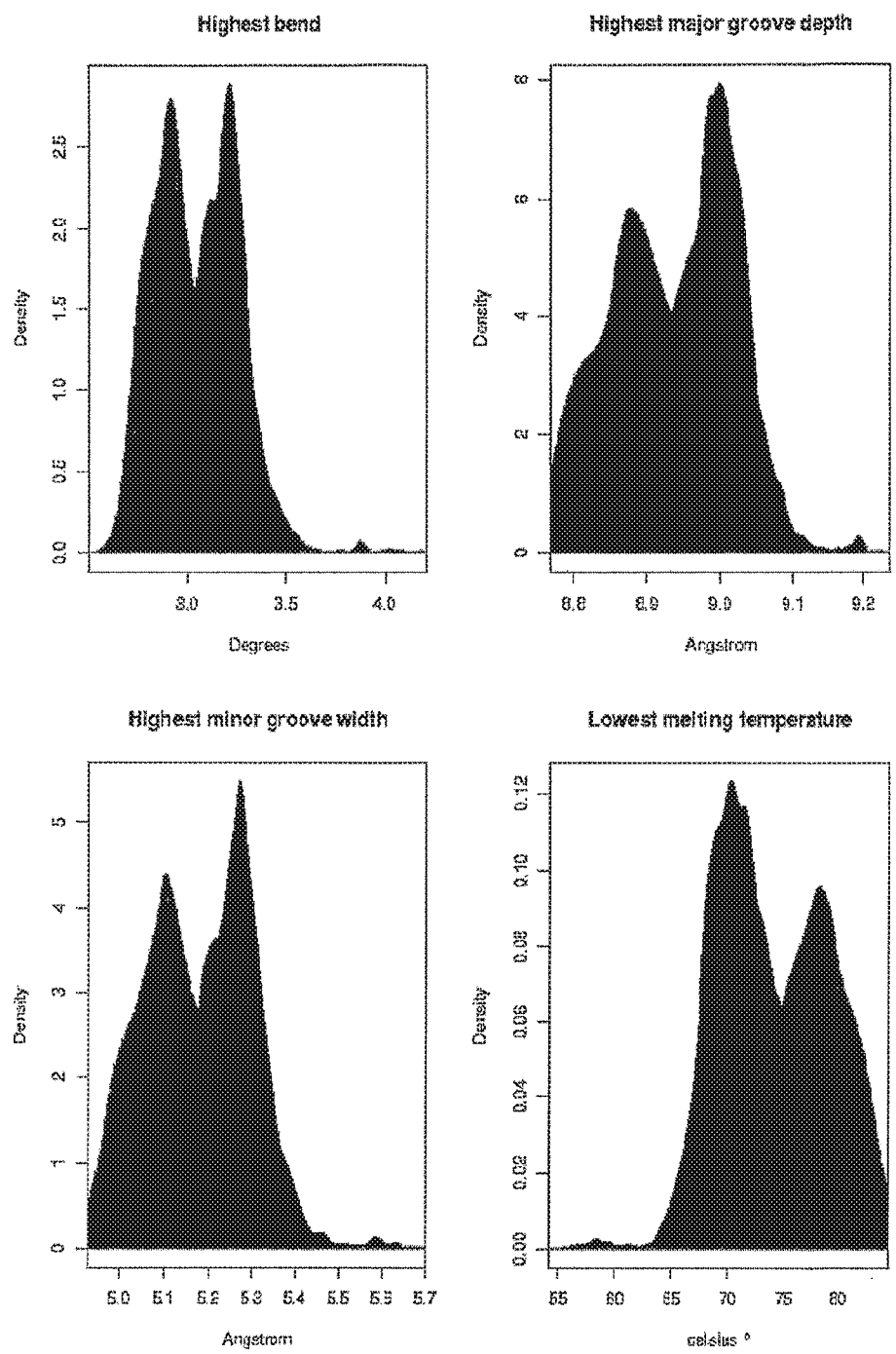
FIG. 1 shows the distribution plots of MARs and non-MARs sequences. Histograms are density plots (relative frequency divided by the bin width) relative to the score of the observed parameter. The density histogram for human MARs in the SMARt DB database is shown in black, while the density histogram for the human chromosome 22 is in grey.

The present invention relates to a purified and isolated DNA sequence having protein production increasing activity characterized in that said DNA sequence comprises at least one bent DNA element, and at least one binding site for a DNA binding protein.

Certain sequences of DNA are known to form a relatively "static curve", where the DNA follows a particular 3-dimensional path. Thus, instead of just being in the normal B-DNA conformation ("straight"), the piece of DNA can form a flat, planar curve also defined as bent DNA (Marini, et al., 1982 "Bent helical structure in kinetoplast DNA", *Proc. Natl. Acad. Sci. USA*, 79: 7664-7664).

Surprisingly, Applicants have shown that the bent DNA element of a purified and isolated DNA sequence having protein production increasing activity of the present invention usually contains at least 10% of dinucleotide TA, and/or at least 12% of dinucleotide AT on a stretch of 100 contiguous base pairs. Preferably, the bent DNA element contains at least 33% of dinucleotide TA, and/or at least 33% of dinucleotide AT on a stretch of 100 contiguous base pairs. These data have been obtained by the method described further.

According to the present invention, the purified and isolated DNA sequence usually comprises a MAR nucleotide sequence selected from the group comprising the sequences SEQ ID Nos 1 to 27 or a cLysMAR element or a fragment thereof. Preferably, the purified and isolated DNA sequence is a MAR nucleotide sequence selected from the group comprising the sequences SEQ ID Nos 1 to 27, more preferably the sequences SEQ ID Nos 24 to 27.

Encompassed by the present invention are as well complementary sequences of the above-mentioned sequences SEQ ID Nos 1 to 27 and the cLysMAR element or fragment, which can be produced by using PCR or other means.

An "element" is a conserved nucleotide sequences that bears common functional properties (i.e. binding sites for transcription factors) or structural (i.e. bent DNA sequence) features.

A part of sequences SEQ ID Nos 1 to 27 and the cLysMAR element or fragment refers to sequences sharing at least 70% nucleotides in length with the respective sequence of the SEQ ID Nos 1 to 27. These sequences can be used as long as they exhibit the same properties as the native sequence from which they derive. Preferably these sequences share more than 80%, in particular more than 90% nucleotides in length with the respective sequence of the SEQ ID Nos 1 to 27.

The present invention also includes variants of the aforementioned sequences SEQ ID Nos 1 to 27 and the cLysMAR element or fragment, that is nucleotide sequences that vary from the reference sequence by conservative nucleotide substitutions, whereby one or more nucleotides are substituted by another with same characteristics.

The sequences SEQ ID Nos 1 to 23 have been identified by scanning human chromosome 1 and 2 using SMAR SCAN, showing that the identification of novel MAR sequences is feasible using the tools reported thereafter whereas SEQ ID No 24 to 27 have been identified by scanning the complete human genome using the combined SMAR SCAN method.

Figure 3:
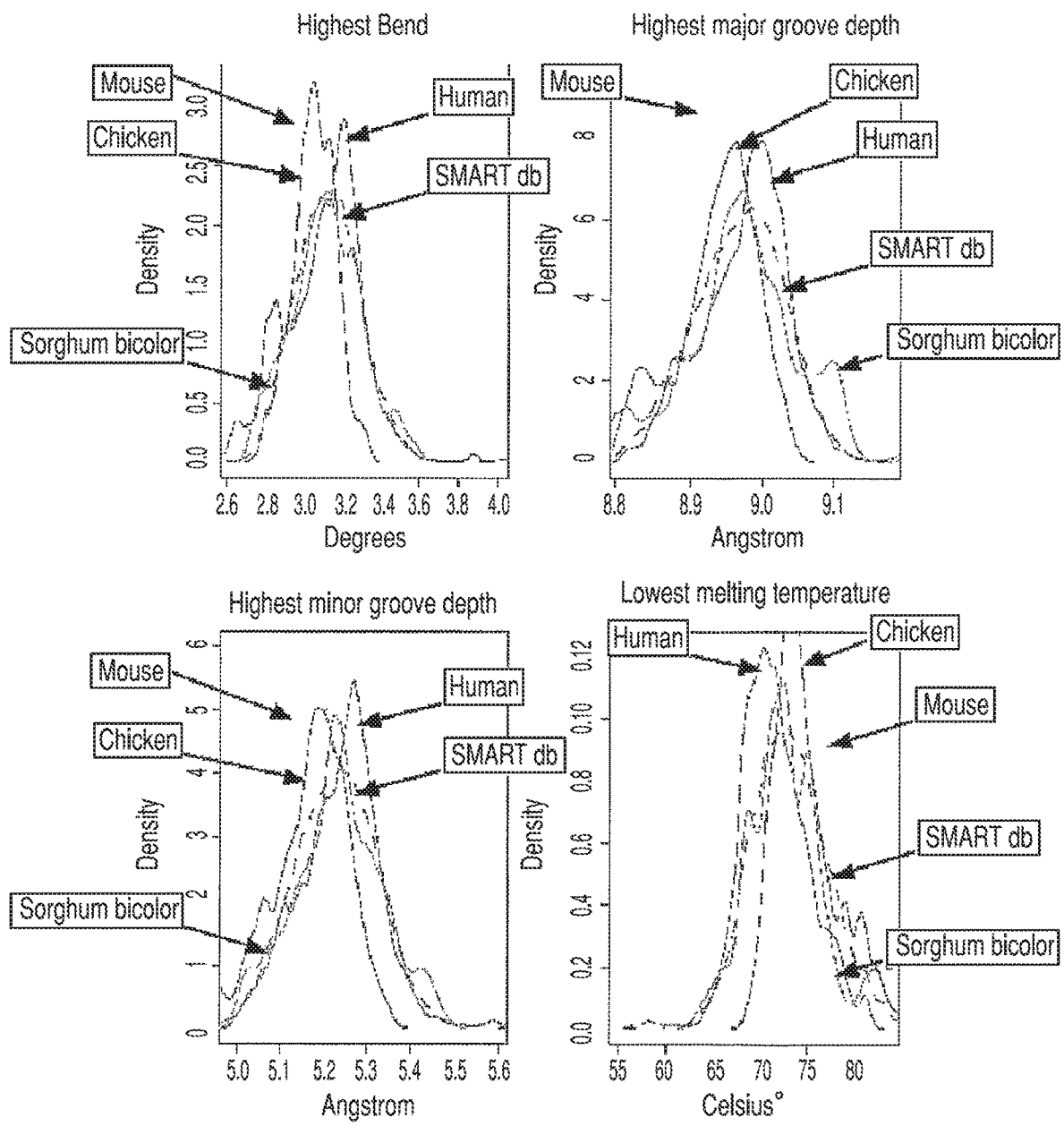
FIG. 3 shows the distribution plots of MAR sequences by organism. MAR sequences from SMARt DB of other organisms were retrieved and analyzed. The MAR sequences density distributions for the mouse, the chicken, the sorghum bicolor and the human are plotted jointly.

In a first step, the complete chromosome 1 and 2 were screened to identify bent DNA element as region corresponding to the highest bent, major groove depth, minor groove width and lowest melting temperature as shown in FIG. 3. In a second step, this collection of sequence was scanned for binding sites of regulatory proteins such as SATB1, GATA, etc. as shown in the FIG. 8B) yielding sequences SEQ ID 1-23. Furthermore, sequences 21-23 were further shown to be located next to known gene from the Human Genome Data Base.

With regard to SEQ ID No 24 to 27 these sequences have been yielded by scanning the human genome according to the combined method and were selected as examples among 1757 MAR elements so detected.

Molecular chimera of MAR sequences are also considered in the present invention. By molecular chimera is intended a nucleotide sequence that may include a functional portion of a MAR element and that will be obtained by molecular biology methods known by those skilled in the art.

Particular combinations of MAR elements or fragments or sub-portions thereof are also considered in the present invention. These fragments can be prepared by a variety of methods known in the art. These methods include, but are not limited to, digestion with restriction enzymes and recovery of the fragments, chemical synthesis or polymerase chain reactions (PCR).

Therefore, particular combinations of elements or fragments of the sequences SEQ ID Nos 1 to 27 and cLysMAR elements or fragments are also envisioned in the present invention, depending on the functional results to be obtained. Elements of the cLysMAR are e.g. the B, K and F regions as described in WO 02/074969, the disclosure of which is hereby incorporated herein by reference, in its entirety. The preferred elements of the cLysMAR used in the present invention are the B, K and F regions. Only one element might be used or multiple copies of the same or distinct elements (multimerized elements) might be used (see FIG. 8 A)).

By fragment is intended a portion of the respective nucleotide sequence. Fragments of a MAR nucleotide sequence may retain biological activity and hence bind to purified nuclear matrices and/or alter the expression patterns of coding sequences operably linked to a promoter. Fragments of a MAR nucleotide sequence may range from at least about 100 to 1000 bp, preferably from about 200 to 700 bp, more preferably from about 300 to 500 bp nucleotides. Also envisioned are any combinations of fragments, which have the same number of nucleotides present in a synthetic MAR sequence consisting of natural MAR element and/or fragments. The fragments are preferably assembled by linker sequences. Preferred linkers are BgIII-BamHI linker.

"Protein production increasing activity" refers to an activity of the purified and isolated DNA sequence defined as follows: after having been introduced under suitable conditions into a eukaryotic host cell, the sequence is capable of increasing protein production levels in cell culture as compared to a culture of cell transfected without said DNA sequence. Usually the increase is 1.5 to 10 fold, preferably 4 to 10 fold. This corresponds to a production rate or a specific cellular productivity of at least 10 pg per cell per day (see Example 11 and FIG. 13).

As used herein, the following definitions are supplied in order to facilitate the understanding of this invention.

"Chromatin" is the protein and nucleic acid material constituting the chromosomes of a eukaryotic cell, and refers to DNA, RNA and associated proteins.

A "chromatin element" means a nucleic acid sequence on a chromosome having the property to modify the chromatine structure when integrated into that chromosome.

"Cis" refers to the placement of two or more elements (such as chromatin elements) on the same nucleic acid molecule (such as the same vector, plasmid or chromosome).

"Trans" refers to the placement of two or more elements (such as chromatin elements) on two or more different nucleic acid molecules (such as on two vectors or two chromosomes).

Chromatin modifying elements that are potentially capable of overcoming position effects, and hence are of interest for the development of stable cell lines, include boundary elements (BEs), matrix attachment regions (MARs), locus control regions (LCRs), and universal chromatin opening elements (UCOEs).

Boundary elements ("BEs"), or insulator elements, define boundaries in chromatin in many cases (Bell A and Felsenfeld G. 1999; "Stopped at the border: boundaries and insulators, *Curr Opin Genet Dev* 9, 191-198) and may play a role in defining a transcriptional domain in vivo. BEs lack intrinsic promoter/enhancer activity, but rather are thought to protect genes from the transcriptional influence of regulatory elements in the surrounding chromatin. The enhancer-block assay is commonly used to identify insulator elements. In this assay, the chromatin element is placed between an enhancer and a promoter, and enhancer-activated transcription is measured. Boundary elements have been shown to be able to protect stably transfected reporter genes against position effects in *Drosophila*, yeast and in mammalian cells. They have also been shown to increase the proportion of transgenic mice with inducible transgene expression.

Locus control regions ("LCRs") are cis-regulatory elements required for the initial chromatin activation of a locus and subsequent gene transcription in their native locations (Grosveld, F. 1999, "Activation by locus control regions?" *Curr Opin Genet Dev* 9, 152-157). The activating function of LCRs also allows the expression of a coupled transgene in the appropriate tissue in transgenic mice, irrespective of the site of integration in the host genome. While LCRs generally confer tissue-specific levels of expression on linked genes, efficient expression in nearly all tissues in transgenic mice has been reported for a truncated human T-cell receptor LCR and a rat LAP LCR. The most extensively characterized LCR is that of the globin locus. Its use in vectors for the gene therapy of sickle cell disease and (3-thalassemias is currently being evaluated.

"MARs", according to a well-accepted model, may mediate the anchorage of specific DNA sequence to the nuclear matrix, generating chromatin loop domains that extend outwards from the heterochromatin cores. While MARs do not contain any obvious consensus or recognizable sequence, their most consistent feature appears to be an overall high A/T content, and C bases predominating on one strand (Bode J, Schlake T, RiosRamirez M, Mielke C, Stengart M, Kay V and KlehrWirth D, "Scaffold/matrix-attached regions: structural propreties creating transcriptionally active loci", Structural and Functional Organization of the Nuclear Matrix: International Review of Citology, 162A: 389453, 1995). These regions have a propensity to form bent secondary structures that may be prone to strand separation. They are often referred to as base-unpairing regions (BURs), and they contain a core-unwinding element (CUE) that might represent the nucleation point of strand separation (Benham C and al., Stress induced duplex DNA destabilization in scaffold/matrix attachment regions, J. MoL BioL, 274:181-196, 1997). Several simple AT-rich sequence motifs have often been found within MAR sequences, but for the most part, their functional importance and potential mode of action remain unclear. These include the A-box (AATAAAYAAA (SEQ ID NO: 243)), the T-box (TTWTWTTWTT (SEQ ID NO: 244)), DNA unwinding motifs (AATATATT, AATATT), SATB1 binding sites (H-box, A/T/C25) and consensus Topoisomerase II sites for vertebrates (RNYNNCNNGYNGKTNYNY (SEQ ID NO: 245)) or *Drosophila* (GTNWAYATTNATNNR (SEQ ID NO: 246)).

Ubiquitous chromatin opening elements ("UCOEs", also known as "ubiquitously-acting chromatin opening elements") have been reported in WO 00/05393.

An "enhancer" is a nucleotide sequence that acts to potentiate the transcription of genes independent of the identity of the gene, the position of the sequence in relation to the gene, or the orientation of the sequence. The vectors of the present invention optionally include enhancers.

A "gene" is a deoxyribonucleotide (DNA) sequence coding for a given mature protein. As used herein, the term "gene" shall not include untranslated flanking regions such as RNA transcription initiation signals, polyadenylation addition sites, promoters or enhancers.

A "product gene" is a gene that encodes a protein product having desirable characteristics such as diagnostic or therapeutic utility. A product gene includes, e. g., structural genes and regulatory genes.

A "structural gene" refers to a gene that encodes a structural protein. Examples of structural genes include but are not limited to, cytoskeletal proteins, extracellular matrix proteins, enzymes, nuclear pore proteins and nuclear scaffold proteins, ion channels and transporters, contractile proteins, and chaperones. Preferred structural genes encode for antibodies or antibody fragments.

A "regulatory gene" refers to a gene that encodes a regulatory protein. Examples of regulatory proteins include, but are not limited to, transcription factors, hormones, growth factors, cytokines, signal transduction molecules, oncogenes, proto-oncogenes, transmembrane receptors, and protein kinases.

"Orientation" refers to the order of nucleotides in a given DNA sequence. For example, an inverted orientation of a DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence.

"Eukaryotic cell" refers to any mammalian or non-mammalian cell from a eukaryotic organism. By way of non-limiting example, any eukaryotic cell that is capable of being maintained under cell culture conditions and subsequently transfected would be included in this invention. Especially preferable cell types include, e. g., stem cells, embryonic stem cells, Chinese hamster ovary cells (CHO), COS, BHK21, NIH3T3, HeLa, C2C12, cancer cells, and primary differentiated or undifferentiated cells. Other suitable host cells are known to those skilled in the art.

The terms "host cell" and "recombinant host cell" are used interchangeably herein to indicate a eukaryotic cell into which one or more vectors of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The terms "introducing a purified DNA into a eukaryotic host cell" or "transfection" denote any process wherein an extracellular DNA, with or without accompanying material, enters a host cell. The term "cell transfected" or "transfected cell" means the cell into which the extracellular DNA has been introduced and thus harbors the extracellular DNA. The DNA might be introduced into the cell so that the nucleic acid is replicable either as a chromosomal integrant or as an extra chromosomal element.

"Promoter" as used herein refers to a nucleic acid sequence that regulates expression of a gene.

"Co-transfection" means the process of transfecting a eukaryotic cell with more than one exogenous gene, or vector, or plasmid, foreign to the cell, one of which may confer a selectable phenotype on the cell.

The purified and isolated DNA sequence having protein production increasing activity also comprises, besides one or more bent DNA element, at least one binding site for a DNA binding protein.

Usually the DNA binding protein is a transcription factor. Examples of transcription factors are the group comprising the polyQpolyP domain proteins.

Another example of a transcription factor is a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors are preferred. Most preferred are SATB1, NMP4, MEF2 and polyQpolyP domain proteins.

SATB1, NMP4 and MEF2, for example, are known to regulate the development and/or tissue-specific gene expression in mammals. These transcription factors have the capacity to alter DNA geometry, and reciprocally, binding to DNA as an allosteric ligand modifies their structure. Recently, SATB1 was found to form a cage-like structure circumscribing heterochromatin (Cai S, Han H J, and Kohwi-Shigematsu T, "Tissue-specific nuclear architecture and gene expression regulated by SATB1" Nat Genet, 2003. 34(1): p. 42-51).

Yet another object of the present invention is to provide a purified and isolated cLysMAR element and/or fragment, a sequence complementary thereof, a part thereof sharing at least 70% nucleotides in length, a molecular chimera thereof, a combination thereof and variants.

More preferably, the cLysMAR element and/or fragment are consisting of at least one nucleotide sequence selected from the B, K and F regions.

A further object of the present invention is to provide a synthetic MAR sequence comprising natural MAR element and/or fragments assembled between linker sequences.

Preferably, the synthetic MAR sequence comprises a cLysMAR element and/or fragment a sequence complementary thereof, a part thereof sharing at least 70% nucleotides in length, a molecular chimera thereof, a combination thereof and variants. Also preferably, linker sequences are BgIII-BamHI linker.

Another aspect of the invention is to provide a method for identifying a MAR sequence using a Bioinformatic tool comprising the computing of values of one or more DNA sequence features corresponding to DNA bending, major groove depth and minor groove width potentials and melting temperature. Preferably, the identification of one or more DNA sequence features further comprises a further DNA sequence feature corresponding to binding sites for DNA binding proteins, which is also computed with this method.

Preferably, profiles or weight-matrices of said bioinformatic tool are based on dinucleotide recognition.

The bioinformatic tool used for the present method is preferably, SMAR SCAN, which contains algorithms developed by Gene Express and based on Levitsky et al., 1999. These algorithms recognize profiles, based on dinucleotides weight-matrices, to compute the theoretical values for conformational and physicochemical properties of DNA.

Preferably, SMAR SCAN uses the four theoretical criteria also designated as DNA sequence features corresponding to DNA bending, major groove depth and minor groove width potentials, melting temperature in all possible combination, using scanning windows of variable size (see FIG. 3). For each function used, a cut-off value has to be set. The program returns a hit every time the computed score of a given region is above the set cut-off value for all of the chosen criteria. Two data output modes are available to handle the hits, the first (called "profile-like") simply returns all hit positions on the query sequence and their corresponding values for the different criteria chosen. The second mode (called "contiguous hits") returns only the positions of several contiguous hits and their corresponding sequence. For this mode, the minimum number of contiguous hits is another cut-off value that can be set, again with a tunable window size. This second mode is the default mode of SMAR SCAN Indeed, from a semantic point of view, a hit is considered as a core-unwinding element (CUE), and a cluster of CUEs accompanied by clusters of binding sites for relevant proteins is considered as a MAR. Thus, SMAR SCAN considers only several contiguous hits as a potential MAR.

To tune the default cut-off values for the four theoretical structural criteria, experimentally validated MARs from SMARt DB were used. All the human MAR sequences from the database were retrieved and analyzed with SMAR SCAN using the "profile-like" mode with the four criteria and with no set cut-off value. This allowed the setting of each function for every position of the sequences. The distribution for each criterion was then computed according to these data (see FIGS. 1 and 3).

The default cut-off values of SMAR SCAN for the bend, the major groove depth and the minor groove width were set at the average of the 75th quantile and the median. For the melting temperature, the default cut-off value should be set at the 75th quantile. The minimum length for the "contiguous-hits" mode should be set to 300 because it is assumed to be the minimum length of a MAR (see FIGS. 8 and 9). However, one skilled in the art would be able to determine the cut-off values for the above-mentioned criteria for a given organism with minimal experimentation.

Preferably, DNA bending values are comprised between 3 to 5° (radial degree). Most preferably they are situated between 3.8 to 4.4°, corresponding to the smallest peak of FIG. 1.

Preferably the major groove depth values are comprised between 8.9 to 9.3 Å (Angström) and minor groove width values between 5.2 to 5.8 Å. Most preferably the major groove depth values are comprised between 9.0 to 9.2 Å and minor groove width values between 5.4 to 5.7 Å.

Preferably the melting temperature is comprised between 55 to 75° C. (Celsius degree). Most preferably, the melting temperature is comprised between 55 to 62° C.

The DNA binding protein of which values can be computed by the method is usually a transcription factor preferably a polyQpolyP domain or a transcription factor selected from the group comprising SATB1, NMP4, MEF2, S8, DLX1, FREAC7, BRN2, GATA 1/3, TATA, Bright, MSX, AP1, C/EBP, CREBP1, FOX, Freac7, HFH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or a combination of two or more of these transcription factors.

However, one skilled in the art would be able to determine other kinds of transcription factors in order to carry out the method according to the present invention.

In case SMAR SCAN is envisaged to perform, for example, large scale analysis, then, preferably, the above-mentioned method further comprises at least one filter predicting DNA binding sites for DNA transcription factors in order to reduce the computation.

The principle of this method combines SMAR SCAN to compute the structural features as described above and a filter, such as for example, the pfsearch, (from the pftools package as described in Bucher P, Karplus K, Moeri N, and Hofmann K, "A flexible search technique based on generalized profiles", Computers and Chemistry, 20:324, 1996) to predict the binding of some transcription factors.

Examples of filters comprise, but are not limited to, pfsearch, MatInspector, RMatch Professional and TRANSFAC Professional This combined method uses the structural features of SMAR SCAN and the predicted binding of specific transcription factors of the filter that can be applied sequentially in any order to select MARs, therefore, depending on the filter is applied at the beginning or at the end of the method.

The first level selects sequences out of the primary input sequence and the second level, consisting in the filter, may be used to restrain among the selected sequences those which satisfy the criteria used by the filter.

In this combined method the filter detects clusters of DNA binding sites using profiles or weightmatrices from, for example, MatInspector (Quandt K, Frech K, Karas H, Wingender E, Werner T, "MatInd and MatInspector New fast and versatile tools for detection of consensus matches in nucleotide sequence data", *Nucleic Acids Research,* 23, 48784884, 1995.). The filter can also detect densities of clusters of DNA binding sites.

The combined method is actually a "wrapper" written in Perl for SMAR SCAN and, in case the pfsearch is used as a filter, from the pftools. The combined method performs a two level processing using at each level one of these tools (SMAR SCAN or filter) as a potential "filter", each filter being optional and possible to be used to compute the predicted features without doing any filtering.

If SCAN is used in the first level to filter subsequences, it has to be used with the "all the contiguous hits" mode in order to return sequences. If the pfsearch is used in the first level as first filter, it has to be used with only one profile and a distance in nucleotide needs to be provided. This distance is used to group together pfsearch hits that are located at a distance inferior to the distance provided in order to return sequences; The combined method launches pfsearch, parses its output and returns sequences corresponding to pfsearch hits that are grouped together according to the distance provided. Then whatever the tool used in the first level, the length of the subsequences thus selected can be systematically extended at both ends according to a parameter called "hits extension".

Figure 20:
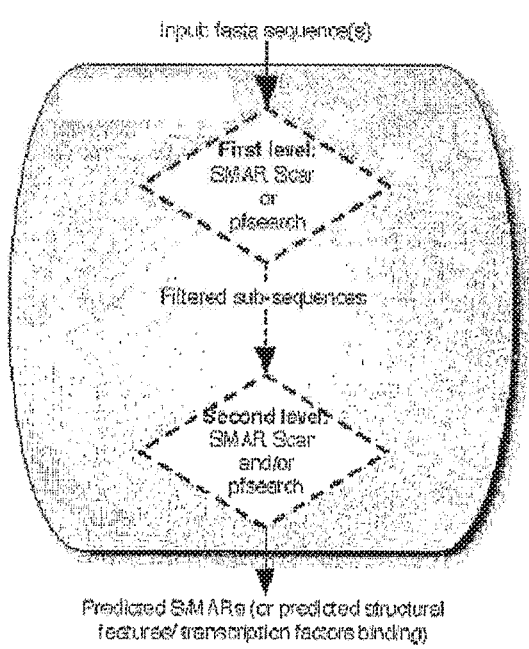
FIG. 20 depicts the effect of the induction of hematocrit in mice injected by MAR-network.

The second and optional level can be used to filter out sequences (already filtered sequences or unfiltered input sequences) or to get the results of SMAR SCAN and/or pfsearch without doing any filtering on these sequences. If the second level of combined method is used to filter, for each criteria considered cutoff values (hit per nucleotide) need to be provided to filter out those sequences (see FIG. 20).

Another concern of the present invention is also to provide a method for identifying a MAR sequence comprising at least one filter detecting clusters of DNA binding sites using profiles or weightmatrices. Preferably, this method comprises two levels of filters and in this case, SMAR SCAN is totally absent from said method. Usually, the two levels consist in pfsearch.

Also embraced by the present invention is a purified and isolated MAR DNA sequence identifiable according to the method for identifying a MAR sequence using the described bioinformatic tool, the combined method or the method comprising at least one filter.

Analysis by the combined method of the whole human genome yielded a total of 1757 putative MARs representing a total of 1 065 305 base pairs. In order to reduce the number of results, a dinucleotide analysis was performed on these 1757 MARs, computing each of the 16 possible dinucleotide percentages for each sequence considering both strands in the 5' to 3' direction.

Surprisingly, Applicants have shown that all of the "super" MARs detected with the combined method contain at least 10% of dinucleotide TA on a stretch of 100 contiguous base pairs. Preferably, these sequences contain at least 33% of dinucleotide TA on a stretch of 100 contiguous base pairs.

Applicants have also shown that these same sequences further contain at least 12% of dinucleotide AT on a stretch of 100 contiguous base pairs. Preferably, they contain at least 33% of dinucleotide AT on a stretch of 100 contiguous base pairs.

Another aspect of the invention is to provide a purified and isolated MAR DNA sequence of any of the preceding described MARs, comprising a sequence selected from the sequences SEQ ID Nos 1 to 27, a sequence complementary thereof, a part thereof sharing at least 70% nucleotides in length, a molecular chimera thereof, a combination thereof and variants.

Preferably, said purified and isolated MAR DNA sequence comprises a sequence selected from the sequences SEQ ID Nos 24 to 27, a sequence complementary thereof, a part thereof sharing at least 70% nucleotides in length, a molecular chimera thereof, a combination thereof and variants. These sequences 24 to 27 correspond to those detected by the combined method and show a higher protein production increasing activity over sequences 1 to 23.

The present invention also encompasses the use of a purified and isolated DNA sequence comprising a first isolated matrix attachment region (MAR) nucleotide sequence which is a MAR nucleotide sequence selected from the group comprising a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants or a MAR nucleotide sequence of a cLysMAR element and/or fragment, a sequence complementary thereof, a part thereof sharing at least 70% nucleotides in length, a molecular chimera thereof, a combination thereof and variants for increasing protein production activity in a eukaryotic host cell.

Said purified and isolated DNA sequence usually further comprises one or more regulatory sequences, as known in the art e.g. a promoter and/or an enhancer, polyadenylation sites and splice junctions usually employed for the expression of the protein or may optionally encode a selectable marker. Preferably said purified and isolated DNA sequence comprises a promoter which is operably linked to a gene of interest.

The DNA sequences of this invention can be isolated according to standard PCR protocols and methods well known in the art.

Promoters which can be used provided that such promoters are compatible with the host cell are, for example, promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters. Such regulatory sequences direct constitutive expression.

Furthermore, the purified and isolated DNA sequence might further comprise regulatory sequences which are capable of directing expression of the nucleic acid preferentially in a particular cell type (e. g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBOJ. 8: 729-733) and immunoglobulins (Banerji, et al., 1983. Cell 33: 729-740; Queen and Baltimore, 1983. Cell 33:741-748), neuron-specific promoters (e. g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e. g., milk whey promoter; U.S. Pat. No. 4,873,316 and European Application No. 264,166).

Developmentally-regulated promoters are also encompassed. Examples of such promoters include, e.g., the murine hox promoters (Kessel and Gruss, 1990. Science 249: 374-379) and thea-fetoprotein promoter (Campes and Tilghman, 1989. Genes Dev. 3: 537-546).

Regulatable gene expression promoters are well known in the art, and include, by way of non-limiting example, any promoter that modulates expression of a gene encoding a desired protein by binding an exogenous molecule, such as the CRE/LOX system, the TET system, the doxycycline system, the NFkappaB/UV light system, the Leu3p/isopropylmalate system, and the GLVPc/GAL4 system (See e. g., Sauer, 1998, Methods 14 (4): 381-92; Lewandoski, 2001, Nat. Rev. Genet 2 (10): 743-55; Legrand-Poels et al., 1998, J. Photochem. Photobiol. B. 45: 18; Guo et al., 1996, FEBS Lett. 390 (2): 191-5; Wang et al., PNAS USA, 1999, 96 (15): 84838).

However, one skilled in the art would be able to determine other kinds of promoters that are suitable in carrying out the present invention.

Enhancers can be optionally included in the purified DNA sequence of the invention then belonging to the regulatory sequence, e.g. the promoter.

The "gene of interest" or "transgene" preferably encodes a protein (structural or regulatory protein). As used herein "protein" refers generally to peptides and polypeptides having more than about ten amino acids. The proteins may be "homologous" to the host (i.e., endogenous to the host cell being utilized), or "heterologous," (i.e., foreign to the host cell being utilized), such as a human protein produced by yeast. The protein may be produced as an insoluble aggregate or as a soluble protein in the periplasmic space or cytoplasm of the cell, or in the extracellular medium. Examples of proteins include hormones such as growth hormone or erythropoietin (EPO), growth factors such as epidermal growth factor, analgesic substances like enkephalin, enzymes like chymotrypsin, receptors to hormones or growth factors, antibodies and include as well proteins usually used as a visualizing marker e.g. green fluorescent protein.

Preferably the purified DNA sequence further comprises at least a second isolated matrix attachment region (MAR) nucleotide sequence selected from the group comprising
   a purified and isolated DNA sequence having protein production increasing activity,
   a purified and isolated MAR DNA sequence identifiable according to the method for identifying a MAR sequence using the described bioinformatic tool, the combined method or the method comprising at least one filter,
   the sequences SEQ ID Nos 1 to 27,
   a purified and isolated cLysMAR element and/or fragment,
   a synthetic MAR sequence comprising natural MAR element and/or fragments assembled between linker sequences,
a sequence complementary thereof, a part thereof sharing at least 70% nucleotides in length, a molecular chimera thereof, a combination thereof and variants. The isolated matrix attachment region (MAR) nucleotide sequence might be identical or different. Alternatively, a first and a second identical MAR nucleotide sequence are used.

Preferably, the MAR nucleotide sequences are located at both the 5' and the 3' ends of the sequence containing the promoter and the gene of interest. But the invention also envisions the fact that said first and or at least second MAR nucleotide sequences are located on a sequence distinct from the one containing the promoter and the gene of interest.

Embraced by the scope of the present invention is also the purified and isolated DNA sequence comprising a first isolated matrix attachment region (MAR) nucleotide sequence which is a MAR nucleotide sequence selected from the group comprising
   a purified and isolated DNA sequence having protein production increasing activity,
   a purified and isolated MAR DNA sequence identifiable according to the method for identifying a MAR sequence using the described bioinformatic tool, the combined method or the method comprising at least one filter,
   the sequences SEQ ID Nos 1 to 27,
   a purified and isolated cLysMAR element and/or fragment,
   a synthetic MAR sequence comprising natural MAR element and/or fragments assembled between linker sequences,
a sequence complementary thereof, a part thereof sharing at least 70% nucleotides in length, a molecular chimera thereof, a combination thereof and variants that can be used for increasing protein production activity in a eukaryotic host cell by introducing the purified and isolated DNA sequence into a eukaryotic host cell according to well known protocols. Usually applied methods for introducing DNA into eukaryotic host cells applied are e.g. direct introduction of cloned DNA by microinjection or microparticle bombardment; electrotransfer; use of viral vectors; encapsulation within a carrier system; and use of transfecting reagents such as calcium phosphate, diethylaminoethyl (DEAE)—dextran or commercial transfection systems like the Lipofect-AMINE 2000 (Invitrogen). Preferably, the transfection method used to introduce the purified DNA sequence into a eukaryotic host cell is the method for transfecting a eukaryotic cell as described below.

The purified and isolated DNA sequence can be used in the form of a circular vector. Preferably, the purified and isolated DNA sequence is used in the form of a linear DNA sequence as vector.

As used herein, "plasmid" and "vector" are used interchangeably, as the plasmid is the most commonly used vector form. However, the invention is intended to include such other forms of expression vectors, including, but not limited to, viral vectors (e. g., replication defective retroviruses, adenoviruses and adeno-associated viruses), which serve equivalent functions.

The present invention further encompasses a method for transfecting a eukaryotic host cell, said method comprising
  a) introducing into said eukaryotic host cell at least one purified DNA sequence comprising at least one DNA sequence of interest and/or at least one purified and isolated DNA sequence comprising a MAR nucleotide sequence or other chromatin modifying elements,
  b) subjecting within a defined time said transfected eukaryotic host cell to at least one additional transfection step with at least one purified DNA sequence comprising at least one DNA sequence of interest and/or with at least one purified and isolated DNA sequence comprising a MAR nucleotide sequence or other chromatin modifying elements
  c) selecting said transfected eukaryotic host cell.

Preferably at least two up to four transfecting steps are applied in step b).

In order to select the successful transfected cells, a gene that encodes a selectable marker (e. g., resistance to antibiotics) is generally introduced into the host cells along with the gene of interest. The gene that encodes a selectable marker might be located on the purified DNA sequence comprising at least one DNA sequence of interest and/or at least one purified and isolated DNA sequence consisting of a MAR nucleotide sequence or other chromatin modifying elements or might optionally be co-introduced in separate form e.g. on a plasmid. Various selectable markers include those that confer resistance to drugs, such as G418, hygromycin and methotrexate. The amount of the drug can be adapted as desired in order to increase productivity Usually, one or more selectable markers are used. Preferably, the selectable markers used in each distinct transfection steps are different. This allows selecting the transformed cells that are "multi-transformed" by using for example two different antibiotic selections.

Any eukaryotic host cell capable of protein production and lacking a cell wall can be used in the methods of the invention. Examples of useful mammalian host cell lines include human cells such as human embryonic kidney line (293 or 293 cells subcloned for growth in suspension culture, Graham et al., J. Gen Virol 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/-DHFR (CHO, Urlaub and Chasin, *Proc. Natl. Acad. Sci. USA*, 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV4O (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Preferably, the selected transfected eukaryotic host cells are high protein producer cells with a production rate of at least 10 pg per cell per day.

Most preferred for uses herein are mammalian cells, more preferred are CHO cells.

The DNA sequence of interest of the purified and isolated DNA sequence is usually a gene of interest preferably encoding a protein operably linked to a promoter as described above. The purified and isolated DNA sequence comprising at least one DNA sequence of interest might comprise additionally to the DNA sequence of interest MAR nucleotide sequence or other chromatin modifying elements.

Purified and isolated DNA sequence comprising a MAR nucleotide sequence are for example selected from the group comprising the sequences SEQ ID Nos 1 to 27 and/or particular elements of the cLysMAR e.g. the B, K and F regions as well as fragment and elements and combinations thereof as described above. Other chromatin modifying elements are for example boundary elements (BEs), locus control regions (LCRs), and universal chromatin opening elements (UCOEs) (see Zahn-Zabal et al. already cited). An example of multiple transfections of host cells is shown in Example 12 (Table 3). The first transfecting step (primary transfection) is carried out with the gene of interest (SV40EGFP) alone, with a MAR nucleotide sequence (MAR) alone or with the gene of interest and a MAR nucleotide sequence (MAR-SV40EGFP). The second transfecting step (secondary transfection) is carried out with the gene of interest (SV40EGFP) alone, with a MAR nucleotide sequence (MAR) alone or with the gene of interest and a MAR nucleotide sequence (MAR-SV40EGFP), in all possible combinations resulting from the first transfecting step.

Preferably the eukaryotic host cell is transfected by:
  a) introducing a purified DNA sequence comprising one DNA sequence of interest and additionally a MAR nucleotide sequence,
  b) subjecting within a defined time said transfected eukaryotic host cell to at least one additional transfection step with the same purified DNA sequence comprising one DNA sequence of interest and additionally a MAR nucleotide sequence of step a).

Also preferably, the MAR nucleotide sequence of the of the purified and isolated DNA sequence is selected form the group comprising
  a purified and isolated DNA sequence having protein production increasing activity,
  a purified and isolated MAR DNA sequence identifiable according to the method for identifying a MAR sequence using the described bioinformatic tool, the combined method or the method comprising at least one filter,
  the sequences SEQ ID Nos 1 to 27,
  a purified and isolated cLysMAR element and/or fragment,
  a synthetic MAR sequence comprising natural MAR element and/or fragments assembled between linker sequences,
a sequence complementary thereof, a part thereof sharing at least 70% nucleotides in length, a molecular chimera thereof, a combination thereof and variants.

Surprisingly, a synergy between the first and second transfection has been observed. A particular synergy has been observed when MAR elements are present at one or both of the transfection steps. Multiple transfections of the cells with pMAR alone or in combination with various expression plasmids, using the method described above have been carried out. For example, Table 3 shows that transfecting the cells twice with the pMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. This proves that the presence of MAR elements at each transfection step is of particular interest to achieve the maximal protein synthesis.

As a particular example of the transfection method, said purified DNA sequence comprising at least one DNA sequence of interest can be introduced in form of multiple unlinked plasmids, comprising a gene of interest operably linked to a promoter, a selectable marker gene, and/or protein production increasing elements such as MAR sequences.

The ratio of the first and subsequent DNA sequences may be adapted as required for the use of specific cell types, and is routine experimentation to one ordinary skilled in the art.

The defined time for additional transformations of the primary transformed cells is tightly dependent on the cell cycle and on its duration. Usually the defined time corresponds to intervals related to the cell division cycle.

Therefore this precise timing may be adapted as required for the use of specific cell types, and is routine experimentation to one ordinary skilled in the art.

Preferably the defined time is the moment the host cell just has entered into the same phase of a second or a further cell division cycle, preferably the second cycle.

This time is usually situated between 6 h and 48 h, preferably between 20 h and 24 h after the previous transfecting event.

Also encompassed by the present invention is a method for transfecting a eukaryotic host cell, said method comprising co-transfecting into said eukaryotic host cell at least one first purified and isolated DNA sequence comprising at least one DNA sequence of interest, and a second purified DNA comprising at least one MAR nucleotide selected from the group comprising:
  a purified and isolated DNA sequence having protein production increasing activity,
  a purified and isolated MAR DNA sequence identifiable according to the method for identifying a MAR sequence using the described bioinformatic tool, the combined method or the method comprising at least one filter,
  the sequences SEQ ID Nos 1 to 27,
  a purified and isolated cLysMAR element and/or fragment,
  a synthetic MAR sequence comprising natural MAR element and/or fragments assembled between linker sequences,
a sequence complementary thereof, a part thereof sharing at least 70% nucleotides in length, a molecular chimera thereof, a combination thereof and variants.

Said first purified and isolated DNA sequence can also comprise at least one MAR nucleotide as described above.

Also envisioned is a process for the production of a protein wherein a eukaryotic host cell is transfected according to the transfection methods as defined in the present invention and is cultured in a culture medium under conditions suitable for expression of the protein. Said protein is finally recovered according to any recovering process known to the skilled in the art.

Given as an example, the following process for protein production might be used.

The eukaryotic host cell transfected with the transfection method of the present invention is used in a process for the production of a protein by culturing said cell under conditions suitable for expression of said protein and recovering said protein. Suitable culture conditions are those conventionally used for in vitro cultivation of eukaryotic cells as described e.g. in WO 96/39488. The protein can be isolated from the cell culture by conventional separation techniques such as e.g. fractionation on immunoaffinity or ion-exchange columns; precipitation; reverse phase HPLC; chromatography; chromatofocusing; SDS-PAGE; gel filtration. One skilled in the art will appreciate that purification methods suitable for the polypeptide of interest may require modification to account for changes in the character of the polypeptide upon expression in recombinant cell culture.

The proteins that are produced according to this invention can be tested for functionality by a variety of methods. For example, the presence of antigenic epitopes and ability of the proteins to bind ligands can be determined by Western blot assays, fluorescence cell sorting assays, immunoprecipitation, immunochemical assays and/or competitive binding assays, as well as any other assay which measures specific binding activity.

The proteins of this invention can be used in a number of practical applications including, but not limited to:
1. Immunization with recombinant host protein antigen as a viral/pathogen antagonist.
2. Production of membrane proteins for diagnostic or screening assays.
3. Production of membrane proteins for biochemical studies.
4. Production of membrane protein for structural studies.
5. Antigen production for generation of antibodies for immuno-histochemical mapping, including mapping of orphan receptors and ion channels.

Also provided by the present invention is a eukaryotic host cell transfected according to any of the preceding transfection methods. Preferably, the eukaryotic host cell is a mammalian host cell line.

As already described, example of useful mammalian host cell lines include human cells such as human embryonic kidney line (293 or 293 cells subcloned for growth in suspension culture, Graham et al., *J. Gen Virol* 36, 59 (1977)), human cervical carcinoma cells (HELA, ATCC CCL 2), human lung cells (W138, ATCC CCL 75), human liver cells (Hep G2, HB 8065); rodent cells such as baby hamster kidney cells (BHK, ATCC CCL 10), Chinese hamster ovary cells/-DHFR (CHO, Urlaub and Chasin, *Proc. Natl. Acad. Sci. USA,* 77, 4216 (1980)), mouse sertoli cells (TM4, Mather, *Biol. Reprod* 23, 243-251 (1980)), mouse mammary tumor (MMT 060562, ATCC CCL51); and cells from other mammals such as monkey kidney CV1 line transformed by SV4O (COS-7, ATCC CRL 1651); monkey kidney cells (CV1 ATCC CCL 70); African green monkey kidney cells (VERO-76, ATCC CRL-1587); canine kidney cells (MDCK, ATCC CCL 34); buffalo rat liver cells (BRL 3A, ATCC CRL 1442); myeloma (e.g. NS0)/hybridoma cells.

Most preferred for uses herein are CHO cells.

The present invention also provides for a cell transfection mixture or Kit comprising at least one purified and isolated DNA sequence according to the invention.

The invention further comprises a transgenic organism wherein at least some of its cells have stably incorporated at least one DNA sequence of a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Preferably, some of the cells of the transgenic organisms have been transfected according the methods described herein.

Also envisioned in the present invention is a transgenic organism wherein its genome has stably incorporated at least one DNA sequence of a purified and isolated DNA sequence having protein production increasing activity, a purified and isolated MAR DNA sequence identifiable according to the method for identifying a MAR sequence using the described bioinformatic tool, the combined method or the method comprising at least one filter, the sequences SEQ ID Nos 1 to 27, a purified and isolated cLysMAR element and/or fragment, a synthetic MAR sequence comprising natural MAR element and/or fragments assembled between linker sequences, a sequence complementary thereof, a part thereof sharing at least 70% nucleotides in length, a molecular chimera thereof, a combination thereof and variants.

Transgenic eukaryotic organisms which can be useful for the present invention are for example selected form the group comprising mammals (mouse, human, monkey etc) and in particular laboratory animals such as rodents in general, insects (*drosophila*, etc), fishes (zebra fish, etc.), amphibians (frogs, newt, etc.) and other simpler organisms such as *c. elegans*, yeast, etc.

Yet another object of the present invention is to provide a computer readable medium comprising computer-executable instructions for performing the method for identifying a MAR sequence as described in the present invention.

The foregoing description will be more fully understood with reference to the following Examples. Such Examples, are, however, exemplary of methods of practicing the present invention and are not intended to limit the scope of the invention.

EXAMPLES

Example 1: SMAR SCAN and MAR Sequences

A first rough evaluation of SMAR SCAN was done by analyzing experimentally defined human MARs and non-MAR sequences. As MAR sequences, the previous results from the analysis of human MARs from SMARt Db were used to plot a density histogram for each criterion as shown in FIG. 1. Similarly, non-MAR sequences were also analyzed and plotted. As non-MAR sequences, all Ref-Seq-contigs from the chromosome 22 were used, considering that this latter was big enough to contain a negligible part of MAR sequences regarding the part of non-MAR sequences.

The density distributions shown in FIG. 1 are all skewed with a long tail. For the highest bend, the highest major groove depth and the highest minor groove width, the distributions are right skewed. For the lowest melting temperature, the distributions are left-skewed which is natural given the inverse correspondence of this criterion regarding the three others. For the MAR sequences, biphasic distributions with a second weak peak, are actually apparent. And between MAR and non-MAR sequences distributions, a clear shift is also visible in each plot.

Among all human MAR sequences used, in average only about 70% of them have a value greater than the 75th quantile of human MARs distribution, this for the four different criteria. Similarly concerning the second weak peak of each human MARs distribution, only 15% of the human MAR sequences are responsible of these outlying values. Among these 15% of human MAR sequences, most are very well documented MARs, used to insulate transgene from position effects, such as the interferon locus MAR, the beta-globin locus MAR (Ramezani A, Hawley T S, Hawley R G, "Performance- and safety-enhanced lentiviral vectors containing the human interferon-beta scaffold attachment region and the chicken beta-globin insulator", *Blood*, 101: 4717-4724, 2003), or the apolipoprotein MAR (Namciu, S, Blochinger K B, Fournier R E K, "Human matrix attachment regions in-sulate transgene expression from chromosomal position effects in *Drosophila melanogaster*", *Mol. Cell. Biol.*, 18:2382-2391, 1998).

Figure 2:
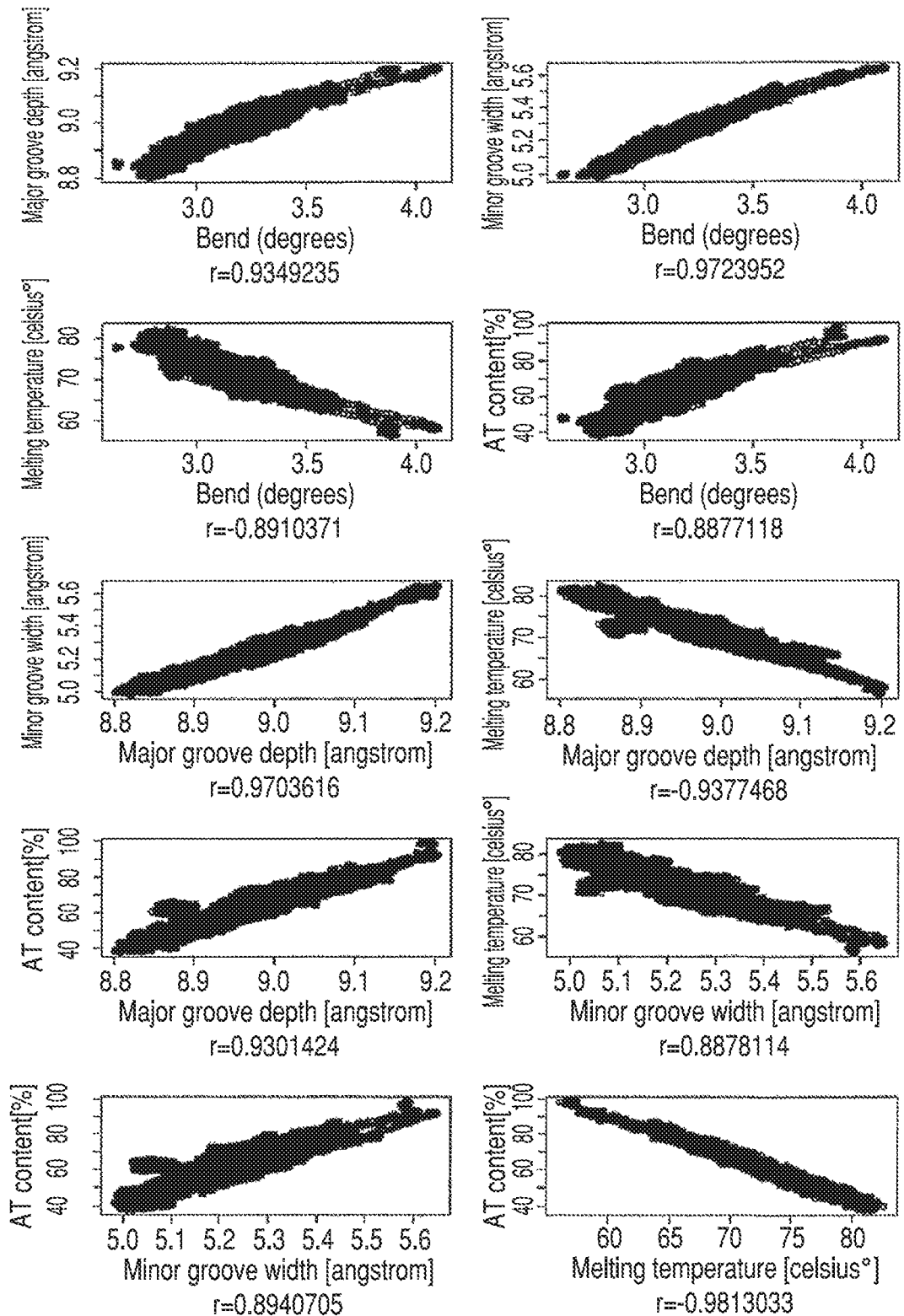
FIG. 2 shows Scatterplots of the four different criteria used by SMAR SCAN and the AT-content with human MARs from SMARt DB.

Always with the same data, human MAR sequences were also used to determine the association between the four theoretical structural properties computed and the AT-content. FIG. 2 represents the scatterplot and the corresponding correlation coefficient r for every pair of criteria.

Example 2: Distribution Plots of MAR Sequences by Organism

MAR sequences from SMARt DB of other organisms were also retrieved and analyzed similarly as explained previously. The MAR sequences density distributions for the mouse, the chicken, the sorghum bicolor and the human are plotted jointly in FIG. 3.

Example 3: MAR Prediction of the Whole Chromosome 22

All RefSeq contigs from the chromosome 22 were analyzed by SMAR SCAN using the default settings this time. The result is that SMAR SCAN predicted a total of 803 MARs, their average length being 446 bp, which means an average of one MAR predicted per 42 777 bp. The total length of the predicted MARs corresponds to 1% of the chromosome 22 length. The AT-content of the predicted regions ranged from 65.1% to 93.3%; the average AT-content of all these regions being 73.5%. Thus, predicted MARs were AT-rich, whereas chromosome 22 is not AT-rich (52.1% AT).

SMARTest was also used to analyze the whole chromosome 22 and obtained 1387 MAR candidates, their average length being 494 bp representing an average of one MAR predicted per 24 765 bp. The total length of the predicted MARs corresponds to 2% of the chromosome 22. Between all MARs predicted by the two softwares, 154 predicted MARs are found by both programs, which represents respectively 19% and 11% of SMAR SCAN and SMARTest predicted MARs. Given predicted MARs mean length for SMAR SCAN and SMARTest, the probability to have by chance an overlapping between SMAR SCAN and SMARTest predictions is 0.0027% per prediction.

Figure 4:
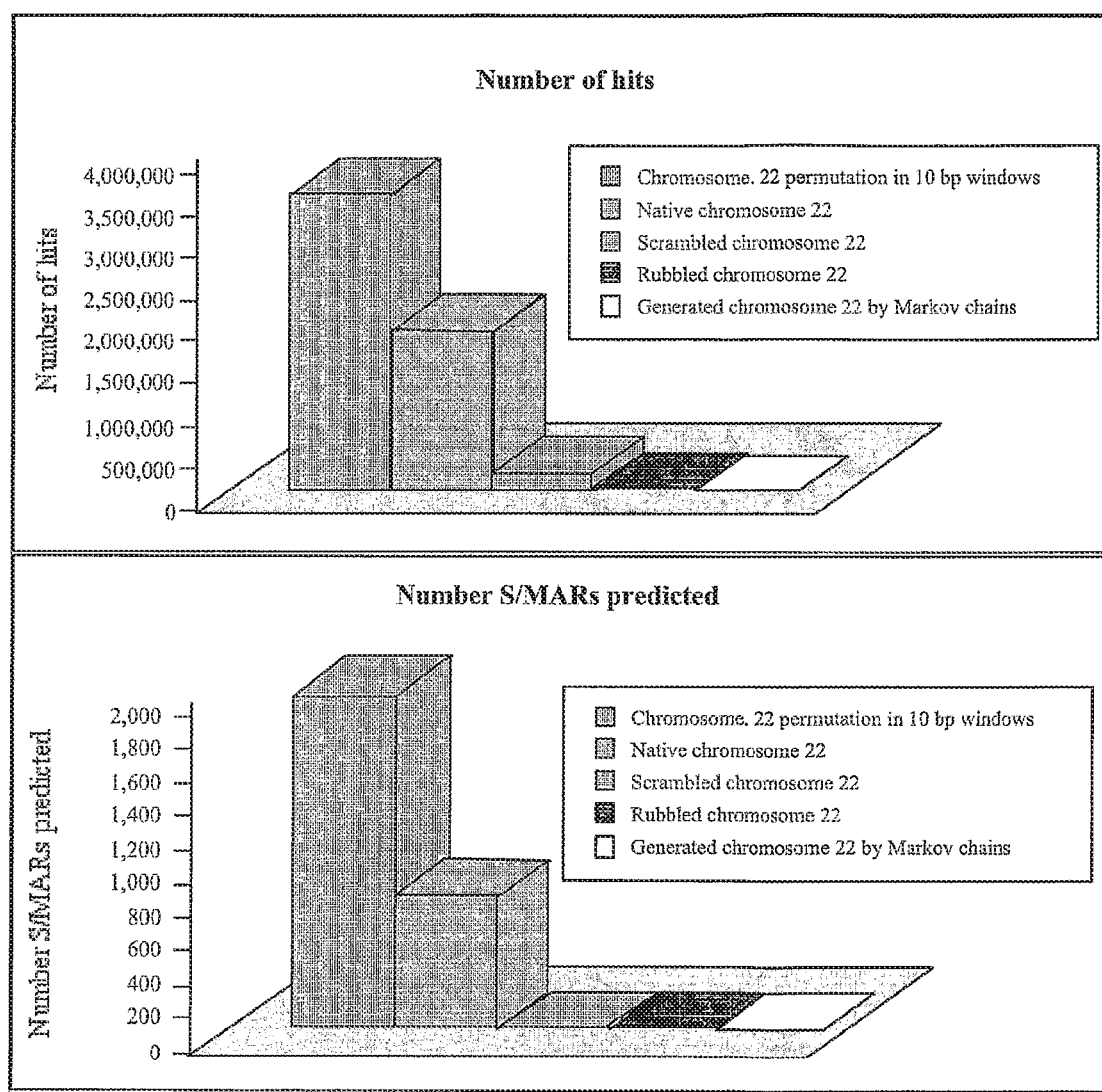
FIG. 4 shows SMAR SCAN predictions on human chromosome 22 and on shuffled chromosome 22. Top plot: Average number of hits obtained by SMAR SCAN with five: rubbled, scrambled, shuffled within nonoverlapping windows of 10 bp, order 1 Markov chains model and with the native chromosome 22. Bottom plot: Average number of MARs predicted by SMAR SCAN in five: rubbled, scrambled, shuffled within non-overlapping windows of 10 bp, order 1 Markov chains model and with the native chromosome 22.

To evaluate the specificity of SMAR SCAN predictions, SMAR SCAN analyses were performed on randomly shuffled sequences of the chromosome 22 (FIG. 4). Shuffled sequences were generated using 4 different methods: by a segmentation of the chromosome 22 into non-overlapping windows of 10 bp and by separately shuffling the nucleotides in each window; by "scrambling" which means a permutation of all nucleotides of the chromosome; by "rubbling" which means a segmentation of the chromosome in fragments of 10 bp and a random assembling of these fragments and finally by order 1 Markov chains, the different states being the all the different DNA dinucleotides and the transition probabilities between these states being based on the chromosome 22 scan. For each shuffling method, five shuffled chromosome 22 were generated and analyzed by SMAR SCAN using the default settings. Concerning the number hits, an average of 3 519 170 hits (sd: 18 353) was found for the permutated chromosome 22 within non-overlapping windows of 10 bp, 171 936,4 hits (sd: 2 859,04) for the scrambled sequences and 24 708,2 hits (sd: 1 191,59) for the rubbled chromosome 22 and 2 282 hits in average (sd: 334,7) for the chromosomes generated according to order 1 Markov chains models of the chromosome 22, which respectively represents 185% (sd: 0.5% of the mean), 9% (sd: 1.5%), 1% (sd: 5%) and 0.1% (sd: 15%) of the number of hits found with the native chromosome 22. For the number of MARs predicted, which thus means contiguous hits of length greater than 300, 1 997 MARs were predicted with the shuffled chromosome 22 within windows of 10 bp (sd: 31.2), only 2.4 MARs candidates were found in scrambled sequences (sd: 0.96) and none for the rubbled and for the sequences generated according to Markov chains model, which respectively represents 249% and less than 0.3% of the number of predicted MARs found with the native chromosome 22. These data provide indications that SMAR SCAN detects specific DNA elements which organization is lost when the DNA sequences are shuffled.

Figure 9:
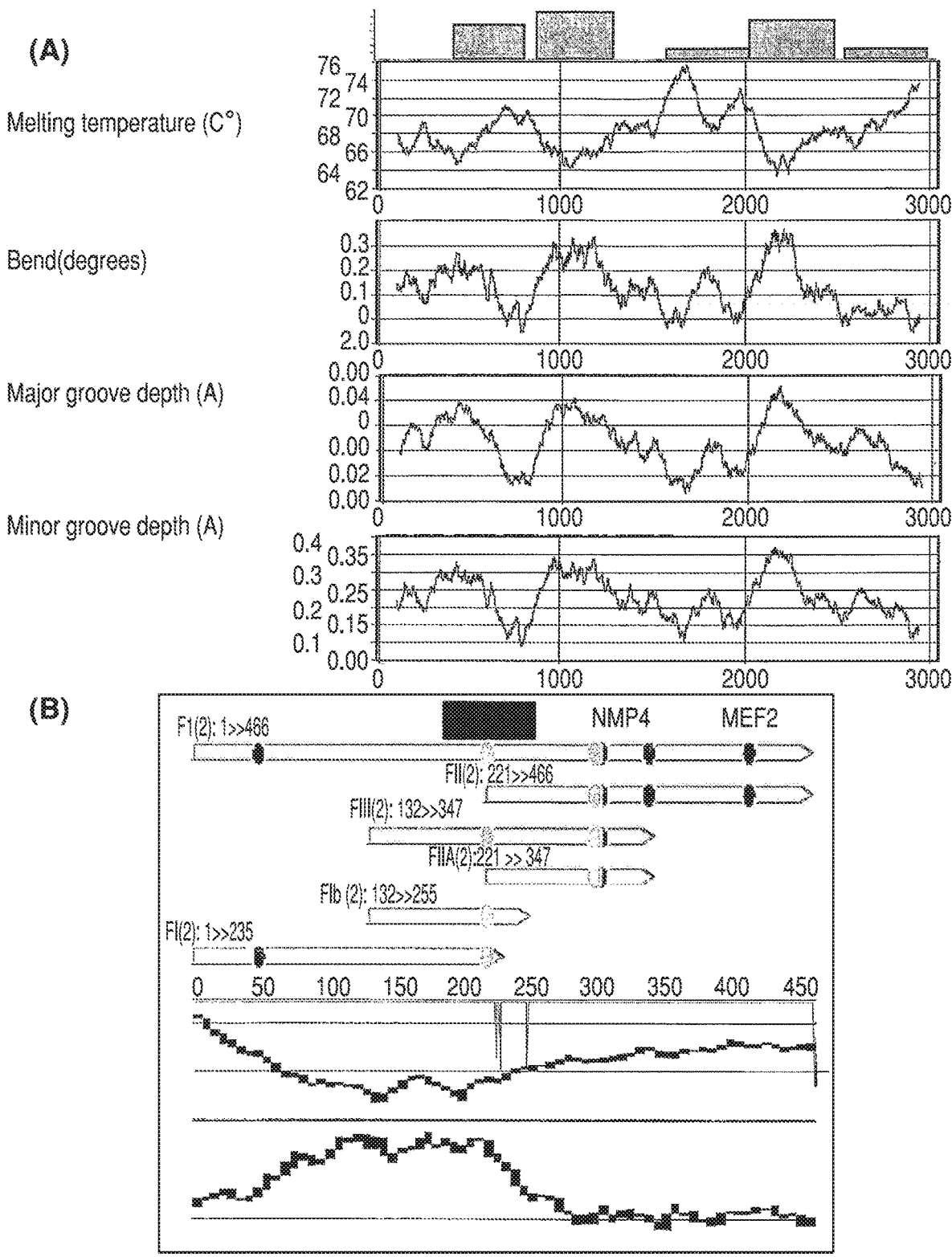
FIG. 9 shows the correlation of DNA physico-chemical properties with MAR activity.

Example 4: Analysis of Known Matrix Attachment Regions in the Interferon Locus with SMAR SCAN The relevance of MAR prediction by SMAR SCAN was investigated by analyzing the recently published MAR regions of the human interferon gene cluster on the short arm of chromosome 9 (9p22). Goetze et al. (already cited) reported an exhaustive analysis of the WP18A10A7 locus to analyze the suspected correlation between BURs (termed in this case stress-induced duplex destabilization or SIDD) and in vitro binding to the nuclear matrix (FIG. 9, lower part). Three of the SIDD peaks were in agreement with the in vitro binding assay, while others did not match matrix attachment sites. Inspection of the interferon locus with SMAR SCAN (FIG. 9, top part) indicated that three major peaks accompanied by clusters of SATB1, NMP4 and MEF2 regulators binding sites correlated well with the active MARs. Therefore, we conclude that the occurrence of predicted CUEs and binding sites for these transcription factors is not restricted to the cLysMAR but may be a general property of all MARs. These results also imply that the SMAR SCAN program efficiently detects MAR elements from genomic sequences.

Example 5: Accuracy of SMAR SCAN Prediction and Comparison with Other Predictive Tools The accuracy of SMAR SCAN was evaluated using six genomic sequences for which experimentally determined MARs have been mapped. In order to perform a comparison with other predictive tools, the sequences analyzed are the same with the sequences previously used to compare MAR-Finder and SMARTest. These genomic sequences are three plant and three human sequences (Table 1) totalizing 310 151 bp and 37 experimentally defined MARs. The results for SMARTest and MAR-Finder in Table 1 come from a previous comparison (Frisch M, Frech K, Klingenhoff A, Cartharius K, Liebich I and Werner T, In silico pre-diction of scaffold/matrix attachment regions in large genomic sequences, Genome Research, 12:349-354, 2001.). MAR-Finder has been used with the default parameters excepted for the threshold that has been set to 0.4 and for the analysis of the protamine locus, the AT-richness rule has been excluded (to detect the non AT-rich MARs as was done for the protamine locus).

TABLE 1

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| *Oryza Sativa* putative ADP-glucose pyrophosphorylase subunit SH2 and putative NADPH dependant reductase A1 genes (U70541). [4] | 30.034 | 0.0-1.2 | – | – | – |
| | | 5.4-7.4 | 6.5-7.0 | – | – |
| | | | 15.2-15.7 | 15.7-15.9 | 15.6-16 |
| | | | 16.2-16.6 | – | – |
| | | 17.3-18.5 | 17.6-18.3 | 17.5-18.4 | 17.6-18.2 |
| | | 20.0-23.1 | 19.6-20.1 | 19.8-20.4 | 21.6-22 |
| | | | 20.7-21.3 | 21.3-21.5 | – |
| | | | 23.6-23.9 | 23.9-24.2 | 23.4-23.8 |
| | | | 25.0-25.4 | 24.7-25.1 | – |
| | | | 27.5-27.9 | – | – |
| *Sorghum bicolor* ADP-glucose pyrophophorylase subunit SH2, NADPH-dependant reducatse A1-b genes (AF010283). [4] | 42.446 | 0.0-1.5 | – | – | – |
| | | 7.1-9.7 | – | – | 7.4-7.7 |
| | | | 21.3-21.9 | – | 21.5-21.8 |
| | | 22.4-24.7 | 22.9-24.0 | 23.2-24.2 | 22.9-23.2 |
| | | | – | – | 23.6-24.0 |
| | | | 27.3-27.6 | 26.9-27.5 | 27.3-27.6 |
| | | 32.5-33.7 | – | – | 33.4-33.9 |
| | | 41.6-42.3 | – | – | – |

TABLE 1-continued

Evaluation of SMAR SCAN accuracy

| Sequence, description and reference | Length (kb) | Experimentally defined MARs positions (kb) | SMARTest prediction positions (kb) | MAR-Finder prediction positions (kb) | SMAR Scan prediction positions (kb) |
|---|---|---|---|---|---|
| *Sorghum bicolor* BAC clone 110K5 (AF124045). [37] | 78.195 | ~0.9 | – | – | – |
| | | ~5.8 | – | – | – |
| | | ~6.3 | – | – | – |
| | | ~9.3 | – | – | – |
| | | ~15.0 | 15.1-15.8 | – | – |
| | | ~18.5 | – | – | – |
| | | ~21.9 | 21.7-22.0 | – | 21.4-21.9 |
| | | ~23.3 | – | – | – |
| | | ~25.6 | – | – | – |
| | | ~29.1 | – | – | 29.2-29.5 |
| | | ~34.6 | – | – | – |
| | | – | – | – | 39.0-40.0 |
| | | ~44.1 | 44.1-44.5 | – | – |
| | | ~48.5 | 47.9-49.5 | 47.9-49.4 | 48.1-48.6 |
| | | – | – | – | 48.8-49.3 |
| | | ~57.9 | – | – | – |
| | | ~62.9 | 63.1-63.7 | – | – |
| | | ~67.1 | – | – | – |
| | | ~69.3 | – | – | – |
| | | ~73.7 | 74.3-74.7 | – | 74.3-74.6 |
| Human alpha-1-antitrypsin and corticosteroid binding globulin intergenic region (AF156545), [35] | 30.461 | 2.6-6.3 | 5.5-6.0 | 3.0-3.2 | 5.4-5.8 |
| | | | – | 5.1-6.0 | – |
| | | 22.0-30.4 | 25.7-26.2 | 24.9-25.3 | 25.8-26.4 |
| | | | 27.5-27.8 | 25.5-25.8 | |
| | | | – | 26.2-26.4 | – |
| | | | – | 27.5-28.2 | – |
| Human protamine locus (U15422). [24] | 53.060 | 8.8-9.7 | – | 8.0-8.9* | – |
| | | 32.6-33.6 | – | 33.9-34.8* | – |
| | | 37.2-39.4 | – | 33.9-34.8* | – |
| | | 51.8-53.0 | – | –* | – |
| Human beta-globin locus (U01317), [21] | 75.955 | 1.5-3.0 | – | – | 2.3-2.6 |
| | | 15.6-19.0 | 18.0-18.4 | 15.5-16.0 | 15.3-15.6 |
| | | | – | 18.0-18.4 | – |
| | | | 34.4-34.9 | – | – |
| | | 44.7-52.7 | – | 50.6-50.8 | – |
| | | | 56.6-57.1 | 56.5-57.2 | – |
| | | 60.0-70.0 | 59.8-60.3 | 58.1-58.5 | 62.8-63.1 |
| | | | 65.6-66.0 | 63.0-63.6 | – |
| | | | 67.6-67.9 | 68.7-69.3 | 66.3-66.7 |
| | | | 68.8-69.1 | – | – |
| Sum(kb) | 310.151 | at least 56.1 | 14.5 | 13.8 | 9.5 |
| Total numbers: | | 37 | 28 | 25 | 22 |
| Average kb/predicted MAR | | | 11.076 | 12.406 | 14.097 |
| True positives [number of experimentally defined MAR found] | | | 19[14] | 20[12] | 17[14] |
| False positives | | | 9 | 5 | 5 |
| False negatives | | | 23 | 25 | 23 |
| Specificity | | | 19/28 = 68% | 20/25 = 80% | 17/22 = 77% |
| Sensitivity | | | 14/37 = 38% | 12/37 = 32% | 14/37 = 38% |

Six different genomic sequences, three plant and three human sequences, for which experimentally defined MARs are known, were analyzed with MAR-Finder, SMARTest and SMAR SCAN. True positive matches are printed in bold, minus (–) indicates false negative matches. Some of the longer experimentally defined MARs contained more than one in silico prediction, each of them was counted as true positive match. Therefore, the number of true in silico predictions is higher than the number of experimentally defined MARs found. Specificity is defined as the ratio of true positive predictions, whereas sensitivity is defined as the ratio of experimentally defined MARs found. *AT-rich rule excluded using MAR-Finder.

SMARTest predicted 28 regions as MARs, 19 (true positives) of these correlate with experimentally defined MARs (specificity: 68%) whereas 9 (32%) are located in non-MARs (false positives). As some of the longest experimentally determined MARs contains more than one in silico prediction, the 19 true positives correspond actually to 14 different experimentally defined MARs (sensitivity: 38%). MARFinder predicted 25 regions as MARs, 20 (specificity: 80%) of these correlate with experimentally defined MARs corresponding to 12 different experimentally defined MARs (sensitivity: 32%). SMAR SCAN predicted 22 regions, 17 being true positives (specificity: 77%) matching 14 different experimentally defined MARs (sensitivity: 38%).

As another example, the same analysis has been applied to human chromosomes 1 and 2 and lead to the determination of 23 MARs sequences (SEQ ID N°1 to 23). These sequences are listed in Annex 1 in ST25 format.

Example 6: Analyses of the Whole Genome Using the Combined Method (SMAR SCAN-pfsearch)

In order to test the potential correlation between the structural features computed by SMAR Scan® and the S/MAR functional activity, the whole human genome has been analyzed with the combined method with very stringent parameters, in order to get sequences with the highest values for the theoretical structural features computed, which are called "super" S/MARs below. This was done with the hope to obtain predicted MAR elements with a very potential to increase transgene expression and recombinant protein production. The putative S/MARs hence harvested were first analyzed from the bioinformatics perspective in an attempt to characterize and classify them.

In the second level processing, predicted transcription factors binding have been sought in the sequences selected from the previous step without doing any filtering on these sequences.

The analysis by the combined method of the whole human genome came up with a total of 1757 putative "super" S/MARs representing a total of 1 065 305 bp (0.35% of the whole human genome). Table 2 shows for each chromosome: its size, its number of genes, its number of S/MARs predicted, its S/MARs density per gene and its kb per S/MAR. This table shows that there are very various gene densities per S/MAR predicted for the different chromosomes (standard deviation represents more than 50% of the mean of the density of genes per S/MAR predicted and the fold difference between the higher and the lower density of genes per S/MAR is 6.5). Table 2 also shows that the kb per S/MAR varies less that the density of genes per S/MAR (standard deviation represents 25% of the mean of kb per S/MAR and the fold difference between the higher and the lower kb per S/MAR is 3.2).

TABLE 2

Number of S/MARs predicted per chromosome.

| Chromosome | Number of genes per chromosome | Size of the chromosome (millions bp) | Number of S/MARs predicted | Density of genes per S/MAR | Kb per S/MAR |
|---|---|---|---|---|---|
| 1 | 2544 | 230 | 85 | 29.9 | 2705 |
| 2 | 1772 | 241 | 143 | 12.3 | 1685 |
| 3 | 1406 | 198 | 101 | 13.9 | 1960 |
| 4 | 1036 | 190 | 118 | 8.7 | 1610 |
| 5 | 1233 | 180 | 116 | 10.6 | 1551 |
| 6 | 1247 | 170 | 94 | 13.2 | 1808 |
| 7 | 1383 | 160 | 179 | 7.7 | 1754 |
| 8 | 942 | 145 | 77 | 12.2 | 1883 |
| 9 | 1100 | 119 | 48 | 22.9 | 2479 |
| 10 | 1003 | 133 | 71 | 14.1 | 1873 |
| 11 | 1692 | 132 | 67 | 25.2 | 1970 |
| 12 | 1278 | 131 | 78 | 16.3 | 1679 |
| 13 | 506 | 97 | 70 | 7.2 | 1385 |
| 14 | 1168 | 88 | 36 | 32.4 | 2444 |
| 15 | 895 | 83 | 35 | 25.5 | 2371 |
| 16 | 1107 | 81 | 41 | 27 | 1975 |
| 17 | 1421 | 80 | 37 | 38.4 | 2162 |
| 18 | 396 | 75 | 51 | 7.7 | 1470 |
| 19 | 1621 | 56 | 36 | 45.02 | 1555 |
| 20 | 724 | 60 | 28 | 25.8 | 2142 |
| 21 | 355 | 34 | 18 | 19.7 | 1888 |
| 22 | 707 | 34 | 28 | 25.2 | 1214 |
| X | 1168 | 154 | 170 | 6.8 | 905 |
| Y | 251 | 25 | 30 | 8.3 | 833 |
| Sum | 26 955 | 3 050 | 1 757 | 457 | 433 12 |
| Mean | 1 123 | 127 | 73 | 19 | 1 804 |
| Sd | 510 | 72.8 | 45 | 10 | 462 |

The number of genes per chromosome corresponds to the NCBI human genome statistics (Build 34 Version 3) (National Center for Biotechnology Information, The NCBI handbook [Internet]. Bethesda (Md.): National Library of Medicine (U.S.), October Chapter 17, The Reference Sequence (RefSeq) Project, 2002 based on GenBank annotations. Chromosome sizes are the sum of the corresponding human RefSeq (National Center for Biotechnology Information, The NCBI handbook [Internet]. Bethesda (Md.): National Library of Medicine (U.S.), October Chapter 17, The Reference Sequence (RefSeq) Project, 2002 (release 5) contig lengths.

6.1 S/MARs Predicted from the Analysis of the Whole Human Genome

As whole human genome sequence, all human RefSeq (National Center for Biotechnology Information, The NCBI handbook [Internet]. Bethesda (Md.): National Library of Medicine (US), October. Chapter 17, The Reference Sequence (RefSeq) Project, 2002 contigs (release 5) were used and analyzed with the combined method, using SMAR SCAN as filter in the first level processing, employing default settings except for the highest bend cutoff value, whereas a stringent threshold of 4.0 degrees (instead of 3.202 degrees) has been used for the DNA bending criterion.

6.2 Bioinformatics Analysis of "Super" MARS for Transcription Factor Binding Sites The 1757 predicted "super" S/MARs sequences obtained previously by SMAR SCAN were then analyzed for potential transcription factors binding sites. This has been achieved using RMatch™ Professional (Kel A E, Gossling E, Reuter I, Cheremushkin E, KelMargoulis O V, Wingender E, MATCH: A tool for searching transcription factor binding sites in DNA sequences, Nucleic Acids Res. 31(13):35769, 2003), a weight matrixbased tool based on TRANSFAC (Wingender E, Chen X, Fricke E, Geffers R, Hehl R, Liebich I, Krull M, Matys V, Michael H, Ohnhauser R, Pruss M, Schacherer F, Thiele S, Urbach S, The TRANSFAC system on gene expression regulation, Nucleic Acids Research, 29(1):2813, 2001). Match™ 2.0 Professional has been used with most of the default settings Match™ analysis was based on TRANSFAC Professional, release 8.2 (20040630). The sums of all transcription factors binding prediction on the 1757 sequences analyzed according to Match™ are in Table 3. Based on this table, only the transcription factors totalizing at least 20 hits over the 1757 sequences analyzed were considered for further analyses.

Hereafter are some of the human transcription factors that are the most often predicted to bind on the 1757 putative S/MAR sequences and their Match description: Cdc5 (cell division control protein 5) a transcriptional regulator/repressor, Nkx3A a homeodomain protein regulated by androgen, POU1F1 (pituitaryspecific positive transcription factor 1) which is specific to the pituitary and stimulates cells proliferation. Thus, in addition to SATB1, NMP4 and MEF2, other transcription factors can participate in the activity of MARs.

| AP1 | 1 | AR | 2 | Bach2 | 1 | Brn2 | 1 |
|---|---|---|---|---|---|---|---|
| C/EBP | 20 | C/EBPgamma | 5 | CDP CR3 | 1 | COMP1 | 2 |
| CREBP1 | 34 | Cdc5 | 858 | Cdx2 | 35 | Evi1 | 472 |
| FOX | 78 | FOXD3 | 79 | FOXJ2 | 244 | FOXP3 | 29 |
| Freac7 | 272 | GATA1 | 2 | GATA3 | 142 | GATA4 | 125 |
| HFH1 | 12 | HFH3 | 1 | HLF | 275 | HNF1 | 337 |
| HNF3alpha | 23 | HNF3beta | 71 | HP1 | 2 | Lhx3 | 22 |
| MEF2 | 114 | MRF2 | 57 | Myc | 18 | NKX3A | 849 |
| Nkx25 | 2 | Oct1 | 191 | PBX | 5 | POU1F1 | 483 |
| POU3F2 | 11 | POU6F1 | 29 | Pax3 | 3 | Pax6 | 20 |
| Pit1 | 505 | SRF | 8 | TEF | 2852 | TFIIA | 14 |
| TTF1 | 1 | V$MTATA_B | 4 | VBP | 53 | Vmw65 | 1 |
| XFD1 | 65 | XFD2 | 418 | XFD3 | 2 | | |

Table 3 is a summary of all transcription factors binding prediction (totalizing 20 hits or more) on the 1757 sequences analyzed.

6.3 Bioinformatics Analysis of Predicted "Super" MARs for Dinucleotide Frequencies Various computer analyses were performed in order to easily identify "super" S/MAR sequences using an explicit criterion that could be identified without computing. Among those, a di-nucleotide analysis was performed on the 1757 superMARs, computing each of the 16 possible dinucleotide percentage for each sequence considering both strands in the 5'>3' direction.

A summary (min., max., median, mean, 25th percentile and 75th percentile) as well as the histograms of each dinucleotide percentage over the 1757 S/MAR sequences are respectively presented in Table 4. A similar analysis was performed on randomly selected sequences from the human genome, representing randomly selected non-S/MAR sequences (which might however contain some MARs). Table 5 represents respectively a summary of the dinucleotide content analysis for these sequences.

TABLE 4

Dinucleotide percentages over the 1757 S/MAR sequences

|  | AA % | AC % | AG % | AT % |
|---|---|---|---|---|
| Minimum | 0.000 | 0.0000 | 0.0000 | 18.50 |
| 25th percentile | 4.234 | 0.9372 | 0.1408 | 32.11 |
| Median | 7.843 | 2.2408 | 0.4777 | 34.68 |
| Mean | 7.184 | 3.2117 | 1.0865 | 34.32 |

TABLE 4-continued

Dinucleotide percentages over the 1757 S/MAR sequences

| 75th percentile | 10.110 | 4.7718 | 1.5096 | 36.94 |
|---|---|---|---|---|
| Maximum | 17.290 | 12.9479 | 8.1230 | 50.00 |

|  | CA % | CC % | CG % | CT % |
|---|---|---|---|---|
| Minimum | 0.0000 | 0.00000 | 0.0000 | 0.0000 |
| 25th percentile | 0.9695 | 0.00000 | 0.0000 | 0.1408 |
| Median | 1.9776 | 0.00000 | 0.0000 | 0.4777 |
| Mean | 2.6977 | 0.14123 | 0.2709 | 1.0865 |
| 75th percentile | 3.7543 | 0.09422 | 0.1256 | 1.5096 |
| Maximum | 10.4061 | 4.24837 | 7.4410 | 8.1230 |

|  | GA % | GC % | GG % | GT % |
|---|---|---|---|---|
| Minimum | 0.00000 | 0.0000 | 0.00000 | 0.0000 |
| 25th percentile | 0.08696 | 0.0000 | 0.00000 | 0.9372 |
| Median | 0.32616 | 0.0000 | 0.00000 | 2.2408 |
| Mean | 0.63347 | 0.2104 | 0.14123 | 3.2117 |

TABLE 4-continued

Dinucleotide percentages over the 1757 S/MAR sequences

| 75th percentile | 0.83333 | 0.1914 | 0.09422 | 4.7718 |
|---|---|---|---|---|
| Maximum | 5.77889 | 9.8795 | 4.24837 | 12.9479 |

|  | TA % | TC % | TG % | TT % |
|---|---|---|---|---|
| Minimum | 28.63 | 0.00000 | 0.0000 | 0.000 |
| 25th percentile | 33.48 | 0.08696 | 0.9695 | 4.234 |
| Median | 35.22 | 0.32616 | 1.9776 | 7.843 |
| Mean | 35.29 | 0.63347 | 2.6977 | 7.184 |
| 75th percentile | 37.14 | 0.83333 | 3.7543 | 10.110 |
| Maximum | 50.00 | 5.77889 | 10.4061 | 17.290 |

Considering the results of the predicted S/MAR elements and of the nonS/MAR sequences in the summary tables, noticeable differences can be noticed in the AT et TA dinucleotide contents between these two groups of sequences. AT and TA represent respectively at least 18.5% and 28.6% of the dinucleotide content of the predicted S/MAR sequences, whereas the minimum percentages for the same dinucleotides in nonS/MAR sequences are respectively 0.3% and 0%. Similarly, the maximum CC and GG content in S/MAR sequences is 4.2%, whereas in nonS/MAR sequences the percentages for these two dinucleotides can amount up to 20.8%.

Figure 17:
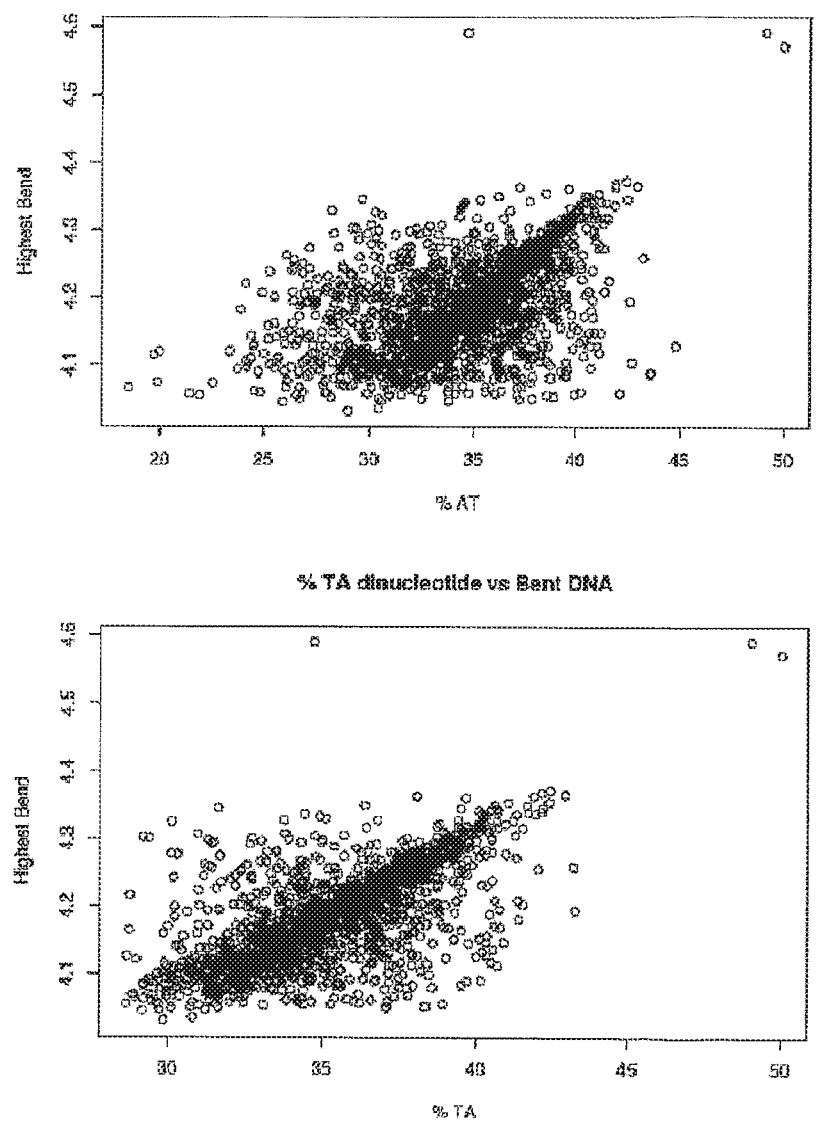
FIG. 17 represents the scatterplot for the 1757 S/MAR sequences of the AT (top) and TA (bottom) dinucleotide percentages versus the predicted DNA bending as computed by SMAR SCAN.
Figure 18:
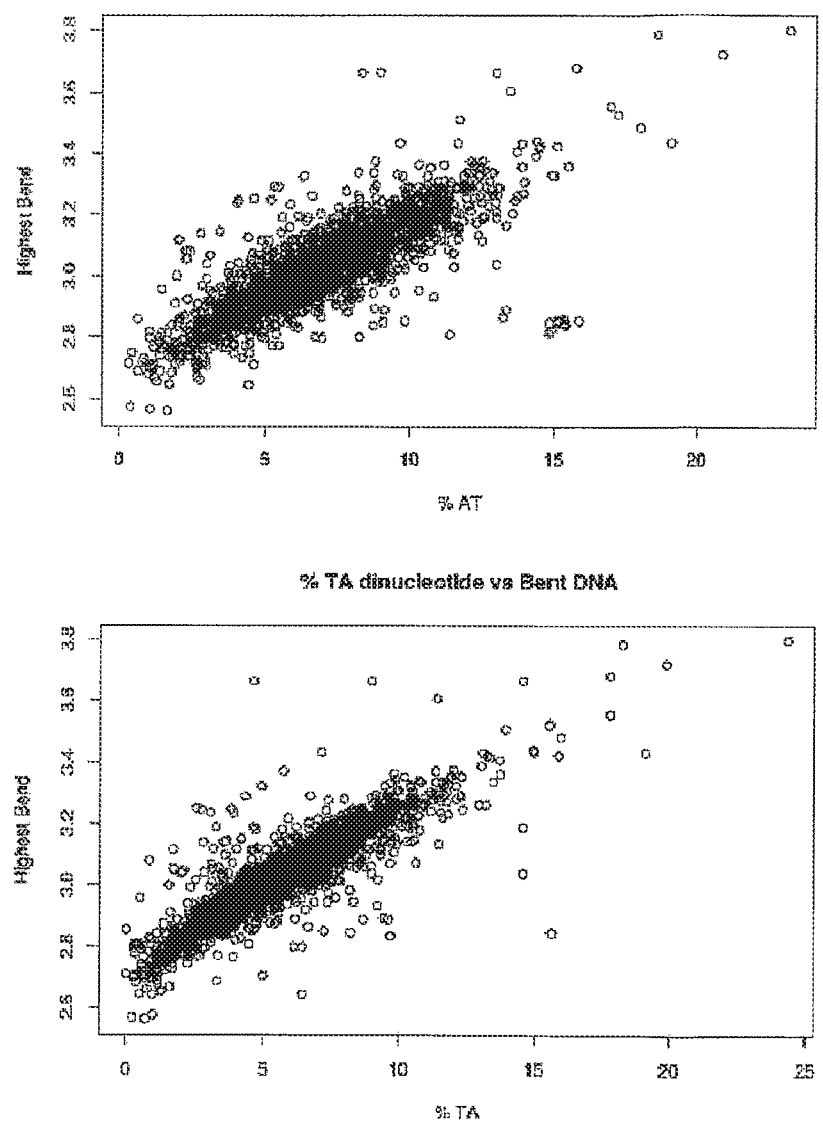
FIG. 18 represents the dinucleotide percentage distribution plots over the 1757 non-S/MARs sequences.

The correlation between AT and TA dinucleotide percentages and the DNA highest bend as computed by SMAR SCAN is depicted in FIG. 17 for the predicted S/MAR sequences and in FIG. 18 for the nonS/MAR sequences. The different scatterplots of these figures show that the TA percentage correlates well with the predicted DNA bend as predicted by SMAR SCAN.

TABLE 5

Dinucleotide percentages over the 1757 nonS/MAR sequences summary

|  | AA % | AC % | AG % | AT % |
|---|---|---|---|---|
| Minimum | 0.000 | 1.735 | 1.512 | 0.3257 |
| 25th percentile | 7.096 | 4.586 | 6.466 | 5.1033 |
| Median | 9.106 | 5.016 | 7.279 | 6.8695 |
| Mean | 8.976 | 5.054 | 7.184 | 7.0108 |
| 75th percentile | 10.939 | 5.494 | 7.969 | 8.7913 |
| Maximum | 17.922 | 13.816 | 12.232 | 23.1788 |
|  | CA % | CC % | CG % | CT % |
| Minimum | 3.571 | 0.8278 | 0.0000 | 1.512 |
| 25th percentile | 6.765 | 4.1077 | 0.4727 | 6.466 |
| Median | 7.410 | 5.5556 | 0.8439 | 7.279 |
| Mean | 7.411 | 5.9088 | 1.2707 | 7.184 |
| 75th percentile | 8.010 | 7.2460 | 1.5760 | 7.969 |
| Maximum | 15.714 | 20.8415 | 12.6074 | 12.232 |
|  | GA % | GC % | GG % | GT % |
| Minimum | 1.319 | 0.4967 | 0.8278 | 1.735 |
| 25th percentile | 5.495 | 3.2615 | 4.1077 | 4.586 |
| Median | 6.032 | 4.4092 | 5.5556 | 5.016 |
| Mean | 6.065 | 4.7468 | 5.9088 | 5.054 |
| 75th percentile | 6.602 | 5.8824 | 7.2460 | 5.494 |
| Maximum | 10.423 | 16.0000 | 20.8415 | 13.816 |
|  | TA % | TC % | TG % | TT % |
| Minimum | 0.000 | 1.319 | 3.571 | 0.000 |
| 25th percentile | 3.876 | 5.495 | 6.765 | 7.096 |
| Median | 5.625 | 6.032 | 7.410 | 9.106 |
| Mean | 5.774 | 6.065 | 7.411 | 8.976 |
| 75th percentile | 7.464 | 6.602 | 8.010 | 10.939 |
| Maximum | 24.338 | 10.423 | 15.714 | 17.922 |

Four of the novel super MARs were randomly picked and analyzed for AT and TA dinucleotide content, and compared with the previously known chicken lysMAR, considering windows of 100 base pairs (Table 6).

Surprisingly, Applicants have shown that all of the super MARs have AT dinucleotide frequencies greater than 12%, and TA dinucleotides greater than 10% of the total dinucleotides analyzed in a window of 100 base pairs of DNA. The most efficient MARs display values around 34% of the two dinucleotide pairs.

TABLE 6

Summary of % AT and TA dinucleotide frequencies of experimentally verified MARs

| CLysMAR (average of CUEs) | AT %: 12.03 | TA %: 10.29 |  |
|---|---|---|---|
| P1_68 | AT %: 33.78 | TA %: 33.93 | SEQ ID No. 25 |
| P1_6 | AT %: 34.67 | TA %: 34.38 | SEQ ID No. 24 |
| P1_42 | AT %: 35.65 | TA %: 35.52 | SEQ ID No. 26 |
| Mean value for all human "super"MARs | AT %: 34.32 | TA %: 35.29 |  |
| Mean value for all human non-MARs | AT %: 7.01 | TA %: 5.77 |  |

6.4 Analysis of Orthologous Intergenic Regions of Human and Mouse Genomes

In order to get an insight on S/MAR evolution, orthologous intergenic regions of human and mouse genomes have been analyzed with SMAR SCAN. The data set used is composed of 87 pairs of complete orthologous intergenic regions from the human and mouse genomes (Shabalina S A, Ogurtsov A Y, Kondrashov V A, Kondrashov A S, Selective constraint in intergenic regions of human and mouse genomes, Trends Genet, 17(7):3736, 2001) (average length~12 000 bp) located on 12 human and on 12 mouse chromosomes, the synteny of these sequences was confirmed by pairwise sequence alignment and consideration of the annotations of the flanking genes (experimental or predicted).

Analysis of the 87 human and mouse orthologous intergenic sequences have been analyzed with SMAR SCAN using its default settings. Analysis of the human sequences yielded a total of 12 S/MARs predicted (representing a total length of 4 750 bp), located on 5 different intergenic sequences.

Among the three human intergenic sequences predicted to contain a "super" S/MAR using SMAR SCAN stringent settings, one of the corresponding mouse orthologous intergenic sequence is also predicted to contain a S/MAR (human EMBL ID: Z96050, position 28 010 to 76 951 othologous to mouse EMBL ID: AC015932, positions 59 884 to 89 963). When a local alignment of these two orthologous intergenic sequences is performed, the best local alignment of these two big regions correspond to the regions predicted by SMAR SCAN) to be S/MAR element. A manual search for the mouse orthologs of the two other human intergenic sequences predicted to contain a "super" S/MAR was performed using the Ensembl Genome Browser. The mouse orthologous intergenic sequences of these two human sequences were retrieved using Ensembl orthologue predictions (based on gene names), searching the orthologous mouse genes for the pairs of human genes flanking these intergenic regions.

Because SMAR SCAN has been tuned for human sequences and consequently yields little "super"MARs with mouse genomic sequences, its default cutoff values were slightly relaxed for the minimum size of contiguous hits to be considered as S/MAR (using 200 bp instead of 300 bp). Analysis by SMAR SCAN of these mouse sequences predicted several S/MARs having high values for the different computed structural features. This finding suggests that the human MAR elements are conserved across species.

Example 7: Dissection of the Chicken Lysozyme Gene 5'-MAR

The 3000 base pair 5'-MAR was dissected into smaller fragments that were monitored for effect on transgene expression in Chinese hamster ovary (CHO) cells. To do so, seven fragments of ~400 bp were generated by polymerase chain reaction (PCR). These PCR-amplified fragments were contiguous and cover the entire MAR sequence when placed end-to-end. Four copies of each of these fragments were ligated in a head-to-tail orientation, to obtain a length corresponding to approximately half of that of the natural MAR. The tetramers were inserted upstream of the SV40 promoter in pGEGFPControl, a modified version of the pGL3Control vector (Promega). The plasmid pGEGFPControl was created by exchanging the luciferase gene of pGL3Control for the EGFP gene from pEGFP-N1 (Clontech). The 5'-MAR-fragment-containing plasmids thus created were co-transfected with the resistance plasmid pSVneo in CHO-DG44 cells using LipofectAmine 2000 (Invitrogen) as transfection reagent, as performed previously (Zahn-Zabal, M., et al., "Development of stable cell lines for production or regulated expression using matrix attachment regions" *J Biotechnol*, 2001. 87(1): p. 29-42.). After selection of the antibiotic (G-418) resistant cells, polyclonal cell populations were analyzed by FACS for EGFP fluorescence.

Figure 5:
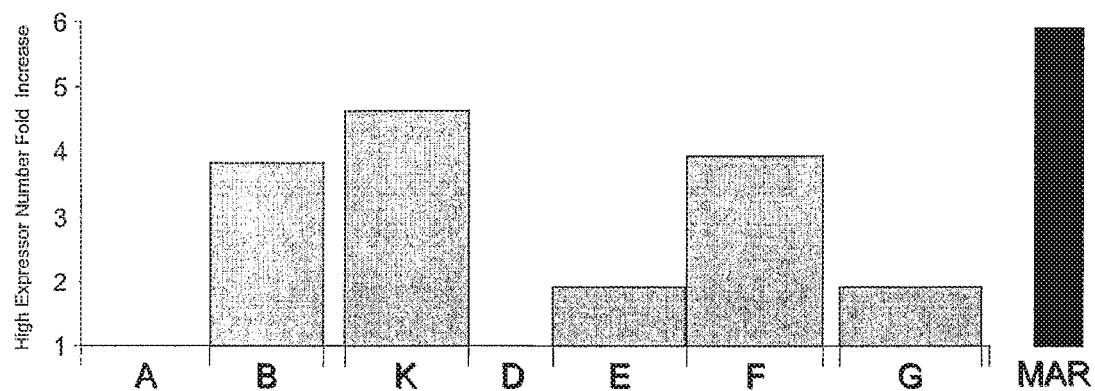
FIG. 5 shows the dissection of the ability of the chicken lysozyme gene 5'-MAR to stimulate transgene expression in CHO-DG44 cells. Fragments B, K and F show the highest ability to stimulate transgene expression. The indicated relative strength of the elements was based on the number of high-expressor cells.

Transgene expression was expressed at the percentile of high expressor cells, defined as the cells which fluorescence levels are at least 4 orders of magnitude higher than the average fluorescence of cells transfected with the pGEGF-PControl vector without MAR. FIG. 5 shows that multimerized fragments B, K and F enhance transgene expression, despite their shorter size as compared to the original MAR sequence. In contrast, other fragments are poorly active or fully inactive.

Example 8: Specificity of B, K and F Regions in the MAR Context

Figure 6:
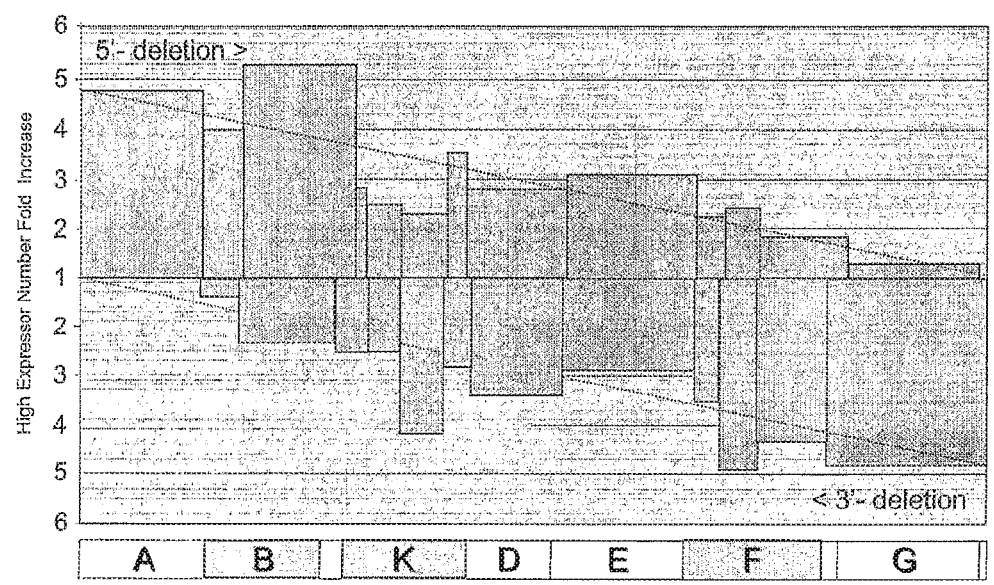
FIG. 6 shows the effect of serial-deletions of the 5'-end (upper part) and the 3'-end (lower part) of the 5'-MAR on the loss of ability to stimulate transgene expression. The transition from increased to decreased activity coincide with B-, K- and F-fragments.

The 5'-MAR was serially deleted from the 5'-end (FIG. 6, upper part) or the 3'-end (FIG. 6, lower part), respectively. The effect of the truncated elements was monitored in an assay similar to that described in the previous section. FIG. 6 shows that the loss of ability to stimulate transgene expression in CHO cells was not evenly distributed.

In this deletion study, the loss of MAR activity coincided with discrete regions of transition which overlap with the 5'-MAR B-, K- and F-fragment, respectively. In 5' deletions, activity was mostly lost when fragment K and F were removed. 3' deletions that removed the F and b elements had the most pronounced effects. In contrast, flanking regions A, D, E and G that have little or no ability to stimulate transgene expression on their own (FIG. 5), correspondingly did not contribute to the MAR activity in the 5'- and 3'-end deletion studies (FIG. 6).

Example 9: Structure of the F Element

Figure 7:
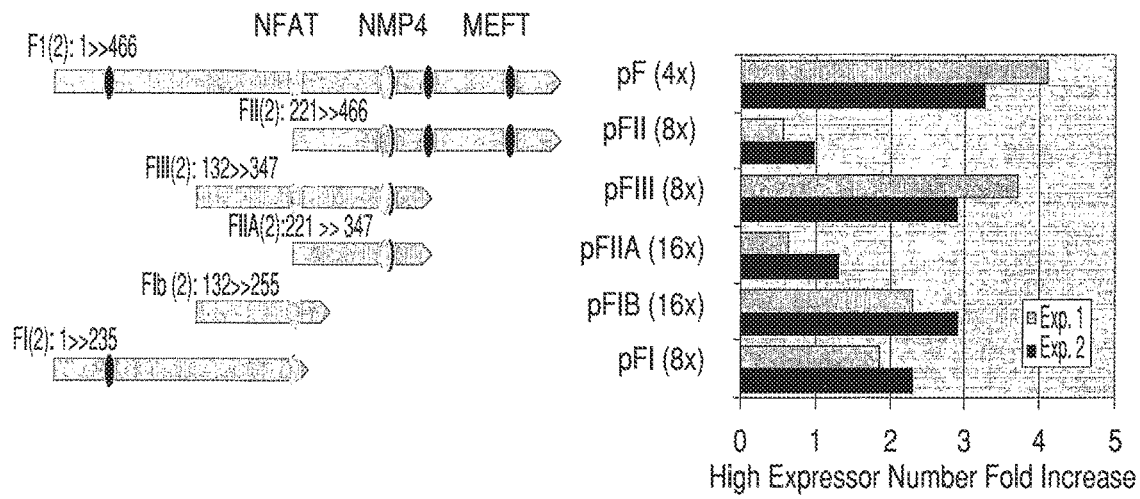
FIG. 7 shows that portions of the F fragment significantly stimulate transgene expression. The F fragment regions indicated by the light grey arrow were multimerized, inserted in pGEGFP Control and transfected in CHO cells. The element that displays the highest activity is located in the central part of the element and corresponds to fragment FIII (black bar labelled minimal MAR). In addition, an enhancer activity is located in the 3'-flanking part of the FIII fragment (dark grey bar labeled MAR enhancer).

The 465 bp F fragment was further dissected into smaller sub-fragments of 234, 243, 213 bp and 122, 125 and 121 bp, respectively. Fragments of the former group were octamerized (8 copies) in a head-to-tail orientation, while those of the latter group were similarly hexa-decamerized (16 copies), to maintain a constant length of MAR sequence. These elements were cloned in pGEGFPControl vector and their effects were assayed in CHO cells as described previously. Interestingly, fragment FIII retained most of the activity of the full-length F fragment whereas fragment FII, which contains the right-hand side part of fragment FIII, lost all the ability to stimulate transgene expression (FIG. 7). This points to an active region comprised between nt 132 and nt 221 in the FIB fragment. Consistently, multiple copies of fragments FI and FIB, which encompass this region, displayed similar activity. FIIA on its own has no activity. However, when added to FIB, resulting in FIII, it enhances the activity of the former. Therefore FIIA appears to contain an auxiliary sequence that has little activity on its own, but that strengthens the activity of the minimal domain located in FIB.

Figure 8:
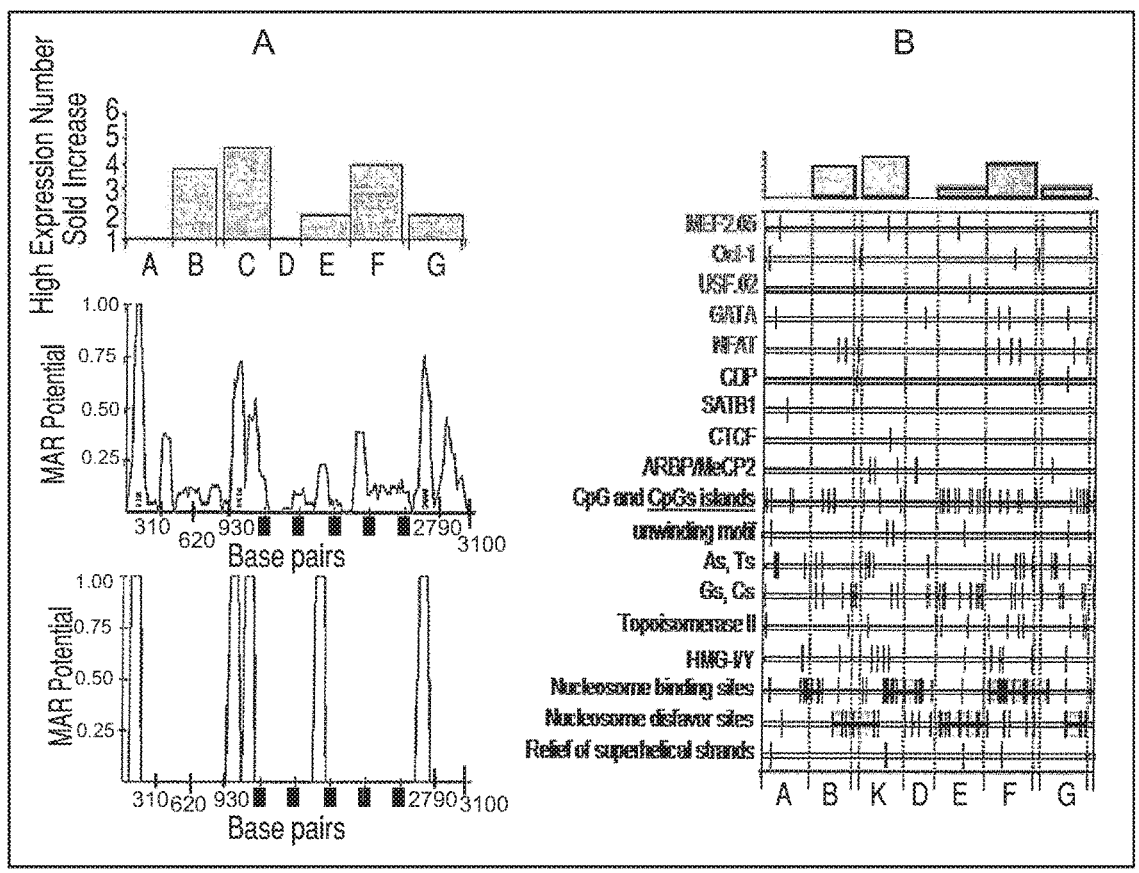
FIG. 8 shows a map of locations for various DNA sequence motifs within the cLysMAR.

Analysis of the distribution of individual motifs within the lysozyme gene 5'-MAR is shown in FIG. 8 A, along with some additional motifs that we added to the analysis.

Most of these motifs were found to be dispersed throughout the MAR element, and not specifically associated with the active portions. For instance, the binding sites of transcription factors and other motifs that have been associated with MARs were not preferentially localized in the active regions. It has also been proposed that active MAR sequences may consist of combination of distinct motifs. Several computer programs (MAR Finder, SMARTest, SIDD duplex stability) have been reported to identify MARs as regions of DNA that associate with the DNA matrix. They are usually based on algorithms that utilizes a predefined series of sequence-specific patterns that have previously been suggested as containing MAR activity, as exemplified by MAR Finder, now known as MAR Wiz. The output of these programs did not correlate well with the transcriptionally active portions of the cLysMAR. For instance, peaks of activity obtained with MAR Finder did not clearly match active MAR sub-portion, as for instance the B fragment is quite active in vivo but scores negative with MAR Finder (FIG. 8B, compare the top and middle panels). Bent DNA structures, as predicted by this program, did not correlate well either with activity (FIG. 8B, compare the top and bottom panels). Similar results were obtained with the other available programs (data not shown).

The motifs identified by available MAR prediction computer methods are therefore unlikely to be the main determinants of the ability of the cLysMAR to increase gene expression. Therefore, a number of other computer tools were tested. Surprisingly, predicted nucleosome binding sequences and nucleosome disfavoring sequences were found to be arranged in repetitively interspersed clusters over the MAR, with the nucleosome favoring sites overlapping the active B, K and F regions. Nucleosome positioning sequences were proposed to consist of DNA stretches that can easily wrap around the nucleosomal histones, and they had not been previously associated with MAR sequences.

Nucleosome-favoring sequences may be modeled by a collection of DNA features that include moderately repeated sequences and other physico-chemical parameters that may allow the correct phasing and orientation of the DNA over the curved histone surface. Identification of many of these DNA properties may be computerized, and up to 38 different such properties have been used to predict potential nucleosome positions. Therefore, we set up to determine if specific components of nucleosome prediction programs might correlate with MAR activity, with the objective to construct a tool allowing the identification of novel and possibly more potent MARs from genomic sequences.

To determine whether any aspects of DNA primary sequence might distinguish the active B, K and F regions from the surrounding MAR sequence, we analyzed the 5'-MAR with MAR SCAN. Of the 38 nucleosomal array prediction tools, three were found to correlate with the location of the active MAR sub-domains (FIG. 9A). Location of the MAR B, K and F regions coincides with maxima for DNA bending, major groove depth and minor groove width. A weaker correlation was also noted with minima of the DNA melting temperature, as determined by the GC content. Refined mapping over the MAR F fragment indicated that the melting temperature valley and DNA bending summit indeed correspond the FIB sub-fragment that contains the MAR minimal domain (FIG. 9B). Thus active MAR portions may correspond to regions predicted as curved DNA regions by this program, and we will refer to these regions as CUE-B, CUE-K and CUE-F in the text below. Nevertheless, whether these regions correspond to actual bent DNA and base-pair unwinding regions is unknown, as they do not correspond to bent DNA as predicted by MAR Wiz (FIG. 9B).

Example 10: Imprints of Other Regulatory Elements in the F Fragment

Nucleosome positioning features may be considered as one of the many specific chromatin codes contained in genomic DNA. Although this particular code may contribute to the activity of the F region, it is unlikely to determine MAR activity alone, as the 3' part of the F region enhanced activity of the minimal MAR domain contained in the FIB portion. Using the MatInspector program (Genomatix), we searched for transcription factor binding sites with scores higher than 0.92 and found DNA binding sequences for the NMP4 and MEF2 proteins in the 3' part of the F fragment (FIG. 8B).

Figure 10:
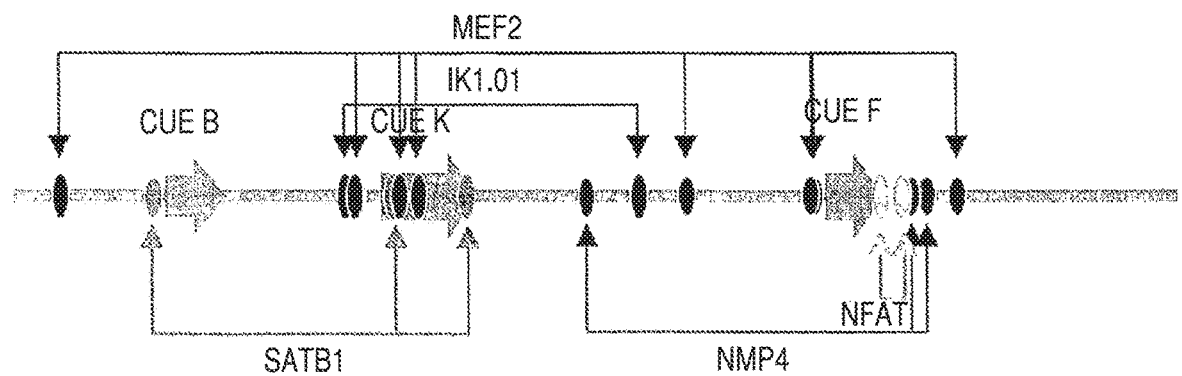
FIG. 10 shows the distribution of putative transcription factor binding sites within the 5'-cLysMAR. Large arrows indicate the position of the CUE elements as identified with SMAR SCAN.

To determine whether any of these transcription factor-binding sites might localize close to the B and K active regions, the entire 5'-MAR sequence was analyzed for binding by NMP4 and MEF2 and proteins reported to bind to single-stranded or double-stranded form of BURs. Among those, SATB1 (special AT-rich binding protein 1) belongs to a class of DNA-binding transcription factor that can either activate or repress the expression of nearby genes. This study indicated that specific proteins such as SATB1, NMP4 (nuclear matrix protein 4) and MEF2 (myogenic enhancer factor 2), have a specific distribution and form a framework around the minimal MAR domains of cLysMAR (FIG. 10). The occurrence of several of these NMP4 and SATB1 binding sites has been confirmed experimentally by the EMSA analysis of purified recombinant proteins (data not shown).

Figure 11:
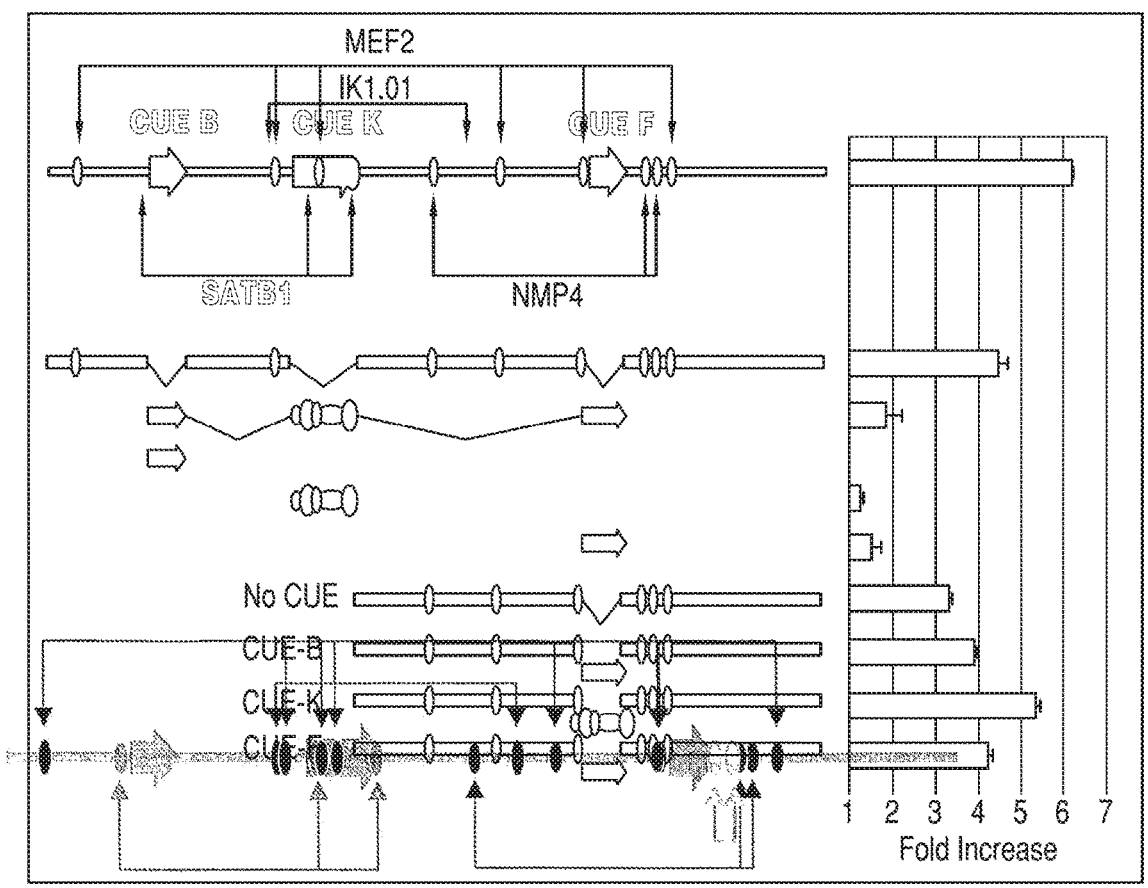
FIG. 11 shows the scheme of assembly of various portions of the MAR. The indicated portions of the cLysMAR were amplified by PCR, introducing BgIII-BamHI linker elements at each extremity, and assembled to generate the depicted composite elements. For instance, the top construct consists of the assembly of all CUE and flanking sequences at their original location except that BgII-BamHII linker sequences separate each element.

Example 11: Construction of Artificial MARs by Combining Defined Genetic Elements To further assess the relative roles of the various MAR components, the cLysMAR was deleted of all three CUE regions (FIG. 11, middle part), which resulted in the loss of part of its activity when compared to the complete MAR sequence similarly assembled from all of its components as a control (FIG. 11, top part). Consistently, one copy of each CUE alone, or one copy of each of the three CUEs assembled head-to-tail, had little activity in the absence of the flanking sequences. These results strengthen the conclusion that optimal transcriptional activity requires the combination of CUEs with of flanking sequences. Interestingly, the complete MAR sequence generated from each of its components, but containing also BgIII-BamHI linker sequences (AGATCC) used to assemble each DNA fragment, displayed high transcriptional activity (6 fold activation) as compared to the 4.8 fold noted for the original MAR element in this series of assays (see FIG. 5).

We next investigated whether the potentially curved DNA regions may also be active in an environment different from that found in their natural MAR context. Therefore, we set up to swap the CUE-F, CUE-B and CUE-K elements, keeping the flanking sequences unchanged. The sequences flanking the CUE-F element were amplified by PCR and assembled to bracket the various CUEs, keeping their original orientation and distance, or without a CUE. These engineered ~1.8 kb MARs were then assayed for their ability to enhance transgene expression as above. All three CUE were active in this context, and therefore there action is not restricted to one given set of flanking sequences. Interestingly, the CUE-K element was even more active than CUE-F when inserted between the CUE-F flanking sequences, and the former composite construct exhibited an activity as high as that observed for the complete natural MAR (4.8 fold activation). What distinguishes the CUE-K element from CUE-F and CUE-B is the presence of overlapping binding sites for the MEF-2 and SatB1 proteins, in addition to its CUE feature. Therefore, fusing CUE-B with CUE-F-flanking domain results in a higher density of all three binding sites, which is likely explanation to the increased activity. These results indicate that assemblies of CUEs with sequences containing binding sites for proteins such as NMP4, MEF-2, SatB1, and/or polyPpolyQ proteins constitute potent artificial MAR sequences.

Example 12: Expression Vectors

Figure 12:
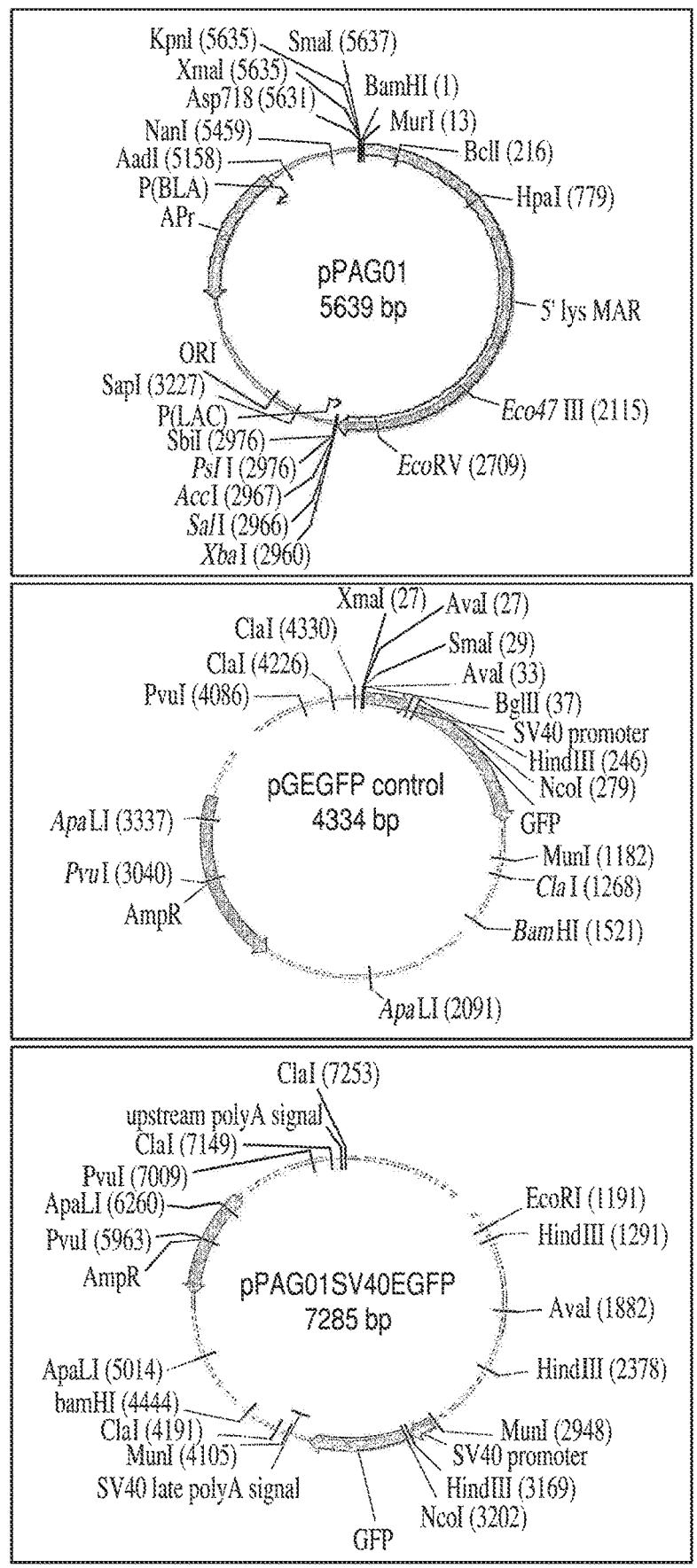
FIG. 12 represents the plasmid maps.

Three expression vectors according to the present invention are represented on FIG. 12.

Plasmid pPAG01 is a 5640 bp pUC19 derivative. It contains a 2960 bp chicken DNA fragment cloned in BamH1 and XbaI restriction sites. The insert comes from the border of the 5'-end of the chicken lyzozyme locus and has a high A/T-content.

Plasmid pGEGFP (also named pSV40EGFP) control is a derivative of the pGL3-control vector (Promega) in which the luciferase gene sequence has been replaced by the EGFP gene sequence form the pEGFP-N1 vector (Clontech). The size of pGEGFP plasmid is 4334 bp.

Plasmid pUbCEGFP control is a derivative of the pGL3 wit an Ubiquitin promoter.

Plasmid pPAG01GFP (also named pMAR-SV40EGFP) is a derivative of pGEGFP with the 5'-Lys MAR element cloned in the MCS located just upstream of the SV40 promoter. The size of the pPAG01EGF plasmid is 7285 bp.

Example 13: Effect of the Additional Transfection of Primary Transfectant Cells on Transgene Expression One day before transfection, cells were plated in a 24-well plate, in growth medium at a density of $1.35 \times 10^5$ cells/well for CHO-DG44 cells. 16 hours post-inoculum, cells were transfected when they reached 30-40% confluence, using Lipofect-AMINE 2000 (hereinafter LF2000), according to the manufacturer's instructions (Invitrogen). Twenty-seven microliters of serum free medium (Opti-MEM; Invitrogen) containing 1.4 µl of LF2000 were mixed with 27 µl of Opti-MEM containing 830 ng of linear plasmid DNA. The antibiotic selection plasmid (pSVneo) amounted to one tenth of the reporter plasmid bearing the GFP transgene. The mix was incubated at room temperature for 20 min, to allow the DNA-LF2000 complexes to form. The mixture was diluted with 300 µl of Opti-MEM and poured into previously emptied cell-containing wells. Following 3 hours incubation of the cells with the DNA mix at 37° C. in a $CO_2$ incubator, one ml of DMEM-based medium was added to each well. The cells were further incubated for 24 hours in a $CO_2$ incubator at 37° C. The cells were then transfected a second time according to the method described above, except that the resistance plasmid carried another resistance gene (pSVpuro). Twenty-four hours after the second transfection, cells were passaged and expanded into a T-75 flask containing selection medium supplemented with 500 µg/ml G-418 and 5 µg/ml puromycin. After a two week selection period, stably transfected cells were cultured in 6-well plates. Alternatively, the cell population was transfected again using the same method, but pTKhygro (Clontech) and pSVdhfr as resistance plasmids. The expression of GFP was analyzed with Fluorescence-activated cell sorter (FACS) and with a Fluoroscan.

Figure 13:
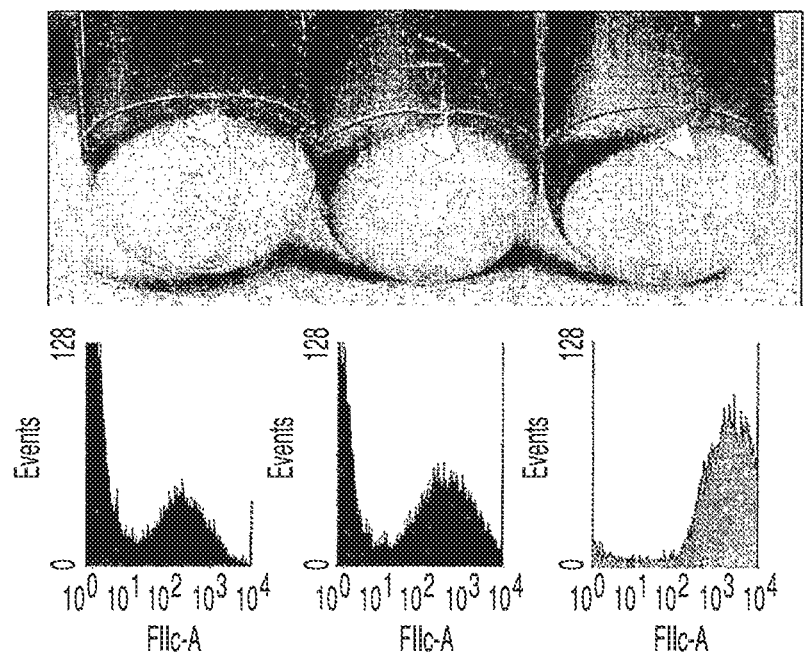
FIG. 13 shows the effect of re-transfecting primary transfectants on GFP expression. Cells (CHO-DG44) were co-transfected with pSV40EGFP (left tube) or pMAR-SV40EGFP (central tube) and pSVneo as resistance plasmid. Cells transfected with pMAR-SV40EGFP were re-transfected 24 hours later with the same plasmid and a different selection plasmid, pSVpuro (right tube). After two weeks selection, the phenotype of the stably transfected cell population was analyzed by FACS.

FIG. 13 shows that the phenotype of the twice-transfected cells (hereafter called secondary transfectants) not only was strongly colored, such that special bulb and filter were not required to visualize the green color from the GFP protein, but also contained a majority of producing cells (bottom right-hand side FACS histogram) as compared to the parental population (central histogram). This level of fluorescence corresponds to specific cellular productivities of at least 10 pg per cell per day. Indeed, cells transfected only one time (primary transfectants) that did not express the marker protein were almost totally absent from the cell population after re-transfection. Bars below $10^1$ units of GFP fluorescence amounted 30% in the central histogram and less than 5% in the right histogram. This suggested that additional cells had been transfected and successfully expressed GFP.

Strikingly, the amount of fluorescence exhibited by re-transfected cells suggested that the subpopulation of cells having incorporated DNA twice expressed much more GFP than the expected two-fold increase. Indeed, the results shown in Table 2 indicate that the secondary transfectants exhibited, on average, more than the two-fold increase of GFP expected if two sets of sequences, one at each successive transfection, would have been integrated independently and with similar efficiencies. Interestingly, this was not dependent on the promoter sequence driving the reporter gene as both viral and cellular promoter-containing vectors gave a similar GFP enhancement (compare lane 1 and 2). However, the effect was particularly marked for the MAR-containing vector as compared to plasmids without MAR- (lane 3), where the two consecutive transfections resulted in a 5.3 and 4.6 fold increase in expression, in two distinct experiments.

TABLE 7

Effect of re-transfecting primary transfectants at 24 hours interval on GFP expression. Two independent experiments are shown. The resistance plasmid pSVneo was co-transfected with various GFP expression vectors. One day post-transfection, cells were re-transfected with the same plasmids with the difference that the resistance plasmid was changed for pSVpuro. Cells carrying both resistance genes were selected on 500 µg/ml G418 and 5 µg/ml puromycin and the expression of the reporter gene marker was quantified by Fluoroscan. The fold increases correspond to the ratio of fluorescence obtained from two consecutive transfections as compared to the sum of fluorescence obtained from the corresponding independent transfections. The fold increases that were judged significantly higher are shown in bold, and correspond to fluorescence values that are consistently over 2-fold higher than the addition of those obtained from the independent transfections.

| Type of plasmids | Primary transfection | Secondary transfection | EGFP fluorescence Fold increase |
|---|---|---|---|
| pUbCEGFP | 4'992 | 14'334 | 2.8 |
| pSV40EGFP | 4'324 | 12'237 | 2.8 |
| pMAR-SV40EGFP | 6'996 | 36'748 | 5.3 |
| pUbCEGFP | 6'452 | 15'794 | 2.5 |
| pSV40EGFP | 4'433 | 11'735 | 2.6 |
| pMAR-SV40EGFP | 8'116 | 37'475 | 4.6 |

The increase in the level of GFP expression in multiply transfected cells was not expected from current knowledge, and this effect had not been observed previously.

Taken together, the data presented here support the idea that the plasmid sequences that primarily integrated into the host genome would facilitate integration of other plasmids by homologous recombination with the second incoming set of plasmid molecules. Plasmid recombination events occur within a 1-h interval after the plasmid DNA has reached the nucleus and the frequency of homologous recombination between co-injected plasmid molecules in cultured mammalian cells has been shown to be extremely high, approaching unity (Folger, K. R., K. Thomas, and M. R. Capecchi, Nonreciprocal exchanges of information between DNA duplexes coinjected into mammalian cell nuclei. Mol Cell Biol, 1985. 5(1): p. 59-69], explaining the integration of multiple plasmid copies. However, homologous recombination between newly introduced DNA and its chromosomal homolog normally occurs very rarely, at a frequency of 1 in $10^3$ cells receiving DNA to the most [Thomas, K. R., K. R. Folger, and M. R. Capecchi, High frequency targeting of genes to specific sites in the mammalian genome. Cell, 1986. 44(3): p. 419-28.]. Thus, the results might indicate that the MAR element surprisingly acts to promote such recombination events. MARs would not only modify the organization of genes in vivo, and possibly also allow DNA replication in conjunction with viral DNA sequences, but they may also act as DNA recombination signals.

Example 14: MARs Mediate the Unexpectedly High Levels of Expression in Multiply Transfected Cells If MAR-driven recombination events were to occur in the multiple transfections process, we expect that the synergy between the primary and secondary plasmid DNA would be affected by the presence of MAR elements at one or both of the transfection steps. We examined this possibility by multiply transfections of the cells with pMAR alone or in combination with various expression plasmids, using the method described previously. Table 3 shows that transfecting the cells twice with the pMAR-SV40EGFP plasmid gave the highest expression of GFP and the highest degree of enhancement of all conditions (4.3 fold). In contrast, transfecting twice the vector without MAR gave little or no enhancement, 2.8-fold, instead of the expected two-fold increase. We conclude that the presence of MAR elements at each transfection step is necessary to achieve the maximal protein synthesis.

TABLE 8

| Primary transfection | | Secondary transfection | | |
|---|---|---|---|---|
| Type of plasmid | EGFP-fluorescence | Type of plasmid | EGFP-fluorescence | Fold increase |
| pMAR | 0 | pMAR | 0 | 0 |
|  |  | pSV40EGFP | 15'437 | 2.3-2.5 |
|  |  | pMAR-SV40EGFP | 30'488 | 2.6-2.7 |
| pMAR-SV40EGFP | 11'278 | pMAR-SV40EGFP | 47'027 | 4.3-5.3 |
|  |  | pMAR | 12'319 | 1.0-1.1 |
| pSV40EGFP | 6'114 | pSV40EGFP | 17'200 | 2.8 |
|  |  | pMAR | 11'169 | 1.8-2.3 |

Interestingly, when cells were first transfected with pMAR alone, and then re-transfected with pSV40EGFP or pMAR-SV40EGFP, the GFP levels were more than doubled as compared to those resulting from the single transfection of the later plasmids (2.5 and 2.7 fold respectively, instead of the expected 1-fold). This indicates that the prior transfection of the MAR can increase the expression of the plasmid used in the second transfection procedure. Because MARs act only locally on chromatin structure and gene expression, this implies that the two types of DNA may have integrated at a similar chromosomal locus. In contrast, transfecting the GFP expression vectors alone, followed by the MAR element in the second step, yielded little or no improvement of the GFP levels. This indicates that the order of plasmid transfection is important, and that the first transfection event should contain a MAR element to allow significantly higher levels of transgene expression.

If MAR elements favored the homologous recombination of the plasmids remaining in episomal forms from the first and second transfection procedures, followed by their co-integration at one chromosomal locus, one would expect that the order of plasmid transfection would not affect GFP levels. However, the above findings indicate that it is more favorable to transfect the MAR element in the first rather than in the second transfection event. This suggests the following molecular mechanism: during the first transfection procedure, the MAR elements may concatemerize and integrate, at least in part, in the cellular chromosome. This integrated MAR DNA may in turn favor the further integration of more plasmids, during the second transfection procedure, at the same or at a nearby chromosomal locus.

Example 15: MARs as Long Term DNA Transfer Facilitators

If integrated MARs mediated a persistent recombination-permissive chromosomal structure, one would expect high levels of expression even if the second transfection was performed long after the first one, at a time when most of the transiently introduced episomal DNA has been eliminated. To address this possibility, the cells from Table 3, selected for antibiotic resistance for three weeks, were transfected again once or twice and selected for the incorporation of additional DNA resistance markers. The tertiary, or the tertiary and quaternary transfection cycles, were performed with combinations of pMAR or pMAR-SV40EGFP, and analyzed for GFP expression as before.

TABLE 9

MARs act as facilitator of DNA integration.

| | Tertiary transfection | | Quaternary transfection | |
|---|---|---|---|---|
| Type of plasmid | EGFP-fluorescence | Fold increase | Type of plasmid | EGFP-fluorescence | Fold increase |
| pMAR | 18368 | 2.2 | pMAR | 43'186 | 2.4 |
| pMAR-SV40EGFP | 16544 | 2.0 | pMAR-SV40EGFP | 140'000 | 7.6 |
| | | | pMAR-SV40EGFP | 91'000 | 5.5 |
| | | | pMAR | 33'814 | 2.0 |

The pMAR-SV40EGFP/pMAR-SV40EGFP secondary transfectants were used in a third cycle of transfection at the end of the selection process. The tertiary transfection was accomplished with pMAR or pMAR-SV40EGFP, and pTKhygro as selection plasmid, to give tertiary transfectants. After 24 hours, cells were transfected again with either plasmid and pSVdhfr, resulting in the quaternary transfectants which were selected in growth medium containing 500 μg/ml G-418 and 5 μg/ml puromycin, 300 μg/ml hygromycin B and 5 μM methotrexate. The secondary transfectants initially exhibited a GFP fluorescence of 8300. The fold increases correspond to the ratio of fluorescence obtained from two consecutive transfections as compared to the sum of fluorescence obtained from the corresponding independent transfections. The fold increases that were judged significantly higher are shown in bold, and correspond to fluorescence values that are 2-fold higher than the addition of those obtained from the independent transfections.

These results show that loading more copies of pMAR or pMAR-SV40EGFP resulted in similar 2-fold enhancements of total cell fluorescence. Loading even more of the MAR in the quaternary transfection further enhanced this activity by another 2.4-fold. This is consistent with our hypothesis that newly introduced MAR sequences may integrate at the chromosomal transgene locus by homologous recombination and thereby further increase transgene expression.

Figure 14:
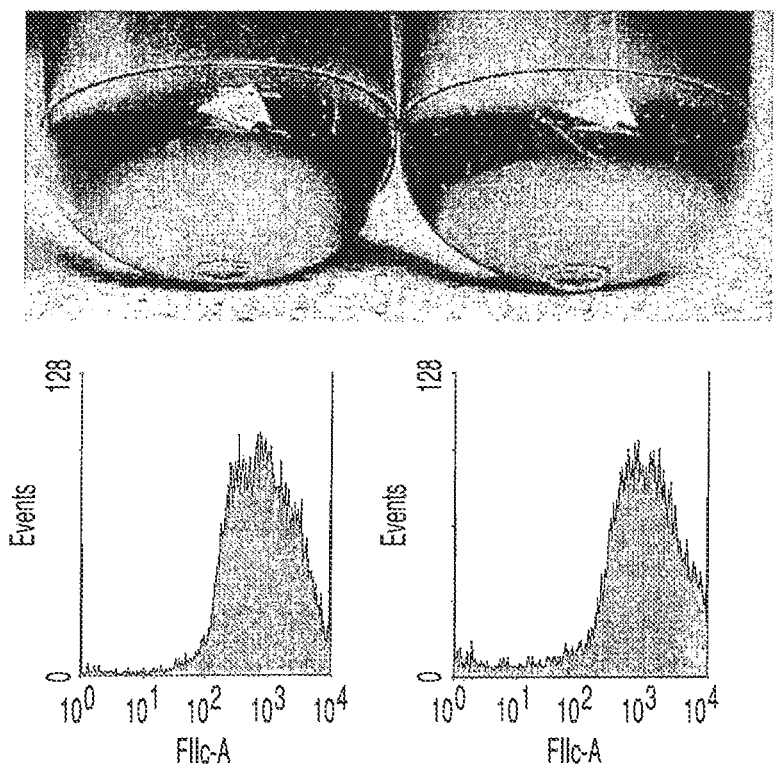
FIG. 14 shows the effect of multiple load of MAR-containing plasmid. The pMAR-SV40EGFP/pMAR-SV40EGFP secondary transfectants were used in a third cycle of transfection at the end of the selection process. The tertiary transfection was accomplished with pMAR or pMAR-SV40EGFP to give tertiary transfectants. After 24 hours, cells were transfected again with either plasmid, resulting in the quaternary transfectants (see Table 4).
Figure 15:
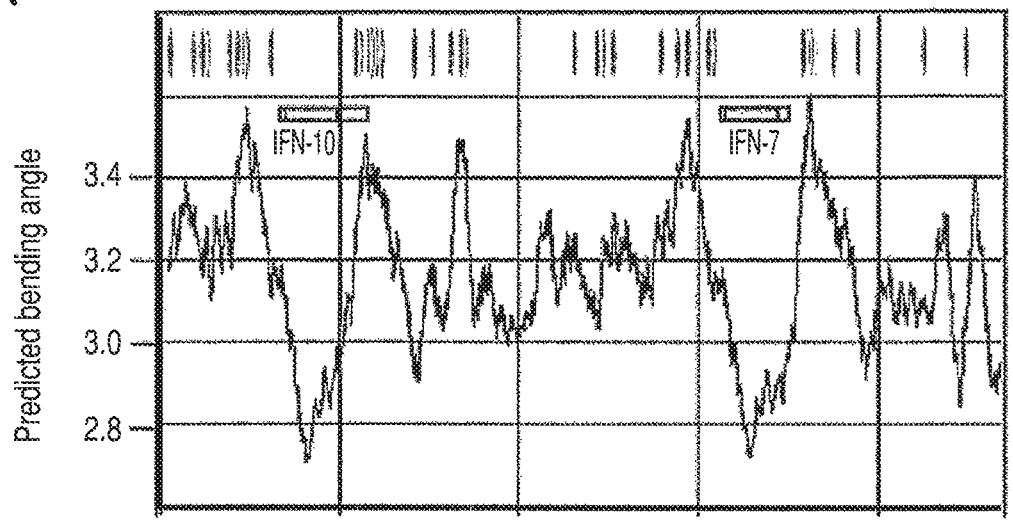
FIG. 15 shows comparative performance of SMAR prediction algorithms exemplified by region WP18A10A7. (A) SMAR SCAN analysis was performed with default settings. (B) SIDD analysis (top curve and left-hand side scale), and the attachment of several DNA fragments to the nuclear matrix in vitro (bar-graph, right-hand side scale) was taken from Goetze et al (Goetze S, Gluch A, Benham C, Bode J, "Computational and in vitro analysis of destabilized DNA regions in the interferon gene cluster: potential of predicting functional gene domains." *Biochemistry*, 42:154-166, 2003).
Figure 15:
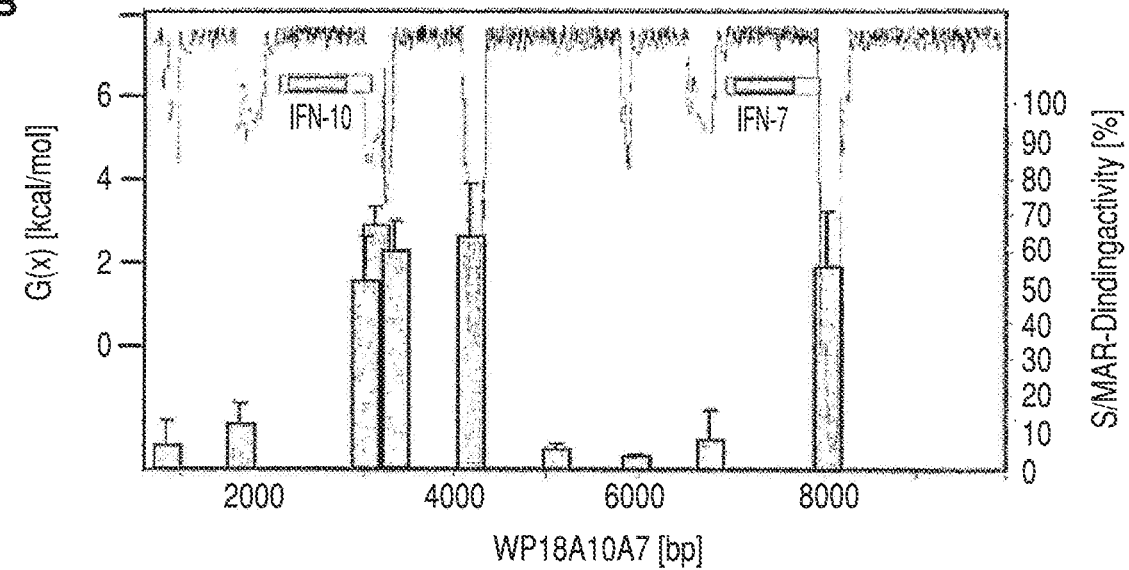

When the cells were transfected a third and fourth time with the pMAR-SV40EGFP plasmid, GFP activity further increased, once again to levels not expected from the addition of the fluorescence levels obtained from independent transfections. GFP expression reached levels that resulted in cells visibly glowing green in day light (FIG. 14). These results further indicate that the efficiency of the quaternary transfection was much higher than that expected from the efficacy of the third DNA transfer, indicating that proper timing between transfections is crucial to obtain the optimal gene expression increase, one day being preferred over a three weeks period.

We believe that MAR elements favor secondary integration events in increasing recombination frequency at their site of chromosomal integration by relaxing closed chromatin structure, as they mediate a local increase of histone acetylation (Yasui, D., et al., SATB1 targets chromatin remodelling to regulate genes over long distances. *Nature*, 2002. 419(6907): p. 641-5.]. Alternatively, or concomitantly, MARs potentially relocate nearby genes to subnuclear locations thought to be enriched in trans-acting factors, including proteins that can participate in recombination events such as topoisomerases. This can result in a locus in which the MAR sequences can bracket the pSV40EGFP repeats, efficiently shielding the transgenes from chromatin-mediated silencing effects.

Figure 19:
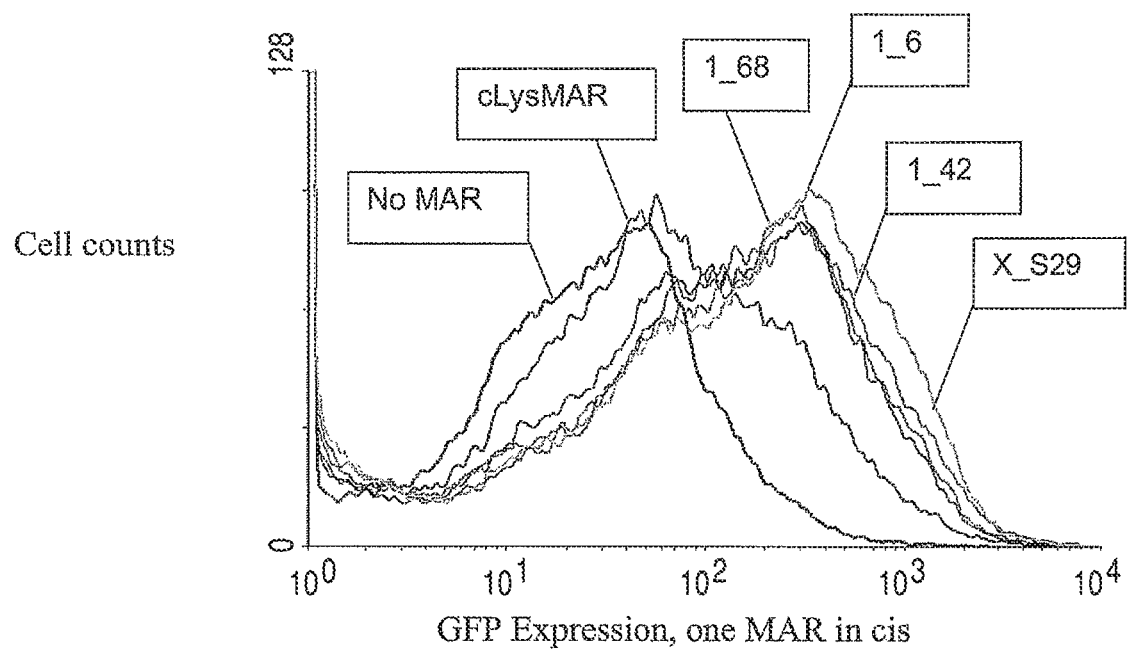
FIG. 19 shows the effect of various S/MAR elements on the production of recombinant green fluorescent protein (GFP). Populations of CHO cells transfected with a GFP expression vector containing or a MAR element, as indicated, were analyzed by a fluorescence-activated cell sorter (FACS), and typical profiles are shown. The profiles display the cell number counts as a function of the GFP fluorescence levels.

Example 16: Use of MARs Identified with SMAR SCAN II to Increase the Expression of a Recombinant Protein Four MAR elements were randomly selected from the sequences obtained from the analysis of the complete human genome sequence with SMAR SCAN or the combined method. These are termed 1_6, 1_42, 1_68, (where the first number represents the chromosome from which the sequence originates, and the second number is specific to the predicted MAR along this chromosome) and X_S29, a "super" MAR identified on chromosome X. These predicted MARs were inserted into the pGEGFPControl vector upstream of the SV40 promoter and enhancer driving the expression of the green fluorescent protein and these plasmids were transfected into cultured CHO cells, as described previously (Zahn-Zabal, M., et al., *Development of stable cell lines for production or regulated expression using matrix attachment regions*. J Biotechnol, 2001. 87(1): p. 29-42). Expression of the transgene was then analyzed in the total population of stably transfected cells using a fluorescent cell sorter (FACS) machine. As can be seen from FIG. 19, all of these newly identified MARs increased the expression of the transgene significantly above the expression driven by the chicken lysosyme MAR, the "super" MAR X_S29 being the most potent of all of the newly identified MARs.

Example 17: Effect on Hematocrit of In Vivo Expression of mEpo by Electrotransfer of Network System with and without Human MAR (1-68)

The therapeutic gene encodes EPO (erythropoietin), an hormone used for the treatment of anemia. The EPO gene is placed under the control of a doxycycline inducible promoter, in a gene switch system described previously called below the Network system (Imhof, M. O., Chatellard, P., and Mermod, N. (2000). A regulatory network for efficient control of transgene expression. J. Gene. Med. 2, 107-116.). The EPO and regulatory genes are then injected in the muscle of mice using an in vivo electroporation procedure termed the electrotransfer, so that the genes are transferred to the nuclei of the muscle fibers. When the doxycycline antibiotic is added to the drinking water of the mice, this compound is expected to induce the expression of EPO, which will lead to the elevation of the hematocrit level, due to the increase in red blood cell counts mediated by the high levels of circulating EPO. Thus, if the MAR improved expression of EPO, higher levels of hematocrit would be expected.

In vivo experiments were carried out on 5 week-old C57BL6 female mice (Iffa Credo-Charles River, France). 30 µg of plasmid DNA in normal saline solution was delivered by trans-cutaneous injections in the tibialis anterior muscle. All injections were carried out under Ketaminol (75 mg/kg) and Narcoxyl (10 mg/kg) anesthesia. Following the intramuscular injection of DNA, an electrical field was applied to the muscle. A voltage of 200 V/cm was applied in 8 ms pulses at 1 Hz (Bettan M, Darteil R, Caillaud J M, Soubrier F, Delaere P, Branelec D, Mahfoudi A, Duverger N, Scherman D. 2000. "High-level protein secretion into blood circulation after electric pulse-mediated gene transfer into skeletal muscle". Mol Ther. 2: 204-10).

16 mice were injected by the Network system expressing EPO without the 1_68 MAR and 16 other mice were injected with the Network system incorporating the MAR in 5' of the promoter/enhancer sequences driving the expression of the activator and EPO genes. In each group, half of the mice were submitted to doxycycline in drinking water from the beginning of the experiment (day 0—the day of electrotransfer) and in the other half, doxycycline was put in drinking water starting at day 21.

Blood samples were collected using heparinated capillaries by retro-orbital punction at different times after the injection of plasmids. Capillaries were centrifugated 10 minutes at 5000 rpm at room temperature and the volumetric fraction of blood cells is assessed in comparison to the total blood volume and expressed as a percentile, determining the hematocrit level.

Figure 16:
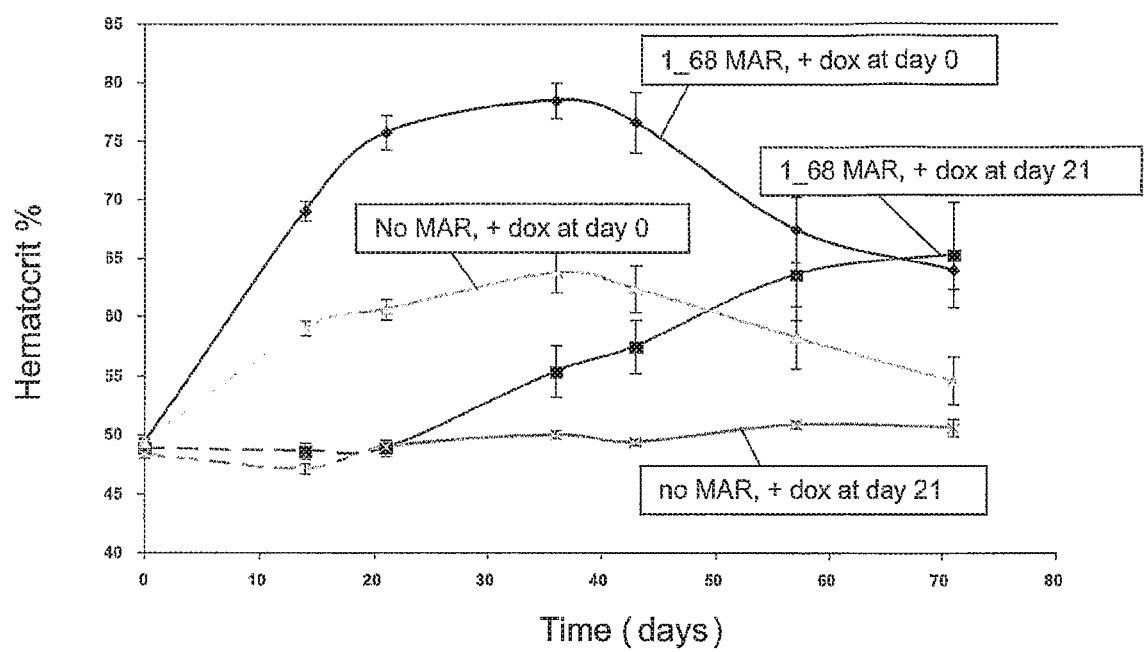
FIG. 16 represents the results of a gene therapy-like protocol using MARs. The group of mice injected by MAR-network, induced from the beginning of the experiment, display a better induction of the hematocrit in comparison of mice injected by original network without MAR. After 2 months, hematocrits in "MAR-containing group" is still at values higher (65%) than normal hematocrit levels (45-55%).

As can be deduced from FIG. 16 The group of mice injected by MAR-network, induced from the beginning of the experiment, display a better induction of the hematocrit in comparison of mice injected by original network without MAR. After 2 months, haematocrits in "MAR-containing group" is still at values higher (65%) than normal hematocrit levels (45-55%).

More importantly, late induction (day 21) is possible only in presence of MAR but not from mice where the Network was injected without the MAR. Thus the MAR likely protects the transgenes from silencing and allows induction of its expression even after prolong period in non-inducing conditions.

Overall, the MAR element is able to increase the expression of the therapeutic gene as detected from its increased physiological effect on the hematocrit.

The invention claimed is:

1. A host cell comprising:
a DNA sequence comprising:
a) at least one bent DNA element comprising at least 33% of the dinucleotide TA and/or at least 33% of the dinucleotide AT on a stretch of 100 contiguous base pairs,
b) at least one binding site for a DNA binding protein, wherein said DNA sequence is
(i) a fragment of SEQ ID NO: 26 which share at least 90% nucleotides in length with SEQ ID NO: 26,
(ii) a sequence that has at least 90% sequence identity with a nucleic acid sequence having SEQ ID NO: 26, or
(iii) a sequence complementary to the sequence of (ii), wherein the DNA sequence is heterologous to said host cell.

2. The host cell of claim 1, wherein said bent DNA element comprises at least five contiguous AT or TA dinucleotides.

3. The host cell of claim 2, wherein said bent DNA element comprises at least 10 contiguous AT or TA dinucleotides.

4. The host cell of claim 1, wherein said DNA binding protein is a transcription factor.

5. The host cell of claim 4, wherein the transcription factor is a polyQpolyP domain protein.

6. The host cell of claim 5, wherein said transcription factor is selected from the group consisting of: SATB1, NMP4, MEF2, S8, DLX1, FREAC7, BRN2, GATA 1/3, TATA, Bright, MSX, AP1, C/EBP, CREBP1, FOX, Freac7, HGH1, HNF3alpha, Nkx25, POU3F2, Pit1, TTF1, XFD1, AR, C/EBPgamma, Cdc5, FOXD3, HFH3, HNF3 beta, MRF2, Oct1, POU6F1, SRF, V$MTATA_B, XFD2, Bach2, CDP CR3, Cdx2, FOXJ2, HFL, HP1, Myc, PBX, Pax3, TEF, VBP, XFD3, Brn2, COMP1, Evil, FOXP3, GATA4, HFN1, Lhx3, NKX3A, POU1F1, Pax6, TFIIA or Vmw65 and a combination of two or more of said transcription factors.

7. The host cell of claim 1, wherein the DNA sequence has a melting temperature of between 55 and 75° and a DNA bending value of more than 4 radial degrees and wherein said binding protein is a transcription factor.

8. The host cell of claim 7, wherein the melting temperature of the DNA is between 55 and 62°.

9. The host cell of claim 1, wherein said DNA sequence is a sequence which deviates from SEQ ID NO: 26 by one or more nucleotide substitutions.

10. The host cell of claim 9, wherein said bent DNA element comprises at least five contiguous AT or TA dinucleotides.

11. The host cell according to claim 1, wherein the DNA sequence is part of a vector.

12. The host cell according to claim 1, wherein said purified and isolated DNA sequence is
(i) the sequence that has at least 90% sequence identity with a nucleic acid sequence having SEQ ID NO: 26, or
(ii) the sequence complementary to the sequence of (i).

13. A vector comprising a DNA sequence comprising:
(i) a sequence that has at least 90% sequence identity with a nucleotide sequence having SEQ ID NO: 26, or
(ii) a sequence complementary to the sequence of (i); or
(iii) a fragment of SEQ ID NO: 26 which shares at least 90% nucleotides in length with SEQ ID NO: 26; and at least one virus promoter or a heterologous mammalian promoter.

14. A cell transfection mixture or kit comprising at least one of the vectors according to claim 13.

15. A vector comprising a DNA sequence comprising:
(i) a sequence that has at least 90% sequence identity with a nucleotide sequence having SEQ ID NO: 26, or
(ii) a sequence complementary to the sequence of (i); or
(iii) a fragment of SEQ ID NO: 26 which shares at least 90% nucleotides in length with SEQ ID NO: 26; and at least one virus promoter or a heterologous mammalian promoter and a gene of interest.

16. The vector of claim 15, wherein said vector further comprises a purified and isolated DNA sequence comprising at least one bent DNA element and at least one binding site for a DNA binding protein.

17. The vector of claim 16, wherein said purified and isolated DNA sequence is 5' and 3' to said gene of interest.

18. The vector of claim 16, wherein said purified and isolated DNA sequence comprises at least 10% of the dinucleotide TA and/or at least 12% of the dinucleotide AT on a stretch of 100 contiguous base pairs.

19. The vector of claim 16, wherein said purified and isolated DNA sequence is a MAR nucleotide sequence with sequence ID NO: 26, or a sequence complementary to sequence ID NO: 26.

20. The vector of claim 19, wherein said purified and isolated DNA sequence has a melting temperature of between 55 and 75° and a DNA bending value of more than 4 radial degrees.

21. A cell transfection mixture or kit comprising at least one of the vectors according to claim 15.

22. The vector of claim 16, wherein said bent DNA element comprises at least five contiguous AT or TA nucleotides and wherein said binding protein is a transcription factor and has a DNA bending value of more than 4 radial degrees.

23. The vector of claim 15, wherein said gene of interest encodes a heterologous protein.

24. The vector of claim 23, further comprising an enhancer sequence.

25. The vector of claim 15, wherein said at least one promoter is operably linked to said gene of interest.

26. The vector of claim 15, wherein said DNA sequence has a melting temperature of between 55 and 75° and a DNA bending value of more than 4 radial degrees and wherein said binding protein is a transcription factor.

27. The vector of claim 15, wherein the DNA sequence is SEQ ID NO: 26, is a sequence complementary thereto or is the fragment of SEQ ID NO: 26 which shares at least 90% nucleotides in length with SEQ ID NO: 26.

28. The vector of claim 27, wherein the gene of interest encodes an antibody or fragment thereof.

29. The vector of claim 15, wherein said DNA sequence is SEQ ID No: 26 or a sequence complementary thereof.

30. A eukaryotic host cell transfected with at least one vector comprising at least one DNA sequence comprising:
    a) at least one bent DNA element comprising at least 33% of the dinucleotide TA and/or at least 33% of the dinucleotide AT on a stretch of 100 contiguous base pairs,
    b) at least one binding site for a DNA binding protein,
    c) at least one virus promoter or a heterologous mammalian promoter, wherein said DNA sequence is
    Matrix Attachment Region (MAR) nucleotide sequence with SEQ ID NO: 26, or
    a sequence complementary to sequence ID NO: 26, or
    a sequence having at least 90% identity with said SEQ ID NO: 26.

31. The host cell of claim 30, further comprising at least one DNA sequence of interest on said vector or on a separate vector.

32. The host cell of claim 31, wherein said at least one DNA sequence of interest is a gene of interest that encodes a heterologous protein.

33. The host cell of claim 32, wherein said at least one DNA sequence and said at least one DNA sequence of interest are on the same vector.

34. The host cell of claim 32, wherein said at least one DNA sequence and said at least one DNA sequence of interest are on separate vectors.

35. The host cell of claim 30, wherein said at least one DNA sequence has a melting temperature of between 55 and 75° and a DNA bending value of more than 4 radial degrees and wherein said binding protein is a transcription factor.

36. The host cell of claim 30, wherein said at least one purified and isolated DNA sequence is SEQ ID NO: 26, a sequence complementary thereof, or a fragment of sequences SEQ ID NO: 26 which shares at least 90% nucleotides in length with the respective sequence of the SEQ ID NO: 26 and wherein said binding protein is a transcription factor.

37. The host cell according to claim 30, wherein the host cell is a high recombinant protein producing cell with a production rate of at least 10 pg per cell per day.

38. A cell transfection mixture or kit comprising at least one DNA sequence selected from the group consisting of:
    (i) a sequence that has at least 90% sequence identity with a nucleotide sequence having SEQ ID NO: 26,
    (ii) a sequence complementary to the sequences of (i); and
    (iii) a fragment of SEQ ID NO: 26 which shares at least 90% nucleotides in length with SEQ ID NO: 26.

39. A synthetic Matrix Attachment Region (MAR) sequence comprising:
    linker sequences and, assembled between the linker sequences, one of the following sequences:
    (i) MAR sequence ID NO: 26, or
    (ii) a sequence complementary to sequence ID NO: 26, or
    (iii) a fragment of SEQ ID Nos 26 which shares at least 90% nucleotides in length with the respective sequence of the SEQ ID NO: 26.

40. The synthetic Matrix Attachment Region (MAR) sequence of claim 39, comprising:
    (i) MAR sequence SEQ ID NO: 26,
    (ii) a sequence complementary to the sequences of (i),
    wherein said sequence comprises at least 33% of dinucleotide TA and/or at least 33% of dinucleotide AT on a stretch of 100 continuous base pairs, and
    a transcription factor binding site.

41. The synthetic MAR sequence of claim 40, wherein the linkers are a BglII linker and a BamHI linker.

42. A method for transfecting a eukaryotic host cell, said method comprising
    a) providing a host cell according to claim 1,
    b) subjecting said eukaryotic host cell to at least one additional transfection step with at least one purified and isolated DNA sequence of interest, and
    c) selecting said transfected eukaryotic host cell.

43. The method of claim 42, wherein said DNA sequence of interest is a gene of interest coding for a protein operably linked to a promoter.

44. The method of claim 42, wherein said purified and isolated DNA sequence is a MAR nucleotide sequence
    with sequence ID NO: 24, 26, or 27, or
    a sequence complementary to sequence ID NO: 24, 26, or 27, or
    a sequence having at least 90% identity with said SEQ ID NO: 24, 26, or 27.

45. A method for transfecting a eukaryotic host cell, said method comprising co-transfecting into said eukaryotic host cell at least one first purified and isolated DNA sequence comprising at least one DNA sequence of interest, and a second DNA comprising at least one DNA sequence of claim 1.

46. The method of claim 42, wherein said at least one additional transfection step is performed between 6 hours and 48 hours after the introduction of a first DNA sequence comprising the DNA sequence of (i), (ii) or (iii).

* * * * *

SEQUENCE LISTING

```
<160> NUMBER OF SEQ ID NOS: 246

<210> SEQ ID NO 1
<211> LENGTH: 320
<212> TYPE: DNA
<213> ORGANISM: Homo sapiens
<220> FEATURE:
<221> NAME/KEY: misc_binding
<222> LOCATION: (1)..(320)
<223> OTHER INFORMATION: MAR of human chromosome 1, nt from 36686 to
      37008
<220> FEATURE:
<221> NAME/KEY: misc_binding
<222> LOCATION: (1)..(320)
<223> OTHER INFORMATION: MAR of human chromosome 1, genomic contig;
      36686 to 37008

<400> SEQUENCE: 1
ttatattatg ttgttatata tattatatta tgttattaga ttatattatg ttgttatatt       60
atataataat attatattat atattatata ttatattata taatatataa taatattata      120
taattatata ttacattata taatatataa taatattata taattatata ttacattata      180
taatatataa taatattata taataatata taattatata atatataata atattatata      240
atattatata atattatata atatataaat ataataataat atattatata ttatataata      300
gtatataata ttatataata                                                 320

<210> SEQ ID NO 2
<211> LENGTH: 709
<212> TYPE: DNA
```

```
<213> ORGANISM: Homo sapiens
<220> FEATURE:
<221> NAME/KEY: misc_binding
<222> LOCATION: (1)..(709)
<223> OTHER INFORMATION: MAR of human chromosome 1, nt from 142276 to
      142984
<220> FEATURE:
<221> NAME/KEY: misc_binding
<222> LOCATION: (1)..(709)
<223> OTHER INFORMATION: MAR of human chromosome 1, genomic contig;
      142276 to 142984

<400> SEQUENCE: 2
tacaatatat tttctattat atatattttg tattatatat aatatacaat atattttcta      60
ttatatataa tatattttgt attatatata ttacaatata ttttgtatta tataatatat     120
aatacaatat ataatatatt gtattatata ttatataata caatatatta tatattgtat     180
tatatattat ataaatacct ataaatata ttgtattata tattatatat aatactatat     240
aatatatttt attatatatt atatataata caatatataa tatattgtat tataatacaa     300
tgtattataa tgtattatat tgtattatat attatatata atacaatata taataatata     360
ttataatata taataataat ataatatatt attgtattat atattatata     420
atacaatata taatatattg tattatatat attttattac ataatatata taatacatta     480
tataatatat tttgtattat ataatatata ttttattatg tattatagat aatatatttt     540
attatatatt atatataata caatatataa tatattttgt attgtatata atatataata     600
caatatataa tatattgtat tatatataat attaatatat tttgtattat atatttatat    660
tttatattat aattatgttt tgcattatat atttcatatt atatatacc              709

<210> SEQ ID NO 3
<211> LENGTH: 409
<212> TYPE: DNA
<213> ORGANISM: Homo sapiens
<220> FEATURE:
<221> NAME/KEY: misc_binding
<222> LOCATION: (1)..(409)
<223> OTHER INFORMATION: MAR of human chromosome 1, nt from 1368659 to
      1369067
<220> FEATURE:
<221> NAME/KEY: misc_binding
<222> LOCATION: (1)..(409)
<223> OTHER INFORMATION: MAR of human chromosome 1, genomic contig;
      1368659 to 1369067

<400> SEQUENCE: 3
tacacataaa tacatatgca tatatattat gtatatatac ataaatacat atgcatatac      60
attatgtata tatacataaa tacatatgca tatacattat gtatatatac ataaatacat     120
atgcatatac attatgtata tatacataaa tacatatgca tatacattat gtatatatac     180
ataaatacat atgcatatac attatgtata tatacataaa tacatatgca tatacattat     240
gtatatatac ataaatacat atgcatatat tatatacata aattatatta tatacataat     300
acatatacat atattatgtg tatatataca taaatacata tacatatatt atgtgtatat     360
atacatgata catatacata tattatgtat atatatacat aaatacata              409

<210> SEQ ID NO 4
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig;
```

2839089 to 2839482

<400> SEQUENCE: 4

| tatgtatata tacacacata tgtatatata cacacatatg tatatacgta tatatgtata | 60 |
| tatacacaca tatgtatata cgtatatatg tatatataca cacatatgta tatacgtata | 120 |
| tatgtatata tacacacata tgtatatacg tatatatgta tatatacaca catatgtata | 180 |
| tatgtatata tacacacata tgtatatacg tatatatgta tatatacaca catgtgtata | 240 |
| tatatataca catatgtata tatgtatata tacacacata tgtatatatg tgtatgtata | 300 |
| tatacacaca tatgtatata tacacatata tatgtatata tacacacata cttatatata | 360 |
| cacatatata tgtatatata cacatatgta taca | 394 |

<210> SEQ ID NO 5
<211> LENGTH: 832
<212> TYPE: DNA
<213> ORGANISM: Homo sapiens
<220> FEATURE:
<221> NAME/KEY: misc_binding
<222> LOCATION: (1)..(832)
<223> OTHER INFORMATION: MAR of human chromosome 1, genomic contig;
      1452269 to 1453100

<400> SEQUENCE: 5

| tatattacta tatatacaat atacatatta ctatatatac catgtattac tatatatatc | 60 |
| tactatatat attactatat atacaaaata tatattacta tatatacaat atacatatta | 120 |
| ctatatatac catatattac tatatatatc tactatatat attactatat atacaaaata | 180 |
| tatattacta tatatactat atattactgt atatacaata tatattacta tatatatact | 240 |
| atatattact atatatacac tatatattac tatatataca caatatatat attactatat | 300 |
| atacacaatg tatataacta tatatacaat atatattact atatatacta tatatattac | 360 |
| tatacatact atatattact ctatatatac aatatatata ttacaatata tactacatat | 420 |
| tactacatat actttatata ttactatata tactatatat tactgtatat acaatatata | 480 |
| ttactaaaata tacacaatat atattactat atatacacaa tatatatatt actatatata | 540 |
| cacattatat atgactatat atacacacta tatatattac tatatataca caatatataa | 600 |
| ctatatatac acagtataca tattactata tacacaat atatatatta ctatatatac | 660 |
| actatatatt actatatata cacaaatatat attactctat gtatacacta tatatattac | 720 |
| tatatataca gaatatatat aactatatat acactatatt actatatata ctatatatta | 780 |
| ctatatgtac tatatatatt actatatata ctatatatta ctatatatac ac | 832 |

<210> SEQ ID NO 6
<211> LENGTH: 350
<212> TYPE: DNA
<213> ORGANISM: Homo sapiens
<220> FEATURE:
<221> NAME/KEY: misc_binding
<222> LOCATION: (1)..(350)
<223> OTHER INFORMATION: MAR of human chromosome 1, genomic contig;
      831495 to 831844

<400> SEQUENCE: 6

| aatatataat atataaaatat taatatgtat tatataaatat atattaatat attatattat | 60 |
| attactatat aaataatatt aatatattat attaaaatat taataaatat atcatattaa | 120 |
| atattatatt aattaaaatat taataaatat attatattaa tatatttata tattaaaacct | 180 |
| ataacatatg catatactta tttatatata acatgcatgt acttatttat atatacaata | 240 |

```
tatatttata tattatataa tatattatat gtatttatat attatatatc atatattata      300
tgtatttata tattatatat catataatat atatatttat attatatata                 350
```

<210> SEQ ID NO 7
<211> LENGTH: 386
<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of human chromosome 1, genomic contig;
      1447225 to 1447610

<400> SEQUENCE: 7

```
acatttaatt taattatata ctgctatata taattaaatc tatatatcta tataacttat       60
aatttatttt aatttaatta tatatactat atagttatat atacatatat gtaattatat      120
atagtataat tatagtatat atgtatatat aatgtaagta aatatatagt atatatttat      180
atatactata tatttataca tatgtcttta tatatactaa tatatataca catatgtaat      240
atgtacatat ggcatatatt ttatagtgta tatatacata tatgtaatat atagtaat        300 atgtaaaatat atagtacata tttaattata tggtaatata tacacatata tgtaaatatgt   360 gtattatagt acatatttta tagtat                                          386
```

<210> SEQ ID NO 8
<211> LENGTH: 585
<212> TYPE: DNA
<213> ORGANISM: Homo sapiens
<220> FEATURE:
<221> NAME/KEY: misc_binding
<222> LOCATION: (1)..(585)
<223> OTHER INFORMATION: MAR of human chromosome 1, genomic contig;
      4955365 to 4955949

<400> SEQUENCE: 8

```
atacacacat atacacatat gtacgtatat atactatata tacacacata tacacatatg       60
tacgtatata tactatatat acacacatat acacatatgt acgtatatat actatatata     120
cacacatata cacatatgta cgtatatata ctatatatac acacatatac acatgtgtac     180
gtatatatac tatatataca cacatataca catatgtacg tatatattat atacacac       240 atacacatat atgtacgtat atactatata tacacaca tatacacata tgtacgtata       300
tatactatat atacacacat atacacatat gtacgtatat atactatata tacacacata    360
tacacatatg tacgtatata tactatatat acacacatat acacatatgt acgtatatat     420
actatatata cacacatata cacatatgta cgtatatata ctatatatac acacatatac     480
acatgtgtac gtatatatac tatatataca cacatataca catgtgtacg tatatatact     540
atatataccc atacacatac gtatatacgt acatatatat acgta                     585
```

<210> SEQ ID NO 9
<211> LENGTH: 772
<212> TYPE: DNA
<213> ORGANISM: Homo sapiens
<220> FEATURE:
<221> NAME/KEY: misc_binding
<222> LOCATION: (1)..(772)
<223> OTHER INFORMATION: MAR of human chromosome 1, genomic contig;
      5971862 to 5972633

<400> SEQUENCE: 9

```
agtaaacata tatatagtaa atatatatag tgtatatata gtaaatatat atagtgcata       60
```

```
tatatagtgc atatatatag tgtatatata gtaaatatat agtgtatata tatagtaaat    120
atatatagtg tatatatagt aaatatatat agtaaatata tatatactat atatagtaaa    180
tatatatata ctatatatag taaatatata tatagtatat atatagtaaa tatatatata    240
gtatatatat agtaaatata tatatagtat atatatagta aatatatata tagtatatat    300
agtaaatata tatagtatat atatagtaaa tatatatata gtatatatat agtaaatata    360
tatatagtat atatatagta aatatatata tagtatatat atagtaaata tatatagtat    420
atatatagta aatatatata gtatatatat agtaaatata tatagtatat atatagtaaa    480
tatatataca ctgtatatat atagtaaata tatatacact gtatatatat agtaaatata    540
tatacactgt atatatatag taaatatata tacactgtat atatatagta aatatatata    600
cactgtatat acatagtaaa tatatataca ctgtatatac atagtaaata tatatacact    660
gtatatacat agtaaatata tatacactgt atatacatag taaatatata tacagtgtat    720
atacatagta aatatatata cagtgtatat acatagtaaa tatatataca gt           772

<210> SEQ ID NO 10
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of human chromosome 1, genomic contig;
      6221897 to 6222200

<400> SEQUENCE: 10
atatataata tataattta tattatatat aatatataat atatataatt atattatata     60
ttatatataa tatattatat attatatata taatatatat tatatattaa atatatatta   120
tatatataat atatattata tattaaatat attattatata taatatatat attatatata   180
atatatataa tatatattat atatatatta tatattatat atatatatta tatatatata   240
atatatataa tatatattat atataatata tattatatat atataatata tataatatat   300
atta                                                                 304

<210> SEQ ID NO 11
<211> LENGTH: 311
<212> TYPE: DNA
<213> ORGANISM: Homo sapiens
<220> FEATURE:
<221> NAME/KEY: misc_binding
<222> LOCATION: (1)..(311)
<223> OTHER INFORMATION: MAR of human chromosome 1, genomic contig;
      9418531 to 9418841

<400> SEQUENCE: 11
tatatataat atttatatat aatattcatg tatttatata taaatattta tatatttata     60
tataaatatt tatatattta tatataaata tttatatatt tatatataat atttatacat   120
tatatataat atttatatat tatatataat atttatatat aatatttata tattatatat   180
aatatttata tatttatatg taaatatata attttatata tgtatgtata atatatattt   240
tatatatgta tgtataatat atttatatata tgtatgtata atatattatt atatataata   300
tataatttat a                                                         311

<210> SEQ ID NO 12
<211> LENGTH: 302
<212> TYPE: DNA
```

```
<213> ORGANISM: Homo sapiens
<220> FEATURE:
<221> NAME/KEY: misc_binding
<222> LOCATION: (1)..(302)
<223> OTHER INFORMATION: MAR of human chromosome 1, genomic contig;
      15088789 to 15089090

<400> SEQUENCE: 12
atataatata tatattatat atataaatat atataaatat ataacatata tattatatat      60
aaatatatat aaatatataa catatatatt atatatataa atatatataa atatataaca     120
tatatattat atatataaat atatataaat ataacata tattattat ataaaatat         180 atatttata tttatatata taatatatat aaatatataa tatatattta tatatataat     240
atatataaat ataatatata tatatttata taatatatat ataaatatat aatatataat     300
at                                                                   302

<210> SEQ ID NO 13
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of human chromosome 1, genomic contig;
      6791827 to 6792287

<400> SEQUENCE: 13
tatataatat atattatata tacacatata taatatatat tatatataca catatataat      60
atatattata tatacacata tataatatat attatatata cacatatata atatatatta    120
tatatacaca tatataatat atattatata tacacatata taatatatat tatatataca    180
catatataat atatattata tacacatata taatatatat attatatata cacatatata    240
atatatatta tatatacaca tatgtaatat atattataca cacacatata atatatatta    300
tatacacata tataatatat attatatata catatataat atatattata tacacatata    360
tataatatat attatatata cacatatata atatatatta tatatacaca tataatatat    420
aatatataca catatataat atatatatta tatatgcaca t                        461

<210> SEQ ID NO 14
<211> LENGTH: 572
<212> TYPE: DNA
<213> ORGANISM: Homo sapiens
<220> FEATURE:
<221> NAME/KEY: misc_binding
<222> LOCATION: (1)..(572)
<223> OTHER INFORMATION: MAR of human chromosome 1, genomic contig;
      163530 to 164101

<400> SEQUENCE: 14
atattataat tatatatatt atatataatt atataaaata tatattataa ttatatatat      60
tttatataat atatatatta taattaatat attatatata atatatatat tatatataat    120
atatatatta tatatattat atataatata tataatatat ataatatata ataatatata    180
tatattatat ataatatata atatatataa tatattataa tataatatat ataatatata    240
ataatatata tataatatat aatataatat aatatatata atatatataa tatataatat    300
aatatataat atatataata taatatataa tatatataat aaatatata ttataatata    360 atatatataa tatataatat aatatatata atataatata taatatataa tatataatat    420
atatttaata tatttattaa ttatttgtta tatatttatt aatatataat atataatata    480
```

```
tttaatatat tataactata tattatatta taattatata tattatatat atacaattat      540
aattatatat tatatatact tataatatat at                                    572

<210> SEQ ID NO 15
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of human chromosome 1, genomic contig;
      1842332 to 1842688

<400> SEQUENCE: 15
tatatctata tatctctata tatatataat atagataata tctatatata taatatagat       60
aatattatct atataataa tagataatat tatctatata taatatagat aatattatct      120
atatataaaa ttatattata tctatatata ttatatatat aaaattatat tatatctata     180
tataatatag ataatatcta tatataaata gataatatct atatatataa tatagatatt     240
atctatatta tagatataga taatattatc tatattatag atattatcta tatataaatat    300 agataatatt atctatatta tatatataat atatctatat tatctataat attatct        357

<210> SEQ ID NO 16
<211> LENGTH: 399
<212> TYPE: DNA
<213> ORGANISM: Homo sapiens
<220> FEATURE:
<221> NAME/KEY: misc_binding
<222> LOCATION: (1)..(399)
<223> OTHER INFORMATION: MAR of human chromosome 1, genomic contig;
      2309560 to 2309958

<400> SEQUENCE: 16
attatatata atatatatta tatattatat atatcaagca gcagatataa tatataatat       60
atataatata tataatatat attgtatatt atataatata taatatatat aatatatatt      120
gtatattata taatatataa tatataataat atatattgta tattataataa tatataatat   180 ataataatata tattgtatat tatataatat ataatatatg taatatatta tgtaatatat    240
tatataatat atattatata ttatatataa tatatattat ataataata tattacataa     300 tatattacat atattacgta atatatgtta tatattacat ataatatata acatatatta    360
cgtaatatat gtaatatatt acatataata tatacatta                            399

<210> SEQ ID NO 17
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of human chromosome 1, genomic contig;
      2231759 to 2232152

<400> SEQUENCE: 17
atatatactt ataaattata tacttatata tacttataaa ttatatactt atatatactt       60
ataaattata tacttatata tacttataaa ttatatactt atatatactt ataaattata     120
tacttatata tacttataaa ttatatactt atatatactt ataaattata tacttatata    180
tacttataaa ttatatactt atatataatt ataaattata tacttatata taattataaa    240
ttatatactt atatataatt ataaattata tacttatata taattataaa ttatatactt    300
```

```
atatataatt ataaattata tacatatata taattataaa ttatatacat ataaatttat    360
aaattatata catatataat tataaattat atac                                 394

<210> SEQ ID NO 18
<211> LENGTH: 387
<212> TYPE: DNA
<213> ORGANISM: Homo sapiens
<220> FEATURE:
<221> NAME/KEY: misc_binding
<222> LOCATION: (1)..(387)
<223> OTHER INFORMATION: MAR of human chromosome 1, genomic contig;
      7406524 to 7406910

<400> SEQUENCE: 18
tatattatat ataatatata ttatatataa taaaataat atattata tataatatat         60 aaataatata taatatataa ataatatata atatataata tataaataat ataatatata    120
taacatataa atatatata taatatataa ataatatata taatatataa ataatatata     180
taatatataa aaatatataa tatataatac atatataaat aatatattat attatatatg    240
atacataata tattatatat aatatattat atgatacata atatattata tagaatatat    300
tatatgatac ataatatatt atagaata tattatatga tacataatat attatatgat      360
acataatata ttatatataa tatatta                                        387

<210> SEQ ID NO 19
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of human chromosome 1, genomic contig;
      9399572 to 9399941

<400> SEQUENCE: 19
catatataca tatatacaca tatatacaca tatatataca catacatatg tacacatata     60
tatacacata tgtatacaca tatatacaca tatatacaca catatataca catatataca    120
cacatatata cacatatata cacatatata cacatataca catatataca catatataca    180
tatatacaca tatatataat atacacacat atatatacac atatatacac acatatatac    240
acatatatac acatatatat acacatatat acacatatat acatatatac acatatatat    300
acatatatac acatatatac atatatacac atatatacat atatacacac atatatacac    360
atacatatac                                                            370

<210> SEQ ID NO 20
<211> LENGTH: 377
<212> TYPE: DNA
<213> ORGANISM: Homo sapiens
<220> FEATURE:
<221> NAME/KEY: misc_binding
<222> LOCATION: (1)..(377)
<223> OTHER INFORMATION: MAR of human chromosome 1, genomic contig;
      12417411 to 12417787

<400> SEQUENCE: 20
attatatata atacatataa ttatatattt atatataaat tataataaat acatataatt     60
atatatttat atataaatta tataataaa atacatataa ttacatatat ttataaatta     120 taataaaatac atataattac atatatttat atatgaatta tatataataa atacatataa    180
ttatatatat ttatatgtag attatatata aatatatata atttatatat ataataatat    240
```

| | |
|---|---|
| atataattta tatatataat tatatatata ataaatatat ataatttata tatataatta | 300 |
| tatatataat aaatatataa taatatatat aatttatata taaattata tatataataa | 360 |
| atatatataa tttatat | 377 |

<210> SEQ ID NO 21
<211> LENGTH: 1524
<212> TYPE: DNA
<213> ORGANISM: Homo sapiens
<220> FEATURE:
<221> NAME/KEY: misc_binding
<222> LOCATION: (1)..(1524)
<223> OTHER INFORMATION: MAR of human chromosome 1, genomic contig; 1643307 to 1644830

<400> SEQUENCE: 21

| | |
|---|---|
| tataaatata tataaatata taaatatata taaatatata aatatatata aatatatata | 60 |
| aatatataaa aatatataaa tatatataaa tatatataaa tatataaaaa cataaaaata | 120 |
| tatataaata tatataaata tataaaaata taaaatata taaatatata aaatataca | 180 |
| aatatataaa tatatacata aatatatata aatatatata aatataaaa aatatatata | 240 |
| aatatataaa tatatataaa tatatataaa tatatataaa tatataaaaa tatatataaa | 300 |
| tatataaata taaaaata tatataaata taaaatata taaatatata taaatatata | 360 |
| aatatataaa taaatataag tatttatgaa tatatatgaa tataaaata tataaaaaat | 420 |
| atatataaat atataaatat atataaatat ataaatatat acatatatac atatataaat | 480 |
| aaataaaatat aagtatttat gaatatatat gaatatataa atatataaaa aatatatata | 540 |
| aatatataaa tatatataaa taaatatata taaaatata taaaatata tataaatata | 600 |
| taaatatata taaatatata aatatatata aatatatata aatatataaa tatatataaa | 660 |
| tatatataaa tatataaata tataaaatata taaatatata taaatatata taaatatata | 720 |
| aatataaata tataaatata taaatatata taaatatata taaatatata taaatatata | 780 |
| taaatatata taaatatata taaatatata aatatatata aatatatata taaatatata | 840 |
| taaatatata aatatataaa tatataaaaa tatataacaa tatataaata tatataaaaa | 900 |
| tatataacaa tatataaata taaatatata taaaatata taacaatata taaatataaa | 960 |
| tatatataaa tatataaata taaatataaa aaatatatat aaatatataa atatatataa | 1020 |
| atatataaat gtataaatat atataaaaat ataacaat atataaatat ataaatatat | 1080 |
| aacaatatat aaatatataa aaatatataa caatatataa atataaatat atataaaaat | 1140 |
| atataacaat atataaaatat aaatatatat ataaatatat aaatataaat ataaaaata | 1200 |
| tatataaata tataaatata tatataaata tatataaata tataaatgta taaatatata | 1260 |
| taaatatata aatatataaa aatatataaa tatatataaa tatatataaa tatataaata | 1320 |
| taaatatata aatatatata aatatataaa taaatatata taaacatata taaatatata | 1380 |
| taaataaaca tatataaaga tatataaaga tataaagata tataaatata taaatatata | 1440 |
| aagatatata aatatataaa gatatataaa tatataaaga tatataaata tataaagata | 1500 |
| tataaatata atatataaat atat | 1524 |

<210> SEQ ID NO 22
<211> LENGTH: 664
<212> TYPE: DNA
<213> ORGANISM: Homo sapiens
<220> FEATURE:
<221> NAME/KEY: misc_binding
<222> LOCATION: (1)..(664)

<223> OTHER INFORMATION: MAR of human chromosome 1, genomic contig;
      1398763 to 1399426

<400> SEQUENCE: 22

```
acacatatat atataaaata tatatatata cacacatata tataaaatat atatatatac      60
acacatatat ataaaatata tatatacaca catatatata aaatatatat atacacacat     120
atatataaaa tatatatata cacacatata tataaaatat atatatacac acatatatat     180
aaaatatata tatacacaca tatatataaa atatatatat acacacatat atataaaata     240
tatatataca cacatatata taaaatatat atatacacac atatatataa aatatatata     300
tacacacata tatataaaat atatatatac acacatatat aaaatatata tatacacaca     360
tatataaaat atatatatac acatatatat aaaatatata tatacacata tatataaaat     420
atatatacac acatatatat aaaatatata tatacacaca tatatataaa atatatatat     480
acacatatat ataaaatata tatacacaca tatatataaa atatatatat atacacatat     540
atataaaata tatatacaca catatatata aagtatatat atacacacat atatataaaa     600
tatatatata cacatatata taaaatatat atacacat atatataaaa tatatatata     660
caca                                                                  664
```

<210> SEQ ID NO 23
<211> LENGTH: 1428
<212> TYPE: DNA
<213> ORGANISM: Homo sapiens
<220> FEATURE:
<221> NAME/KEY: misc_binding
<222> LOCATION: (1)..(1428)
<223> OTHER INFORMATION: MAR of human chromosome 2, genomic contig;
      17840365 to 17841792

<400> SEQUENCE: 23

```
aatttattat atattatata ttatatatat tatatatatt atatattata tatattatat      60
atattatata ttatatatat tatatattat atatttatat ataatatata tctaatatat     120
atattagata taatatatat ctaatatata tatattttat atataaata tatctctaat     180 atatatattt tatatgtata taatatatct ctaatatata tatatttat atgtatataa     240 tatatctcta atatatatat ttttatata taatatatct ctaatatata tattttatat     300
atataatata tatctaatat atataatata tatattagat atataaaa tatatatgat     360 atatttatta tatatataat atataatata taatatatat attatattat atacatatat     420
attatataca atatatatta tatatatttt atatacatta tatattatat atattttata     480
tacaatatat attatatatt ttatatacaa tatatattat atatattta tattttata     540 tacaatatat attatatata ttttatatat aatatatatt atatatattt tatataatat     600
atattatata tattttatat ataatatata ttatataaat tatatataat atatattata     660
ataaattata atattttta tatatataat atgtattta tataataat attataatat     720 atatttata tataatatat tataatatat atttatata taatatatta taatatatat     780
tttatattat aatatattat aatatatatt ttatatataa tatattataa tatatattt     840 atatataata tattataata tatttat atataatata ttataatata tatattataa     900
tatatatttt atatataata tattatcata tatatattaa atatatatt tatatataat     960 atatttaat atatatatta taatatatat tttatatata atatattata atatatatat    1020
tataatatat attttatata taatatatta taatatatat tttatatata atatattata    1080
atatatattt tatatataat atattataat atatatttta tatataatat aatatatatt    1140
```

```
ttatatataa tatattataa tatatatttt atatataata tattataata tatatttat    1200 atataatata ttataatata tattttatat ataatatatt ataatatata ttttatatat    1260
aatatattat aatatatatt ttatatataa tatattataa tatatattttt atatataata   1320 tattataata tatattttat atataatata ttaattaaat ttattaattt attaattatt    1380
aatatttatt atattattaa ttaataatat ataaattatt aatatata                 1428
```

<210> SEQ ID NO 24
<211> LENGTH: 4624
<212> TYPE: DNA
<213> ORGANISM: Homo sapiens
<220> FEATURE:
<221> NAME/KEY: misc_binding
<222> LOCATION: (1)..(4624)
<223> OTHER INFORMATION: MAR 1_6 of chromosome 1

<400> SEQUENCE: 24

```
ggatcttaaa tctattttat ttatttattt ttcatgtggc caataccctc caccccttc     60 ttctgtctct ttcaacttat tgtggttacc ttgaggctac ctgagacagt aggcttgggt   120
ggggaagtat gcattctaag tgtaaagttt gatgagcttt gacaaatgtc aacccatgta   180
ccagaacatt ttcatcaccc ataaaatctc ccttgtgtca cttgccagtc agtgtctatt   240
ctagtatcca actcctggct ccaagaaacc attgaactgt tttctgtcac tataaattag   300
atttgtcttt tctagagttt catgtaaatg gaatcataca ctaagtactc tttgtgcctg   360
gcttctgctc agcataatgt ttttgagaat cattcatgct gctgcatgtt ttcagtagtt   420 catttttta aataggtgaa ttgtaactca ttctgtgaat ataccatatt ctgtcttcca    480
tttatctgtt agtggatctt taggtcgttt ctagttttgg gctattgcaa ataaagctgc   540
tgtaaatatt aatgcacaag ttttccatgt tcatatgttt catttcactt aggaaaatac   600
ctaagagagg aattgcacat attaaaaaaa ttttaaaaac tactaagctg ttctccaaaa   660
tggttgtaca atttttattc ccaagagcaa tatgagtgtt taattgctcc acattctcac   720
caacacttgg tgcttgttag tttttatttc attgttttca ttgttatgtc tgtgaggcag   780
cattgatgtg catgtctctg agtgtcatct tagcggtgat gctgagcatc agttcacgtc   840
cttataggcc gtttgtatat ctgctttgtg aaatgtctgt tcaaatcttt tgcctatttt   900
aaattgagtt gtgttcgtct tcttaggatt aagtaatgag ttaaaatat ttctgataca    960 aatctttcat tatatatttc taatgctttc tcatctatag tttatttcct catattcttt   1020
aactgtatct tttgaagagc aaattttact tttgattatg cccaatttat caagtttta    1080 tatggctctt ttgattatgc ccataatcac attagacttt gcctaaccca gtttgcaga    1140 gattttttct tttatgcttt tatctagaaa ttttgtagtt ttaggtttta aaaaagttta   1200
atttatttat ttgagacagg gtattgctct ttacatatac tggagtgcag tgatgcaatc   1260
atggctcact gcagcctcaa cctcttgggc tcaagcggtt ctcccatctc agagtcctga   1320
gtagctggcc aggtgcatgc cagcttcaat gtgttttttca tttgcatttc cctgataatt   1380
attgacgttg agcatttttt tcatatatca gttagctatt tgtacgtctt cttttgagaa   1440
acatctattc gggtcttttg cccatttttaa agtcagatgg tttgtttgtc agctattgag   1500
ttgtttgagt tccttgtata ttctggatat taccatcttg tcagatgcac agtttgcaaa   1560
tttttttttt ctatttttgta ggttgtctct ttctctgttg tttcctccgg tatgcagaag   1620 tttttttagtg tgatgtaatt tcatttgtct gtttttgctt ttgttgcctg tactttctta   1680
```

```
ttcttatcca aaaaatctttt atctagatca atgtcacgaa gagtttctcc tctgttttct    1740
tcgagtagtt ttttataatt tgggtatac  atttaagtct ttaatctatt tggaattgat    1800
ttttgcatat ggtgagagat cagagtctaa tttcatactt ttggatgtgg aaagctagtt    1860
ttttcagcac catttattga agagactgtc tcttctccaa tgtgtgttct ttgtgccttc    1920
gtcaaaaatc agttggctgt gcgtggattt atttctgtgt tctctatttt gttccattgg    1980
tctagtttta gccttaaatt taggtctgca atttttttt  ttttgtatat ggtgtgaagt    2040
aagagtcaaa gttcattatt tttcatatgg atatgtaatt actccagtac catcatttag    2100
tttgaatgga ctgtcctttc tccatggaat tacatgggca tcttttgtct gaaaccaatt    2160
atgtatgttt acgtatgtgt atgtttatgc atatgttata ggtttaatat atattaatat    2220
atataatata taatatataa atattaatat gtattatata atatatatta atatattata    2280
ttatattact atataaataa tattaatata ttatattaaa atattaataa atatatcata    2340
ttaaatatta tattaattaa atattaataa atatattata ttaatatatt tatatattaa    2400
acctataaca tatgcatata cttatttata tataacatgc atgtacttat ttatatatac    2460
aatatatatt tatatattat ataatatatt atatgtattt atatattata tatcatatat    2520
tatatgtatt tatatattat atatcatata atatatatat ttatattata tatattatat    2580
gatatataat attatataat gtattaatat atattaaacc tatatttata attctggact    2640
cactattttg tttcattggt gtctgtgtgt atctaaccct atgccaataa tgtactatct    2700
taattaccat agctttatag taagctttga aatcagatag tgtatttttt atcattgttt    2760
tttaaaataa tagtttatct ttttatttga atttgtaatc agctagtcag tttctgcaaa    2820
aagcttactg ggattttgct tggaattatg ttacatctgt agcatgtact atccaatatt    2880
ctagccttta tccacatgtg gctattaagg tttaaattaa ttaaattaaa atttaattaa    2940
ttaaaattaa aacttaataa ttggttcctc attcacacta ccatatgtca agtgttcaat    3000
agccacatat ggtcaatgtc ttggaaaagt caatacagta catttccatt attgcagtaa    3060
gttctgtcaa acagcactat cgtagaccga ttaggagaga actgacttaa cagtattgga    3120
tgctccagtc aatgaacatc tttttttttt tcatttattt cagtagtctc tgcagtatat    3180
tatagatttc agtttacata ttttgcatat attttattaa atgtataacg gtagaagtac    3240
tattattgga tgatgtgttc tatagatgta ttttaggtca agtttgttga tagtgttgtt    3300
taaatctcgt atacctcttg attttttttat ttacttgttc tttgaattac tgagacagga    3360
atgttatatc cttaactata tttgtgaatt tattcacttc ttccttcagt tctgttaact    3420
tttgcttagg tgcttttttaa aaatgaaact ttcaatctct gccttttaat tgtagcattt    3480
agaccattta cattcaatgt aattatcaat atcagtttat ttaagtctga agttgtgcaa    3540 ttttttcctct acctatatta taaatctttc tatatacaaa acacatgcta tgttttctgc    3600
atatgtttta aatgacaccc ggaaagcatt gacactattt ttgctttagg ttatctttca    3660
aagatgttaa aaatgagaaa gaaatattct gcatttatcc atacacttat tatttgcaaa    3720 ggtttttttta ataccttttg tgtagatttc agttaccaac ttgtatttcc ttcagcttga    3780
agaacttaca atttcttgta ggacaggtct ctgacaacaa attatctcag cttttctttg    3840
tctaaaaaag ttattgcctt tattttttaaa atatattttc actggatatt gaattttagg    3900
tgataatctt tttttttttg ttagcacttt aaatatgtct tctaatgtcc tcttgctttc    3960
atagtttctg atgagaagtc tactgttatt agtatctctt tgtgtgtgtc tctcttttt    4020 ccctctctgc tattatggct attttttttt tttttttttt ttttggtcac tggtgtcagc    4080
```

```
aatttaatta tggtgtgcct tggtatgttt tgtgtgtgtg tgtgtgtgtg tgtgtgtgtg    4140
tgtgtgtgtg tagctgatgt tctttgagct ttagaatctg tgagtttgta gttttcatca    4200 attattttt cttttcattc cttttattta ctcatgttcg tgttttattt tatattttta    4260
agaattttgt gcgtatttgt aataactgtt taaatgtcat ttgtgaattc cattgcttct    4320
aggtaggatt ctattgacag atatttttc cctgacgaga ggtcatactt tccttattct    4380
tcatgtatct agtggttttt ggttgaatac tggatatttt gaattttatg ggagtgctga    4440
attctacaat attccttaaa aatgtgttgg attttgtttt agcagatagc tatcttactt    4500
gaagatcaat ttcatattt ttgatgttca tttttcatt tattaaagaa taggtccatg    4560
gtagagttta ctgatatcaa cctttctggt gtctctaata aatgcaacat attcaataag    4620
atcc                                                                4624

<210> SEQ ID NO 25
<211> LENGTH: 3616
<212> TYPE: DNA
<213> ORGANISM: Homo sapiens
<220> FEATURE:
<221> NAME/KEY: misc_binding
<222> LOCATION: (1)..(3616)
<223> OTHER INFORMATION: MAR 1_68 of chromosome 1

<400> SEQUENCE: 25
gactctagat tataccaacc tcataaaata agagcatata taaaagcaaa tgctcttatc      60
ttgcagatcc ctgaactgag gaggcaagat cagtttggca gttgaagcag ctggaatctg     120
caattcagag aatctaagaa aagacaaccc tgaagagaga gacccagaaa cctagcagga     180
gtttctccaa acattcaagg ctgagggata aatgttacat gcacagggtg agcctccaga     240
ggcttgtcca ttagcaactg ctacagtttc attatctcag ggatcacaga ttgtgctacc     300
tattgcctac catctgaaaa cagttgcttc ctatatttca tccagtttaa tatttattta     360
aaccaagaag gttaatctgg caccagctat tccgttgtga gtggatgtga agtaccaat      420 tccattctgt tttactatta actatccttt gccttaatat gtatcagtag gtggcttgtt     480
gctaggaaat attaaatgaa tggcatgttt cataggttgt gtttaaagtt gttttttgag     540
ttaaatcttt ctttaataat actttctgat gtcaaaaaca cttagaagtc atggtgttga     600
acatctatat agggttggat ctaaaatagc ttcttaacct ttcctaacca ctgttttgt      660 ttgtttgttt ttaactaagc atccagtttg ggaaattctg aattagggga atcataaaag     720
gtttcatttt agctgggcca cataaggaaa gtaagatatc aaattgtaaa aatcgttaag     780
aacttctatc ccatctgaag tgtgggttag gtgcctcttc tctgtgctcc cttaacatcc     840 tatttatct gtatatatat atattcttcc aaatatccat gcatgggaaa aaaaatctga     900
tcataaaaat attttaggct gggagtggtg gctcacgcct gtaatcccag cactttggga     960
ggctgaggtg gcggatcat gaggtcaaga gatcagacc atcctgacca atatggtgaa    1020
accccatctc tactaaagat acaaaactat tagctggacg tggtggcacg tgcctgtagt    1080
cccagctact cgggaggctg aggcaggaga acggcttgaa cccaggaggt ggaggttgca    1140
gtgagctgag atcgcgccac tgcactccag cctgggcgac agagcgagac tctgtctcaa    1200
aaaaaaaata tatatatata tatatataca catatatata taaaatatat atatatacac    1260
acatatatat ataaaatata tatatataca cacatatata taaaatatat atatatacac    1320
acatatatat aaaatatata tatacacaca tatatataaa atatatatat acacacatat    1380
```

```
ataaaaata tatatataca cacatatata taaaatatat atatacacac atatatataa      1440
aatatatata tacacacata tatataaaat atatatatac acacatatat ataaaatata      1500
tatatacaca catatatata aaatatatat atacacacat atatataaaa tatatatata      1560
cacacatata tataaaatat atatatacac acatatataa aatatatata tacacacata      1620
tataaaatat atatatacac atatatataa aatatatata tacacatata tataaaatat      1680
atatacacac atatatataa aatatatata tacacacata tatataaaat atatatatac      1740
acatatatat aaaatatata tatacacata tatataaaat atatatatat acacatatat      1800
ataaaatata tatacacaca tatatataaa gtatatatat acacacatat atataaaata      1860
tatatataca catatatata aaatatatat atacacatat atataaaata tatatataca      1920
catatatata aaaatatata tatatattttt ttaaaatatt ccaattgtct cactttgtgg     1980
atgagaaaaa gaagtagtta gaggtcaagt aacttggcct acatcttttc tcaagattgt      2040
aaactcctag tgagcaataa ccacatcttc attttctttg tataaaacaa gaaagtttag      2100
catgaaaaag gtactcaatt acaaatgtgt tggattgaat tgaagaccct tggaagggga      2160
ttttgtacct gaggatctct ttcttttggc catattgttc aatggacaaa atttagcctt      2220
cgaaggcagg ccgatttgag gttaatacta cctttaccac ttgatagcta tgtgaccttg      2280
gccatgtggt ttcaacagtc tgaacctcat tttctctgtg tatgtgtggt cctccttaca      2340
agtttgtgaa aaatgtgaag tccttagcca tgatagccca ataacagg ctaaatgata       2400
ataggtttat gttcttttcc tttatattct cagataagca ctgtccaagt ttgaggtgtt      2460
ttgaggtctc gcctgatttg gattgtttga gtttatgcta ttctttgaat tctttgagct      2520
gttctgaagc agtgtatcat gaacaaaaac atccccagtt cagtccaaac ccctggttac      2580
atatcattct tatgccatgt tataaccagt ttgagagtgt tccctctgtt attgcattta      2640
agtttcagcc tcacacagaa attcagcagc caatttctaa gccctaagca taaaatctgg      2700
ggtgggggg gggatggcc tgaagagcag cattatgaat agcaccatta taattaatga       2760
tctctcagga agatttacaa tcacaggtag cagataaaac aaatagtact gcttctgcac      2820
ttcccctcct tttattcgct atgaaatttt atgggaaatc agtccagtga aaatgtaag      2880
ctcttaatct ttcccagaaa tcctacctca tttgatgaat actttgaggg aatgaattag      2940
agcatttttt tcttttatag tctacttcgc atttacgaag tgaggacggt agcttaggct      3000
gcctggccaa ctgatgagaa ggtcagaggc atttttagag acctctgttg tctttcattc      3060
atgttcattt tccacaaggc aagtaatttc caacaaatca gtgtcttcat tagtaataag      3120
attattaaca acaataatag tcatagtaac tattcagtga gagtccatta tatatcaggc      3180
attctacaag gtactttata tacatctgag taaacctcac acaattctac agggaggtat      3240
ttctatcccc atttaacaaa taaggaaacg aagtccaagt aaattaactt gcccaaggtc      3300
acacagatag tacctggcag aacaggaatt taaacctaaa tttgtccaac tccaaaagca      3360
gccttctatt tgttataaat gctgcctctc attatcacat attttattat taacaacaac      3420
aaacatacca attagcttaa gatacaatac aaccagataa tcatgatgac aacagtaatt      3480
gttatactat tataataaaa tagatgtttt gtatgttact ataatcttga atttgaatag      3540
aaatttgcat ttctgaaagc atgttcctgt catctaatat gattctgtat ctattaaaat      3600
agtactacat ctagag                                                     3616
```

<210> SEQ ID NO 26
<211> LENGTH: 4660

```
<212> TYPE: DNA
<213> ORGANISM: Homo sapiens
<220> FEATURE:
<221> NAME/KEY: misc_binding
<222> LOCATION: (1)..(4660)
<223> OTHER INFORMATION: MAR 1_42 of chromosome 1

<400> SEQUENCE: 26
gatcccttga ggtcagtagt ttaagaccag cctgaccaac atggtgaaac ccatctctac      60
taaaaataca aaaattagcc aggcgtggtg gcggggcct gtaacccag ctactcagga       120
ggctgaggca caagaatctc ttgaacccgg gaggcggagg ttgcagtgag ctgagattgt     180
gtcactgcac tccagcctgg gcaacagtgc cagactctgc cttaaaaaaa aaaaaaaaa     240
aaaaaaggcc gggcgcggtg gctgacgcct gtaatcccag cactttggga ggccgaggcg     300
ggtggatcat gaggtcagga gatcgagacc acagtgaaac cccgtctcaa ctaaaaatac     360
aaaaaattag ccgggcgcgg tggtgggcgc ttgtagtccc agctactcag gaggctgagg     420
caggagaatg gcgtgaacct gggaggcgga gcttgcagtg agccgagatg gcaccactgc     480
actccagcct gggcgaaaga gtgagactcc gtctcaaaaa aaaaaaaaaa ttagctgggt     540
atggtggtgc gtgcctgtaa tcccagctac tcgggaggct gaggcaggag aatcccttga     600
acctgggagg cggaggttgc agtgatctgc catcctgtca ctgcatcact acactccagc     660
ctgggtgaca gagcgagact ctgtctcaaa aaaaaaaaaa aaaaaaaag ctgggtgtgg     720
tggtatgcac cagctgtagt cccagctact tgggaggctg agttgggggg attgcctgag     780
ccagggaggt cgaggcttca gggagccatg attatgccac tgcactccag cctgggccac     840
agagtgaaac cttctgtcaa aaacaaaaaa acaaaaaaac acagtgtgtt agatcttgct     900
agacttggtg atataattaa gaggccatta tgggcagaac tgtgcccct tccaaaattc     960
atatataaat atatataaat atatataaat ataaatat ataaatatat ataaatatat    1020
ataaatatat aaatatat aaatatataa atatatataa atatatataa atatataaaa    1080
atatataaat atatataaat atatataaat ataaaaac ataaaaatat ataaatat       1140
atataaatat ataaaaatat ataaatatat aaatatataa aaatatacaa atatataaat    1200
atatacataa atatatataa atatatataa atatataaaa atatatataa atatataaat    1260
atatataaat atatataaat atatataaat ataaaaaat atatataaat ataaaatat     1320
ataaaaatat atataaatat ataaatatat aaatatatat aaatatataa atatataaat    1380
aaatataagt atttatgaat atatgaat atataaatat ataaaaaata tatataaata    1440
tataaatata tataaatata taaatatata catatataca tatataaaata aataaatata    1500
agtatttatg aatatatatg aatatataaa tatataaaaa atatatataa atatataaat    1560
atatataaat ataaatatat aaaaatat at aaaaaatat at ataaatatat aaatatatat   1620
aaatatataa atatatataa atatatataa atatatataat atatataaat atatataaat    1680
atataaatat ataaatatat ataaatatat aaatatataa atatataaat               1740
ataaatatat ataaatatat ataaatatat aaatatatat aaatatatat aaatatatat    1800
aaatatatat aaatatataa atatatataa atatatataat aaatatatat aaatatataa    1860
atatataaat atataaaaat ataacaat atataaatat atataaaaat ataacaat        1920
atataaaatat aaatatatat aaaaatatat aacaatatat aaatatataat at           1980
atataaaatat aaatataaaa aatatatata aatatataa tatatataaa tatataaatg    2040
tataaatata tataaaaata tataacaata tataaatata taaatatata acaatatata    2100
```

```
aatatataaa aatatataac aatatatataaa tataaatata tataaaaata tataacaata     2160
tataaaatata aatatatata taaatatata aatataaata taaaaaatat atataaaatat     2220
ataaatatat atataaatat atataaatat ataaatgtat aaatatatat aaatatataa      2280
atatataaaa atatataaat atataaaat atataaaat atataaatat aaatatataa        2340
atatatataa atatataaat ataaatatat aaacatatat aaatatatat aaataaacat      2400
atataaagat ataaaagat ataaagatat aaaatatat aaatatataa agatatataa        2460
atatataaag atatataaat atataaagat ataaatatat ataagatat ataaatataa       2520
tatataaata tataaagata taaatatata atataaaaat atataatat atattaaaaa       2580
tatatacata taaatatatg tatatttttt tgagatgggg tctcgctcag ccacccacgc      2640
tggagtgcag tggcacgagc tcggctcact gcaaccactg tctctcgggt ccaagcaatt      2700
ctgtctcagc ctcccaagta gctgggatta caggcacctg ccatcatgcc cggctaatttt    2760
ttgtattta gtagagatgg agtttcacca tgttggccag gttggtctcg aattcctgac       2820
ctcaggtgat ctgccggcct cggcctccca gtgctgggat tacaggcatg agtcaccacg      2880
cccggcccta tatattttt tgagacaagc tctgtgtctc ccaggctgga gtgcagcagc     2940
atgatcatga ctcactgtag cctagacctc cagggctcaa gtgattctcc cacctcagcc     3000
tcccaagtag ctgggattac aggcatgcac caccaccc agctaattttt tgttttgttt     3060
tgttttggag acagaatctc tctctgtcac ccaggctgga gtgcagtggt gtgatctcag     3120
ctcagtgcaa cctccacctc ctgggttcaa gtgattctca tgcctcagcc tcctgagtag    3180
ctgggactac aggcgtgagc caccacgccc tgataaattt tgtattttt ttttcagatg     3240
gagtctcact ctgtcatact caggctggag tgcagtggcg tgattttggt ttattgcaac    3300
ctctgcttcc tgggttcaag cgattctcct gcctcagcct ccagagtagc tgggattaca   3360
ggcgcctgcc accatgccca cctagctaac ttttttttt ttttttttga gatagagtct    3420
cactctgtca cccaggctgg agtgcaatgg ggcgatattg gctcactaca acctccacct   3480
cccaggttca agcgattctc ctgcctcagc ctcctgagta gctgggatta caggtgggtg   3540
ccaccacgcc agactaatat ttgtattatt agtagagacg gggtttcacc acattggtca   3600
ggctggttc gaactcctgg cctcaggtga tctgcctgcc tcggcctccc aaagtgctgg    3660
gattacaggc atgagccact gcggctggcc caatttttgc atttttttgg tagagacggg   3720
ggtttcacta tgcttcccag gctggtctca aactcctgga ctcaagcgat ctgcctgtct   3780
cagcctccca aagtgcaggg attacagtca tgagccacca ctgcacggcc caaaattta   3840
tttatttttat tattattatt attttttaga tggagtctcc ttctgttgcc agattggaat  3900
gcagtgccac gatctcagct cactgcaacc tcccctcct gggatcaagt gattcttttt    3960
ttttaagac tctgtctcaa aaaaaagaa aaaaaaaaa aatatatata tatatatata      4020
tatacacgaa ttttgggcca ggcacagtgg cttatgcctg taatcccagc actttgggag   4080
ggccgaggtg ggtggatcac aaggtcagga gtttgagacc agcctggcca atatggtgaa   4140
accctgtctc tactaaaaaa tacaaaaatt agctgggcgt ggtggcacga gcctgtaatc   4200
ctggctactc tggaggctaa gcaggagaaa tcgcttgaac cggggaggca gaggttgcag  4260
tgagccagga tcgcatcact gcactccagc ctgggtaaca gagcaagact ctgtctcaaa   4320
aaacaaacaa aacaaacaa aacaaaataa ataacggtgc aaaattgaat atgcctttt     4380
gactctctaa atgcctcaga tccatttacc ctggggattt gtccttttcta gccccaccac  4440
catctcccct ctggaagact gctgacctat aaggataaag accagactct tgagcaggca   4500
```

-continued

| | |
|---|---|
| cttagggtct tcctgcccat ccctatcccc aactcccct cagtaatttt ggctactagt | 4560 |
| atttctccac atctgaggct atcgtgggtc tcccttcagt ggtcatgaag gacaaggttg | 4620 |
| gagaagtttg ccctcgtgag tctgatgagg gattgggtgg | 4660 |

<210> SEQ ID NO 27
<211> LENGTH: 3354
<212> TYPE: DNA
<213> ORGANISM: Homo sapiens
<220> FEATURE:
<221> NAME/KEY: misc_binding
<222> LOCATION: (1)..(3354)
<223> OTHER INFORMATION: MAR X_S29 of chromosome X

<400> SEQUENCE: 27

| | |
|---|---|
| gatcccttta taaaaccaca atataatgga gtgctataat ttcaaacagt gtttggtctg | 60 |
| ctggcagagt ggtcattcta acagcagtca cagtagagta gaaataagac tgcagtatat | 120 |
| ctaaggcaaa aagctgaggt ttcaggagct tgaaggtaaa gaggaagaaa gaaatgggaa | 180 |
| tgggaattgg aaagacaaat atcgttaaga gaaaattgct tttaggagag gggaaagaat | 240 |
| ctatgtgtac ttaagactat ggaatcaatc ccatttaagc tgggaaacta gtttcatata | 300 |
| taactaataa attttattta cagaatatct atttacctga tctaggcttc aagccaaagg | 360 |
| gactgtgtga aaaaccatca gttctgtcat attcctaaaa aaaaattaaa aagttaaaaa | 420 |
| taaataaata ataaaacttc ttttctttca aaataatcaa ggtgcttatt cacatccatt | 480 |
| ccaatttggg gaaatactta ttttcctatg attagcgaag agaaaagtaa cttgcatttc | 540 |
| aattcaagtt gatacatgtc acttttaaga ggtcaactaa tatttgctag ttgagctaac | 600 |
| catataggct ttaaatactt tcatagtaga aagaaaatga aaatcattag tgaactgtat | 660 |
| aaaatagatc atacttttg aaagaatcag actgaagttt ccgaaaaaaa gaagtaagct | 720 |
| tcaatgaaaa ggtaagtgaa tttagcattt actcagcatc tactatggac ttaacaccta | 780 |
| acagtagata atctgaaggc aaacatattt gtatagggac tgcagaatga tagatgataa | 840 |
| atatcatctc ttctatttga atgaatattt tttcaaatct ttcacacaca gtggtttgct | 900 |
| atggaaagat ttgtagtaca ttaaacaaat ctgaagatgg agttagaaag cttaggctat | 960 |
| gttttgagca aacatataa tttctctgtg attgtttctt catctttcaa atgaggttac | 1020 |
| tgtgaagatt aaatgagata actaaatgat gataaaataa tgtaatctta gcagcacctt | 1080 |
| atttaatctg tgcaacaact ctgtgaagtg agtagggctc agcttcagtc acttctctgc | 1140 |
| catttattaa ctaagatagt ttggaaagtt acccatctct tcagctgtaa aatgatgagg | 1200 |
| atcataccta ttttatgggg ctgcttttag gtacaaatat acaggcaagc actttgttaa | 1260 |
| tactaaagca ttacaccaat tagttttact cttttccatt cacacatgaa attaatgtaa | 1320 |
| tcagaattct gtagattacc taaatcttct gttaacacgt gatatgcagt tcaggttaaa | 1380 |
| tgtcagttga gttaccaaag cacatacata ctcaccaccc tatccaaatc tacaagcctc | 1440 |
| ccagtttgtc ttcactattt tggttaaatt aatatgaatt cctagatgaa aatttcactg | 1500 |
| atccaaatga aataaaaaat atattacaaa actcacacct gtaatctcaa cattttggga | 1560 |
| ggccaaggca ggtagatcac ttgaggccag gagttcaaga ccagcctgat caacatggtg | 1620 |
| aaaccctgtc tctactaaaa atacaaaaat tagccaggtg tggtggcatg tgcctgtagt | 1680 |
| cctacctact cgggaggctg aggcacaaga atcgcttgaa tgtgggaggt ggaggttgca | 1740 |
| gtgacctgag atcgtgccac tgcactccag cctaggcaac agagtgagat catgtgtcat | 1800 |

```
atatatatat atatatatat atatatatat atatatatac acacacacac acatatatat  1860
atacacatat atatacgtat atatatatat gtatatatat acatatatat acatatatat  1920
atatacgtat atatatacgt atatatatat caatgtaaat tatttgggaa atttggtatg  1980
aatagtcttc cctgtgaaca cagatcataa aatcatatat caagcagaca aataagtagt  2040
agtcacttat atgcttatac ttgtaactta aagtaaaaga attacaaaag catatgacaa  2100
agactaattt taagatatcc taatttaaat tgttttctaa aagtgtgtat accattttac  2160
ctatcatatg aataatttag aaacatgttt ataaaattaa tgtccaaatc cattcaaaag  2220
ttttgtaatg cagatcaccc acaacaacaa agaatcctag cctattaaaa aagcaacacc  2280
acctacatat aatgaaatat tagcagcatc tatgtaacca aagttacaca gtgaatttgg  2340
gccatccaac actttgagca aagtgttgaa ttcatcaaat gaatgtgtaa tcatttactt  2400
actaatgcca atacacttta aggtaatctt aagtagaaga gatagagttt agaatttttt  2460
aaatttatct cttgttgtaa agcaatagac ttgaataaat aaattagaag aatcagtcat  2520
tcaagccacc agagtatttg atcgagattt cacaaactct aactttctga tacccattct  2580
cccaaaaacg tgtaacctcc tgtcgatagg aacaacccac tgcagggatg tttctcgtgg  2640
aaaaaggaaa tttcttttgc attggtttca gacctaactg gttacaagaa aaaccaaagg  2700
ccattgcaca atgctgaagt acttttttca aatttaaaat ttgaaagttg ttcttaaaat  2760
ctatcattta ttttaaaata cggatgaatg agaaagcata gatttgataa agtgaattct  2820
tttctgcaat ctacagacac ttccaaaaat cactacagac actacagaca ctacagaaaa  2880
tcataaataa acaagtgcta gtatcaatat ttttaccaaa aaatggcatt cttagaattt  2940
tttataggct agaaggtttg tacaaactaa tctgccacgg attttaaaat atgagtgaat  3000
aaattatatt gcaaaaaaaa tcaggttaca gagaactggc aaggaagact cttatgtaaa  3060
acacagaaaa catacaaaac gtattttaa dacaaataaa aacagaactt gtacctcaga  3120
tgatactgga gattgtgttg acatattagc attatcactg tcttgctaaa acataaaaat  3180
aaaaagatgg aagatgaaat tacaatacaa atgatgattt aaacatataa aaggaaaata  3240
aaaattgttc tgaccaacta ctaaaggaag acctactaaa gatatgccat ccagcacatt  3300
gccactctac atgtggtctg taaaccagca gcatagggat cctctagcta gagt         3354
```

<210> SEQ ID NO 28
<211> LENGTH: 677
<212> TYPE: DNA
<213> ORGANISM: Homo sapiens
<220> FEATURE:
<221> NAME/KEY: misc_binding
<222> LOCATION: (1)..(677)
<223> OTHER INFORMATION: MAR of chromosome 1 genomic contig; 12803267..
       12803943

<400> SEQUENCE: 28

```
ttatatagta tatataatag tatatatatt atagtataca taatagtata tattatatag    60
tatacataat agtatatatt ataatataca taattgtata tatcatatag tatacattat   120
agtatatatc atatagtata cattatagta tatatcatat agtatacatt atatagtata   180
tatcatatag tatacattat agtatatatc atatagtata cattatagta tatatcatat   240
agtatacgta atagtatata tcatatagta tacgtaatag tatatatcat atagtatacg   300
taatagtata tatcatatag tatacgtaat agtatatatc atatagtata cgtaatagta   360
tatatcatat agtatacgta atagtatata tcatatagta tacgtaatag tatatatcat   420
```

| | |
|---|---|
| atagtatacg taatagtata tatcatatag tatacgtaat agtatatatc atatagtata | 480 |
| tattatatag tatatatcat atagtatata ttatatagta tatatcatat agtatatatt | 540 |
| atatagtata tatcatatag tatatattat atagtatata tcatatagta tatataatag | 600 |
| tatatatcat atagtatata taatagtata tatcatatag tatatatact atactatatt | 660 |
| atatatagta tacataa | 677 |

```
<210> SEQ ID NO 29
<211> LENGTH: 332
<212> TYPE: DNA
<213> ORGANISM: Homo sapiens
<220> FEATURE:
<221> NAME/KEY: misc_binding
<222> LOCATION: (1)..(332)
<223> OTHER INFORMATION: MAR of chromosome 1 genomic contig; 13079684..
      13080015

<400> SEQUENCE: 29
```

| | |
|---|---|
| ttaattatat tatatatatt atataattat atattaatat atattaatta tattatatat | 60 |
| attatataat tatatattaa tatatattaa ttatattata tatattatat aattatatat | 120 |
| taatatatat taattatatt atatatatta taattatata tattaatata tattaattat | 180 |
| attatatata ttatatatta taattatata ttatataatt ataatatata tgttaatata | 240 |
| atatatataa ttaatatata attaaaacta tttaattata tgtatattat atataatatg | 300 |
| tattatttaa ataataaata tattatttat at | 332 |

```
<210> SEQ ID NO 30
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAr of chromosome 1 genomic contig; 15682296..
      15682774

<400> SEQUENCE: 30
```

| | |
|---|---|
| acaagtacat atatatatag tatatatata caagtacata tatatagtat atatatatat | 60 |
| acaagtacat atatatagta tatatatata tacaagtaca tatatatagt atatatatat | 120 |
| acaagtacat atatatagta tatatatata caagtacata tatatatagt atatatatat | 180 |
| acaagtacat atatatagta tatatatata caagtacata tatatatagt atatatatat | 240 |
| acaagtacat atatatagta tatatatata caagtacata tatatatagt atatatatat | 300 |
| acaagtacat atatatatag tatatatata tacaagtaca tatatatata gtatatatat | 360 |
| atacaagtac atatatatag tatatatata tatatacaag tacatatata tagtgtatat | 420 |
| atatatatac aagtacatat atatacttgt attagtatat atatatatat atacaagta | 479 |

```
<210> SEQ ID NO 31
<211> LENGTH: 531
<212> TYPE: DNA
<213> ORGANISM: Homo sapiens
<220> FEATURE:
<221> NAME/KEY: misc_binding
<222> LOCATION: (1)..(531)
<223> OTHER INFORMATION: MAr of chromosome 1 genomic contig; 15694611..
      15695141

<400> SEQUENCE: 31
```

| | |
|---|---|
| tataatatat ataatacata atagatatat tatattatat aatagatata taattataaa | 60 |

```
cataataata tataatgaat ataatataaa ataaatataa taaaatatat aatatatcta    120
ttatgtatta tatattatat atgtttatat ataatataat tatatatgtt tatatataat    180
ataattatat atgtttatat ataatataat tatatattat atattataga tataaatatat   240 aatatactat atattataga tataaatatat aatatactat atattataga tataaatatat   300 aatatactat atattataga tataaatatat aatatactat atattataga tataaatatat   360 aatatactat atattataga tataaatatat aatatatatt atatattata gataaaatatat 420 ataatatatt atatattata tctatatata atatattgta tattatatat aatatattgt    480
atattatata taatatattg tatattatat ataatatatt gtatattata t             531
```

<210> SEQ ID NO 32
<211> LENGTH: 378
<212> TYPE: DNA
<213> ORGANISM: Homo sapiens
<220> FEATURE:
<221> NAME/KEY: misc_binding
<222> LOCATION: (1)..(378)
<223> OTHER INFORMATION: MAR of chromosome 1 genomic contig; 886276..
      886653

<400> SEQUENCE: 32

```
ttatattata tatcttacat aaattatata tatatattac ataaattata tacaatataa    60
attatataca atataattta tatataaaat ataaattata taaataattt atatataaaa    120
tataaattat ataataaatt tatatataaa atataaatta tgtataaaat ttatatataa    180
aatataaatt gtgtataaaa ttatatataa aatataaatt gtgtataaaa tttatatata   240
aaatataaat tatatataat ttatatatta taatatataat tatatataat atatatcata   300
aaatataaat tatatataat atatatcata agatataaat tatatataat atatatcata   360
agatataaaa tatataat                                                  378
```

<210> SEQ ID NO 33
<211> LENGTH: 595
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 1 genomic contig; 3326732..
      3327326

<400> SEQUENCE: 33

```
aaaatatata aatatatata aaaatatata aaaatatata aatatatata aaaatatata    60
aatatatata aatatatata aaaatatata aatatatata aatatatata aaaatatataa   120 atatatataa aatatatata aatatatata aatatatata aaaatataaa tatatataaa    180
aatataaata tatataaata tatataaaaa taaaatatata tataaatata tataaatata   240
taaatatata taaatatata taaatatata aatatatata aatatatata aatatatata    300
aatatataaa tatataaaaa tatataaaa tatataaata tataaaata tataaatata     360 taaaatatata tataaatata taaaatatata taaaatatata tataaatata            420 tataaatata tatatata aatatatata aatatatata taaatatata taaatatata     480
tatatatata taaatatata taaatatata taaatatata tataaatata taaatatata   540
tataaatata tatataaata tatataaata tatataaa tatat                     595
```

<210> SEQ ID NO 34
<211> LENGTH: 738

```
<212> TYPE: DNA
<213> ORGANISM: Homo sapiens
<220> FEATURE:
<221> NAME/KEY: misc_binding
<222> LOCATION: (1)..(738)
<223> OTHER INFORMATION: MAR of chromosome 1 genomic contig; 4485716..
      4486453

<400> SEQUENCE: 34
ataatagata atatatatta tatgatagat atataaatata ttatataata tataatatat      60
tatatatcta tcatataata tatataatat aaatatatt atatatctat catataatat       120
aatatatata atatataata tatatcatat tatattgtat ataatatata tcatattata      180
ttgtatataa tatatatcat attatattgt ataatatata tcatatta tattgtatat        240 aatatatatc atattatatt gtatataata tatatcatat tatattgtat ataatatata      300
tcatattata ttgtatataa tatatatcat attatattgt ataatatata tcatatta        360 tattgtatat aatatatatc atattatatt gtatataata tatatcatat tatattgtat      420
ataatatata tcatattata ttgtatataa tatatatcat attatattgt ataatatata      480
tatcatatta tattgtatat aatatatatc atattatatc tattatattg tatataaatat     540 atattatata ttatctatta tattgtatat aatatatatt atatattatc tattatattg      600 tatataaatat atattatata ttatctatta tattgtatat aatatataat aaatatagta     660 tatataaatag ataatatata gtatatatga tatattatat atactatata ttatatatca     720
tatatactat atactata                                                    738

<210> SEQ ID NO 35
<211> LENGTH: 386
<212> TYPE: DNA
<213> ORGANISM: Homo sapiens
<220> FEATURE:
<221> NAME/KEY: misc_binding
<222> LOCATION: (1)..(386)
<223> OTHER INFORMATION: MAR of chromosome 1 genomic contig; 5423067..
      5423452

<400> SEQUENCE: 35
taaatatata aaaatatata taaaaatata aaaatattta tataaatata taaaaatatt      60
tatataaata tataaatata taaatatata tttatataaa tataaaatata tataaatata    120 taaatatata tttatataaa tataaaatata tatttata taaatatata aatatatata      180
aaatatataa atatatattt atataaatat ataaaatatata taaaatata taaatatata    240 tattttatat aaaatatataa atatatataa aatatataaa tatatatt ttatataaat      300 atataaatat atataaaata taaaatata tatattttat atttttatat ataaaatac       360 atatatttca tatatcacat atatga                                          386

<210> SEQ ID NO 36
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 1 genomic contig; 5805559..
      5806142

<400> SEQUENCE: 36
taaatatttt taaatatatat atattttata atatataatt tatattataa tgtgtacata     60
atatatatta taatataata tatataatac tgtatatatt attatatata ttataatata    120
```

-continued

```
tattattata tattatatta tatataatat aatatatatt ataatatatt atattataca      180
tattataatg tattataata tatatttatat tatatatttat aatatatatt atattatata      240
ttataatata tattatatta tatattataa tatatattat attatattat atatattata      300
atacatatta taatacatat tatataatat attataatat gtattataat acatattata      360
taatatatta taatatatta tatataataa tatattataa tacatattat ataatatata      420
tattatgtat attatatata atatatatta caatgtatat tatgtatatt atatatatta      480
tatatcatat aatatatatt atatataata tgatatataa tatatattat ataatatatt      540
atatgatata tataatatgt attacatgta atatatatca taat                       584
```

<210> SEQ ID NO 37
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig; 10802644..
      10802988

<400> SEQUENCE: 37

```
tgtatatata tactatatat atactatata tatagtgtat atatatacta tatatatact       60
atatatatag tgtatatata tactatatat atagtatata gtatatatag taatatatat      120
atatagtata tatatacact atatatagta tatatagtat atatatattg tgtatatagt      180
atatatatag tgtatatata gtatatatat attgtatata tagtatatat attgtgtata      240
tatagtatat atatagtata tatagtatat atagtatata tatagtatat atatactata      300
tatatagtgt atatatattg tatatatata ctatatatat agtat                     345
```

<210> SEQ ID NO 38
<211> LENGTH: 474
<212> TYPE: DNA
<213> ORGANISM: Homo sapiens
<220> FEATURE:
<221> NAME/KEY: misc_binding
<222> LOCATION: (1)..(474)
<223> OTHER INFORMATION: MAR of chromosome 1 genomic contig; 13496468..
      13496941

<400> SEQUENCE: 38

```
atattatata taatataatt atatctataa ttatatatta tatataatat aattatatat       60
ctataattat atattatata taatatatat tatatataat atataattat ataataattta     120 tataatataa tatataatat ataattatat ataattatat aataatatat ataatatata     180
attatatata atttatataa taatatatat aaatatataat tatatatatt tatataatat     240
aattatatat aatatataat tatatataat ttataataata taattatata taatatataa     300
ttatatataa tttatataat ataattatat aaattatat attatatata atttatataa       360
tataattata taatatatat aattatatat aatatataat tatataataat tatatataat    420 atataattat atataattta taaatataaa ttatatatta tatatattat atat             474
```

<210> SEQ ID NO 39
<211> LENGTH: 483
<212> TYPE: DNA
<213> ORGANISM: Homo sapiens
<220> FEATURE:
<221> NAME/KEY: misc_binding
<222> LOCATION: (1)..(483)
```

<223> OTHER INFORMATION: MAR of chromosome 1 genomic contig; 2509163..
    2509645

<400> SEQUENCE: 39

| caaaatacat aatatatat agtattatat aatagtatgt atagttataa tatatagtat | 60 |
|---|---|
| aattacaata tatgatatgg tttatatatt atatatagta taatataata taacataata | 120 |
| ctattataat atataaacta tataatatat actattataa tatatgaact attataatat | 180 |
| ataaactata tataatatat aatatgtact attataatat ataaactatt ataatataat | 240 |
| atataaacta ttataataca taaactatta taatatatat aatactatgt atacatatat | 300 |
| tacattatgt acatactaca ttatgtatta tgtatgtata tatacacaaa atacataata | 360 |
| tataatagta ttatataata gtatatatag ttataaatata tagtataatt acaatatata | 420 |
| atatggttta tatattatat atagtataat acaatataac ataatactat tatatataaa | 480 |
| cta | 483 |

<210> SEQ ID NO 40
<211> LENGTH: 641
<212> TYPE: DNA
<213> ORGANISM: Homo sapiens
<220> FEATURE:
<221> NAME/KEY: misc_binding
<222> LOCATION: (1)..(641)
<223> OTHER INFORMATION: MAR of chromosome 1 genomic contig; 2776349..
    2776989

<400> SEQUENCE: 40

| tgttatatat atataacata gatattatat atacatgtta tatatataac atagatatta | 60 |
|---|---|
| tatatacatg ttatatatat aacatagata ttatatatat aacatagata ttatatatac | 120 |
| atgttatata taacatagat attatatata catgttatat ataacagata ttatatatac | 180 |
| atgttatata taacatagat attatatatg tatgttatat ataacataga tattatatat | 240 |
| gtttatataa tatataacat atgtttaaca tatataaatat ataacatgtt tatataatat | 300 |
| ataacataat tatatgttat atatgatata aaacatatat attatatacg ttatatgtaa | 360 |
| tatataacat atattgtata cgttatatgt aatatataac atatattgta tacgttatat | 420 |
| gtaatatata acatatattg tatacgttat atgtaatata taacatatat tgcatacgtt | 480 |
| atatgtaata tataacatat attgtatacg ttatatgtaa tatgtaacat atattgtata | 540 |
| cgttatatgt aatatgtaat atataataca taacatgtt atatataaca tatatgtata | 600 |
| taacatatat ataacatata taacatatat gttatatatt a | 641 |

<210> SEQ ID NO 41
<211> LENGTH: 745
<212> TYPE: DNA
<213> ORGANISM: Homo sapiens
<220> FEATURE:
<221> NAME/KEY: misc_binding
<222> LOCATION: (1)..(745)
<223> OTHER INFORMATION: MAR of chromosome 1 genomic contig; 2858703..
    2859447

<400> SEQUENCE: 41

| atatttatat atgtaataat atataatata tttatatgta tttgtatatg taataaatata | 60 |
|---|---|
| tatataataa aatatgtaat aatatataat atatttatat ataaatatat tatattatat | 120 |
| atatattatt atatttataa tataatatat atttatatta tatattataa atatatatta | 180 |
| tataatatat attataaata tatattatat aatatatatt ataaatatat attatattat | 240 |

```
atattataaa tatatattat ataatatata ttataaatat atattatata atatatatta    300
taaatatata ttatatttat aatatatatt tttgtatatt atatattata tattataaat    360
attattatat ttataatata ttatatattt tatatataat atatgatata tattataaat    420
atatcttata aatatatata tttatatata tatattataa atatataaat ataaatatat    480
aatataatat aatataatat aataaatata atatataata tatataatat ataataaata    540
taataaaaat aaatatatca taaaatata aatataaata taaatatatc atataaatat    600
atatatttat atgatatatt atagtatata taaatatatt tatatattat aaaatattta    660
tataatatat aattataata tatttatata taaaattaa ctaatatata taaactaata    720
taatatataa tgtaataata tagta                                         745

<210> SEQ ID NO 42
<211> LENGTH: 307
<212> TYPE: DNA
<213> ORGANISM: Homo sapiens
<220> FEATURE:
<221> NAME/KEY: misc_binding
<222> LOCATION: (1)..(307)
<223> OTHER INFORMATION: MAR of chromosome 1 genomic contig; 945522..
      945828

<400> SEQUENCE: 42
catatataat atatattacc tatgttatat aggtcatata taacataaat atattacata     60
tatgtaatat atattaaata taaatatata acatatatgt gtaactatat atgtaaatat    120
gtacatatac atatatgtaa atatataata tatatttaca ttatattata taatatatat    180
ttacattata tatttatata tacattatat atatttacat tataaatatt tatataaatat   240 atatttacat tatattacat tatataaaat acaatatatt acattataat acattataac    300
agataaa                                                             307

<210> SEQ ID NO 43
<211> LENGTH: 357
<212> TYPE: DNA
<213> ORGANISM: Homo sapiens
<220> FEATURE:
<221> NAME/KEY: misc_binding
<222> LOCATION: (1)..(357)
<223> OTHER INFORMATION: MAR of chromosome 1 genomic contig; 3402743..
      3403099

<400> SEQUENCE: 43
aatattatat taaatataat atattaatat ttaatatatt taatataata ttaaataaat     60
atattataaa taaattataa tatataaata tatattatgt atttatgtat aatatataaa    120
aattatatat aatatatata tttttataaa tatataaata tataataaat aaatatatta    180
aataaataat aatatattaa atattaatat attaaatatt atatattaaa tataatatgt    240
aatatgaaat atattaaata ttatatatta aatataaata taatgtgaaa atatattaaa    300
tattatatat taaatataat atataatatg aaatatatta aatattatat attaaat      357

<210> SEQ ID NO 44
<211> LENGTH: 323
<212> TYPE: DNA
<213> ORGANISM: Homo sapiens
<220> FEATURE:
<221> NAME/KEY: misc_binding
<222> LOCATION: (1)..(323)
<223> OTHER INFORMATION: MAR of chromosome 1 genomic contig; 3485830..
      3486152
```

<400> SEQUENCE: 44

```
atatttatag actatatatt tatatattta gtgtatttgt atactatata tttatatagt    60
tagtatattt gtatactata tatttatata tttagtatat ttgtatacta tatatttata   120
tatttagaat atttgtatac tatatattta tatatttagt atatttgtat actatatatt   180
tagtatattt gtatactata tatttatata tttagtatat ttgtatacta tatatttata   240
tatttagtat atttatatac tatatactta tatatttagt atatttatat actatatact   300
tatatattta gtatatttat ata                                           323
```

<210> SEQ ID NO 45
<211> LENGTH: 498
<212> TYPE: DNA
<213> ORGANISM: Homo sapiens
<220> FEATURE:
<221> NAME/KEY: misc_binding
<222> LOCATION: (1)..(498)
<223> OTHER INFORMATION: MAR of chromosome 1 genomic contig; 3548336..
  3548833

<400> SEQUENCE: 45

```
aattattact atattgttaa tataattatt ataatatata atataattat atcactatta    60
ttatattata gtattaatat aatagtgtat aacattaata taatatagta ttaatataat   120
agcgtataac attaatataa tatagtatta ataatatagc gtaacatt aatataaat     180 agtattaata taatagtgta tattaatata atagtatt aatatataat attaatataa    240
tatatcaata taatagtata taatataata taatatatca ataaatagt atataatata   300 atataatata tcaatataat agtatataat ataatataat atatcaatat aatagtatat   360
aatattaata taatataata tcaatataat agtatataat attaatatat taatataata   420
gtatataata ttaatgtaat ataatattaa cataatgtat ataataatat aatagtatat   480
aatactaata taatataa                                                 498
```

<210> SEQ ID NO 46
<211> LENGTH: 400
<212> TYPE: DNA
<213> ORGANISM: Homo sapiens
<220> FEATURE:
<221> NAME/KEY: misc_binding
<222> LOCATION: (1)..(400)
<223> OTHER INFORMATION: MAr of chromosome 1 genomic contig; 4595109..
  4595508

<400> SEQUENCE: 46

```
aaatatatta tattatatat tatatattat tcaatatact ataatatata ttatatatgt    60
ttaatacaat atataaatatt tacatatatt cccatttatt tatataacat atattatatg  120
atattatata ttactccata taatataata tattatacat aatatattac tcagtataat   180
acataatata tataatatat tactcggtat aatatataat attatatgtt atgcaatata   240
atatataata ttatatataa tacattattc aataataaat ataatattat ataataaca    300 ttattcaata taatatataa tacactattc aataataat acaatattat ataataaca    360 ttattcaata taatatatat tatataatat atatatttat                         400
```

<210> SEQ ID NO 47
<211> LENGTH: 403
<212> TYPE: DNA
<213> ORGANISM: Homo sapiens
<220> FEATURE:
<221> NAME/KEY: misc_binding

```
<222> LOCATION: (1)..(403)
<223> OTHER INFORMATION: MAr of chromosome 1 genomic contig; 7205509..
      7205911

<400> SEQUENCE: 47
agtatatata tgtgtatata tatgagtata tatatgtgta tatatatgag tatatatatg    60
tgtatatata tgagtatata tatgtgtata tatgagtata tatatatgtg tatatatatg   120
agtatatata tgtgtatata tatgagtata tatatgtgta tatatatgag tatatatatg   180
tgtatatata tgagtatata tatgtgtata tatgagtata tatatgtgta tatatgagta   240
tatatatatg tgtatatatg tgagtatata tatgtgtata tatgagtata tatgtgtata   300
tatatatgag tatacatatg tgtatatata tgagcatata tgtgtatata tatgagtata   360
tatatgtgta tatatgagta tatatatgtg tatatatatg agt                      403

<210> SEQ ID NO 48
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig; 7507280..
      7507588

<400> SEQUENCE: 48
tataaaatat atattattta tatattatat ataaaatata tattatatta tatattatag    60
atataataaa taaataatat ataatatatt atataaattat ttatacataa ttatatataa   120
ttatatgtaa ttgtacaatt atatataatt atatacaatt atacacataa ttatatacaa   180
ttatacaatt atatacataa ttatatatat aaatatacata attatatatt aattatacaa   240
ttatatacat aattatatat aattatacaa ttatatacat aattattatg tatattatat   300
tatataata                                                            309

<210> SEQ ID NO 49
<211> LENGTH: 516
<212> TYPE: DNA
<213> ORGANISM: Homo sapiens
<220> FEATURE:
<221> NAME/KEY: misc_binding
<222> LOCATION: (1)..(516)
<223> OTHER INFORMATION: MAR of chromosome 1 genomic contig; 3581085..
      3581600

<400> SEQUENCE: 49
atatatatat atatatatat atttatatat atatatatta atatatatta tatataaaaa    60
tatataaaat ttatatatat aatttatata tataaaaata tataaaattt atatatataa   120
tttatatata taaaaatata taaaatttat atatataatt tatatatata aaatatatata  180 aaatttatat ataaatttta tatatataaa aatatataaa atttatatat ataatttata   240
tatataaaaa tatataaaat ttatatatat aatttatata tataaaaata tataaaattt   300
atatatataa tttatatata taaaatatat aaattatata taattatata tatataatat   360
aaaattatat ataaattat atataaata taaaattata tataatta tatatataat      420 ataaaattat atatatattg tatatatata aaatatacaa aatttatata tataaaaatat   480 aaaatataca taaaaataaa tatatataat ttatat                              516

<210> SEQ ID NO 50
<211> LENGTH: 534
```

```
<212> TYPE: DNA
<213> ORGANISM: Homo sapiens
<220> FEATURE:
<221> NAME/KEY: misc_binding
<222> LOCATION: (1)..(534)
<223> OTHER INFORMATION: MAR of chromosome 1 genomic contig; 3084851..
      3085384

<400> SEQUENCE: 50
atataatata tatgactata tattttatat tatattctat ttcaataaaa tatttatatt    60
ttattatata ttataatata taattatata tgtaataata tataatatat aatatatatt   120
ttatattata ttttatattt atttttatat tttatattat attttattat atatattata   180
atatataatt atatatgcaa taatatatta tatattataa tatataatta tatatgcaat   240
aatatattat atattataat ataaattat atatgcaata atatattata gattataata    300
tataattata tatgcaataa tatattatat attatatatt agataatata ttaatatata   360
ttataacata taatatataa catataatat ataaatatatt atctaatata taatataaca   420
tataatatat aatatattat ataatatatt attacatata taatatattg taatatataa   480
tattacatat atcttcaaaa agagttatgt gtatataata catatatata ccat           534

<210> SEQ ID NO 51
<211> LENGTH: 583
<212> TYPE: DNA
<213> ORGANISM: Homo sapiens
<220> FEATURE:
<221> NAME/KEY: misc_binding
<222> LOCATION: (1)..(583)
<223> OTHER INFORMATION: MAR of chromosome 1 genomic contig; 160087..
      160669

<400> SEQUENCE: 51
tatttatata aaatatataa aatatattat atataaatat attatatata atatatttat    60
atattataca atatatttat atattatata taatatattt tatataatat acataatata   120
ttttatatat tatatataat atattttata taatgtac aatatatttt atatattata    180
tataatatat tttatatata ctatacaata tattttatat attatatatt ttatatatat   240
ttttcatgta acatatatat tttatatata atatatatac catataatat atatttttata   300 tataatatat ataccatata taatatattt tatatataat atgtatatca tatatagtat   360
attttatata taataggtat accatatata atatatttta tatataatag gtataacata   420
tataatatat tttatatata atatgtatac catatataat atattttata tattatagat   480
accatatgta atatacttta tatataatat agataccata tgtaatatac tttatatata   540
atatagatac catatgtaat atactttata tataatatag ata                     583

<210> SEQ ID NO 52
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 1 genomic contig; 4350424..
      4350737

<400> SEQUENCE: 52
tatgtgtata taaatatatg tatatatgtg tatataaata tatataaata tatgtatata    60
tgtatatata catatattta tatataaata tatgcatata tttatatata aaatatatgc   120
atatatgtat atatataaaa tatatacata tatgtatata tataaaatat atacatatat   180
```

```
gtatatatat aaaatatata catatatgta tatatataaa atatatacat atatgtatat      240 ataaaaata tatacatata tgtatatata taaaatatat acatatattt atatatataa      300
aataccaagt ctta                                                       314
```

<210> SEQ ID NO 53
<211> LENGTH: 828
<212> TYPE: DNA
<213> ORGANISM: Homo sapiens
<220> FEATURE:
<221> NAME/KEY: misc_binding
<222> LOCATION: (1)..(828)
<223> OTHER INFORMATION: MAR of chromosome 1 genomic contig; 8443267..
      8444094

<400> SEQUENCE: 53

```
tattatataa ttatatatac tatataatta tataatatat agttatatag tatatataat       60
atatataata tatactatag tatatataat atatataata tatactatag tatatataat      120
atataattat atataatata taaatatag tatatatatt atatatatta tatatatata       180
atatatatat aatatatata ataagtata taaatatat aattatatat aatatataat       240
atagtatata taatatataa tatatatata attatatact ataatatata taatatataa      300
ttatatatta tatactatag tatatattat tatatataat agatataata tatataatta      360
ttatataata tagtatatat aatatataat tatatataat agatataata taatataatt      420
atatataata tagtatatat aatatataat tatattatat tatatataat ataaattat       480 aatatataat tatattatat aatatatata atatataatt atattatata attatattat      540
ataatatata taatatataa ttatattata taatatatat aatatataat tatattatat      600
aatatatata atatataatt atattatata atatatataa tataattata tattatataa      660
tatatataat ataaattat atattatata taatatagta tatatataat gtaattatat      720
atcatataat atataacatt gtatataata tataattaca tattatataa tgtatataat      780 ataaattat atacattata taatatagta taaattata tattatgt                    828
```

<210> SEQ ID NO 54
<211> LENGTH: 573
<212> TYPE: DNA
<213> ORGANISM: Homo sapiens
<220> FEATURE:
<221> NAME/KEY: misc_binding
<222> LOCATION: (1)..(573)
<223> OTHER INFORMATION: MAR of chromosome 1 genomic contig; 8703190..
      8703762

<400> SEQUENCE: 54

```
tatattatat ataaaatata catataatat acctataata tacatataat atataatata       60
tattatgtac atataatata catataatat ataatatata taatgtacat ataatataca      120
tataatatat gttatatatt atatataaaa tataggatat atataatata gaatatatat      180
actatattgt atatataaga tatataatat atagtatata tactatataa tatataatat      240
atagtatata taatatataa tatagaatat atatacaata tataatatag aatataggat      300
atatatagaa tatacatata taatatgtat atattatata ttatattata tattatataa      360
aaatatataa tatataatat aaaatatatt tatatattat ataatataaa atatattata      420
tattatatat tatataataat aaaatatatt atattatata tattatatat aaaatatatt      480
atatattata tattatatat aaaatatatat tatatattat atattatata taaaaatata      540
```
ttatatatta tatataaaaa tatatattat tac                                573

<210> SEQ ID NO 55
<211> LENGTH: 597
<212> TYPE: DNA
<213> ORGANISM: Homo sapiens
<220> FEATURE:
<221> NAME/KEY: misc_binding
<222> LOCATION: (1)..(597)
<223> OTHER INFORMATION: MAR of chromosome 1 genomic contig; 8819076..
      8819672

<400> SEQUENCE: 55
acatatctta tatataaaat atataaatat acacatattt tatatataat atatattata     60
tatatgaaat atacacatat ttttatatat ataatatata tattatatat aatatatgca   120
tatattatat ataaaatata tatattatat ataaaatatg catatatttat ataatatata   180 taatatataa aatatataat atatattata tattatatat aatatatatt atatataata   240
catatatata atataataata tatataaaat ataatatata tattatataa tatatatata   300
aatatatata atatatatat aatatatata ttatatataa aatatatatt atatgtaaaa   360
tatataaaat atataatata tatattatat gtaaaatata tattatatat aaaatatata   420
atatataaaa tatatattat atataaaata tataatatat aaaatatata atatatataa   480
aatatataat atatataaat atatattata taaaaatatt ataatatata taaatatata   540
ttatatataa aatatataat atatataaat atatattata tataaaatat atattat     597

<210> SEQ ID NO 56
<211> LENGTH: 646
<212> TYPE: DNA
<213> ORGANISM: Homo sapiens
<220> FEATURE:
<221> NAME/KEY: misc_binding
<222> LOCATION: (1)..(646)
<223> OTHER INFORMATION: MAr of chromosome 1 genomic contig; 759619..
      760264

<400> SEQUENCE: 56
taatatatat aatatatatt atataataat atataaatata tattatatta taatatataa     60
tatattatat aataatatat attatataat ataataataat atataataata catattatttt   120 aataatatat aatatatatt ataataataat ataataatata tattatataa taatatacat   180
tatattatat aatatataat atataataata tatattatat aataatatat aatatatatt   240
atagaatgat atattagata ttatataatt atatatataa tattatatat tatataataa   300 tataataataat atattatata attatatata taatatttata tattatataa ttatatataa   360
tatattatat aattatatat ataatattat atattatata attatatata atatatatta   420
tataattata tatataatac tatatattat ataattatat ataatactat atattatata   480
atttatataa ttatatatat tatatattat ataattatat atattatata ttatataata   540
acatatatat tatatattat ataataacat atatattata tattatataa tacatatata   600
ttatatatta tataatacat tattatataa tatataatat atatta                  646

<210> SEQ ID NO 57
<211> LENGTH: 752
<212> TYPE: DNA
<213> ORGANISM: Homo sapiens
<220> FEATURE:
<221> NAME/KEY: misc_binding
<222> LOCATION: (1)..(752)
<223> OTHER INFORMATION: MAR of chromosome 1 genomic contig; 1226710..

-continued

```
     1227461

<400> SEQUENCE: 57
taaacatata tataaatata tataaatata tatataaata tatataaata tataaatata    60
taaatatata tgaatatata aatatatata aatatatatg aatatataaa tatatatata   120
aatatatata aatatatata taaatatata taaatatata taaatatata taaatatata   180
taaataaata tataaatata tataaatata taaatatata tataaatatg taaataaata   240 tataaaata tataaatata tataaatata taaatatata tatagaaata tatatagaaa   300
tatatataaa tatatataga aatatataga aatatatata gaatatatata taaatatata   360 taaatataga aatatatata aatatatata aatatatata gaatatatata atatatataa   420 atatatataa atatataaat atatatataa atatatatat aaatatatat aaatatatat   480
aaatatatat aaatatatat aaatatatat attaatatat aaatctatat taatatatat   540
taatatataa atctatatta atatatatta atatatatat taatatatat taatatataa   600
atatatatat taatatataa atatatataa atatatatgt aaatatatat ataaatatat   660
ataaatatat ataaatatac atataaatat atatataaat atatataaat atatatataa   720
atatatataa atatatatat aaatatatat aa                                 752

<210> SEQ ID NO 58
<211> LENGTH: 300
<212> TYPE: DNA
<213> ORGANISM: Homo sapiens
<220> FEATURE:
<221> NAME/KEY: misc_binding
<222> LOCATION: (1)..(300)
<223> OTHER INFORMATION: MAR of chromosome 1 genomic contig; 1119049..
      1119348

<400> SEQUENCE: 58
taatatacat tttatataat atatgtaata tatatttat atatatgtaa tatatatttt    60 ataatata tgtaatatat atttatata tatgtaaat atattttata taatatatgt       120
aatatatatt ttatataata tatgtaaat atatttata taatatatgt aatatatatt    180
ttatataata tatgtaatat atatttata taatatatgt aatatatatt ttatataata   240
tatgtaatat atatttata taatatatgt aatatatatt ttatatat gtaatacata   300

<210> SEQ ID NO 59
<211> LENGTH: 617
<212> TYPE: DNA
<213> ORGANISM: Homo sapiens
<220> FEATURE:
<221> NAME/KEY: misc_binding
<222> LOCATION: (1)..(617)
<223> OTHER INFORMATION: MAR of chromosome 1 genomic contig; 3603613..
      3604229

<400> SEQUENCE: 59
aaaatataat atatataata tataatatat ataatatatt atatataaaa tatataatat    60
ataatatata taataaaata tacataatat ataatgtata ataaaatata cataatatat   120
aatatataat aaatatataa tatataatat ataataaaat ataatata taatatataa    180 taaatatat aatatattat atataataaa atataataa tattatatat aataaaatat    240
ataatatatt atataataa aaatataa tatattatat ataataaaat atataatata    300
ttatatataa taaatatat aatatattat ataataaa atataataa tataaatat     360 aataatatat ataatatata atatatataa taaatatat aatatatata atatatataa   420
```

```
taaaatatat aatatataat atatataata aaatatatat gatatataat atatataata      480
aaatatatga tatataatat ataataaaa atatataata tataatataa tatataatat       540
atatactaaa aaatatataa tatataataa aaaatatata atatataata tatataatat      600
ataataaaat atatata                                                     617
```

<210> SEQ ID NO 60
<211> LENGTH: 674
<212> TYPE: DNA
<213> ORGANISM: Homo sapiens
<220> FEATURE:
<221> NAME/KEY: misc_binding
<222> LOCATION: (1)..(674)
<223> OTHER INFORMATION: MAR of chromosome 1 genomic contig; 2592460..
      2593133

<400> SEQUENCE: 60

```
taagcttata tatatatata agcttatata tatatatata agcttatata tatatagaaa      60
gcttatatat atatagaaag cttatatata taagaagctt atatataaaa gcttatgtat      120
aaatatatat aaatatattt atttatgctt atagatacat ataaaatat atttatttat      180 atttatatat aaacatatat ttatatatat ttatataata tttatttatt ataaaataa      240 atatataata aataataaat atatataata tatttattgt attatttata taaatttatt     300 aatataaatat ataataaaat aataattata taaatatata aatatctata aatatatata    360
aatatatata atatctataa atatatataa ataaaatat ataataatc tataaaatata      420 gataaatata aatatatata atatctataa atatagataa atataaatat ataaactat     480 ataaaatat ataaactat ataaaatat ataataaat ataataact atatatataa         540 ctatatatat aaatatatat aactatatat ataaatatat ataaaatat ataaactat      600 atatataaat atataaact atatataaat atatataaa atatatataa ctatatatat      660
aaatatatat ataa                                                       674
```

<210> SEQ ID NO 61
<211> LENGTH: 1694
<212> TYPE: DNA
<213> ORGANISM: Homo sapiens
<220> FEATURE:
<221> NAME/KEY: misc_binding
<222> LOCATION: (1)..(1694)
<223> OTHER INFORMATION: MAR of chromosome 1 genomic contig; 2891680..
      2893373

<400> SEQUENCE: 61

```
atatgtaata catatattat atatgcatat atacatgcat atgtatatac atatattata      60
tatgcatata tacatgcata tgtatataca tatataaagt atgattatat ataatatata     120
catgtatatg tatatacatg tatatattat attatatatt attatacat attattatgt     180 ctatatataa tataatatat acatattaat aatataatac ataatataat ataatatatt     240
atataataca taatataata taatatatta taatacat aatataatat aatatattat      300
atgatacata atataatata atatattata tgatacataa tataatataa tacatattaa    360
taatatatta ttattattaa tataatatat acatattaat atacatacat atatattata    420
ttatatataa tatacatata atataatatg taatattata taaaatataa tacataatat    480
aatacatatt aataatatat tattaataag ataaatatata tgtatctata atatatacat    540
atatgtatat gtatgtatat attatagata tacatgttta tacatgtata tattatagat    600
```

```
atatacatgt atatacatgt atatattata gatatataca tgtatatacg tatatattat    660
agatatacat gtatatatgt atatatatta tagatataat atatacaaga ataaagaat    720 atatataata taatatataa tacacataat acgtatatat tatatataca tgtatattat    780
atatgtacat atatacatgt atattatata tacatgtata ttatatatac atgcatatta    840
tatatatttt tatatataat atccatgtat attatgtata tttgtgtata ttatatatac    900
atgtatatta tatatacatg catattatat atattttat ataaatatc catatatatt    960 atgtatattt gtgtatatta tatatacaca tatattatat atacatggat attatatata   1020
cacatatatt atatatacat atatattata tatacacata tattatatat acatgtatat   1080
tatatataca cgtatattat atatacacac gtatattata tatacacgta tattatatat   1140
acacacgtat attatatata cacgtatatt atatatacac acgtatatta tatatacacg   1200
tatattatat atacacacgt atattatata tacgtatata ttatatatac acacgtatat   1260
tatatataca cgtatattat atatacacac gtatattata tatacacgta tattatatat   1320
acacacgtat attatatata cacgtatatt atatatacac acgtatatta tatatacatg   1380
tatattatat atacatgtat attatatata cacatgtata ttatatatac atgtatatta   1440
tatatacaca tgtatattat atatgcatgt atattatata tacacatgta tattatatat   1500
acacatgtat attatatata catatatatt atatatacat gtatattatg tacatatata   1560
tattatatat acatgtatat tatagataca tatatattaa atatacatgt atattatgta   1620
tacatatata ttaaatatac atgtatattg tatacacata tatattatat acatgtatat   1680
tacatgtata cata                                                    1694
```

<210> SEQ ID NO 62
<211> LENGTH: 587
<212> TYPE: DNA
<213> ORGANISM: Homo sapiens
<220> FEATURE:
<221> NAME/KEY: misc_binding
<222> LOCATION: (1)..(587)
<223> OTHER INFORMATION: MAR of chromosome 1 genomic contig; 3432560..
     3433146

<400> SEQUENCE: 62

```
gaattatata tatatagctg aattatatac atatataata tatacaatat atattatata     60
tttatatatg atatatacaa tatatattac atattatata tacaatatat aatatataat    120
atataatatt atatattata tattgtatat aatatatatt atataacatt atataatata    180
taatattata tattatatat tgtatataat atatattata taacattata taatatatac    240
tattatatat taaatatat aatatataat aatatataat agtatatatt atatatattg    300 tatatatttat atataaatat ataatatata atatatatta tataatatat attatataat    360
atatattatt atatattata tatttatata taatatatat tatatatatt atatttata    420 tataaatata taatatataa taatatataa tttaatatat ataatatata caatatataa    480
tataatatat attaatatat ataatatata caatatataa tatataatat ataatatata    540
atataaatta ttatatataa tatatattat atatagctga attatat              587
```

<210> SEQ ID NO 63
<211> LENGTH: 313
<212> TYPE: DNA
<213> ORGANISM: Homo sapiens
<220> FEATURE:
<221> NAME/KEY: misc_binding
<222> LOCATION: (1)..(313)

<223> OTHER INFORMATION: MAR of chromosome 1 genomic contig; 3805392..
       3805704

<400> SEQUENCE: 63

```
tatataatat gtatattatg taatatttta tatagcatat atgtatatta tatataatct    60
tttatatata gtataataa tgtatattat attatata attatataat tatgtattat    120
ataaaatata ttatataata taaattata tatttttga aatatagatt atatataata   180
tatatggcag tgagctgaga tataatatat attatctata ctatataata tatattat    240 atactctata ttatatatgt atatattata taatatat acatatataa tgtgtatata    300
ttatatataa taa                                                    313
```

<210> SEQ ID NO 64
<211> LENGTH: 349
<212> TYPE: DNA
<213> ORGANISM: Homo sapiens
<220> FEATURE:
<221> NAME/KEY: misc_binding
<222> LOCATION: (1)..(349)
<223> OTHER INFORMATION: MAR of chromosome 1 genomic contig; 4521378..
       4521726

<400> SEQUENCE: 64

```
ttatatacac tatataatat gtatttatat atacttatat acactatata tgtatttata   60
tataattata tacactatat aatatgtatt tatatataat tatatacact atataaatatg  120 tatttatata taattatata cactatataa tatgtattta tatataattg tatacactat  180
ataatgtata tttatatata attgtataca ctatataatg tatatttatg tataattgta  240
tacactatat aatgtatatt tatgtataat tgtatacact ataatgta tatttatgta   300 taattgtata taccatataa tgtatattta tgtataattg tatatacca              349
```

<210> SEQ ID NO 65
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 1 genomic contig; 3240166..
       3240665

<400> SEQUENCE: 65

```
ttaatatata atatatatta tatatttata tattaatata taatatatat ttatatataa    60
tatatattat atatttatat tacatatatt tatatgttaa tatatatttt atatatttat  120
atattttata tatttatata ttatatattt atatattata tttatatatt atatattat  180 attatatatt tatatatatt atttatatat tatatattta tattatatat ttatatattg   240
tatatttata ttatatattt atatattgta tttatatatt atatttat atactatata   300 tatttatata tattatatat ttatatatta tatataattta tatatattat atatttat   360 attatatata tttatatata ttatatattt atattttata tatttatatat  tatatttat   420 atatttatat atatttatata tttatatata atatatata tatatttat ctatatattt   480 atatattaat atatattata                                             500
```

<210> SEQ ID NO 66
<211> LENGTH: 866
<212> TYPE: DNA
<213> ORGANISM: Homo sapiens
<220> FEATURE:

<221> NAME/KEY: misc_binding
<222> LOCATION: (1)..(866)
<223> OTHER INFORMATION: MAR of chromosome 1 genomic contig; 409429..
      410294

<400> SEQUENCE: 66

```
atatatataa tatattatat atattatata ttatatatat aatacatata ttatatatat    60
aatatataat acatatatta tatatattat atttatata taatatataa tacatatatt   120
atatataata tataatatat aatatattat ataatataat tatataatta taaatataaa   180
tataatatat aatattatat aattatataa tatataataat tatattatat attataaata   240
ttatataata tatatattac aaatatatat tatatatatt ataaatatta tataacatat    300
atattatata atatatataa tataatatat ataaaaaat aaatatata agatatatat     360
aatatatgat atatatgata tataatatat gatatatatg atatatataa tatatgatat    420
atatgatata tatgatatat ataatatatg atatatatga tatatatgat atatgatata    480
tatgatatat gatatatatg atatatatga tatatgatat atatgatata tatgatatat    540
gatatatatg atatatatga tatatgatat gatatatata atatgatata tgatatatat    600
aatatatgat atatatgata tatgatatgt aatatatatg atatattata tataaatatat   660
aatatataca taatatataa tataatatat ataaatatata taatatgtga tatatataat   720
atatgatata tgatatatga tatatattat aaatatata taatatatat tatatataat    780
atatattata taatatatat aatatatatt atatataata tataagatat aagatataat   840
atatataata tataatatat ataata                                       866
```

<210> SEQ ID NO 67
<211> LENGTH: 335
<212> TYPE: DNA
<213> ORGANISM: Homo sapiens
<220> FEATURE:
<221> NAME/KEY: misc_binding
<222> LOCATION: (1)..(335)
<223> OTHER INFORMATION: MAR of chromosome 1 genomic contig; 614754..
      615088

<400> SEQUENCE: 67

```
acccaatata tgtgtatata tgtatgtata tatacatata catacataca tatatgtaca    60
tacatatata catacataca tatatatgta catacatata tacatacata catatataca   120
tataacatat atacacacat atatacagat atacatatat acatacatat atacatataa   180
catatataca tacatatata catataacac atacatacat acatatatac atacaacata   240
tatacataca tatatacata tgtatacata catatatgta tacatatatg tacatatata   300
tgtatacata tatgtatata tatattgtta tatat                             335
```

<210> SEQ ID NO 68
<211> LENGTH: 455
<212> TYPE: DNA
<213> ORGANISM: Homo sapiens
<220> FEATURE:
<221> NAME/KEY: misc_binding
<222> LOCATION: (1)..(455)
<223> OTHER INFORMATION: MAR of chromosome 1 genomic contig; 1299520..
      1299974

<400> SEQUENCE: 68

```
ggatatatat attattagtt gttatattat tatatattat atatattatt atatataata    60
tattatatca tatatattat tatatataat atattatatc atatatatta ttatataata   120
```

```
tattatatca tatatattat tatatataat atatattata tatattatta tatataatat      180
atattatata tattattatg taaatatat atattatata ttatttatat atatataaat       240
tatataataa tataaatta attatacata tatacatata taagtataca tataatatat       300
ttatatagta tatataaata tatatacaat atatttatat attatatatt atatataaat     360
atatacaata tatttatatc atatatttta tatatgatac atataatata tattatatat     420
gatatataat atatatcata tatgatatat aacat                                 455

<210> SEQ ID NO 69
<211> LENGTH: 404
<212> TYPE: DNA
<213> ORGANISM: Homo sapiens
<220> FEATURE:
<221> NAME/KEY: misc_binding
<222> LOCATION: (1)..(404)
<223> OTHER INFORMATION: MAR of chromosome 1 genomic contig; 1970778..
      1971181

<400> SEQUENCE: 69
atatataata tgtataatat ataatatata tcatatattg ttctatgtat attacatata      60
atatgcatta tatattatat attgcatata atatgcatta tatattatat attgcatata    120
atatgcatta tatattatat attgcatata atatgcatta tatattatat attgcatata    180
atatgcatta tatattatat attgcatata atatgcatta tatattatat attgcatata    240
atatgcatta tatattatat aatatataca catataaaat ataaattta tatatattta     300 tatatattta catttattat atatttatta tatataaata tatttttata tattacttat    360
atattatata taatatatat aatatatata ttatatataa tata                      404

<210> SEQ ID NO 70
<211> LENGTH: 605
<212> TYPE: DNA
<213> ORGANISM: Homo sapiens
<220> FEATURE:
<221> NAME/KEY: misc_binding
<222> LOCATION: (1)..(605)
<223> OTHER INFORMATION: MAR of chromosome 1 genomic contig; 3562918..
      3563522

<400> SEQUENCE: 70
tatatatata aaatacatat atattatata tattatatat aatacatata ttatatatta     60
tatataatac acgtatataa tatataatat ataatacata taatatatat gatatataat    120
acatataata tatatgatat ataatacata taatatatat atgatatata atacatatat    180
aatatatatt atatataata catatataat atatattata taatacat atataatata    240 tattatatat aatacatata taatatatat tatatataat acatatataa tatatattat   300
ataatacata taatatatat attatataat acatgtatat aatatatatt atatataata    360
catatatatt ataataaca tgtatataat atatattata taatacat atattattata     420 tattatatat taatatattt ataaatagt aatatataat attaatatat tatatatatt    480
aatattatat ataatacata tattatatat aatataaata tataatac atataataata    540 cacatattat atataataca tatattatat ataatatata tattatatat aatatatg     600 taata                                                                 605

<210> SEQ ID NO 71
<211> LENGTH: 317
<212> TYPE: DNA
<213> ORGANISM: Homo sapiens
```

```
<220> FEATURE:
<221> NAME/KEY: misc_binding
<222> LOCATION: (1)..(317)
<223> OTHER INFORMATION: MAR of chromosome 1 genomic contig; 189743..
      190059

<400> SEQUENCE: 71 tatttttat  atttatatat  tatatatatt  tttatgtga  atatattata  tataaaatta     60
tataatttta  ctacatataa  tatataaaat  tatataattt  tactacatat  aatatataaa    120
attatataat  tttactatat  ataatatata  aaattatata  attttatata  taatatatat    180
tataatatat  attatatgca  atatatatta  tatattatat  ataatatata  tgtatatttt    240
tgtatataaa  atatataata  tataatatat  ttatagacaa  taatatataa  tataatatat    300
aaaattttat  atataaa                                                      317

<210> SEQ ID NO 72
<211> LENGTH: 522
<212> TYPE: DNA
<213> ORGANISM: Homo sapiens
<220> FEATURE:
<221> NAME/KEY: misc_binding
<222> LOCATION: (1)..(522)
<223> OTHER INFORMATION: MAR of chromosome 1 genomic contig; 229111..
      229632

<400> SEQUENCE: 72
gatatatata  tttatatata  taaaagatat  atattattta  tatataaaga  tatatattta     60
tatatataaa  agatatatat  tatttatata  taaaaagat   atatatttat  atatatgata    120
tatattattt  atatatataa  aagatatata  tttatatata  tgatatatat  tatttatata    180
taaaagatat  ataaaaga    tatatattat  ttatatatat  aaaagatata  tatataaaag    240
atatatatta  tttatatata  taaatgatat  atattattta  tatataaaag  atatatatta    300
tttatatata  aaagatatat  attatttata  tatataaaag  atacatatat  aaaagatata    360
tatttatata  taaaagatat  atatatttat  atataaaaga  tacatatatt  tatatatata    420
aaagatatat  atatttttat  atataaaata  tatattatat  atataaaaga  tatatataaa    480
tatatatatc  ttttatatat  aaaagatata  tataaatata  ta                      522

<210> SEQ ID NO 73
<211> LENGTH: 1110
<212> TYPE: DNA
<213> ORGANISM: Homo sapiens
<220> FEATURE:
<221> NAME/KEY: misc_binding
<222> LOCATION: (1)..(1110)
<223> OTHER INFORMATION: MAR of chromosome 1 genomic contig; 1138030..
      1139139

<400> SEQUENCE: 73
tatgtatgta  tacataatat  attatatatg  tatattatgt  atacataata  tattatatat     60
gtatattatg  tatacataat  atattatata  tgtatattat  gtatacataa  tatattatat    120
attatatgta  tattatgtat  acataatata  ttatatatta  tatgtatatt  atgtatacat    180
aatatatatt  atattatatg  tatattatgt  atacataata  tattatatat  tatatgtata    240
ttatgtatac  ataatatatt  atattatata  tgtatattat  gtatacataa  tatattatat    300
attatatgta  tattatgtat  acataatata  ttatatatta  tatgtatatt  atgtatacat    360
aatatatatt  atattatatg  tatattatgt  atacataata  tattatatat  tatatgtata    420
ttatgtatac  ataatatatt  atattatata  tgtatattat  gtatacataa  tatattatat    480
```

| | |
|---|---|
| attatatgta tattatgtat acataatatt tatatattat atgtatatta tgtatacata | 540 |
| atatattata tattatatgt atattatgta tacataatat gtacacataa tatttatata | 600 |
| ttatatgtat attatgtata cataatattt atatattata tgtatattat gtatacataa | 660 |
| tatttatata ttatatgtat attatgtata cataatattt atatattata tgtatattat | 720 |
| gtatacataa tatttatata ttatatgtat attatgtata cataatatat tatatattat | 780 |
| atgtatatta tgtatacata atatattata tattatatgt atattatgta tacataatat | 840 |
| attatatatt atatgtatat tatgtataca taatatttat attatatg tatattatgt | 900 |
| atacataata tattatatat tatgtatata ttatgtatac ataatatatt atatattata | 960 |
| tgtatattat gtatacataa tatattatat attatatatg tatattatgt atacataata | 1020 |
| tattatatat tatatgtata tattatgtat tatattatat attatgtata ttatagatta | 1080 |
| tgtatgcata cataatatgt attgtatatt | 1110 |

<210> SEQ ID NO 74
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig; 2863407..
      2863927

<400> SEQUENCE: 74

| | |
|---|---|
| aatatatata aatatataaa tatatataaa tatatataca tataaatata taaatatata | 60 |
| tatgtaaata tatgtaaata tatgtaaata tatgtatatg tatatatatg taaatgtatg | 120 |
| taaatatata taaatatatg taaatatata taaatatacg taaatatata aatatatata | 180 |
| actatatata aatatatata aatatataaa tataaaatata taaatatata taaatatata | 240 |
| taaataaata catataaaata tataaataaa tacatataaa tatatataaa tatataaaaa | 300 |
| tatatataaa tatatatata aatatataaa catataaaata tataaaata tatataaaata | 360 |
| tataaataca taaaatatat aaatatatat aaatatataa atatatataa atatagataa | 420 |
| atatagataa atatatataaat atataaat ataaaatat agataaatat ataaatatat | 480 |
| aaatataaat ataaaaaat atataaat atataaaaat a | 521 |

<210> SEQ ID NO 75
<211> LENGTH: 560
<212> TYPE: DNA
<213> ORGANISM: Homo sapiens
<220> FEATURE:
<221> NAME/KEY: misc_binding
<222> LOCATION: (1)..(560)
<223> OTHER INFORMATION: MAR of chromosome 1 genomic contig; 5712303..
      5712869

<400> SEQUENCE: 75

| | |
|---|---|
| atataattat atatatatta tatattatat ataattatat attatatata atgtataatt | 60 |
| atatattata tataatatat ataaatatat atattttta taaaatatata ttatatattt | 120 |
| atatattata tataaattta tatatataaa tttatatata ttatatatat ttatatatta | 180 |
| tatattgtat atatttatat attacatatt gtatatattt atatatataa tattatatat | 240 |
| ttatatatta tatattatat atttatatat tatatattat atatatttat atattatata | 300 |
| taaattattt atatataata tataaatata tattatataa tataaatttg tatatataat | 360 |

```
atatatttat attatatata aaatatttat attatatata aaatataata taaatatata    420 catataaat atatattata tatttataat tatatattat ataaataca tataatatat      480 aatatataat acatatatat catatatgaa atatatatca tatattatac atattatata    540
taacatatat attatatatc                                                560
```

<210> SEQ ID NO 76
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 1 genomic contig; 8578812..
   8579290

<400> SEQUENCE: 76

```
tatggtatac atatagtata tatggggtac atatatggta tatatatggg ttatatatat    60
gatatatatt atatatgtat atggtatata tatggtatat atattataca tgcatatggt   120
atgtatatgg tatatatatg atatatacat atggtgtata tatatgttat atgatata     180 tataaggtat atatatggta tatataaggt atatatagta tatatatggt atatataagg   240
tatatattgt atatatatgg tatatataag gtatatatat tgtatatatg gtatatatat   300
ggtttatata tatggtgtgt atatatggtg tttatataca cactttatat actatatatt   360
atatacacac tatatataat atatattata tatagttaaa tatatggtat atgcaattag   420
atatatggta tatgtaatta tatatatggt atatagatgg tgtatatatg gtatatata    479
```

<210> SEQ ID NO 77
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 1 genomic contig; 8579294..
   8579770

<400> SEQUENCE: 77

```
tatagtatat atacacacta taggtaatat actacatatt atatacacac tataaataaa    60
atatataata tataaatttt tctatatagt atatattata tattgtatat actatatata   120
atatatacta tagacagtag atactttata tactatagac agtatatact atatactgta   180
tacactatag acagtatata ctatatactg tatacagtat atgtagtgta tatgtagtgt   240
atataatata tagtatatat tatctatact atacagta tatatagtgt atacataata    300
tatattatat attatatata ctatatacag tatacatagt gtatatgtag tgtataaat    360 atataatgtg tatataaaat atatatacta tatataaata atattatata taatatatac   420
actatatata ctatagatac actatatatt cactatatat actatatata ctatata      477
```

<210> SEQ ID NO 78
<211> LENGTH: 331
<212> TYPE: DNA
<213> ORGANISM: Homo sapiens
<220> FEATURE:
<221> NAME/KEY: misc_binding
<222> LOCATION: (1)..(331)
<223> OTHER INFORMATION: MAR of chromosome 1 genomic contig; 8580024..
   8580354

<400> SEQUENCE: 78

```
actatatgtt atatacataa gatatagtat ataccatata ttatatacat tatatatagt    60
gtatactata tataatgtat ataatatata gtatatatac actatatata ctatgtatat   120
atacactata tatactatgt atatatacac tatatatact atgtatatat acactatata   180
tactatgtat atacacacta tatatactat gtatatatac actatatata ctatgtatat   240
atacactata tatactatgt atatatacac tatatatact atgtatatat agtgtatata   300
tactgtatat gttatagtgt atatatagta t                                   331

<210> SEQ ID NO 79
<211> LENGTH: 410
<212> TYPE: DNA
<213> ORGANISM: Homo sapiens
<220> FEATURE:
<221> NAME/KEY: misc_binding
<222> LOCATION: (1)..(410)
<223> OTHER INFORMATION: MAR of chromosome 1 genomic contig; 8580705..
      8581114

<400> SEQUENCE: 79
tatagtctat attatataca gtctatataa tatatagtat atactatata tactttttcct   60 cattctgact atatactata tatatactat atatagtata tgtagtgtat atatacacca  120
tatatactat atatagtata cataccatat atagtatact atacatacca tatatagtat  180
acataccgta tatagtatac tatacttacc atatatagta tacatactat ataatata    240 tctggtgtat atatacacta tatatactat atatactata tagtatatat gtacactatt   300
tatagtattt atagtatata tactgtatat atagtatgta gtatatatac tatatattat   360
gtagactata tataatatag actatgtgta gagtatatat actatatata              410

<210> SEQ ID NO 80
<211> LENGTH: 433
<212> TYPE: DNA
<213> ORGANISM: Homo sapiens
<220> FEATURE:
<221> NAME/KEY: misc_binding
<222> LOCATION: (1)..(433)
<223> OTHER INFORMATION: MAR of chromosome 1 genomic contig; 12979167..
      12979599

<400> SEQUENCE: 80
atatataata tatatgtc ctatatataaa aatatatcat atatataaat atatatgata    60
tattttatat attaaatata taattatata taaatatata tttatatata aatatattat  120
ttcaatatat ataaatatat ttaaatatat ttaaatagaa tattaaatat ataaatatat  180
aattatattt aatatataaa tatatattaa atatataatt atatttaata tatataaata  240
tatattaaat ataaattat atatttatat atttattata tataaatata tatttgttct   300
aaataaatat atattctaaa tatataatat tttatatattat ataatatat atataaaata  360 tataataaat atataaatata taaataaata aatatttatt ataaaataca taaaatattt   420
aaatatatat taa                                                       433

<210> SEQ ID NO 81
<211> LENGTH: 385
<212> TYPE: DNA
<213> ORGANISM: Homo sapiens
<220> FEATURE:
<221> NAME/KEY: misc_binding
<222> LOCATION: (1)..(385)
<223> OTHER INFORMATION: MAR of chromosome 1 genomic contig; 16336644..
      16337028
```

```
<400> SEQUENCE: 81
tttatataaa tatctatata aataaatata taaatatata aatataaata tatataaata      60
tataaataaa tatataaata tatataaata taaatatata tataactatg aatttatatt     120
tatataaata tatatctata tgaatataaa tatatattta taaaatata aatatatata      180 taaatatata tatttatata gatataaata tatatataaa tatatatatt tatatagata     240
taaatatata tctatatatg aatatatatc tataggaata taaatatata tctatataaa     300
tataaatata taagtatata aatatatata aatatatatc tatataaata taaatatata     360
tataaatata aatatatata taaat                                           385

<210> SEQ ID NO 82
<211> LENGTH: 363
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 1 genomic contig; 20624448..
      20624810

<400> SEQUENCE: 82
tatatatata gttatatata tatttatata tatagttata tatatatttt tatatagtta      60
tatatatagt tatatatata gttatatata tagttatata tatatagtta tatatatagt     120
tatatatata tagttatata tatagttata tatatagtta tatatatagt tatatatata     180
tagttatata tatagttata tatatatagt tatatatata gttatatata tatagttata     240
tatatagtta tatatatagt tatatatata gttatatata tagttatata tatatagtta     300
tatatatata gttatatata tagttatata tatagttata tatatatata gttatatata     360
tag                                                                   363

<210> SEQ ID NO 83
<211> LENGTH: 310
<212> TYPE: DNA
<213> ORGANISM: Homo sapiens
<220> FEATURE:
<221> NAME/KEY: misc_binding
<222> LOCATION: (1)..(310)
<223> OTHER INFORMATION: MAR of chromosome 1 genomic contig; 566025..
      566334

<400> SEQUENCE: 83
tatatataat atatattgta tatattatat attgtatata taatatatat tgtatatatt      60
atatattgta tatataatat atattgtata tattatatat tgtatatata atatatatat     120
tgtatatatt atatattgta tatataatat atatattgta tatattatat attgtatata     180
taatatatat attgtatata ttatatattg tatatataat atatatattg tatatattat     240
atattgtata tataatatat atattgtata tattatatat agtatatatt atatatagta     300
tatataatat                                                            310

<210> SEQ ID NO 84
<211> LENGTH: 1236
<212> TYPE: DNA
<213> ORGANISM: Homo sapiens
<220> FEATURE:
<221> NAME/KEY: misc_binding
<222> LOCATION: (1)..(1236)
<223> OTHER INFORMATION: MAR of chromosome 1 genomic contig; 1171429..
      1172664
```

```
<400> SEQUENCE: 84
aaagtattat atgtattata tgtatatgta ttatatatta catatgtatt atatataata     60
tatattatat attattatat attatatatt atatattatt atttatataa tgtattatat    120
attatatagt atatatagta tatataatgt attatatatt atagtatata tatagtatat    180
ataatgtatt atatatagta tatataatgt attatatagt atatatacta tataatgtat    240
tacatattat gtatagtata tgtaatgtat tatatattat atagtatatg taatgtatta    300
tatgtattat atagtatata ttatatatga tgtattattt agtatatata atatatatga    360
tgtattatat aacatatata atatatatga tgtattatat agcatgtata gtatatatga    420
tgtattatat agcatgtata gtatatatga tgtattatat atagcatgta tagtatatat    480
gatgtattat atatagcatg tatagtatat atgatgtatt atatatagca tgtatagtat    540
atatgatgta ttatatatag catgtatagt atatgatg tattatatat agcatgtata    600
gtatatatga tgtattatat atagcatgta tagtatatat gatgtattat atatagcatg    660
tatagtatat atgatgtatt atatatagca tgtatagtat atatgatgta ttatatatag    720
catgtatagt atatgatg tattatatat agcatgtata gtatatatga tgtattatat    780
attatatatg gtatatatga tgtattatat attatatatg gtatatatga tgtattatat    840
attatatatg gtatatatga tgtattatat attatatata atatatga tgtattatat    900 attatatata atatatga tgtattatat atgatgtatt atatataata tatatgatgt    960
attatatata ttattatcta ttatatacga tgtattatat gcaagttatt atgtataata   1020
tataatgtat tatatattat ataatgtata atatataaat ataaatatat ataattatgt   1080
ataaatatag aaatatatac attatacatt atatacatta taatgtataa tatataaata   1140
tattatatat aaatgtatac attatatata aatatattat atacattata tataaaatat   1200
gtatatagtt attataccctt atatatacta aacagt                            1236

<210> SEQ ID NO 85
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig; 1925173..
      1925481

<400> SEQUENCE: 85
atatatttat ataaatatat tttatataaa tatatattat ataatattat aatatatgtt     60
atattatata tattttatac aatatataat atatattata tatattttat acaatatata    120
atatatatta tatatatttt ataataatata taatatatat tatatatatt ttatacaata    180
tataatatat attatatatt ataatatata tattatatat attttatata atatataata    240 tatatttta acaatatata atgtatatca ttatattata taatgtatat catattatat    300
aatgtatat                                                             309

<210> SEQ ID NO 86
<211> LENGTH: 312
<212> TYPE: DNA
<213> ORGANISM: Homo sapiens
<220> FEATURE:
<221> NAME/KEY: misc_binding
<222> LOCATION: (1)..(312)
<223> OTHER INFORMATION: MAR of chromosome 1 genomic contig; 4396756..
      4397067
```

<400> SEQUENCE: 86

```
cacagtgtat atatagtata tatactgtat atatactgtg tatatacact gtatatacac    60
agtgtatata cagtatatat actatatata cactgtgtat atatagtata tataaattct   120
aggaatatat atactatata tatactatat atataaattc taggaatata tacacactat   180
atatacacta tatatacaca tatatacact atatatatta tacacatata ttatatatat   240
acactatata tacacgagat ataaacata tacactatat actatacata acatatatac   300
tatatatact at                                                       312
```

<210> SEQ ID NO 87
<211> LENGTH: 398
<212> TYPE: DNA
<213> ORGANISM: Homo sapiens
<220> FEATURE:
<221> NAME/KEY: misc_binding
<222> LOCATION: (1)..(398)
<223> OTHER INFORMATION: MAR of chromosome 1 genomic contig; 56057..
      56454

<400> SEQUENCE: 87

```
atatatatta catattatat ataaatata tattatataa tatatattat attatataat     60 ataaatata aatataat aaattatatt ataaatata taatataat ataatataa        120 ttatataaat ataatatata ttttattata taatatata tatattatat aaatataata   180 taaaattat ataatataat atatatta taatataata tattttatta taaaatata      240 tattatatta taatatat attttattat ataatata ttatatatt atagaatata      300 atatatattt tattataaa tatatattat ataaatata ttatatttat ataacata      360 tattattata taaaatatgt ataatatata ttatataa                          398
```

<210> SEQ ID NO 88
<211> LENGTH: 391
<212> TYPE: DNA
<213> ORGANISM: Homo sapiens
<220> FEATURE:
<221> NAME/KEY: misc_binding
<222> LOCATION: (1)..(391)
<223> OTHER INFORMATION: MAR of chromosome 1 genomic contig; 56984..
      57374

<400> SEQUENCE: 88

```
tactataata catattatat ataatattat atactatata ttactatatt attatattat    60
atataattaa actatattat agtatataat ataatatata tactatatgt aatattacta   120
tgatactgat attatattat ataaattaa attatattat attaatatat aaattatata   180
taatacataa tatataaatt atattatatt atttatatat aatgtatgcc ataatattta   240
tatataatgc attatatata atttatatat aatgcattaa ataaaatta tatataatgc   300 attatatata attatatata atgcattata taatttat atttaatata taaatttata   360
tttaatatat ttatatatta tatataataa a                                  391
```

<210> SEQ ID NO 89
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 1 genomic contig; 469547..
      469855

```
<400> SEQUENCE: 89
atatatatgt aatatatatg ttatatatgt aatatatatg ttatgttata tatgttatat    60
atatgttata tataatatat atgttatata tacgttatat gttatatata tgttatatat   120
aatatatgtt atatatacgt tatatgttat atatgttata tataatatat gttatatata   180
atatatgtta tatatgttat ataatatata tgttatatat attatatata atatatgtta   240
tatatattat ataaatatata taatatatgt gatatataat ataaaatata tgtgatatat   300
attatatat                                                            309

<210> SEQ ID NO 90
<211> LENGTH: 441
<212> TYPE: DNA
<213> ORGANISM: Homo sapiens
<220> FEATURE:
<221> NAME/KEY: misc_binding
<222> LOCATION: (1)..(441)
<223> OTHER INFORMATION: MAR of chromosome 1 genomic contig; 546190..
      546630

<400> SEQUENCE: 90
atacacaaca tatgtgtata tatatagtat atatacacaa catatgtgta tatatatagt    60
atatatacac aatatatgtg tatatatata gtatatatac acaatatatg tgtatatata   120 gtataaaatat atactatata tagtatatat agtataaata tatactatat atagtatata   180
catagtataa atatatacta tatatagtat atacatagta taaatatata ctatatatag   240
tatatacata gtataaatat atactatata tagtatatac atagtataaa tatatactat   300
atatagtata tacatagtat aaatatatac tatatatagt atatacatag taaaatata   360 tactatatat agtatataca tagtataaat atatactata tatagtatat acatagtata   420
aatatatact atatatagta t                                              441

<210> SEQ ID NO 91
<211> LENGTH: 1367
<212> TYPE: DNA
<213> ORGANISM: Homo sapiens
<220> FEATURE:
<221> NAME/KEY: misc_binding
<222> LOCATION: (1)..(1367)
<223> OTHER INFORMATION: MAR of chromosome 1 genomic contig; 124643..
      126009

<400> SEQUENCE: 91
atatttatat gatatataat atatataata ttatatataa tattatatat gatatataac    60
attatataat attatatatg atatatatta tatatattat atatgatata taatatatat   120
aatatttatt atgatattat atatcatata taatatataa aatattatat atgatatata   180
atatatataa tattatatat attatatata ttatatatca tatataaatat tctaaatata   240 taatatttata tgatatataa gattatatac attatatata atatataata ttatatga    300 tatataaatat tatatacatt atatataata taatgtat ataatattat atattatata   360
tttatattat atacaatgta taatattata tatcatata tatttatat tatatacaat    420 gtatataata ttatatatca tatataatat tatatacaat gtatataata tatattatat   480
atatttatat tatatacaat gtatataata tattatatta tatttatat tatatacaat    540 gtatataata tatattatat atatttatat tatatacaat gtatacaata ttatatatta   600
tatattatat atttatatta tatacaatgt atatattata tattatatat ttatattata   660
```

```
tacaatgtat atattatata ttatatattt atattatata caatgtatat attatatatt    720
atatatttat attatataca atgtatatat tatatattat atatttatat tatatacaat    780
gtatatatta tatattatat atttatatta tatataatgt atgtaatatt atatattata    840
tatttatatt atatataatg tatgtaatat tatatattat atatttatat tatatataat    900
gtatgtaata ttatatatta tatatttata ttatatataa tgtatgtaat attatatatt    960
atatatttat attatatata atgtatgtaa tattatatat tatatattta tattatatat   1020
aatgtatgta atattatata ttatatattt attatatata taatgtatgt aatattatat   1080
attatatatt tatattatat ataatgtatg taatattata tattatatat ttatattata   1140
tataatgtat gtaatattat atttatata tttatattat ataatgtata tgtaatatta   1200
tatattatat atttatatta tatataatgt atataatatt atattatata tatttatatt   1260
gtatataata ttatatatta tatatttata ttgtatataa tatatattat atatttatat   1320
tgtatataat attatatatt atatatttat attatatata atgtata              1367

<210> SEQ ID NO 92
<211> LENGTH: 458
<212> TYPE: DNA
<213> ORGANISM: Homo sapiens
<220> FEATURE:
<221> NAME/KEY: misc_binding
<222> LOCATION: (1)..(458)
<223> OTHER INFORMATION: MAR of chromosome 1 genomic contig; 58908..
      59365

<400> SEQUENCE: 92
tatatgatat atatgatata tatgggatat atatgatata tatgatatat atggtatata     60
tatgatatat agtatatatg atatatatgg tatatatatg atatatagta tatatgatat    120
atatggtata tatgatatat agtatatatg atatatatgg tatatatggt atatatatga    180
tatatgatat atatgatata tatgatatat gatatatatg atatatatga tatatatggt    240
atatatgata tatatggtat atatggtata tatatgatat atatgatata tatggtatat    300
atatgatata tatgatatat atggtatata tatgatatat atgatatata tggtatatat    360
atgatatata tgatatatat ggtatatata tgatatatat gatatatatc atatatatgg    420
tatatatatg atatatatga tatatatcat atatatgg                           458

<210> SEQ ID NO 93
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 1 genomic contig; 306867..
      307196

<400> SEQUENCE: 93
ataatatata aatatatatg atatatatct atatatatca tatataaata tatatgatat     60
atatctatat atatcatata taaatatata tgatatataa atatatatga tatatatcta    120
tatatatcat atataaatat atatgatata taaatatata tgatatatat ctatatatat    180
catatataaa tatatatgat atatctat atcatatata taaatatata tgatatatat     240
ctatatatat catatataaa tatatatgat atctatctat atatcatata taaaatatata    300 tatgatatct atctatatat atcatatata                                    330
```

```
<210> SEQ ID NO 94
<211> LENGTH: 353
<212> TYPE: DNA
<213> ORGANISM: Homo sapiens
<220> FEATURE:
<221> NAME/KEY: misc_binding
<222> LOCATION: (1)..(353)
<223> OTHER INFORMATION: MAR of chromosome 1 genomic contig; 636899..
      637251

<400> SEQUENCE: 94
tatgtataca tatacacata tacgtatata tatacatata tacacatata cgtatatata      60
tacgtataca tacatatgta tatgtatacg tatacacaca tatgtatatg tatacgtata     120
cacacatata cgtatatatg tatacgtata cacacatata cgtatatgta tacatatata     180
tgtgtacata tacgtatata cgtatatgta tacatatata cgtttatgta tatatacgta     240
tatacgtata tatgtatatg tatacatata tacatatatg tgtatatacg tatatacgta     300
tatgtgtata tatacaatat acatacatgc acatatatgt gtatatgcac ata            353

<210> SEQ ID NO 95
<211> LENGTH: 345
<212> TYPE: DNA
<213> ORGANISM: Homo sapiens
<220> FEATURE:
<221> NAME/KEY: misc_binding
<222> LOCATION: (1)..(345)
<223> OTHER INFORMATION: MAR of chromosome 1 genomic contig; 1435510..
      1435854

<400> SEQUENCE: 95
atcatatata ttatatatca tatatatgat atataaaaat tatatatcat atatatgata      60
tataaaaatt atatatatca tatataatat atataatata ttatatatat aaattatata     120
taatatatat aaattatata tatcatatat atgatatata atttatatat catatatatg     180
atatatataa tatattattt atatataata tattatatat tatataatat gtaaatatata    240 ttatatatta catattatat tatttataaa taatattta taatatatat aatattatat      300
aatatagaat attatatatt atatattaca tattatataa tatat                     345

<210> SEQ ID NO 96
<211> LENGTH: 521
<212> TYPE: DNA
<213> ORGANISM: Homo sapiens
<220> FEATURE:
<221> NAME/KEY: misc_binding
<222> LOCATION: (1)..(521)
<223> OTHER INFORMATION: MAR of chromosome 1 genomic contig; 39695..
      40215

<400> SEQUENCE: 96
tatatatata atagatatta tatatctatt atatatctat tatatatata atagatatta      60
tatatctatt atatatataa tagatattat atatctatta tatatataat agatattata     120
tatctattat atataatata tatctattat atattatata tctattatat ataatatata     180
tctattatat atattatata tctattatat ataataaga tattatatat ctattatata      240
taatatatat ctattatata ttatatatct attatatata tgtatctatt atatatatta     300
tgtatctatt atataaata tatatctatt atatatatat tatataat atatatta         360 tatattatat atctattata taaatatat atctattata tatttatat atctattata       420 tatattatat atctattata taaatatat atctattata tatttatat atctattata       480 tataatatat attatatata tattatatat tgtatatcta t                         521
```

<210> SEQ ID NO 97
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 1 genomic contig; 1286007..
      1286490

<400> SEQUENCE: 97

```
atatcatata tattatatat catatatatg atatataaaa attatatatc atatatatga      60
tatatataaa ttatatatat catatataat atatataata tattatatat ataaattata     120
tataatatta tatataaatt atatatcaca tatatgacat ataaattata tatcacatat     180
atgatatata atttatatat cacatatatg atatataatt tatatatcat atatatgata     240
tataatttat atatcatata tatgatatat aatttatata tcatatatat gatatatata     300
atatattatt tatatataat atattatata ttatataata tgtaatatat attatatatt     360
atataatatg taatatatat tatatattac atatattatt atttataaat aatatttttat    420 aatatatata atattatata atagaata ttatatatta tatattacat attatataat      480
atat                                                                  484
```

<210> SEQ ID NO 98
<211> LENGTH: 244
<212> TYPE: DNA
<213> ORGANISM: Homo sapiens
<220> FEATURE:
<221> NAME/KEY: misc_binding
<222> LOCATION: (1)..(244)
<223> OTHER INFORMATION: MAR of chromosome 1 genomic contig; 73556..
      73879

<400> SEQUENCE: 98

```
attatatatt atattatata atatataata atattatata attatatatt acattatata     60
atatataata atattatata ataatatata attatataat ataatataat attatataat    120
attatataat attatataat atataaatat ataatataat atattatatt ataaatagt     180 atatatttata ttatataata tatgttatta tattatataa tataaactat tatataatat   240
aata                                                                 244
```

<210> SEQ ID NO 99
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 1 genomic contig; 179038..
      179500

<400> SEQUENCE: 99

```
tacaatatat tttctattat atatattttg tattatatat aatatacaat atattttcta     60
ttatatataa tatattttgt attatatata ttacaatata ttttgtatta tataatatat    120
aatacaatat aatatattgt attatataat atataatact atataaatata ttgtattata   180 tattatatat aatactatat aatatatttt attatatatt atatataata ctatataata   240
tattttatta tatattatat ataatacaat atataatata ttgtattata atacaatgta    300
ttataatgta ttatatataa tatataatac aatatataat attatatata tttatatata    360
```

```
tatatatttt gtattatata ttttgtatta tatatatttt gtattatata tttatatttt    420
atattataat tatgttttgc attatatatt tcatattata tat                      463

<210> SEQ ID NO 100
<211> LENGTH: 390
<212> TYPE: DNA
<213> ORGANISM: Homo sapiens
<220> FEATURE:
<221> NAME/KEY: misc_binding
<222> LOCATION: (1)..(390)
<223> OTHER INFORMATION: MAR of chromosome 1 genomic contig; 55617..
      56006

<400> SEQUENCE: 100
tgtataatat atatacttta tatataaatat atatacttta tatatatact atatactaat    60
atatataata tatactatat ataatatata ctaatatata taatatatac actatatata    120
atatatacta atatatatta tatatacttt ataatatata tactaatata tataatatat    180
atactttata tataatatat actaaatatat ataatgtata tactttatat ataatatata    240
ctaatatata atatatatac tttatatata atatatacta atatatatta tatatacttt    300
atatataaaa tatatactta tatattatat atgcttatat ataatatata cactaatata    360
taatatatat actttatata ttatattta                                      390

<210> SEQ ID NO 101
<211> LENGTH: 582
<212> TYPE: DNA
<213> ORGANISM: Homo sapiens
<220> FEATURE:
<221> NAME/KEY: misc_binding
<222> LOCATION: (1)..(582)
<223> OTHER INFORMATION: MAR of chromosome 2 genomic contig; 1157405..
      1157986

<400> SEQUENCE: 101
tgtatatgta tatatacaca tacgcacata tatgtatatg tatatataca catacgcaca    60
tatatgtata tgtatatata cacatacgca catatatgta tatgtatatg tatatgtata    120
tatacacata tacacatata tgtatatgta tatatacaca tatacacata tatgtatatg    180
tatatataca catatacaca tatatgtata tgtatatata cacatacaca tatatgtata    240
tgtatatgta tatatacaca tacacatata tgtatatgta tatgtatata tacacatata    300
cacatatata catatatgta tacatatatg tgtatatata tacacatata tatacatata    360
tgtatacata tatgtgtata tatacacata tatatacata tatacatata catatatatg    420
tgtatgtata tatacacata tatacatata tgtatatgtg tatatatatt agacagatat    480
atatgtacat atatcatatat atgtatatgt atatgtatat gtatatgtat atgtatatgt    540
atatgcatat ataatataca tatacatata tgtatatgta ta                       582

<210> SEQ ID NO 102
<211> LENGTH: 322
<212> TYPE: DNA
<213> ORGANISM: Homo sapiens
<220> FEATURE:
<221> NAME/KEY: misc_binding
<222> LOCATION: (1)..(322)
<223> OTHER INFORMATION: MAR of chromosome 2 genomic contig; 1858638..
      1858959

<400> SEQUENCE: 102
acaccatata tacaccatat atatacatac catatatata ccatatatat acataccata    60
```

```
tatataccat atatatacat accatatata caccatatat atacatacca tatatataca      120
ccatatatat acataccata tatataccat atatatacat accatatata taccatatat      180
atacatacca tatatataca ccatatatat acataccata tatatacacc atatatatac      240
ataccatata tataccatat atacaccata tatatacacc atatatacac accatatata      300
ccatatatat acaccatata ta                                               322
```

<210> SEQ ID NO 103
<211> LENGTH: 914
<212> TYPE: DNA
<213> ORGANISM: Homo sapiens
<220> FEATURE:
<221> NAME/KEY: misc_binding
<222> LOCATION: (1)..(914)
<223> OTHER INFORMATION: MAR of chromosome 2 genomic contig; 5712196..
      5713109

<400> SEQUENCE: 103

```
aaatatatat tctatatata gaaaatatat attctatata tatagaatat atatagaata       60
tatattctat atatattcta tatatataga atatatatat aaaacatata ttctatatat      120
aaaatatata ttctatatat ataaaatata tattctatat atatagaatg tatataaaat      180
atatattcta tatatataga atgtatataa aatatatatt ctatatatat agaatgtata      240
taaaatatat attctatata tagaatgtat atataaaata tatattctat atatatagaa      300
tatatataac atatatatga aatatatata aaatatatat aaatacatat ttctatatat      360
aaatatatat aaatacatat ttctatatat aaatatatat caatacatat ttctatatat      420
aaatatatat aaatatatat tcatatatat aaaaatatat aaatatatat tcatatatat      480
aaatatatat tgaatatata ttctctatat ataaaatata taatatatat attatatata      540
taaaatatat ataaatatata ttatatatat aaaatatata taatatatat tcatatatat      600
aaattatata taaatatata ttcatatata taatatatat aaatatttat ttcatatata      660
aaatatattt aaatatatat ttctatatag aatatatatt ctatatataa aatatatata      720
taaatatatt ttctatatag aaatatatat gaaatatata gaatatatat aaatatatat      780
tatatatact atatatacaa tatatattat ataaaaata tatatacaat atatattcta      840
tatattaata tatagaatat atattaacat atatttcaat atattaatat atgaaatata      900
tataaatatt tcat                                                        914
```

<210> SEQ ID NO 104
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig; 5713613..
      5713982

<400> SEQUENCE: 104

```
tatttcatat ataatatata tataaaatat atatttcata tacataatat atataatata       60
aataaaatat atatttcata tatataatat atataatata tataaaacat atatttcata      120
tataatatat ataaactata tatttcatat ataatatata taaactatat atttcatata      180
cataatatat ataatatata tttcatttat attatatata taatatatat ttcatatata      240
taatatataa aatagatata aatatatata aatatatatt tcatatataa tatatataaa      300
```

```
atatatatta atatatattt tatatataat atatatattt catatataaa tataaaaaaa    360
tatatatttc                                                           370

<210> SEQ ID NO 105
<211> LENGTH: 442
<212> TYPE: DNA
<213> ORGANISM: Homo sapiens
<220> FEATURE:
<221> NAME/KEY: misc_binding
<222> LOCATION: (1)..(442)
<223> OTHER INFORMATION: MAR of chromosome 2 genomic contig; 7481647..
      7482088

<400> SEQUENCE: 105
atataaatta tataatatgt tataataaat ataaatatat tatataacat gttatataat    60
atataacatg ttatataata taaacatgt tatataaat ataacatgtt atataatata     120
taacatgtta tataatatat tatgtaatat gttatataat atataaata ttatataaca    180 tgttatataa tataacatg ttatataaat atgttatata atatataaat atattatatt    240
atatgttata taatataaa atatattata ttatatgtta taatatatat aaatatatta    300
tattatatgt tataataat ataaatatat tatattgtat gttatataat ataaaatat    360 attatattgt atgttatata atataaaat atattatatt gtatgttata taatatataa    420
atatattata ttatatatgt ta                                             442

<210> SEQ ID NO 106
<211> LENGTH: 338
<212> TYPE: DNA
<213> ORGANISM: Homo sapiens
<220> FEATURE:
<221> NAME/KEY: misc_binding
<222> LOCATION: (1)..(338)
<223> OTHER INFORMATION: MAR of chromosome 2 genomic contig; 9594557..
      9594894

<400> SEQUENCE: 106
tatataaata tataccatat atataaaatat atatattcca tatataaata tatatattcc    60
atatatataa atatatatat tccatatata aatatatata ttccatatat ataaatatat    120 ataaaatat atatattcca tatataatat aatatata aatatatata ttcatatata     180
aatatatata tattccatat ataaaaatat atatatattc catatataaa aatatatata    240
tattccatat atataaatat atatatattc catatatata aatatatata tattccatat    300 atataaaatat atatatatt catatatata aatatata                            338

<210> SEQ ID NO 107
<211> LENGTH: 364
<212> TYPE: DNA
<213> ORGANISM: Homo sapiens
<220> FEATURE:
<221> NAME/KEY: misc_binding
<222> LOCATION: (1)..(364)
<223> OTHER INFORMATION: MAR of chromosome 2 genomic contig; 10519720..
      10520083

<400> SEQUENCE: 107
ttatatatat ttataataat atatataagc tatatatatt tatatataat atattatata     60
tattagctat atatatttat ataataatat attatatatt agctatatat atttatatat    120
aataatatat ataagctata tatttatata tattatatat tagctatata tatttatata    180
taatatatta tatattagct atatatttat atataataaa taatatatat attagctata    240
```

```
tatatttata tataataata tatataagct atatatttat atataatata ttatatatta    300
gctatatata tttatatata ataatatatt atatattagc tatatatatt tatatataat    360
atat                                                                 364

<210> SEQ ID NO 108
<211> LENGTH: 342
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig; 11481943..
      11482284

<400> SEQUENCE: 108
tacatataat atataattat atataatata tattatatat tacatatata atatatatat     60
tacatatgta atatatatat tatatatgta atatatatta tatatgtaat atatatatta    120
tatatgtaat atatattata tatatgtaat atatatatta tatatgtaat atatatatta    180
tatgtaatat atatatgtaa tatatatata atatatatgt aatatatata taatatatat    240
gtaatatata tataatatat atgtaatata tattatatat atgtaatata tatatcatat    300
atatgtaata tatatcatat atatgtaata tatatcatat at                       342

<210> SEQ ID NO 109
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig; 13499598..
      13500012

<400> SEQUENCE: 109
tatatatata tatatatata atataatata atatatatat aaatatatat aatataaatt     60
tatatatata tatttatata tacatatata aatatatatt tatatttata taaaatata    120 tataaaatata tataaaatata tatttatata tacatatata aatatatatg ttcataaaa    180 tatatatgta tatatacata tataaaatata tattatatat gtatatatat aatataatat    240
ataataataa tataatatat attatataaa tataatatat tatatataat atatataata    300
tataatatat aatatataat atataaatata tattatattat tatataatat ataaaatata    360
tattatataa tatatataca taatatatat aaataaaatat atataaagat ataaa         415

<210> SEQ ID NO 110
<211> LENGTH: 330
<212> TYPE: DNA
<213> ORGANISM: Homo sapiens
<220> FEATURE:
<221> NAME/KEY: misc_binding
<222> LOCATION: (1)..(330)
<223> OTHER INFORMATION: MAR of chromosome 2 genomic contig; 16370976..
      16371305

<400> SEQUENCE: 110
catttacata tgtatgtata agtatgtata ttcatacttt atacatacat acttataaat     60
atataagtat aatacataca tacttataaa tatataagta taatacatac atacttatac    120
atatataagt ataatacata catacttata catatataag tataatacat acatacttat    180
acatatataa gtataataca tacatactta tacatatataag tataatacat acatacttat    240
```

```
acatatataa gtataataca tacatactta tacatatata agtataatac atacttatta      300
catatgtata taagtatatt acatacttat                                       330
```

```
<210> SEQ ID NO 111
<211> LENGTH: 702
<212> TYPE: DNA
<213> ORGANISM: Homo sapiens
<220> FEATURE:
<221> NAME/KEY: misc_binding
<222> LOCATION: (1)..(702)
<223> OTHER INFORMATION: MAR of chromosome 2 genomic contig; 626641..
      627342

<400> SEQUENCE: 111
```

```
tatatataca catatacata tataatatat atacatatac atatatatta tatatacata       60
tatattacat atatcatata tacatatata ttatatatac atatatatta tatatatcat      120
atatacatat atatattata tattatatat atcatatata catatatatt atatatatta     180
tatatatcat atatacatat atattatata tattatatat acatatatat tatatatatc      240
atataaacat atatattata tatcatat atacatatat attatatata ttatatatat       300
catatataca tatatattat atatatcata taatatatat attatatata ttatatataa      360
tatatattat atatacatat atattatata tacatatata ttatatatac atatatatta      420
tatatacata tatattatat atacatatat attatatata tacatatata ttatatatac      480
atatatatta tatatacata tattatatat acatatatat tatatataca tatattatat      540
atatacatat atattatata tacatatatt atatatatac atatatatta tatatacata      600
tattatatat atacatatat attatatata catatattat atatacatat atattatata      660
tacatatata ttttatatat atataatata tattttatat at                        702
```

```
<210> SEQ ID NO 112
<211> LENGTH: 679
<212> TYPE: DNA
<213> ORGANISM: Homo sapiens
<220> FEATURE:
<221> NAME/KEY: misc_binding
<222> LOCATION: (1)..(679)
<223> OTHER INFORMATION: MAR of chromosome 2 genomic contig; 3196047..
      3196725

<400> SEQUENCE: 112
```

```
atatattata tattcatata tcataaatat atatattata tattcatata ttatatatct       60
atatatttat atattcatat attatatatc tatatattta tatattcata tattatatat      120
ctatttatat attcatatat tatatatcta tatattttat atattcgtat attatatatc      180
tatatattat atattcgtat attatatatc tatatattat gtattcatat atatctatat      240
attatatata ttcatatata ttataaatta tattcatata gtatatatct attataaatg      300
tatattcata tagtatatat ctatatatta taaatataca tatattatat atttatatat      360
tatatattca tatagatcta tatattatat atattcatat atgaatatat atattatatg      420
tatatatatt ataaatatat ttatatagta tagatattat atagtatatg catatttata      480
ttataaataa tttacatagt atatgtatat ttataaatta tatatattta catattacat      540
gtatatttat atattataaa tacatattta catattataa atatatttat atattatgaa      600
tataatttat atattattac atatttacat atatgcatag ttatatatta taaatatgca      660
tttatgtaaa tatatatttt                                                 679
```

<210> SEQ ID NO 113
<211> LENGTH: 728
<212> TYPE: DNA
<213> ORGANISM: Homo sapiens
<220> FEATURE:
<221> NAME/KEY: misc_binding
<222> LOCATION: (1)..(728)
<223> OTHER INFORMATION: MAR of chromosome 2 genomic contig; 3196778..
      3197505

<400> SEQUENCE: 113
tacataaata tatatttaca atatgtaaat atctgatatg taaatatgta tttataatat     60
ataaatatac atataatatg taaatatata aatatacata tactatgtaa atatatgtta    120
tatatacata tactatataa atatagaata taaaatata catatactat ataaatatgt    180
aatatataaa tatatactat ataaatatac atatactata taaatgtatt tataatatat    240
aaatatacat atactatata aattcatata tgaatatata atatataaat atatataata    300
tatgaatata tactcatata taaatatata tgaatatata tttataatat atagatataa    360
tatgaatata tatttataat atatagatat atattatatg aatatatatt taaatatat    420 agatatatac catatgaata tatattatac actatatgaa tatatattta taatatataa    480
atagatatat actatatgaa tatataatat atatactcta tgaatatata atatatatac    540
tatatgaata tattatatac tgtatgaata taatatat agatgtatac tatatgaata    600 taaatatat agatatatat actatatgaa tatatataat atatagatat atactatatg    660
aatatatatg atatatagat atactatata tgaatatata atatatagat atatatttat    720
gatatatg                                                             728

<210> SEQ ID NO 114
<211> LENGTH: 413
<212> TYPE: DNA
<213> ORGANISM: Homo sapiens
<220> FEATURE:
<221> NAME/KEY: misc_binding
<222> LOCATION: (1)..(413)
<223> OTHER INFORMATION: MAR of chromosome 2 genomic contig; 2560638..
      2561050

<400> SEQUENCE: 114
atataaatat atatttatat atttatatata aatatatata tttatatatt tttatataaa     60
tatatatatt tatatatatt tatataaata tatatatta tatatatta taaaatata    120 taaatatata tatttatata aatatataaa atatataaat atatttatat aaatatataa    180
aatatataaa tatatttata taaatatata aaatatataa atatatttat ataaaatat    240 ataaaatata taaatatctt tatatataaa tataaaaat atataaatat ctttatatat    300
aaatatataa aatatataaa tatatttata taaatatata taaaatatat aaatatattt    360
atatacaaat atataaaata tataaatata tttatatata aatatataaa ata         413

<210> SEQ ID NO 115
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig; 4965309..
      4965669

<400> SEQUENCE: 115
tatacgtata tatacatata tatacgtata tatatacata tatatacgta tatatacata     60

```
tgtatatatg tgtgtacatg tatatatata catatgtaca tatatatgta cacatatata      120
tatacatata tatgtacaca tatacatata tatgtacaca tatacatata catatatatg      180
tacacatata tatacatata tatgtacaca catatatata catatatatg tacacacata      240
tatacgtata tatgtacaca catatatacg tatatatatg tacacacata tatacgtata      300
tatatgtaca cacatatata tacgtatata tatgtacaca tatatatata cgtatatata      360
t                                                                     361

<210> SEQ ID NO 116
<211> LENGTH: 325
<212> TYPE: DNA
<213> ORGANISM: Homo sapiens
<220> FEATURE:
<221> NAME/KEY: misc_binding
<222> LOCATION: (1)..(325)
<223> OTHER INFORMATION: MAR of chromosome 2 genomic contig; 5258150..
      5258474

<400> SEQUENCE: 116
tacacacaca tatacatata tacatatata cgtgtatacg tatacgtata tacgtatata       60
tacatatatg tatacgtata cgtatatacg tatatataca tatatgtata cgtatacgta      120
tatacgtata tatacatata tgtatacgta tacgtatata cgtatatata catatatgta      180
tacgtatacg tatatacgta tatatacata catatgtata cgtatacgta tatatgtata      240
tatacgtata tgtatacgta tacatatata cgtatatata cgtatatgta tatgtatata      300
cgtatatgta tatatgtaca tatac                                            325

<210> SEQ ID NO 117
<211> LENGTH: 1508
<212> TYPE: DNA
<213> ORGANISM: Homo sapiens
<220> FEATURE:
<221> NAME/KEY: misc_binding
<222> LOCATION: (1)..(1508)
<223> OTHER INFORMATION: MAR of chromosome 2 genomic contig; 6057499..
      6059006

<400> SEQUENCE: 117
atataatata tataaattat ataatatata aaaattaata tataaatatat ataaattata      60 taatatataa attaattata taatatatat aaattatata atatataaat taattatata     120
atatatataa attatataat acatataaat taattatata atatataaat tatataatat     180
atacaaatta tatactatat taattatata ttatataatt aattatataa tatatataaa     240
ttatatatta ttaaattaat tatataatat ataaattata taatatataa attaattata     300
taatatataa attatataat atataaatta attatataat atataaatta tataatatat     360
aaattaattg tataatatat aaattaatta tataatatat aatatataat taataaataa     420
ttatatatta attatataat taataaataa aataaaata tataattta atatataaata      480 tacatcatat atatcacata tagattatat aatagttata tattatataa taaattatat     540
ataatatata ataaacatat ataacatatg ttatatatta cataaatatag tataatatat     600 aacatatgtt atatattaca taatatagta taatatataa catgttatat attacataat     660
atagtataat atataacata tgttatatat tacataatat agtataatat ataacatatg     720
ttatatatta cataaatatag tataatatat aacatatgtt atatattaca taatatagta     780
taatatataa catgttatat attacataa tatagtatata atatataaca tatgttatat      840
```

```
attacataat atagtataat ataaacata tgttatatat tacataatat agtataatat    900
ataacatatg ttatatatta cataatatag taatatatat aacatatgtt atatattaca    960
taatatagta taatatataa catatgttat atattacata atatagtata atatataaca   1020
tatgttatat attacataat atagtataat ataaacata tgttatatat tacataatat   1080
agtataatat ataacatatg ttatatatta cataatatag taatatatat aacatatgtt   1140
atatattaca taatatagta taatatataa catgttatat attacataat atagtataat   1200 ataaacata tgctatatat tacataatat agtataatat atatgttata tattacataa   1260
tatagtataa tatataacat atgttatata ttacatatta tagtataata tatatgttat   1320
atattatata atatagtata atatataatg tatgttatat attatataat atagtataat   1380 ataaacatg ttatatatta tataatatag taatatatat atgttatata ttatataata   1440
tagtataata tataatatat gttatatatt ataatatata gtaaatata tatgttatat   1500 attatata                                                            1508

<210> SEQ ID NO 118
<211> LENGTH: 415
<212> TYPE: DNA
<213> ORGANISM: Homo sapiens
<220> FEATURE:
<221> NAME/KEY: misc_binding
<222> LOCATION: (1)..(415)
<223> OTHER INFORMATION: MAR of chromosome 2 genomic contig; 7996866..
      7997280

<400> SEQUENCE: 118
caattatata atatacatat tatataattg tataaattat acaatcatat aattatatta     60
tatataatat acataataata taattatata taattatata attttataat ataattatat    120
ataattatat aattatatat aatatatatt ataattatat atataatata tatattatat    180 atatttata taatatataa atatatata taatatatat ataattatat ataataaat      240 atgtaatata taatatatat ataaatata ttatttataa ttatatatta tatatatatt    300 ataaatatata taattataaa taatatatat tataatatat ataataatat atataaatt    360 atatataata atatatatta taattatata taataatata tataatttat ataat        415

<210> SEQ ID NO 119
<211> LENGTH: 526
<212> TYPE: DNA
<213> ORGANISM: Homo sapiens
<220> FEATURE:
<221> NAME/KEY: misc_binding
<222> LOCATION: (1)..(526)
<223> OTHER INFORMATION: MAR of chromosome 2 genomic contig; 8300930..
      8301455

<400> SEQUENCE: 119
tatatcatat gatataattat acaatatatc atataaatatg atatattata tgatatattg     60
tacaatatat catatgatat atgatatatt atacaatata tcatataagg tatatattat    120
atcatatata atatataata taatatatga tataaatatat gatatatgat ataataata    180 tgatatatga tatgatatat ataaatatatg atatgata tatgatatat aatatatgat    240
atatgatata tgatatataa tatgatatat atgatatatg atatgatata tgatatatga    300
tataatatat gatataatat atgatataata ttatatgata tataatatat gataatttt    360 atatgatata taatatatga tatataatat ataatatatg atatgata tattatatca    420 tatataatat ataatataat atatgatata tattatatat ttttatacat tatatatata    480
```

-continued

```
aactatataa caatataaca tattatgtgt ataatatata ttacat         526

<210> SEQ ID NO 120
<211> LENGTH: 402
<212> TYPE: DNA
<213> ORGANISM: Homo sapiens
<220> FEATURE:
<221> NAME/KEY: misc_binding
<222> LOCATION: (1)..(402)
<223> OTHER INFORMATION: MAR of chromosome 2 genomic contig; 8576553..
      8576954

<400> SEQUENCE: 120
atgtatatta tatacaatat agtatatcat atatagtata tattatatag taatgtatta    60
tatataatgt ataatgtata aatatataat atatactaca tactatacta ttatatatac   120
tatatattat atatgataca tatactatat aaatatgctat atattatact ataaatatg   180 ctatatatta tactatataa tatgctatat attatactat ataatatgct atatattata   240
ctatataata tgctatatat tatactatat aaatatctat aaatatgct atatattata    300 ctatataata tactatatat tatactatat aaatatctat ataacatact atatattata   360
tatgatacat atactatatt acatatataa tatatatata ta                      402

<210> SEQ ID NO 121
<211> LENGTH: 477
<212> TYPE: DNA
<213> ORGANISM: Homo sapiens
<220> FEATURE:
<221> NAME/KEY: misc_binding
<222> LOCATION: (1)..(477)
<223> OTHER INFORMATION: MAR of chromosome 2 genomic contig; 8785649..
      8786125

<400> SEQUENCE: 121
tatttatata tatatttata tatatattta tatatatttta tatatatatt tatatatata    60
tttatatata tatttatata tttatatata tatattttta tatatttata tatatattta   120
tatatttata tatatttata tttatatata tatttatata tatttatata tatttatata   180
tatatattta tatatatttta tatatatata tttatatata tttatatata tttatatata   240
tatttatata tatatttata tatatattca tatatattta tatatatatt catatatatt    300
tatatatata ttcatatata tttatatata tatttatata tatatttata tatatttata   360
tatatttata tatatattta tatatatatt tatatatata tatttatata tatatttata   420
tatatatatt tatatatata tttatatata tatatttata tatatattta tatatat      477

<210> SEQ ID NO 122
<211> LENGTH: 773
<212> TYPE: DNA
<213> ORGANISM: Homo sapiens
<220> FEATURE:
<221> NAME/KEY: misc_binding
<222> LOCATION: (1)..(773)
<223> OTHER INFORMATION: MAR of chromosome 2 genomic contig; 10064737..
      10065509

<400> SEQUENCE: 122
atattatata tattacatat atattatatt gtatataata tatatattat attgtatata    60
atatatatat tatattgtat ataatatata tattatattg tatataatat atatattata   120
ttgtatataa tatattatat tgtatatatt atattgtata tattatattg tatacaatat   180
atattatatt gtatacaata tatattatat tgtatataat atattatatt gtatataata   240
```

```
tattatattg tatatattat attgtatata atatattata ttgtatataa tatattatat    300
tgtatatatt atattgtata taatatatta tatgtatata atatagtgta tactatatta    360
tataatatat attatataca atatataata tattgtatat catatatgat atattgtata    420
taatatataa tatatgatat attgtatata atatattata tatgatatat tgtatattat    480
atattatata tgatatattg tatattatat attatatatt gtatattgta tattatatat    540
tatatattgt ataaatatg ttatatattg tatataatat gttatatatt atatattgta    600
tatatgttat atattatgta ttgtatataa tatgttatat attatatatt gtatataatg    660
tattatatat tatatatatt atatattgta taaatgtat tatatattgt atattatata    720
ttatatattg tatataatat attatataca ttatattata tattatatat tgt           773
```

<210> SEQ ID NO 123
<211> LENGTH: 1554
<212> TYPE: DNA
<213> ORGANISM: Homo sapiens
<220> FEATURE:
<221> NAME/KEY: misc_binding
<222> LOCATION: (1)..(1554)
<223> OTHER INFORMATION: MAR of chromosome 2 genomic contig; 1039775..
      1041328

<400> SEQUENCE: 123

```
ataatatatt aaatgtatat ataatatatt aaatataaat atatttataa tatataaata      60
tttatataaa tataaaatat atattaaata taaatatata taaaatatat attaaatata    120
taaaatataa atatatatta aatatatatt aaatatataa aatataaata tatattaaat    180
atattttaaa tatataaaat ataaatatat attaaatata ttttaaatat attaaatata    240
aatatatatt aaatatattt taaatatatt aaatataaat acatatatta aatatatatt    300
atatatataa aatatataaa ataaaatat atattaaata tataaaaat atatatgtta    360 aatatataaa agatatataa aatataaata tatattaaat atatataaaa tatatatata    420
ttaaatatat atattaaata taaatatata taaaatataa atatatgtat taaatatata    480
tattaaatat aaatatatgt attaaatata tattaaatat gaatatatgt attaaatata    540
tattaaatat aaatatatgt attatatata tagaatataa atatatgtat taaatatagt    600
atattaaata taaatatata taaatatatat attaaatatg aatatatata aaatatatat    660
attaaaaata tataatatat aaatatatat aaaatatata tattaaaaat atatataata    720
taaatatata taaatatat attaaaaa tatatataaa atatatatat taaaaatata    780
tataaaatat atatattaaa aatatatata aaatatatat attaaaaata tatattaaat    840
ataaatatat atattaaaa tatatattaa atataactat atattaaata tatattaaat    900
ataactatat attaaatata tattaaatat aactatatat taaatatata ttaaatataa    960
ctatatatta aatatatatt aaatataact atatattaaa tatatattaa ataaactat    1020 atattaaata tatattaaat ataactatat attaaatata tattaaatat aactatatat    1080
taaatatata tgaaatataa ctatatatta aatatatatt aaatataact atatgtatta    1140
aatataaata tatgtcttaa atatatatta aatataaata tatgtattaa atatatatta    1200
aatataaata tgtgtattaa atatatatta aatataaata tgtgtattaa atatatatta    1260
aatataaata tgtgtattaa atatatatta aatataaata tgtgtattaa atatctatat    1320
taaatataaa tatatgtatt aaatatatat taaatataaa tatatattaa atatatatat    1380
taaatataaa tatatattaa atataaaatat atatattaaa tatatatatt aaatataaat    1440
```

-continued

```
atatataaaa tatatatatt aaatataaat ataaatataa aatatatatt aaatataaat    1500
acatatatta aatatatgta ttaaatatat atataaaata tatgtattaa atat          1554

<210> SEQ ID NO 124
<211> LENGTH: 650
<212> TYPE: DNA
<213> ORGANISM: Homo sapiens
<220> FEATURE:
<221> NAME/KEY: misc_binding
<222> LOCATION: (1)..(650)
<223> OTHER INFORMATION: MAR of chromosome 2 genomic contig; 3944813..
      3945462

<400> SEQUENCE: 124
catgatatat tatgtataat atatattata gattacatat aaattatata tataatatat      60
aattatataa tatataatat tatataatat attatatata ttatacaatt atataatata    120
tataatatac aattatataa tatataatat acaattatat aatatataat acaatataat    180
atatatttaa tatattatat aatacatatt taatatatta tatattatat gttatatact    240
aaatatataa tatgtattta atatatacta ttatatatgt aatatattat ataatttatg    300
taacatatta tatattatat atgcaatata ttacatgtta catatatatt acatataata    360
tatgtaatat ataatataca ctatattatt atagtatata atactata ttatgtaatt      420 atataatata gtatattata cactatatta tattatcata taattatata ttatatacta    480
tattacatat atattatgta atataatatg caatatgtta catatataat atatatgtat    540
tatatagtat atatactata gtatatataa aatatatgct ataatatata ttttatatat    600
tatataatac atataatgta tcatatatta tatataatat attttataat                650

<210> SEQ ID NO 125
<211> LENGTH: 441
<212> TYPE: DNA
<213> ORGANISM: Homo sapiens
<220> FEATURE:
<221> NAME/KEY: misc_binding
<222> LOCATION: (1)..(441)
<223> OTHER INFORMATION: MAR of chromosome 2 genomic contig; 5314265..
      5314705

<400> SEQUENCE: 125
tataaatata tatgaaatat atataaatta tatataattt atatatacat atataaatta      60
tatataaatt atatataaat tatatataca tatataaatt atatattata taaaaattg     120 tatatattta tatataaatt gtatatataa tttatatata aattgtatat ataatttata    180
tatacaatgt atatattaat ttatatatac attgtatata taatttatat atacattgta    240
tatacaattt atatatacat tgtatataca atttatatat acattgtata tacaatttat    300
atataaatta tattatttat atatagtata tataaaatata tatactatat ataaattata    360
tatttattta tatattatat tatttatata taaattatat attatttata tatacattat    420 atataaaatta tatattattt a                                              441

<210> SEQ ID NO 126
<211> LENGTH: 1169
<212> TYPE: DNA
<213> ORGANISM: Homo sapiens
<220> FEATURE:
<221> NAME/KEY: misc_binding
<222> LOCATION: (1)..(1169)
<223> OTHER INFORMATION: MAR of chromosome 2 genomic contig; 5953971..
      5955139
```

<400> SEQUENCE: 126

```
atgtattcat attatatatt tatatataaa taatatacat tcatattata tatttatata       60
taaataatat atattcatat tatatattta tatataaata tataaatatat ttatgtataa      120
ataatatata tattcatatt atatatttct atataaataa tatatatatt catattatat      180
atttatatat aaatatataa tatatttata tataaatata taatatattt atatataata      240
tatatattca tattatatat ttatatataa atatataata tatttatata taaataatat      300
atatattcat attatatatt tatatataaa taatatatat tcatattata tatttatata      360
taaataatat atattcatat tatatactta tatataaata atatatattc atattatata      420
cttatatata aataatatat attcatatta tatatttata taaaaataat atatattcat      480
attatatatt tatatataat atatatattc atattatata tttatatatt ctatatattc      540
atattatata tttatatata aataatgtat attcatatta tatatttata tataaaataat    600
gtatattcat attatatatt tatatataaa tatatattca tattatatat ttatatataa      660
atatatattc atattatata tttatatata aatatatatt catattatat atttatataa      720
aatatatata ttcatattat atttatatat aaatatatat attcatatat atatttatat      780
ataatatata tattcatatt atatatttat atataaatata tatattcata ttatatattt     840
atatataaat aatatatata ttcatattat atatttatat ataaataatg tatattcata      900
ttatatattt atatataaat aatgtatatt catattatat atttatatat aaatatatat      960
attcatatta tatatttgta tataaaatata tattcatatt atatatttgt atatatattc    1020
atatatattt atatataaat ataaatatt catattatat ataaatatat atattcatat     1080
tatatattta tatatataaa taatatatat tcatattatt tatatatata aataatatat     1140
attcatatta tttatatata taaataata                                         1169
```

<210> SEQ ID NO 127
<211> LENGTH: 653
<212> TYPE: DNA
<213> ORGANISM: Homo sapiens
<220> FEATURE:
<221> NAME/KEY: misc_binding
<222> LOCATION: (1)..(653)
<223> OTHER INFORMATION: MAR of chromosome 2 genomic contig; 6427669..
      6428321

<400> SEQUENCE: 127

```
tatatatgta tacatatatg tatatatgtg tatatatgta tacatatatg tatatatgtg       60
tatatatgta tacatatatg tatatatgtg tatatatgta tacatatatg tatatatgtg      120
tatatatgta tacatatatg tatatatgtg tatatatgta tacatatatg tatatatgtg      180
tatatatgta tacatatatg tatatatgtg tatatatgta tacatatatg tatacatgtg      240
tacatgtgta tacatatatg tatacatgtg tacatgtgta tacatatatg tatacatgtg      300
tacatgtgta tacatatatg tatatatgtg tatacatata tgtatatatg tgtatatatg      360
tatacatata tgtatataag tgtatatatg tgtatatgta tataagtgta tatatgtgta      420
tatgtatata agtgtatata tgtgtatatg tatataagtg tatatatgtg tatatatgta      480
tacatatatg tatatatgtg tatatatgta tatgtatata agtgtatata tatgtgtata      540
tatgtataca tatatgtgta tatatgta tacatatatg tatatatgtg tatatatgta      600
tacatatatg taaatatgtg tatatatgtg tatatgtata taagtgtata tat             653
```

```
<210> SEQ ID NO 128
<211> LENGTH: 414
<212> TYPE: DNA
<213> ORGANISM: Homo sapiens
<220> FEATURE:
<221> NAME/KEY: misc_binding
<222> LOCATION: (1)..(414)
<223> OTHER INFORMATION: MAR of chromosome 2 genomic contig; 10890453..
      10890866

<400> SEQUENCE: 128
tatattttgt aaatatatat atagtaaata tatgtaaata tatatatttt gtaaatatat        60
atatattttg taaatatatg taaatatata tattttgtaa atatatgtaa atatatatat       120
tttgtaaata tatgtaaata tatatatttt gtaaatatat gtaaatatat atattttgta       180
aatatatgta aatatatata ttttgtaaat ttatgtaaat atatatattt tgtaaatata       240
tgtaaatata tatatatttt gtaaatatat atacatatat attttgtaaa tatataaaca       300
tatatatttt ataaatatat ttataaatat atatattgta aatatattta taaatatatt       360
tataatatat atattgtaaa tatgtttata aatatatata ttgtatatat aaat            414

<210> SEQ ID NO 129
<211> LENGTH: 496
<212> TYPE: DNA
<213> ORGANISM: Homo sapiens
<220> FEATURE:
<221> NAME/KEY: misc_binding
<222> LOCATION: (1)..(496)
<223> OTHER INFORMATION: MAR of chromosome 2 genomic contig; 13952568..
      13953063

<400> SEQUENCE: 129
taatatacat attatatatt atatattgta tatataatat acatattata tattatatat        60
tgtatatata atatacatat tatatattat atattgtata tataatatac atattatata       120
ttatatattg tatatataat atacatatta tatattatat attgtatata taatatacat       180
attatatatt atatattgta tatataatat acatattata tattatatat tgtatatata       240
atatacatat tatatattat atattgtata taatatacat attatatatt atatattatta      300 tatatataat atacatatta tatattatat attgtatata taatatacat attatatatt       360
atatattgta tatataatat acatattata tattatatat tgtatatata atacacatat       420
tatatattat atattgtata taatatacat attatatata ttatatattg tatatataat       480
atacatatta tatatt                                                      496

<210> SEQ ID NO 130
<211> LENGTH: 317
<212> TYPE: DNA
<213> ORGANISM: Homo sapiens
<220> FEATURE:
<221> NAME/KEY: misc_binding
<222> LOCATION: (1)..(317)
<223> OTHER INFORMATION: MAR of chromosome 2 genomic contig; 16942865..
      16943181

<400> SEQUENCE: 130
tctcctagta gttatatata tatatatgtg tatatatata tatcctagta gatatatata        60
tatatatatc ctagtagata tatatatata tatatcctag tagatatata tatatatata       120
tcctagtagt tatatatata tatatatcct aacagttata tatatatata tcctagtagt       180
tatatatata tatcctagta gttatatata tatatatata tcctagtagt tatatatata       240
tatatcctag tagttatata tatatatatc ctagtagtta tatatatata ttatatatta       300
```

```
tataatatat atataat                                                      317

<210> SEQ ID NO 131
<211> LENGTH: 464
<212> TYPE: DNA
<213> ORGANISM: Homo sapiens
<220> FEATURE:
<221> NAME/KEY: misc_binding
<222> LOCATION: (1)..(464)
<223> OTHER INFORMATION: MAR of chromosome 2 genomic contig; 17217049..
      17217512

<400> SEQUENCE: 131
acatactata tatatacaca tactatatat actatataca gtatatagta tacatatact        60
atacatatac atatactata catatacata tacatatact aagtatacgt atatacagta       120
catagtatat gtatactata tagtatgtat atatagcata tagtatgcgt atactctata       180
tagcatatag tatgcatata cgctatatag catatagtat gcatatacta tatatagtat       240
agagtatgcg tatactatat atatagtata gagtatgcgt atactatata tatagtatag       300
agtatgcgta tactatatat atagtataga gtatgcgtat actatatata tagtatagag       360
tatgcgtata ctatatatat agtatagagt atgcgtatac tatatatata gtatagagta       420
tgcgtatact atatatatag tatagagtat gtatatatat agta                        464

<210> SEQ ID NO 132
<211> LENGTH: 430
<212> TYPE: DNA
<213> ORGANISM: Homo sapiens
<220> FEATURE:
<221> NAME/KEY: misc_binding
<222> LOCATION: (1)..(430)
<223> OTHER INFORMATION: MAR of chromosome 2 genomic contig; 19647266..
      19647695

<400> SEQUENCE: 132
tgtaaatata tgtaaatata tatttatatt atatattata taaaaatata atatataata        60
tataatatat aaactatata ttaatataat atatataaac tattatataa atacatatta       120
aatatattat atttttaata tttatatatt aaatataata tatatttaat atttatatat       180
taaatatata atatatttaa tatttatata atatatagca tattttatat ttatattata       240
tataacattt tatatttata tttatattta tatatattta atttatattt atattatatt       300
tatatttata ttatatataa cataattata tatattttca tattgtatat aataaagaaa       360
tgtatatttg ttatatataa tatatattat ataatttatt atatattata taatatatat       420
tatataatat                                                              430

<210> SEQ ID NO 133
<211> LENGTH: 2131
<212> TYPE: DNA
<213> ORGANISM: Homo sapiens
<220> FEATURE:
<221> NAME/KEY: misc_binding
<222> LOCATION: (1)..(2131)
<223> OTHER INFORMATION: MAR of chromosome 2 genomic contig; 20481223..
      20483353

<400> SEQUENCE: 133
tatatataaa tatatttata tttaatatat atttatataa atatattttt atataaatat        60
atatttaata taaatatctt tatatttaat atatatttaa tataaatatc tttatatttta      120 atatatattt atatataaat atatatttat atttaatata tattaatatt taatatacgt       180
```

```
ttatatttaa tatatatttc tatataaata tatttatatt aacatatatt tatatataaa    240
tatatttata tttaatatat ttacatataa atatattttat atgtaatata tttacatata    300
aatatattta tatttaatat atatgcatat gtaaatatat ttatatttaa taatatttat    360
atataaatat atttatattt aataatattt atatataaat atatttatat ttaatatata    420
ttaaatatat atttatattt aatatatatt aatatttaat atatatttat atttaatata    480
tattatatat aaacatatat ttatatttaa tatatattat atataaacat atatttatat    540
ttaatatata ttatatataa acatatattt atatttaata tatatttata tttaatatat    600
tatatataaa catatatttta tatttaatat atatttatat taaatatata ttatatataa    660
acatatattt atatttaata tatatttata ttaaatatat atttatattt aatatatata    720 tattaaaatat atatttatat ttaatatata tttatattaa atatatattt atattaaata    780
tatttatatt taatatatat ttatattaaa tatatattaa atatttaata tatatttata    840
tttaatatat acatatatat ttatatttaa tatatacata tatatttata tttaatatat    900
acatatatat ttatatttaa tatatacata tatatttata tttaatatat aaatttatat    960
tttatatata taaaaatata tatttatatt taatatatat aaatatatat ttatatttaa   1020
tatatatatt tatattgaat atatacataa atatatattt atatttaata tataaacata   1080
tatttatatt tatatattaa atatatattt atatttaata tataaatata tatttatatt   1140
taatatattt atatatacta atatatttat atttaatata tttatatata gatatattta   1200
tatttaatat atttatgtgt attaatatat ttatatttaa tatatttata tattaatata   1260 tttatattttt atatttatat attaatatat ttatatttta tatttatatt ttatatattt   1320
atatattaat atatttatat ttatatatat ttttatatat taataaattt atatttttata   1380 tatttatata ttaataaatt tatattttat acagttatat aaatatattt atatttttata   1440 cagttatata aatatatttta tattttatag ttatataaat atatttatat tttatacagt   1500
tatataaata tatttatatt ttatacagtt atataaatat atttatattt tatacagtta   1560
tataaatata tttatatttt atacagttat ataaatatat ttatattttta tacagttata   1620 taaatatatt tatatttttat acagttatat aaatatattt atatttttata cagttatata   1680 aatatattta tattttatac agtttatataa atatatttat atttttataca gttatataaa   1740 tatatttatg ttttatacat ttatataaat atatttatat tttatacatt tgtatttaat   1800
atatatttat atataaatat attttatatt taatatattt atatataaat atatattgat   1860
atttaatata tatttatata taaatatata ttgatattta atatgtttat atataaaatat   1920 atatttatat ttaatatata tgtttatata tcaatatata tttatatttta atatatattt   1980 acatataaat atatatttat atttgatata tatttatatt tgatatatat tttatatata   2040
ttaatatatt tacatttgat atatatttta tatatattaa tatatttaca tttgatatat   2100
attttatata tattaatata tttacatttg a                                   2131

<210> SEQ ID NO 134
<211> LENGTH: 842
<212> TYPE: DNA
<213> ORGANISM: Homo sapiens
<220> FEATURE:
<221> NAME/KEY: misc_binding
<222> LOCATION: (1)..(842)
<223> OTHER INFORMATION: MAR of chromosome 2 genomic contig; 20483478..
      20484319

<400> SEQUENCE: 134
```

```
tatatattta tgtttaatat atatttatag ataaatatat atttacgttt aatatatatt      60
tatagataaa tatatattta cgtttaatat atatttatct ataaatatat ttacgtttaa     120
tatatattta tatattaata tatttatgtt taatatatat ttatatatat taatatattt     180
atgtttaata tatatttata tattaatata tttatgttta atatatttat atatattaat     240
atatttatgt ttaatatata tttatatgtt aatatatatta ggtatatata tatttatatg    300
ttaatatata tttatattaa tatattatat ttatatataa aagtatatat aatatatata     360
tattatataa attattatat agtatttta tatatattta tatataaatt ttatatattt      420
tatatatata aatatatatt tatatataca ttttatatat aaatatatat ttatatatac     480
attatatata taaatatata tatttatatt ttatatataa atatatatat ttatatatac     540
attttatata ttttatatat gtaaatatat atataaattt tatatattgt atatatatttt    600 ataaattta tatatatatt tatatatata atatatataa tatatataaa ttttatatat      660
attatatata tttatattt atatattata tatttattta tatatattta tatgttatat      720
atatttatat ttatatttat tttttattta tatatttat atatatattt atatatgtat      780
attatatata ttatatatta tataaatatat tatatatatt atattatata tttatattat    840
at                                                                    842

<210> SEQ ID NO 135
<211> LENGTH: 645
<212> TYPE: DNA
<213> ORGANISM: Homo sapiens
<220> FEATURE:
<221> NAME/KEY: misc_binding
<222> LOCATION: (1)..(645)
<223> OTHER INFORMATION: MAR of chromosome 2 genomic contig; 20897566..
      20898210

<400> SEQUENCE: 135
gtatatttat attatatatt ataatatata tattatatat taataaatta tatataatat      60
aatatatatg tatatttata tttatgttat aatatacata taattatata tgtatgtata     120
catgtataca tatacgtata tgtgtatatg tatacatata ggtatatgtg tacatgtata     180
catataggta tatgtatatg tatacatgta tacatataat ataattacat atgtatgtat     240
acatacatat gtaattatat tatatatgta tatgtatatt tatataatat ataatatgta     300
ttatatatta tacatgcata tttatatgta tattatatat acacatataa tataattata     360
tatgtatgta tatacacaca tatatatttta tattatatat gtatattata tacatatatt    420
tatattatat atgtatatat atttatcata tttatatgta atatgcatgt gtaataaata     480
atatacacat ttatatatgt atattatata catatattta tattgtatat gtatatatat     540
ttatatatat ttgtatatca tatatttata tattgtatat ttatgtatat tatatattta    600
tatattatat atgtattata taatatatat gtaaatatat attat                     645

<210> SEQ ID NO 136
<211> LENGTH: 722
<212> TYPE: DNA
<213> ORGANISM: Homo sapiens
<220> FEATURE:
<221> NAME/KEY: misc_binding
<222> LOCATION: (1)..(722)
<223> OTHER INFORMATION: MAR of chromosome 2 genomic contig; 21664541..
      21665262

<400> SEQUENCE: 136
```

```
tataatatat attatattct atataatatg taaaatatat attatattct atataatgta      60
ttatatatag aatataatat attctatgta ttctataatc tatataatac atattatata     120
ttatatagaa tattataaat aatatattct atattatata tagaatatat tctatatgtt     180
tatattctat atattatata tgaaatagta tataaaatat ataatatata tataaaatat     240
gatatataat atatataaaa taatatataa tgtataatat ataaaataat atataatgta     300
taatatataa aataatatat aatgtataat atataaaata atatataatg tatattatat     360
aaaataatat ataatgtata ttatatataa aataatatat aatgtatatt atatataaaa     420
taatatataa tgtatataaa ataatatata atatattata tataaaataa tatataatat     480
attatatata aaataatata tattatatat aaaataatat ataatatatt atatataaaa     540
taatatatat tatatataaa atatatata atatattata tataaaataa tatatattat     600
atataaaata atatatatta tatataaaat aatatatat attatatata taaaataata     660
tataatatat tatataaaaa tataaatata ttatataaaa atataaaata taaaatatta     720
ca                                                                    722
```

<210> SEQ ID NO 137
<211> LENGTH: 305
<212> TYPE: DNA
<213> ORGANISM: Homo sapiens
<220> FEATURE:
<221> NAME/KEY: misc_binding
<222> LOCATION: (1)..(305)
<223> OTHER INFORMATION: MAR of chromosome 2 genomic contig; 22834991..
      22835295

<400> SEQUENCE: 137

```
aatataaaat atatgatata taatacgtat tatatatgta taatacgtat tatatattaa      60
tataatatat ataatacata ttatatatgt atataatata tactaatata taatgtgat     120 acattatata tttacataat atataataca taatatagaa ttataattat atataatca     180 taatatataa ttatatatat tattatatat gtatttatat tatatataat atattatata     240
taatatatat tatataatta tataagtata taattatgtt atatacataa taatatataa     300
tatat                                                                 305
```

<210> SEQ ID NO 138
<211> LENGTH: 352
<212> TYPE: DNA
<213> ORGANISM: Homo sapiens
<220> FEATURE:
<221> NAME/KEY: misc_binding
<222> LOCATION: (1)..(352)
<223> OTHER INFORMATION: MAR of chromosome 2 genomic contig; 25277762..
      25278113

<400> SEQUENCE: 138

```
taatatatat aatatattat atattatata taatatattt tataatatat aaatatatt      60 atatataata tataatatat tttataatat atataatata ttatatataa tatataatat    120 atttataat atataataa tattatatat attatatatt tatatttatt tatatattca     180
taaatatata tttatatata atatattta taatatatta tatataatat ataatatatt    240
ttataatata ttataatata taatatataa tatattttat aatatatata atatataata    300
tattatatat ttatatttat ttatatattc ataaatatat atatttatat ta            352
```

<210> SEQ ID NO 139
<211> LENGTH: 342

```
<212> TYPE: DNA
<213> ORGANISM: Homo sapiens
<220> FEATURE:
<221> NAME/KEY: misc_binding
<222> LOCATION: (1)..(342)
<223> OTHER INFORMATION: MAR of chromosome 2 genomic contig; 25378452..
      25378793

<400> SEQUENCE: 139
tatgtacata tatattttat atattatata taatatatat tatatgatat atataatata      60
ttatataata taatatataa aatatatata atatatatta tattatataa attatattat     120
atatatcata taatatattt tatatattat ataatatata ttatattata tatattttat     180
atattatatt atatttata tatatcatat aatatatatt atattatata ttttatatat     240
tatataatat atattatata tttttatata ttatataata tatattatat attttatata     300
ttatataata catatattat ataataatata atatatatta ta                       342

<210> SEQ ID NO 140
<211> LENGTH: 663
<212> TYPE: DNA
<213> ORGANISM: Homo sapiens
<220> FEATURE:
<221> NAME/KEY: misc_binding
<222> LOCATION: (1)..(663)
<223> OTHER INFORMATION: MAR of chromosome 2 genomic contig; 30209437..
      30210099

<400> SEQUENCE: 140
aatatatatt acatattgta tatatagtat atgtaatgta tataaatatag tatattctat      60 attgtataat agtaatatat agtatatgat atactatata ttacttatca tatatacaat     120
atatattata tcgtatattg tatattatat attgtatata tgtaatatat gatatgtaca     180
tatgttatat atgtataaa tatactatat tatatattgt atattatata catatataac      240
actattatac aatatataat atagcatatt atatacaata tagcatatac aatatataat     300
atagcatatt atatataata tagtatatta tatacaaat ataatatagc atattatata      360
taatataata tagtatatta tatacaaat ataatatagc atacaata tagtatacaa       420 tatataatat agcatataca atatagtata ttatatataa tatataatat agcatgtaca     480
atatagtatg ttatatacaa tatataatat agcatataca atagtatat ttatatacaa      540 tatataatat agcatataca atatattata ttatatacaa tatataatat agcatataca     600
atatagtata ttatatacaa tatataatac agcatataca atagtatat ttacatacag      660 tat                                                                    663

<210> SEQ ID NO 141
<211> LENGTH: 1200
<212> TYPE: DNA
<213> ORGANISM: Homo sapiens
<220> FEATURE:
<221> NAME/KEY: misc_binding
<222> LOCATION: (1)..(1200)
<223> OTHER INFORMATION: MAR of chromosome 2 genomic contig; 31725089..
      31726288

<400> SEQUENCE: 141
tgtacttata tattataatg tatatataaa gtatatactt tatatatact tatatattat      60
aatgtatatt attgtatata agtatatatc ataatatata cttacatatg ctcacatata     120
ttataatgta tattgtatat attatataca tattatatat gtaaatgta tatatacatt      180 atatatgtat aatgtatata tacattatat atgtataatg tatatataca ttatatatgt     240
```

```
ataatgtata taatatatac aatatatgta taatatataa tatatacaat atatgtataa      300
tatacaatat atgtataata tacaatatat gtatagtata taatatatat tatatatgta      360
tagtatatta tatattatat atgtatagta taaatatgt aatgtata tattataata          420 tattatatat aatatctata acaatataat atattgtata tattatatat aatatatatt      480
tatataatat atattatata taatatatta tgtatttatt tatttatat ataatataaa        540 tatatataat ataataata tttattatat attaatataa atttatat taatatatat          600 ttattatata taaataatat ctatgatata aataatatat aatatacatg tatatgttat      660
aatatataca tataatatac atgtgtatat atactataca tgtatatata acatgtatat      720
atatacatgt atatatatta tgtatacatg tatagtatat atacatgtat atatatacat      780
atatactata catgtatata tacatgtata tatatacata tatactatac atgtatatat      840
acatgtatat atacacatat atactataca tgtatatata catgtatata tatacatgta      900
tgttatatac attattataa tatacatata tagtatacat tatatacatt atataatatg      960
cattattata atataatata cattattata atatacatta ttataatata atatacatta     1020
ttataatata cattattata atatacatta taataatata cattattata atatacatta     1080
taatattgaa gtatatatac tataatatat gtatatatta taatgtatat aatatacatt     1140
attatatata agtatgtatt atatataagt atatattata atatatgtat atacatatat     1200

<210> SEQ ID NO 142
<211> LENGTH: 325
<212> TYPE: DNA
<213> ORGANISM: Homo sapiens
<220> FEATURE:
<221> NAME/KEY: misc_binding
<222> LOCATION: (1)..(325)
<223> OTHER INFORMATION: MAR of chromosome 2 genomic contig; 32147252..
      32147576

<400> SEQUENCE: 142
aaatacaaat atttatttat atataatata taatataata tatttattta tatataatat       60
ataatttata attatataaa tatataatat atttatatat aatatataat tttattatat      120
attaattata tatataataa atatatataa tataatttt tattatatat taattatata      180
tataataaat atatataata tataataata ttatatacat tatatataaa tataaatatt      240
tatataatat ataatataat atatttattt atatataaat atataaatata taattatata      300 aatatataat atatttatat ataac                                             325

<210> SEQ ID NO 143
<211> LENGTH: 507
<212> TYPE: DNA
<213> ORGANISM: Homo sapiens
<220> FEATURE:
<221> NAME/KEY: misc_binding
<222> LOCATION: (1)..(507)
<223> OTHER INFORMATION: MAR of chromosome 2 genomic contig; 32312662..
      32313168

<400> SEQUENCE: 143
attatttata taaatattat atttatatta tttatataaa tattatattt atattattta       60
tataaatatt atatttatat tatttatata aatattatat ttatattatt tatataaata      120
ttatatttat attatttata taaatattat atttatatta tttatataaa tattatattt      180
atattattta tataaatatt atatttatat tatttatata aatattatat ttatattatt      240
```

-continued

| | |
|---|---|
| tatataaata ttatatttat attatttata taaatatttta tttatattat ttatataaat | 300 |
| attatattta tattatttat ataaatattt atttatatta tttatataaa tatttattta | 360 |
| tatttatata aataatatat aaataaatat tttatatgta tataaatatt atttatatta | 420 |
| tttatttaaa taaataatat aaattaatat aaatattaat attatttatt ttattataaa | 480 |
| taatataaat attatattta tatttat | 507 |

<210> SEQ ID NO 144
<211> LENGTH: 339
<212> TYPE: DNA
<213> ORGANISM: Homo sapiens
<220> FEATURE:
<221> NAME/KEY: misc_binding
<222> LOCATION: (1)..(339)
<223> OTHER INFORMATION: MAR of chromosome 2 genomic contig; 33651118..
33651456

<400> SEQUENCE: 144

| | |
|---|---|
| aaatataata tattatttat atataatata aatgatatat tatgtatata taaaatataa | 60 |
| ataatatatt atgtatatat aaaatataaa tattatttat atataaaata taaataatat | 120 |
| ttatatataa aatataaata ttatattatt tatatataaa atataaataa tatattattt | 180 |
| atatataaaa tataaataat atattattta tataaaata atatataaaa tataaatata | 240 |
| tattatatat aaataaaata tatatattat atataaaat ttatatataa tatataaaat | 300 |
| ataatatata tatttaatat ttattatata atatataat | 339 |

<210> SEQ ID NO 145
<211> LENGTH: 461
<212> TYPE: DNA
<213> ORGANISM: Homo sapiens
<220> FEATURE:
<221> NAME/KEY: misc_binding
<222> LOCATION: (1)..(461)
<223> OTHER INFORMATION: MAR of chromosome 2 genomic contig; 45073053..
45073513

<400> SEQUENCE: 145

| | |
|---|---|
| tgtgtataca tatatacgtg tacatataca tatatacatg tgtatatata tacgtgtaca | 60 |
| tatacatata tacatgtgta tatatatgta catatacata tatacatgtg tatacataca | 120 |
| tatatacatg tacatataca tatatacatg tgtatacata catatataca tgtacatata | 180 |
| catatataca tgtgtatact tacatatata catgtacata tacatatata catgtgtata | 240 |
| tatacatata tacacgtaca tacatatata tacatgtaca tatatacatg tatacatata | 300 |
| tacatgtaca tatgtacata tatacatgta tacatatata catgtacata tgtacatata | 360 |
| tacatgtata catatataca tgtacatatg tacatatata catgtataca tatatacata | 420 |
| tgtacatacg cacagataga catatataca tatgtacata c | 461 |

<210> SEQ ID NO 146
<211> LENGTH: 1162
<212> TYPE: DNA
<213> ORGANISM: Homo sapiens
<220> FEATURE:
<221> NAME/KEY: misc_binding
<222> LOCATION: (1)..(1162)
<223> OTHER INFORMATION: MAR of chromosome 2 genomic contig; 45487691..
45488852

<400> SEQUENCE: 146

| | |
|---|---|
| attatattat ctatataaat ctattatatc tattatatta tctatataat atctattata | 60 |

```
tatattatat tatctatata aatctattat atatattata ttatctatat aaatctatta    120
tatatattat attatctata tatctattat atattatatt attatatatt atatataata    180
tctattatat atattatatt atattatatt atatataata tctattatat atattatatt    240
atctatataa tatctattat atattatata ttatattata taatatatct attatatata    300
ttatattata ttatatataa tatctattat atctattata tatattatat atatctatta    360
tatctattat atatattata tataaatatct attatatcta ttatatatat tatatataat    420
atctattata tctattatat tatattatat ataatatcta ttatatctat tatatatatt    480
atatatatct attatatcta ttatatatat tatatataat atctattata tctattatat    540
atattatata taatatctat tatatctatt atatattata tatataatat ctattatatc    600
tattatatat tatatatata atatctatta tatctattat atctattata tatatatcta    660
ttatatctat tatatatatt atatacataa tatctattat atctattata tatattatat    720
atataatatc tattatatct attatatata tactatctat tatatctatt atatatatta    780
tatatgtact atctattata tctattatat ctattatata tatactatct attatatcta    840
ttatatatat tatatatata ctatctatta tatctattat atatattata tatatactat    900
ctattatata tctattatat atattatttt attattatata tagtatctat tacatatatt    960
atattatatt atatataata tctattatat attattatatt atattataaa taatatatat   1020
aatatctgtt atatataata gatattatat taaatatata atatatataa tagatatttat   1080 atatattata ttatataata taatatatat aatataatta atataaaata tatataatat   1140
ataattaata taatatgtaa ta                                             1162

<210> SEQ ID NO 147
<211> LENGTH: 562
<212> TYPE: DNA
<213> ORGANISM: Homo sapiens
<220> FEATURE:
<221> NAME/KEY: misc_binding
<222> LOCATION: (1)..(562)
<223> OTHER INFORMATION: MAR of chromosome 2 genomic contig; 45516233..
      45516794

<400> SEQUENCE: 147
acatattata tatattatat ataatatata ttatatatac atattatata tattatatat     60
aatatatatt atatatacat attatatata ttatatatac atatatatat tgtatataat    120
atatacatat tatatatatt atatatacat attatatatt ataataata tatacatatt    180 atatattata tataaatatt atattatata tataaatatt atatatataa atattatata    240
ttatatataa atattatata tcttatatat aaatataata tataatatat ataatattta    300
tatattatat ataaatatta tatatattat ataatattat atataatata taaatatata    360
tattatataa atattgtata tattatataa atattatata tattatatat aaatatttata    420 tatattatat aaatatatat aaatatataa aatatataaa tatgtaaaat ttatatttat    480
aaatatataa tataaatata taaatataaa tataaattat atataaatata taatatatta    540 tacataatat atactatata ta                                             562

<210> SEQ ID NO 148
<211> LENGTH: 801
<212> TYPE: DNA
<213> ORGANISM: Homo sapiens
<220> FEATURE:
<221> NAME/KEY: misc_binding
<222> LOCATION: (1)..(801)
```

<223> OTHER INFORMATION: MAR of chromosome 2 genomic contig; 45727251..
    45728051

<400> SEQUENCE: 148

```
atatatatat   ataatatata   catatataga   atatatatat   tattatattc   tatatataga        60
atatatatat   agaatatata   tatatagaat   atatatatag   aatatatata   tagaatatat       120
atatagaata   tatatataga   atatatatat   atagaatata   tatatagaat   atatatatat       180
agaatatata   tatatagaat   atatatatat   agaatatata   tatagaatat   atatatatag       240
aatatatata   tagaatatat   atatatagaa   tatatatata   gaatatatat   atatagaata       300
tatatataga   atatatatat   atagaatata   tatatagaat   atatatatat   agaatatata       360
tatagaatat   atatatatag   aatatatata   tagaatatat   atatatagaa   tatatatata       420
gaatatatat   atatagaata   tatatataga   atatatatat   atagaatata   tatatagaat       480
atatatatat   agaatatata   tatagaatat   atatatatag   aatatatata   tagaatatat       540
atatatagaa   tatatatata   gaatatatat   atatagaata   tatatataga   atatatatat       600
atagaatata   tatatagaat   atatatatat   agtatatata   gaatatatat   atatagtata       660
tatagaatat   atatatatag   aatatatata   tagaatatat   atatatagaa   tatatatata       720
gaatatatat   atatagaata   tatatataga   atatatatat   atatagaata   tatatataga       780
atatatatat   atatatagaa   t                                                       801
```

<210> SEQ ID NO 149
<211> LENGTH: 346
<212> TYPE: DNA
<213> ORGANISM: Homo sapiens
<220> FEATURE:
<221> NAME/KEY: misc_binding
<222> LOCATION: (1)..(346)
<223> OTHER INFORMATION: MAR of chromosome 2 genomic contig; 50937238..
    50937583

<400> SEQUENCE: 149

```
taaaattata   tatattatat   ataatatata   atatattata   tataatatat   attataatat        60
atataatata   tattatataa   aatatatattct   atagaatata   tattctatta   tataatatat       120
attctattat   aatatatatt   atataataata  tatattctat   tataatatat   attatatata       180
atatattcta   ttatgatata   tattatatat   aataacatat   attatatata   atatatattc       240
tattatataa   aatatatatt   atataaaata   tatattctat   tatataaaat   atatattata       300
taaaatatat   attatattat   ataaaatata   tattatacta   tatata                         346
```

<210> SEQ ID NO 150
<211> LENGTH: 462
<212> TYPE: DNA
<213> ORGANISM: Homo sapiens
<220> FEATURE:
<221> NAME/KEY: misc_binding
<222> LOCATION: (1)..(462)
<223> OTHER INFORMATION: MAR of chromosome 2 genomic contig; 55672627..
    55673088

<400> SEQUENCE: 150

```
taaatatata   ttatatatta   tattatatat   aatatatttta   tatttatata   tactataatt        60
tatatataat   atatattata   tatataaatat   atttataata   tatatcatat   aaataatata       120
tatttataat   atatatcata   taaataatat   atatttataa   tagatatcat   ataaataata       180
tatatttata   atagatatca   tataaataat   atatatttat   aatagatatc   atataaataa       240
```

```
tatatattta taatagatat catataaata atatatattt ataatatata tcatataaat    300
aatatatatt tataatatat atcatataaa taatatatat ttataatata tatcatataa    360
ataatatata tttataatag atatcatata aataatatat atttataata gatatcatat    420
aaataatata tatttataat agatatcata taaataatat at                       462
```

<210> SEQ ID NO 151
<211> LENGTH: 401
<212> TYPE: DNA
<213> ORGANISM: Homo sapiens
<220> FEATURE:
<221> NAME/KEY: misc_binding
<222> LOCATION: (1)..(401)
<223> OTHER INFORMATION: MAR of chromosome 2 genomic contig; 56081352..
      56081752

<400> SEQUENCE: 151

```
tatacatgta tgtattcgta tatgtatgtt atatatgtat atgtgttata tacatataca    60
tatatacatg tatatgtgtt atatacatat acatatatac atgtatatgt gttatataca   120
tatacatata tacatgtata tgtgttatat acatatacat atatacatgt atatgtgtta   180
tatacatgtg tatgtgtata tgtatatata catatatgtg tatgtgcatg tgtatatata   240
catatatgta tatgtgtata tgtatatata catatatgta tatgtgtatg tgtatacgta   300
tatatacata tatgtgtatg tgtatgtgta tacgtatata tatacatata tgtgtatgtg   360
tatacgtaca tatacatata tgtgtatgtg tatacgtaca t                       401
```

<210> SEQ ID NO 152
<211> LENGTH: 765
<212> TYPE: DNA
<213> ORGANISM: Homo sapiens
<220> FEATURE:
<221> NAME/KEY: misc_binding
<222> LOCATION: (1)..(765)
<223> OTHER INFORMATION: MAR of chromosome 2 genomic contig; 56404208..
      56404972

<400> SEQUENCE: 152

```
tatattatat aaagaatata tattatataa tatgtaaaga atatatatta tataaatatgt   60 aaagaatata tattatatat tatgtaaaga atatatatta tatataatat ataaagaata   120
tatattatat aatatataaa gaatatatat tatatattat ataaagaata tatattatat   180 atatatatata aagaatatat aatatataat atataaagaa tatatattat atataatata   240
taaagaatat atattatata taatatataa agaatatata ttatatattat ataaagaat    300 acatatatat aatatataaa gaatatatat tatataataat atataaagaa tatatattat   360
atataatata taaagaatat atattatata taatatataa agaatatata ttatatataa    420
tatataaaga atatatatta tatataatat ataaagaata tatattatat atattatata    480
aagaatatta tatattatat aaagaatata tattatatat aatatataaa gaataaacat    540
atatactata tataaagaat atacattata tatactatat ataaagaata tacattatat    600
atactatata taaagaatat ataatatata taaagaatat acattatata taatatataa    660
agaatatatt atatattata taaagaatac attatataat aaagaataca ttatatataa    720
tataaagaat acattataat atataaagaa tatatataat atata                    765
```

<210> SEQ ID NO 153
<211> LENGTH: 443
<212> TYPE: DNA
<213> ORGANISM: Homo sapiens

```
<220> FEATURE:
<221> NAME/KEY: misc_binding
<222> LOCATION: (1)..(443)
<223> OTHER INFORMATION: MAR of chromosome 2 genomic contig; 61953416..
      61953858

<400> SEQUENCE: 153
tttatatatt atagataaaa ttatattata ttacatgtaa tatataatat gtaaaatata      60
ttatattaca tatataatat ataatatgta aaatatatta tattcatcat ataatatata     120
atatgtaaaa tatattatat tacatatata atataaaata ttacatataa tatattttac     180
ataaatatat attatctatt acatatttat tatatgtaat aatatgtaca tatgtataaa     240
tatgtatata tttatacata tgtatatatt atatatacat atatatgtat atattatata     300
tacatatata tgtatatatt atattatata tacatatata tgtatatatt atattatata     360
tacatatata tgtatatatt atattatata tacatatata tgtatatata ttataaatat     420
gtataataaa gatttatatg taa                                             443

<210> SEQ ID NO 154
<211> LENGTH: 372
<212> TYPE: DNA
<213> ORGANISM: Homo sapiens
<220> FEATURE:
<221> NAME/KEY: misc_binding
<222> LOCATION: (1)..(372)
<223> OTHER INFORMATION: MAR of chromosome 2 genomic contig; 62076211..
      62076582

<400> SEQUENCE: 154
tatatataat tatatatgta attatatatc agtatatata attatatata attatcaata      60
tatataatta tatataatta tcaatatata taattatcaa tagatatata taattatata     120
tataattata tataattata tatcagtata tatacttata taattatata tatgtatata     180
taattatatg tataaaattat ctataagtat atataactat aatatatatc aattatatat    240
acttatgtat aattatatat actgatatat aattatacat aattatatat atcaattata    300
tataattatg taattatata tatacatata taattatata tatataaatt atatgtaatt    360
atataattac ac                                                        372

<210> SEQ ID NO 155
<211> LENGTH: 484
<212> TYPE: DNA
<213> ORGANISM: Homo sapiens
<220> FEATURE:
<221> NAME/KEY: misc_binding
<222> LOCATION: (1)..(484)
<223> OTHER INFORMATION: MAR of chromosome 2 genomic contig; 62158581..
      62159064

<400> SEQUENCE: 155
attatatata atataaaaat tatacatatt attttattat atattatata cataatatat      60
atatttcata tataatatat attatatata ataaaaata tatattatgt ataattatat     120
ataaaatata ttatataatt atatataaca taaaatatat atatatata attatatata     180 atataaaata tatatataat ataaaatata tattatatgt aattatatat aatataaaat    240
atatatataa tataaaatat atattatata taattataat ataaaatata tattatatag    300
tatatattat ataaaatata tattatatat aattatatat tatataaaat atatattata    360
tataattata taatataaaa tatatattgt atataattat atataaatata aaatatatat    420 aatatatgaa ataagatata tactatatat aatatatata atttacatat aagatatata    480
``` tcat                                                                      484

<210> SEQ ID NO 156
<211> LENGTH: 644
<212> TYPE: DNA
<213> ORGANISM: Homo sapiens
<220> FEATURE:
<221> NAME/KEY: misc_binding
<222> LOCATION: (1)..(644)
<223> OTHER INFORMATION: MAR of chromosome 2 genomic contig; 68145036..
      68145679

<400> SEQUENCE: 156
tatatatatg ctaatatatg taatatatat tatatatatg ctaatatata tatgctaata      60
tataatatat attatatata aatatataat atatatttat ataaatatat aatatattat     120 ataaaatat ataatataaa tatatataat atactcata ttatatatta tgtataacat       180
ataatacata tttgttatat ataatatata tattatatgt tatatattat atttatata      240 taatataaca atatatttta tatttatat gttatatatt atatattata tataatataa      300
cataatatat aatatatatt attatatata ttacatatat tagcaatatt atatataaaa    360
tatatataat atatataaaa tatatataaa aatataaaat atatatcaaa atataaacta    420
tataatatat aaaaatatat tatatataat atataaaaat ataaactata taatatataa    480
aaatatatta tatataatat ataaaaatat attatatatt atatataaaa atatattata   540
tataatatat aaaaatatat ataaaatata aaaatatatat ataaaatata aaaaatatat    600
aaaataatat aaaatatata atatataata atataatata taat                      644

<210> SEQ ID NO 157
<211> LENGTH: 530
<212> TYPE: DNA
<213> ORGANISM: Homo sapiens
<220> FEATURE:
<221> NAME/KEY: misc_binding
<222> LOCATION: (1)..(530)
<223> OTHER INFORMATION: MAR of chromosome 2 genomic contig; 71257289..
      71257818

<400> SEQUENCE: 157
atatctatta tatttatata ctttatataa attatatcta ttatatttat atactttata      60
taaattatat ctattatatt tatatacttt atataaatta tatctattat atttatatac    120
tttatataaa ttatatctat tatatttata tactttatat aaattatatc tattatatttt   180 atatactttta tataaatata taattatatt tatatactttt atataaatat aattataaat   240
atatttatat acttatata aatataatta taaatatatt tatatacttt atataaaatat    300 aattataaat atatttatat acttatata aatataatta taaatatatt tatatacttt     360
ataattatat gttatatttta taattatatt tatataattc ataattatat acattatgtt    420
tatagttata taatttataa ttatatacat tatatttata tttatataat ttataattat    480
ataaattata taaattatat aaattatctt taatttatat tatataatct                530

<210> SEQ ID NO 158
<211> LENGTH: 337
<212> TYPE: DNA
<213> ORGANISM: Homo sapiens
<220> FEATURE:
<221> NAME/KEY: misc_binding
<222> LOCATION: (1)..(337)
<223> OTHER INFORMATION: MAR of chromosome 2 genomic contig; 73413615..
      73413951

<400> SEQUENCE: 158

| acttatatta | tatataacta | tattattgta | tattaatata | aattaatgat | atataatata | 60 |
| ttaattatat | attattatat | gtgatataaa | atacttatat | ttatactgta | tatatgtata | 120 |
| tacacacata | tatgtatata | tgtatatata | cacatatgta | tatatgtata | tgtatatatg | 180 |
| tatactgtat | atatgtatat | acacacatat | atgtatatat | gtatatgtat | atatgtatac | 240 |
| tgtatatatg | tatatacata | tatacatata | tgatatatat | cacatatatg | tgatatataa | 300 |
| atatatttat | ataaatataa | tattaatatt | tatatta | | | 337 |

<210> SEQ ID NO 159
<211> LENGTH: 1340
<212> TYPE: DNA
<213> ORGANISM: Homo sapiens
<220> FEATURE:
<221> NAME/KEY: misc_binding
<222> LOCATION: (1)..(1340)
<223> OTHER INFORMATION: MAR of chromosome 2 genomic contig; 77011049..77012388

<400> SEQUENCE: 159

| atgtatttta | tatagtatat | attatgtatt | atattgatat | aattatataa | caattattta | 60 |
| tatataaaat | aacaaataaa | tatataaaat | aataaatata | tatttattat | taaataataa | 120 |
| atatatattt | attattaaat | aataaatata | taaagtaata | aatatatatt | tatatattaa | 180 |
| ataattcata | tatatttata | tattaaataa | ttcatatata | tttaaataat | taatacatat | 240 |
| ttaaataatt | aatatatatt | tatataatat | atatttatat | attaaataat | taatatatat | 300 |
| ttatagatta | aattaatata | tatttatata | ttaaattaaa | tttaatatat | tatatattta | 360 |
| tataatttaa | atttaataat | ttatataatt | taatttaatt | taatataatt | aaaatatatt | 420 |
| aaacattata | taatatataa | tatatttaat | atataaatat | tatttaatat | ataatatatt | 480 |
| taatatataa | tatatttaat | atataatata | tatttaaatt | ataatatatt | taatatataa | 540 |
| tatatttaat | atataatata | tatttaaatt | ataatatatt | taatatataa | tatatattta | 600 |
| atatataata | tatttaatat | ataatatata | tttaatatat | aatatatttta | atatataata | 660 |
| tatatttaat | gtataatata | tttaatatat | aatatatatt | taatgtataa | tatatttaat | 720 |
| atataatata | tatttgatgt | ataatatatt | taatatatat | ttgatgtata | atatatttaa | 780 |
| tataatatat | atatttgatg | tataatatat | ttaatatata | atatatattt | gatgtataat | 840 |
| atatttaata | tataatatat | atttgatgta | taatatattt | aatatataat | atatatttga | 900 |
| tgtataatat | atttaatata | taatatatat | ttgatgtata | atatatttaa | tatataatat | 960 |
| atatttgatg | tataatatat | ttaatatata | atatatattt | gatgtataat | atatttaata | 1020 |
| tataatatat | atttgatata | taatatattt | aatatataat | atatatttga | tatatattta | 1080 |
| atatataata | tatatttgat | ataatatata | tttaatatat | aatatatatt | tgatatataa | 1140 |
| tatatttaat | atataatata | tatttgatat | ataatatatt | taatatataa | tatatatttg | 1200 |
| atatataata | tatttaatat | ataatatata | tttgatatat | aatatattta | atatataata | 1260 |
| tatatttgat | atataatata | ttttcttatt | aattatttat | atataaatata | taaatatata | 1320 |
| ttaattaatt | atatattaaa | | | | | 1340 |

<210> SEQ ID NO 160
<211> LENGTH: 937
<212> TYPE: DNA
<213> ORGANISM: Homo sapiens
<220> FEATURE:
<221> NAME/KEY: misc_binding
<222> LOCATION: (1)..(937)
<223> OTHER INFORMATION: MAR of chromosome 2 genomic contig; 78226855..
      78227791

<400> SEQUENCE: 160

```
tgtgtatata tacatatatg tgtatctatg tgtatatata catatgtgta tatatacata      60
tatgtgtata tatacatatg tgtatatatg tgtatatatg tgtatatata catatatgtg     120
tatatatgtg tatatatgtg tatatataca tatatgtgta tatatgtgta tatatacata     180
tgtgtatata tgtgtatata tacatatatg tgtatatatg tgtatatata catatatgtg     240
tatatatgtg tatatataca tatatgtgta tatatgtgta tatatgtgta tatatacata     300
tatgtgtata tatgtgtata tacatatata tgtgtatata tgtgtatata tacatatatg     360
tgtatatatg tgtatatgtg tgtatatata catatatgtg tatatacaca catatatgtg     420
tatatatgtg tatatataca tatgtgtata tacatatata tgtgtatata tgtgtatata     480
tacatatatg tgtatatatg tgtatatata catatatgtg tatacataca tatatgtgta     540
tatatgtgta tatatacata tatgtgtata catacatata tgtgtatata tgtgtataca     600
tacatatatg tgtatacata catatatgtg tatatatgtg tatacataca tatatgtgtg     660
tatatatgtg tatacatatg tgtgtatatg tgtatatata catatatgtg tgtatatatg     720
tgtatatata catatatgtg tgtatatatg tgtatatata catatatgtg tgtatatatg     780
tgtatatata catatatgtg tgtatatatg tgtatatata catatatgtg tgtatatatg     840
tgtatatata catatatgtg tgtatatatg tgtatatata catatatgtg tgtatatatg     900
tgtatatata catatatgtg tgtatatatg tgtatat                              937
```

<210> SEQ ID NO 161
<211> LENGTH: 1350
<212> TYPE: DNA
<213> ORGANISM: Homo sapiens
<220> FEATURE:
<221> NAME/KEY: misc_binding
<222> LOCATION: (1)..(1350)
<223> OTHER INFORMATION: MAR of chromosome 2 genomic contig; 79287748..
      79289097

<400> SEQUENCE: 161

```
tatatatatt atatatatag taactgttct attatatata tattatatat atttctgttc      60
tattatatat tatatatatt atattatata ttatatgtaa tatattatat atattataag     120
taatatatta tatatattat atgtaatata ttatatatat tatatgtaat atattatata     180
tattatatgc aatatgttat atatattata tgcaatatgt tatatatatt atatgcaata     240
tattatatat attatatgca atatattata taaatatat gtaatatatt atattatata      300
ttatatgtaa tatcttatat attatatgta atatattata tatattatat gtaatatctt     360
atatatatta tatgtaatat attatatatt atatgtaata tattatctta tatatattat     420
atgtaatata ttatattata tattatatgt aatatatatt atatgtaata tattacatat     480
tatatgtaat atatattata tgtaatatat tacatattat atgtaatata tattatatgt     540
aatatattac atattatatg taatatatta catattatat gtaatatatt atatgtatta     600
tatgtaatat attatatgta ttatatgtaa tatattatat gtattatatg tattatatgt     660
aatatattat atgtaattata tgtaatatat tatatattat atgtaattat attatatgta     720
atatattata ttatatatta tatatattat atgtaatata ttatattata tattatatat     780
```

```
attatatgta atatattata ttatatatta tatatattat atgtaatata ttatattata    840
tattatatat attatatgta atatattata ttatatatta tatatattat atgtaatata    900
ttatattata tattatatat attatatgta atatattata ttatatatta tatatattat    960
atgtaatata ttatattata tattatatat attatatgta atatattata ttatatatta   1020
tatatattat atgtaatata ttatattata tattatatat attatatgta atatattata   1080
ttatatatta tatatattat atgtaatata ttatattata tattatatat attatatgta   1140
atatattata ttatatatta tatatattat atgtaatata ttttatatta tatatattat   1200
attatatatt atatgtaata tattatatta tttattatat attatatatt atatgtaata   1260
tattatatta tttattatat atattatatt atttattata tataatatat tatattatat   1320
atattatatt atatatattt ctgttctaat                                    1350
```

```
<210> SEQ ID NO 162
<211> LENGTH: 332
<212> TYPE: DNA
<213> ORGANISM: Homo sapiens
<220> FEATURE:
<221> NAME/KEY: misc_difference
<222> LOCATION: (1)..(332)
<223> OTHER INFORMATION: MAR of chromosome 2 genomic contig; 81142998..
      81143329

<400> SEQUENCE: 162
ctatgtatat aactatatat aactattata taacttaata agatatataa ctattatata     60
acttaataag ttatatataa ctattatata taacttaata agttatatat aactattata    120
taacttaata agttatatat aactattata taacttatta agttatatat aactatatat    180
aacttaataa gttatatata actattatat aacttaataa gttatatata actattatat    240
aacttaataa gttatatata actattatat aacttaataa gttatatata actatatata    300
acttatatac aacttattaa gctatatata ta                                  332
```

```
<210> SEQ ID NO 163
<211> LENGTH: 327
<212> TYPE: DNA
<213> ORGANISM: Homo sapiens
<220> FEATURE:
<221> NAME/KEY: misc_binding
<222> LOCATION: (1)..(327)
<223> OTHER INFORMATION: MAR of chromosome 2 genomic contig; 84019536..
      84019862

<400> SEQUENCE: 163
actgacagta tacatactgt atatatatac agtatgtata catatacagt atgtatacta     60
tatacagtat gtatactgta tatatatata cagtatgtat actgtatata tatacagtat    120
gtatacgtat gtatactgta tatatgtatt atagtgtata tatgtattat agtgtatata    180
tgtattatat atattatagt gtatgtatta tatgtgtata tacatataat atattataca    240
tatacatatg cacaatatgt atatgtatta tatgtattca tatacatata tgtatatgta    300
taatatatgt atacatataa tacacat                                        327
```

```
<210> SEQ ID NO 164
<211> LENGTH: 407
<212> TYPE: DNA
<213> ORGANISM: Homo sapiens
<220> FEATURE:
<221> NAME/KEY: misc_binding
<222> LOCATION: (1)..(407)
<223> OTHER INFORMATION: MAR of chromosome 2 genomic contig; 1448030..
```

```
                      1448436

<400> SEQUENCE: 164
tatataatat atattacata tatattatat ctatattatt tatattacat atgtaatata    60
tattatattt atattattta tataaatatat tatatatatt atattattta tatgtaaaat   120
atttatattg tttatatata ttatatttat attatttata taaatacat attatatttta   180 tattatttat ataaatata taaataaat atataatata taaaaaata tatatattta     240 atatatctat aatatatatt atatatatta tatataatat atataattgt acatatattt   300
attatatata ttatatatat aatatatatt ataaatataa tatataaata tatttataaa   360
tatatataaa tattatattt atacattata tttatataca tattata              407

<210> SEQ ID NO 165
<211> LENGTH: 1959
<212> TYPE: DNA
<213> ORGANISM: Homo sapiens
<220> FEATURE:
<221> NAME/KEY: misc_binding
<222> LOCATION: (1)..(1959)
<223> OTHER INFORMATION: MAR of chromosome 2 genomic contig; 2117630..
      2119588

<400> SEQUENCE: 165
tatacatgtt atagtgtata tagtatacta atatataatg tatgtatgtg tatacatata    60
cacatataat atacacatat ataatatata tagtatataa taatgtataa tatataatat   120
ataatataaa atgtatagta tactacatat ttatatatag tatatagtat gcatagtaca   180
tatatactat atatgtagta tactatagtg tatatatagt acaccatata tagtataaat   240
atactatata gtatatgtac tatatatata ctatatagta tatacagtat acatatatag   300
tatacctata ctatatagta tatatagtgt gcgtatacta tatagtatat atagtgtgcg   360
tatactatat agtatatata gtgtgcgtat actatatagt atatatagtg tgcgtatact   420
atatagtata tatagtgtgc gtatactata tagtatatat agtatacata tatagtgtgc   480
gtatactata tagtatatat agtatacata tagtatgtgc gtatactata tatagtatac   540
atatatagta tatctagagt atatgtagta tgtatagtat atatagtcta catactgtat   600
atacagtata tatatactct atagtatact atacagtata gtatactata tagtatacaa   660
tatatgtata ctatagaaac acactatata tagtatacta tatatactat atactatata   720
ctatatatag tatactatat atactacata ctatatatag tgtatgtata gtatatataa   780
actatatata gtgtatatag tatatatatt atatataata tatattatat tatattatac   840
tatatattat atgtatatta tagtatatta tactattata tattatatat tatattatat   900
attatataat ataatataat tatatatttat aaaatatata tttttatatt atatattttt   960
aaatatttta taatatatat tttataatat atatattata attatttttat atataaatata  1020 aaatataata aatattttat aatatatatt tttaaaatat aatatttata tattataaaa   1080
atataaatat ataatatatt atatattata taagtataa tatataatat gttatatagt   1140
atcttatact attatactat atatattata tagtgtatat atagtatact atatatagtg   1200
tatatagtgt atactatagt gtatatagtg tatactatag tgtatatagt gtatactata   1260
tacactgtat atagtagtgt atactatata cactgtatat agtagtgtat actatataca   1320
ctgtatatag tagtgtatac tatatacact gtatatagta gtgtatacta tatacactgt   1380
atatagtagt gtatactata tacactgtat atagtagtgt atactatata cactgtatat   1440
```

```
agtagtgtat actatataca ctgtatatag tagtgtatac tatatacact gtatatagta    1500
gtgtatacta tatacactgt atatatagta tattatatat actatatatg tatatatagt    1560
atacatatat attatatata cagtatatat agtatatata ctatgtagta tatatagtat    1620
atatactata tagtatgtat agtatactat atagtatata tagtatatta tatagtatat    1680
atactatata gtatatatag tatattgtat atatagtata tatactatat agtatatata    1740
gtatattgta tatatagtat attgtatata tagtatacat agtatgtata tatagtatat    1800
atagtataca tatatagtat gtacacagta tatatagtct atatgtatac tacatatagt    1860
atacatgtat actatactac atatagtata catgtatact atactacata tagtatacat    1920
gtatagtata ctacatatac tatacatgta tagaatact                           1959

<210> SEQ ID NO 166
<211> LENGTH: 520
<212> TYPE: DNA
<213> ORGANISM: Homo sapiens
<220> FEATURE:
<221> NAME/KEY: misc_binding
<222> LOCATION: (1)..(520)
<223> OTHER INFORMATION: MAR of chromosome 2 genomic contig; 2119984..
      2120503

<400> SEQUENCE: 166
tatgtatgca tcgtatacat atatagtata tatgtgtatg catcgtatac atatatacag      60
tatatatagt atgcatcgta tacatacagt atactatata tacagtatat acagtatact     120
atatatacag tatatacagt atactatata tacagtatat acagtatact gtatatacag     180
tatatacagt atatatagta tactatatat acagtatata tactatgtat tctatatata     240
gtatagtgta catagtatac atatagtata cactatacta tatatagtat actatatata     300
ctctatatag tatatatagt atactatata tagtatatat gtatactata tatagtgtat     360
atatatacta tatagtgtat atatatatac tatatatagt atatatatac actatatatt     420
gtatagtata gtgtatatat agtatagtat atgtatatat acacatgtat acatgtatat     480
atgtatacta atatatacta atatatgtat aaatatatat                           520

<210> SEQ ID NO 167
<211> LENGTH: 954
<212> TYPE: DNA
<213> ORGANISM: Homo sapiens
<220> FEATURE:
<221> NAME/KEY: misc_binding
<222> LOCATION: (1)..(954)
<223> OTHER INFORMATION: MAR of chromosome 2 genomic contig; 2578285..
      2579238

<400> SEQUENCE: 167
tattatatat aactttataa tatataatat atattatata taactttata atatataata      60
tatattatat ataactttat aatatataat atatattata tataacttta taatatataa     120
tatatattat atataacttt ataatatata atatatatta tatataactt tataaatatat    180 aatatatatt atatataact ttataatata taatatatat tatatataac tttataatat     240
ataatatata ttatatataa ctttataata taatatatat attatatata acttataat      300 atataatata tattatatat aactttataa tatataatat atattatata taactttata     360
atatataata tatattatat actatatata atatataact ttataatata taatatatat     420
tatatactat ataactttat aatatatata atatatatta tatattatat ataactttat     480
aatatataat atatattata tataacttta taatatataa tgtatattat atattatata     540
```

```
ttatatatta tatataactt tataatatat aatgtatatt atatattata tataaccttta      600 taatatataa tatataatat aatatataac tttataatat atatatcata tattatatat      660
aactttataa tatatatcat atattatata taactataat atatatatca tatattatat      720
ataactataa tatatatatc atattatata taaacttta taatatatat atcatatatt      780
atatataact ttataatata tatcatatat tatatataac tttataatat atatcatata      840
ttatatataa ctttataata tatttatat ataacttttat aatatatatc atatattata      900 tataaccttta taatatatat catatattat ataaactttt aataatatata tcat           954
```

<210> SEQ ID NO 168
<211> LENGTH: 452
<212> TYPE: DNA
<213> ORGANISM: Homo sapiens
<220> FEATURE:
<221> NAME/KEY: misc_binding
<222> LOCATION: (1)..(452)
<223> OTHER INFORMATION: MAR of chromosome 2 genomic contig; 3836217..
      3836668

<400> SEQUENCE: 168

```
tttatatata aatatatatc ttatatatat ttatatataa tacatatata tcttatatat       60
ataaaatata tatacatatt tatatataaa atacatatgt attatataca tttatatata      120
atacatatgt attatataca attatataat acatatgtat tatatacaat tatataatac      180
atatttataa atatatatat ttatatttat atatatttat atataaataa atatatattt      240
atagatttat ttatatataat atatatttat ataaatatat atttatatat atttatataa      300
atatatattt atatatattt ctatatatat atataaaatat atgtataaaat atatatattt     360 atacatatat tcatataaat atatatattt atacatgtat ttatatgaat atataatttat      420 acatgtaatt atatgaatat atattttatac at                                     452
```

<210> SEQ ID NO 169
<211> LENGTH: 417
<212> TYPE: DNA
<213> ORGANISM: Homo sapiens
<220> FEATURE:
<221> NAME/KEY: misc_binding
<222> LOCATION: (1)..(417)
<223> OTHER INFORMATION: MAR of chromosome 2 genomic contig; 3837666..
      3838082

<400> SEQUENCE: 169

```
gatatatata tttatataaa tatatatata aagagatata tttatatatt tatttatata       60
aatatatttc tttatataaa gatatatgta aatatattta tttatataaa tatatttata      120
tatgtaaata tatatttata tatttatata tttatatatt tatttatata aatatatata      180
tttatatatt tatttatata tataaaaata tataaatata aatatatata aatatatata      240
attataaata tagaaataaa tataaatata aatatataaa tatatataaa tataaatata      300
tataaatata aatatatata aatataaaata taaaatgtata taaatatata aatataaaata     360 tatataaaata tgtataaaata tataaatata taaatatata aaaatatata taaatac          417
```

<210> SEQ ID NO 170
<211> LENGTH: 1197
<212> TYPE: DNA
<213> ORGANISM: Homo sapiens
<220> FEATURE:
<221> NAME/KEY: misc_binding
<222> LOCATION: (1)..(1197)

<223> OTHER INFORMATION: MAR of chromosome 2 genomic contig; 6294846..
      6296042

<400> SEQUENCE: 170

| | | | | | |
|---|---|---|---|---|---|
| tatatactaa | tatgtatata | taaatatata | aatatatata | cacgtgtata | tataaatata | 60 |
| tatgtatata | taaatatata | tacatatatg | tatataaaaa | tatatacgta | tatacgtata | 120 |
| tacgtatata | tagatatata | cgtatatacg | tatacgtata | tatatagata | tatacgtata | 180 |
| tacgtatata | tagatatata | cgtatatacg | tatacgtata | tacatgtgta | tatacgtata | 240 |
| tacacatata | cgtatacatg | tgtatatacg | tatatgtata | cattatatat | acgtatatat | 300 |
| acatatatgt | atacatgtat | atataaatat | atacatatat | gtatatatta | tacatatatg | 360 |
| tatatataat | atatatatta | tatataatat | atatattata | taaatatat | atattatata | 420 |
| taatatatat | attatatata | atatattata | tattatatat | aatatataca | tatataatat | 480 |
| attatatatg | tacatatgta | cataatgtat | atatgtatat | atataaatata | tatgcacatg | 540 |
| tatatataat | atatgtatat | tatatataca | tatgtatata | tgtacatatt | atatatgtat | 600 |
| atatgtacct | attatatata | catatgtata | tatgtaccta | ttatatatac | atatgtatat | 660 |
| atgtacatat | tatatataca | tatgtatata | tgtacatatt | atatatacat | atgtatatat | 720 |
| gtgcatgcat | atataaatata | taatatatta | tagattataa | tattatatac | atatcatata | 780 |
| ttatatactt | atatatacat | gtatatatta | tatacatatt | atatattata | tacatataat | 840 |
| atatgtatat | aatatataca | tatattatat | attatatata | atacattatg | ttatatatta | 900 |
| tgttatataa | tatatattat | ataatataca | tatattatat | ataatatata | catatataat | 960 |
| aaataatata | taattatata | tataatatat | gcatataaat | atgtaatata | ttttatatta | 1020 |
| tatatgatca | tatataatat | gacatattat | atatgattat | atatatgata | tattatatat | 1080 |
| gattatatat | attatatata | aatatatgat | tatatataat | catatatata | aatatatgat | 1140 |
| tatatgatta | tatataaata | tatatatatg | attatatgat | tatatataat | tgattat | 1197 |

<210> SEQ ID NO 171
<211> LENGTH: 362
<212> TYPE: DNA
<213> ORGANISM: Homo sapiens
<220> FEATURE:
<221> NAME/KEY: misc_binding
<222> LOCATION: (1)..(362)
<223> OTHER INFORMATION: MAR of chromosome 2 genomic contig; 6506971..
      6507332

<400> SEQUENCE: 171

| | | | | | |
|---|---|---|---|---|---|
| tatatatagt | gtatactata | tatacgctat | atgcacacat | aaactatata | tacagtatat | 60 |
| aatatgcgta | tactatatac | acagtatata | ctacatgtat | actatatata | gtatataaga | 120 |
| tatatactat | gtatataata | tatatactag | gtatatatat | ccatatatat | actatatact | 180 |
| atagtatata | catatatatg | tacgtatata | tgtatatgta | catatatatg | tagtatgtat | 240 |
| atatatacat | atatacacac | tatagtatat | acatatatat | actatatata | ccctatatag | 300 |
| agtatattat | atacagtata | ctatatatac | tatatatacc | ctatatagag | catgtctatg | 360 |
| ct | | | | | | 362 |

<210> SEQ ID NO 172
<211> LENGTH: 2578
<212> TYPE: DNA
<213> ORGANISM: Homo sapiens
<220> FEATURE:
<221> NAME/KEY: misc_binding
<222> LOCATION: (1)..(2578)
<223> OTHER INFORMATION: MAR of chromosome 2 genomic contig; 6507395..
      6509972

<400> SEQUENCE: 172

```
ggtatactat atatactata gagtatactt tatagtatat ataccatatat tatatatata      60 tacatacact gtatagtata tatggtatat atactatata tggcatatat agtttatata     120
tatactatat atggtatata tagtttatat atatactata tatggtatat atagtttata     180
tataccatat atggtatata tagtttatat agtacatata gtatatatac acactgtata     240
gtatatatta tgtagtatat atactatata tactgtatat atagtataaa tactatatat     300
agtatacact atatactata cactatatat actatatact atatactata tatagtatac     360
tatatagtat atagtatact ctatatgtac tatagagtat actatatata ctatacataa     420
aatattttta tatatagtac agcgtatact atatactata tatagtatac tctatatgta     480
ctatagagtg tagtatatac tatacagtat actctatata tactatacag tacactatat     540
atactatata tagtatattt tatatatagt acagtatata cagtatatat attatactat     600
atgtagtaca tatatagttt agtatatata gtatatatac tatactatat gtactacata     660
tataatagta tatatagtat atatactata ctatatgtag tacatatata gtttagtata     720
tatactagta tatagatata tagttatata gatatataat agtatatata gtatatatag     780
catatatagt atatatgcta tatatactat atagcatata ctatatacta tatatacagt     840
atatatagca tatatagcat atataatata tatacttttg atatacatac tatatacagt     900
atatatagta tatatactgt ataaatatac tatatatacc gtatatgcac actatatgct     960
atatatacta tatacactat atacagtata tatagtacac tatactatat aaagtatata    1020
tagtatacag tacactatac tatatacatt atatatagta tatattatac atagtatata    1080
gtatataaat agtatatata gtatatacag tatatatata gcatacttta tatagtatac    1140
acagtatata gatactatat atgctatata tagtatctat atactgtata ttatatatac    1200
taatatagta tatatgtata tatatactgt atatataata tatacatata tagtatatat    1260
actatacata cacactatac atatgtatat atactataca tactatatac tatatatcct    1320
atatatacta tatagtatat tatatatcct atatatacta tatagtatat tatatatcct    1380
atatatacta tatagtatat tatatatact atataccata tatactatat atactgtata    1440
gtatactata tatactatat agtatactgt atatactata tagtatactg tatatactat    1500
atagtatact gtatatacta tatagtatac tgtatatact atatagtata ctgtatatac    1560
tatatagtat actgtatata ctatatatac tatatagtat actgtatata ctatatagta    1620
tactatatat actatatacc atatatacta tgtatatact atatatagta tatactatgt    1680
atatgctata tatagtatat atagtatata tgctatatat agtatatata gtatatatgc    1740
tatatataca gtctatatat agtatatata ctatatagac tatatatata gcatatatac    1800
tatatatact atatataata tatatggtat atacatagta tctatatgta gtatctatat    1860
atagtaccta tatatactat atataggtac tatatatagt atatatactt tatatagata    1920
ctatatatag tatatatact ttatatagta tatatagtat atgtagcata tatagtatat    1980
atagtatata tagtatatag tatgtatagt atatatagat tatattgtat atacagtata    2040
tatactgtat atactatata aatagtacat acagtatata cagtatatat gtactatata    2100
tagtatatac agtatataca gtatatatgt accatatata gtatatacag tatatacagt    2160
atatatgcac tatatgttat atacagtata tacagtatat atgtactata taaatagaat    2220
```

```
atactctata tacagtatat atgtactata taaatatata cactatgtac agtatatatg    2280
tactatataa atagtatata cactatatac agtatatatg tactatatag tgtatacagt    2340
atatacagta tataggtact atatatggta tatacagtat atatgcacta tatggtatat    2400
acagtatata tgcactatat atggtatata cagtatatat gtactatata tggtatatac    2460
agtatatatg tactatatat ggtatataca gtatatatgt actatatatg gtatatacag    2520
tttatacagt atatatgcac tatatatggt atatacagta tacatgtact atatatgg     2578
```

<210> SEQ ID NO 173
<211> LENGTH: 598
<212> TYPE: DNA
<213> ORGANISM: Homo sapiens
<220> FEATURE:
<221> NAME/KEY: misc_binding
<222> LOCATION: (1)..(598)
<223> OTHER INFORMATION: MAR of chromosome 2 genomic contig; 7770400..
      7770997

<400> SEQUENCE: 173

```
gtgtattgta tatacatata cgtatctacg tatatacata tatgtattgt atatacatat      60
atgtattgta tatacatata tgtatatacg tatatacata tatgtattgt atatacatat     120
atgtatatac gtatatacat atatgtatat acgtatatag atatacatat atatgtattg     180
tatatacata tatgtatata catatataca tatatattga tatacatata tatgtattgt     240
atatacatat acaatatatg tatatataca tatacatata caatatatgt atatacatat     300
atatgtattg tatatacata tatatgtatt gtatatacat atattgatat acatatatgt     360
atatatacat atatgcatat atgtatatat acatatatgc atatatgtat atatacatat     420
atacatatgt acatatatac atatatacat atatgtatat atacatatat acatatgtac     480
atatatacat atatacatat gtacatatat acatatatac atatgtacat atatacatat     540
atagatatat atacacatat atagatatac ttatatgtat atatacatac atacatat      598
```

<210> SEQ ID NO 174
<211> LENGTH: 1048
<212> TYPE: DNA
<213> ORGANISM: Homo sapiens
<220> FEATURE:
<221> NAME/KEY: misc_binding
<222> LOCATION: (1)..(1048)
<223> OTHER INFORMATION: MAR of chromosome 2 genomic contig; 8332422..
      8333469

<400> SEQUENCE: 174

```
cattatatat aatatataat atattattat atataaatata tataacatta tatatagtat      60 atgacata tataacatat attatatata acatatataa aatataacat attatatata        120
acatatataa aatataacat attatatata taacatatat aaaatataac atatattata      180
tataacatgt ataaaatata acatatatta tatataacat gtataaaata taacatatat      240 tataacat gtataaaacta taacatatat tatatataaa atatattata tgttatatat      300
tataaataaa atatattata tgttatatat taacatat tatataaata atatataata        360
tataacatat attatataaa taatatataa catatattat ataaataata tataacataa      420
catatattat ataacatata acatataaca tatttatat ataacatata acatataaca      480
tatattatat ataacatata acatataaca tatttatat ataacatata acatatatta      540
tattatatat aacatataac atatattata ttatatataa catataacat atattatatt      600
```

-continued

```
atatataaca tataacatat attatattat atataacata taacatatat tatattatat    660
ataatatata acatatatat tatatataat atataacata taacatatat tatatataat    720
ataatatata acatatatta tataataatat aatatataac atatattata tataatataa   780
tatataacat atattatata taatataata taacatcat attatatata atataatata     840
taacatatat tatatataat ataatatata acatatatta tatataataat aatatataac   900 atatattata taatataa tataacat ataatatata taacatatag catatataat        960 ataacata taacatatat tatatataac ataacata tattatatat aacatataac       1020
atatataata tgtaacatta tatataac                                      1048

<210> SEQ ID NO 175
<211> LENGTH: 375
<212> TYPE: DNA
<213> ORGANISM: Homo sapiens
<220> FEATURE:
<221> NAME/KEY: misc_binding
<222> LOCATION: (1)..(375)
<223> OTHER INFORMATION: MAR of chromosome 2 genomic contig; 8909678..
      8910052

<400> SEQUENCE: 175
tatatacaca tatatacgta tgaatatata tacacatata cgtatgaata tatatacccca   60 tatacgtatg aatatacaca tatatatacg tacgtatata tatacacata tatacgtacg   120
tatatatata cacatatata cgtacgtata tatatacaca tatatacgta cgaatatata   180
tacacatata tacgtacgaa tatatataca catatatacg tacgaatata tatacacata   240
tatacgtacg aatatatata cacatatata cgtacgaata tatatacaca tatatacgta   300
cgaatatata tacacatata tacgtacgaa tatatataca catatatacg tacgaatata   360
tatacacata tatac                                                    375

<210> SEQ ID NO 176
<211> LENGTH: 563
<212> TYPE: DNA
<213> ORGANISM: Homo sapiens
<220> FEATURE:
<221> NAME/KEY: misc_binding
<222> LOCATION: (1)..(563)
<223> OTHER INFORMATION: MAR of chromosome 2 genomic contig; 10572503..
      10573065

<400> SEQUENCE: 176
atttataata tatatgtata aatatatgta tatatttata tttaaatata tgtatatata    60
tttatattta aatatacgta tatatattta tatttaaata tacgtgtata tatttatatt   120
taaatatacg tgtatatatt tatatttaaa tatacgtgta tatatttata tttaaatata   180
cgtgtatata tttatattta aatatacgtg tatatatta tatttaaata tacgtgtata   240
tatttatatt taaatatacg tgtatatatt tatatttaaa tatacgtgta tatttatatt   300
taaatatacg tgtatatatt tatatttaaa tatgtatgta tttataaata tatatttaaa   360
gtatatattt ataaatgtat acatgtatat ataaatatat atattttaaa tatatattta   420
tatatatatt tatatattta tataagtata tatatatta aatatatgta tatttata     480 tatttatata agtatatata tttaaatata tgtatatatt tataatatat attttaaata   540
tatatttata tatttattat ata                                           563

<210> SEQ ID NO 177
<211> LENGTH: 595
```

```
<212> TYPE: DNA
<213> ORGANISM: Homo sapiens
<220> FEATURE:
<221> NAME/KEY: misc_binding
<222> LOCATION: (1)..(595)
<223> OTHER INFORMATION: MAR of chromosome 2 genomic contig; 11609694..
      11610288

<400> SEQUENCE: 177
tataaatact atatatagta tatataatat tatatatact atatataaat atatgtagta      60
taaataatat ataatataga tatataatat aatataatat gttataaata taaatatatt     120
tatataattt aatttataat atataatata taatatataa tttaatttta taatatataa     180
tatataattt aattttataa tatataatat ataatatgta aattatatat aatttaatat     240
atctaaatta tataatttaa atataaatat aatataaata tatctaacat aatatacata     300
acataaatat atatagtata tatagtacat ataaatatat atagtacata tagtatatat     360
aaatatatag tatatataaa tatagtatat ataaatatat agtatatata tagtatatat     420
aaatatatag tatatataaa tatatatagt atatataaat aatatatagt atataaataa     480
tatatattat taaatataat aataatttat tatatatact atatattatt atgtattata     540
ttatatatat tattttatat ttaatatata ttattttata tattatattt aatat          595

<210> SEQ ID NO 178
<211> LENGTH: 662
<212> TYPE: DNA
<213> ORGANISM: Homo sapiens
<220> FEATURE:
<221> NAME/KEY: misc_binding
<222> LOCATION: (1)..(662)
<223> OTHER INFORMATION: MAR of chromosome 2 genomic contig; 12699804..
      12700465

<400> SEQUENCE: 178
gtatatatat atatatatat atggtgtata tatatatata tatatatggt gtatatatat      60
atatatatat atggtgtata tatatatata tggtgtatat atatatatgc tgtatatata     120
tatggtatat atatatggta tatatatatt tgctatatat atagcagatc tgctatatat     180
atatatttgc tatatatata gcagatctgc tatatatatt tgctatatat atgctatata     240
tatgctacat atatgctata tatatgctat atatatgcta tatatatgct atatatatgc     300
tatatatatg ctacatatat gctatatata tgctacatat atgctatata tatgctatat     360
atatatgcta tatatatgct atatatatat gctatatata tgctatatat atatgctata     420
tatatgctat atatatatgc tatatatatg ctatatatat gctatatata tagcatatat     480
atatagctat atatgctata tatatatagc ttatatatat gctatatatg ctatatatat     540
gctatatata tagctatata tatgctatat atagctatat atatgctaca tatatgctat     600
atatatgcca tatgtatgct atatatatgc tatatatata tgctatatat atgctatata     660
ta                                                                   662

<210> SEQ ID NO 179
<211> LENGTH: 649
<212> TYPE: DNA
<213> ORGANISM: Homo sapiens
<220> FEATURE:
<221> NAME/KEY: misc_binding
<222> LOCATION: (1)..(649)
<223> OTHER INFORMATION: MAR of chromosome 2 genomic contig; 12821904..
      12822552

<400> SEQUENCE: 179
```

```
tatgtaatat tatatatata aattatatat tatacatatg taatattata tatatataaa    60
ttatatatta tacatgtata atattatata tatataaatt atatattata catatgtaat   120
attatatata tataaattat attatataca tatgtaatat tatatatata taaattatat   180
attatacata tgtattatat ataaaatta tatattatac atatataata tatatataaa   240
ttatatatta tacatgtata atatatataa attatatatt atacatatat aatatatata   300
aattatatat tatacatata taatatatat aaattatata ttatacatat ataatatata   360
taaattatat attatacata taatatatat ataaattata tattatacat ataatatata   420
tataaattat atattataca tataatatat atataaatta tatattatac atatataata   480
tatataaatt atatattata catatataat atataaaat tatatattat acatatataa   540
tatatataaa ttatatatta tacatatata atatatataa attatatatt atacatatat   600
aatatatata aattatatat tatacatata taatatatat aaattatat                649

<210> SEQ ID NO 180
<211> LENGTH: 3191
<212> TYPE: DNA
<213> ORGANISM: Homo sapiens
<220> FEATURE:
<221> NAME/KEY: misc_binding
<222> LOCATION: (1)..(3191)
<223> OTHER INFORMATION: MAR of chromosome 2 genomic contig; 15356889..
      15360079

<400> SEQUENCE: 180
tacaattata tataactata aatataatat aatatatatt atctatatta catattaata    60
tataatatat attacctatt aatatataat ataatatata taatatatat tacctattaa   120
tatataatat aatatatata atatatatta cctattaata tataataaaa tatatataat   180
atatattaca tattattata taatatatat tatataacat atataacata tactatatat   240
tatataacat ataataattgt atatgtatta tatatattat atatacttat acataatata   300
taaataatta aatatatgtt ataaatataa caaatatata acatatataa catatataac   360 atatataaa ttcataaaaa tatataatac ataatatata ttatgcaaca tattatataa   420
tatataacat ataatgtata ttatattata tcatatataa tacataaatat ataatatatg   480 atataatata atatattata tatgatataa taatatatat tatatatgtt ataatataat   540
atatattata tataggatat atttataacat attacatatg atataataaa tttatctta   600 tatataggat atattataat atcacata tagcatatat taaaatatat tacatatagt   660
atattatata tactatatgt atatatacat atagtatatt atagtatatt atacagtata   720
tattatatat actatatata gtagtataca gtatatatta tatatactat atatagtagt   780
atacagtata tattatacag tatatattat atacactata ttatatatta tgtataatat   840
atactatata tagtatatta tgtagtatat attaaacata atagatatat agtatatact   900
atagataata gatattatat agtatatagt atatattata taatatatat ataatatata   960
ttatatacat atatgatata tgatatatta tatataatat atataatata taatatatgt  1020
aatataatac atattatata taatatatgt aatataaatat aatatataat atatgtaata  1080
taataatata tattatataa tataacatat ataaatataa taatatatat tatatgatat  1140
aacatacata aatataataa catatataat atatattata tattatattg tatatatgat  1200
atactatata ttcacatta tacattattt ataatatata attaatatat aacatatatt  1260
agataacata taattatatc tgtaacatat ataagatata attacatata taacatatat  1320
```

```
aattatatat atatttatct aattatatat gaaattatat atgacatata aaattatata    1380
ttatatatgt tatatgtatt atatattata tatgttatat atgttatata taacatatat    1440
aacatatata acacacacat ataacatata taacatatat tacatatata acatatataa    1500
cacatatata attatctaac atagataata tatataaat ataatataac atatatatta    1560
tatattatac actctattat attatatata ttatacataa tatataatat atgatata     1620 atataataca ttgtatatac gatataaat atattgtaca tagtataata tacatatata    1680
gtatattatg tataacataa tatatagtat attatgtata acataatata tagtatatta   1740
tgtataacat aatatatagt atattatgta taacataata tatagtatat tatgtataac   1800
ataatatata gtatattatg taacataa tatatagtat attatgtata acataatata    1860
tagtatatta tgtataacat aatatatagt atattatgta taacataata tatagtatat   1920
tatgtataac ataatatata gtatattatg taacataa tatatagtat attatgtata    1980
tataatatac atattatata gtatattatg tatataat atacatatta tatagtatat    2040
tatgtatata taatatacat attatatagt atattatgta tataatat acatattata     2100 tagtatatta tgtatatata atacacatat tatatagtat attatgtata tataatatac   2160
atattatata gtatattatg tatataat atacatatta tatagtatat tatgtatata     2220
taatatacat attatatagt atattatgta tataatat acatattata tagtatatta     2280
tgtatatata atacacatat tatatagtat attatgtata tataatatac atattatata   2340
gtatattatg tatataat atacatgtta tgtagtatat tatgtatata taatatacat     2400
gttatgtagt atattatgta tatataat acatgttatg tagtatatta tgtatatata     2460
atatatataa ggtgtatata tattatgtat atataata taaggtatat atattatgta    2520 tatataata ataaggtg tttatataat gtatataaa tatataaggt atgtatatta      2580
tgtatatata atatgtatat tatataaat atatattatt tatatacatt atgtatctat   2640
ataatatata ttatgtatat attaggtatc tatataata atattatgta tatatattat   2700
gtatctatat aatatatata ttatgtatat atattatgta tctatataat atatatatta  2760
tatgtatatt atgtatctat ataatatata taatgtatat agatatatta tatattatgt  2820
atatatatta tgtatctatt ttatatataa tgtatataga tatacaatat atattatgta  2880
tatattatgt atctatataa tatatattat ttatatagat atatatatta tgtatatata  2940
cataatatat tacatattat gtatatatac ataatatata atatatttatg tatatataca  3000 taatatataa tatattatat attacatata ttatatataa tatattatat tatgtatata  3060
tattatgtat atataatgta tatataaat ataaagtgta tatatattgt gtatatataa    3120
tgtatatata ttacatatat tatgtgtata tatattatac ataatatata tactacatta   3180
tacataatat g                                                        3191
```

<210> SEQ ID NO 181
<211> LENGTH: 314
<212> TYPE: DNA
<213> ORGANISM: Homo sapiens
<220> FEATURE:
<221> NAME/KEY: misc_binding
<222> LOCATION: (1)..(314)
<223> OTHER INFORMATION: MAR of chromosome 2 genomic contig; 728676..
      728989

<400> SEQUENCE: 181

```
tgtgtatata tgtatatata atatatatta tataatatgc atatgtataa aatatgtata    60
```

```
ttatatatgt atattttata tatatgtata tattatatgt atattttata tatgtatatt    120
ttatatatat gtatatatta tatatgtata ttttatatat atgtatatat tatatgtata    180
ttttatatat atgtatatat tatatatgta tattttatat atgtatatat attatatatg    240
tatattttat atatatgtat attttatata tatgtatatc atatatatgt atatattata    300
tatatgtata tctt                                                      314

<210> SEQ ID NO 182
<211> LENGTH: 423
<212> TYPE: DNA
<213> ORGANISM: Homo sapiens
<220> FEATURE:
<221> NAME/KEY: misc_binding
<222> LOCATION: (1)..(423)
<223> OTHER INFORMATION: MAR of chromosome 2 genomic contig; 737493..
      737915

<400> SEQUENCE: 182
ataatatata gtgtctttta tattatctaa tatgtaaatat aatgtatttt atattatgta    60
ttttatatta tataatatat aatataatgt attttatatt atgttata taatatatag     120 tgcattatat attatgttat attatatata ttttatttat ataaattata tattatatgt    180
tattttatat atattatata acatataata taacaatgca ttatatatta taaaatatat    240
aatacattac atatattata taatatataa tacattacat atattatata atatataata    300
cattatcata tattacaaat attacattag tataatagta attataatat aatatattat    360
atattacata tattatatta atgtaatagt aattataata taatatatat tatattttat    420
att                                                                  423

<210> SEQ ID NO 183
<211> LENGTH: 724
<212> TYPE: DNA
<213> ORGANISM: Homo sapiens
<220> FEATURE:
<221> NAME/KEY: misc_binding
<222> LOCATION: (1)..(724)
<223> OTHER INFORMATION: MAR of chromosome 2 genomic contig; 1069556..
      1070279

<400> SEQUENCE: 183
tattataata tattatatac attatattgt atatatacta tatatggtat atatagtata    60
cataatataa aatgtatatt gtaatataca ttatatatat acatagtgta cattatataa    120
tataatataa tgtatattat aatatacatt ataaatataat agtgtactat gtatatagta   180
tatataatgt atattataat gtattatata gtataatata atataatata cattatatag    240
tattgcatta tatatgctat ataatatata atatattatg tatatataca ttatatatac   300
tatattatat agtacatata atgtatatta tatagtatat ataatataat acattataca   360
tacaatatat aatgtatatt atatagtatg tataatgtaa tacattatac atagtacata   420
aagtatatta taatatatta taatatataa tatacattat atattataat gtatataata   480
tattgtatat atactatata taatgtatat acaattatat ataattgtat atacacatgt    540
atatgtatat gtatatatac atgtatatgt atgtgtatat atacatatat gtatatgtat   600
gtgtatatat gtatatgtat atatgtatat gtatacgtat atatgtatat acaatgtata   660
tataatgtat ataaaatatat aatatatata caatatgtat ataatgtata taattatata   720
atat                                                                 724
```

<210> SEQ ID NO 184
<211> LENGTH: 383
<212> TYPE: DNA
<213> ORGANISM: Homo sapiens
<220> FEATURE:
<221> NAME/KEY: misc_binding
<222> LOCATION: (1)..(383)
<223> OTHER INFORMATION: MAR of chromosome 2 genomic contig; 2719918..
      2720300

<400> SEQUENCE: 184
atatttatat tttatatatt atttatatat aaatatatat ttatattttta tatattattt    60 atatataaat atatatttat attttatata ttatttatat ataaatatat atttatattt   120
tatatattat ttatatataa atatatattt atatttata tattatttat atataaatat    180
atatttatat tttatatatt atttatatat aaatatatat ttatattttta tatattattt   240 atatataaat atatatttat attttatata ttatatattt atatattata tatatttata   300
ttaatttgtg tataatatat attattaaat ataataaata tatttatttt tatatattat   360
ataaaaatat ataatatata aaa                                           383

<210> SEQ ID NO 185
<211> LENGTH: 309
<212> TYPE: DNA
<213> ORGANISM: Homo sapiens
<220> FEATURE:
<221> NAME/KEY: misc_binding
<222> LOCATION: (1)..(309)
<223> OTHER INFORMATION: MAR of chromosome 2 genomic contig; 4994249..
      4994557

<400> SEQUENCE: 185
tataatatat aattgttata acattataac aattatatat tatatataat acaattatat    60
aatatatatt ataaattgt aatataataat aaattatat aatatatatt ataataata    120 atatataata tatcatatat gttatatatt ttattatata atatatatta tatataatat    180
tatatataat atatattata taaatatatta tatatataat atatattata taatatattt   240
atatatatta tatataatat atattatata ttaaatatta tatatataat atatataaca   300
ttattgtta                                                           309

<210> SEQ ID NO 186
<211> LENGTH: 740
<212> TYPE: DNA
<213> ORGANISM: Homo sapiens
<220> FEATURE:
<221> NAME/KEY: misc_binding
<222> LOCATION: (1)..(740)
<223> OTHER INFORMATION: MAR of chromosome 2 genomic contig; 5034916..
      5035655

<400> SEQUENCE: 186
tttatatata aaatattata tataatatta tatataaat tttctatata aaatgtgtat     60
ataattatat ataattatat aaaatataat atagaatatc taataatgta taatatataa   120
catataaaaa taatattatt taatatataa tattttatat ataatatttt tatatataat   180
ataatatata ttttatatat aattattaat tatataatta atatataata tatattttat   240
acataattat taattatata taattaaatat ataatatatc ttatacataa ttatcaatta  300
tatataatta atatataata tatattttat acataattat taattatata taattaatat   360
ataatatatc ttatacataa tatatataaa tatattatat ataatatata ttatatataa   420

-continued

```
tattatatat aatatatatt atatatataa aatttatata taatattata tataatatta        480
tatattttat atacaatatg atatataata taatttatat attatatata tttatatata        540
attattatat aaattatata aatataaatt atatatttat ataataattat tataaaaatc       600 attatataat tattataatt ataatatata atataatata atattatata taatatatag        660
tattctatat aaataatata acatatattt tatatagaat attatatata atataatata        720
tattttatat agaatattat                                                    740
```

<210> SEQ ID NO 187
<211> LENGTH: 847
<212> TYPE: DNA
<213> ORGANISM: Homo sapiens
<220> FEATURE:
<221> NAME/KEY: misc_binding
<222> LOCATION: (1)..(847)
<223> OTHER INFORMATION: MAR of chromosome 2 genomic contig; 6074678..
      6075524

<400> SEQUENCE: 187

```
aatatagaca taaatatata tgcataaata tatatatgca taaatatata taaaaatata        60
tataaatata tacataaata tatataaata tatacaaaaa tatatataaa tatataaaaa       120
aatatataaa tatatataca catatataaa tatatataca tacatatata aacatatata       180
cataaatata tatgtataaa tatatataca cataaatata tgtatgaata tatatacata       240
aatatatatg taaatatata tatacataaa tatataaaga tatatacata aatatatata       300
aatatatata cataaatata tataaatata taaaataga tataaaaata tatatataaa       360
tatataaata tatatataaa tatataaata taaaaaata gatatataaa tatatatata       420
aatatataaa tatatatata aatatatata aatatataaa tatatatata aatatatata       480
aatatataaa tatatataaa tatataaata tatatataaa tatataaaaa tatataaata       540
tatataaata tatataaata tataaatata tatataaata tataataaata tataaatata       600 tatataaata taaatatata taaatatata taaatatata taaatatata taaatatata       660
taaatatata aatatatata aatatatata aatatataaa tatataaaaa tatatataaa       720
tatatataaa tatataaata tatataaata tataaatata tatataaata tatataaata       780
tataaatata tatataaaata taaatatata taaatatata aatatatata taaatatata       840
taaatat                                                                 847
```

<210> SEQ ID NO 188
<211> LENGTH: 784
<212> TYPE: DNA
<213> ORGANISM: Homo sapiens
<220> FEATURE:
<221> NAME/KEY: misc_binding
<222> LOCATION: (1)..(784)
<223> OTHER INFORMATION: MAR of chromosome 2 genomic contig; 6108986..
      6109769

<400> SEQUENCE: 188

```
atttatttat atatttaata tataaaatat atatttaata tataaaatgt atatatatac        60
atatattata tataatacaa tatatattat ataatatata tattatatat aatattatat       120 attatatttat aatataaatat atattatata taatataata tatattatat attattatat      180
ataatataat atatattata tattattata taatataaa tatatattat attattatat         240
atataatata atatatatta tatattatta tatataaaat aatatatatt atatatatat        300
tttatatata taatatataa tatatatatt atatatatat tttatatata taatatataa        360
```

```
tatatatatt atatatatat tttatatata taatatataa tatatatatt atatatatat    420
tttatatgta taatatataa tatatatatt atatatatat tatatatata taatatgtaa    480
tatatatatt atatatatat tatatatata tatatatta tacataaaat atatattata    540
tataatatat ataatatata ttatatataa aatatatttt atgtataata tatattatat    600
ataatatata atgtatattt atatataaaa tatatatttta tatacaatgt atatttatat    660
ataaaatata tatttatata caatgtatat ttatataaat atgtgtttaa tatatgaaat    720
atatatttat ataatatata tatttaatct ataaaatata tattaaatat atatttatat    780
ttaa                                                                 784

<210> SEQ ID NO 189
<211> LENGTH: 381
<212> TYPE: DNA
<213> ORGANISM: Homo sapiens
<220> FEATURE:
<221> NAME/KEY: misc_binding
<222> LOCATION: (1)..(381)
<223> OTHER INFORMATION: MAR of chromosome 2 genomic contig; 10389032..
      10389412

<400> SEQUENCE: 189
tatacacata tagagtatat agagtatata tagagtatat ctatagagta tatatgtata    60
tagagtatat aatacagcct accatatata tagtatacat atatatatac tctatatact   120
atatatatag tgtgtatata tatagtatag accctaccat atatatatat aggagtatat   180
atatatacac actcctacta tatatagtat gtatatagag agtatataga gtatatatac   240
agtatatata cacagtatat atatgccata tagtatatct atatacttat atatagtatg   300
tatctatata cttatatata gtatgtatct atatactata tatgtatgt atctatatac   360 tatatagagt atatatgtat a                                             381

<210> SEQ ID NO 190
<211> LENGTH: 507
<212> TYPE: DNA
<213> ORGANISM: Homo sapiens
<220> FEATURE:
<221> NAME/KEY: misc_difference
<222> LOCATION: (1)..(507)
<223> OTHER INFORMATION: MAR of chromosome 2 genomic contig; 11097807..
      11098313

<400> SEQUENCE: 190
aattatatat aatttattat ataaattttt atatttataa tatttttata tacatatttt    60
atatatcttt ataattatat attacatata taatattata taatatatat aatatatata   120
atatatatta tatattatat aatatatatt atatatatta tatataatat ataatatata   180
tataatatat ataatatata taatatataa tatatattat ataatatata ttatatataa   240
tatatattat atataatata tattatatat aatatataat atataatata tatataacat   300
ataataatat attacacata atttatatat aattttttata taattatata tatttatata   360
tttttatata attatatata tttatatatt tttatataat tatatatatt tatatatttt   420
tatataatta tatatataat ttttatataa atatatataa ttttatataa ttttatataa   480
ttataaaata tataattata tataatt                                        507

<210> SEQ ID NO 191
<211> LENGTH: 329
<212> TYPE: DNA
```

```
<213> ORGANISM: Homo sapiens
<220> FEATURE:
<221> NAME/KEY: misc_binding
<222> LOCATION: (1)..(329)
<223> OTHER INFORMATION: MAR of chromosome 2 genomic contig; 11234628..
      11234956

<400> SEQUENCE: 191
ttatagttaa atatataaat ataaaatata cagttttata cagtatatat aaaatataca      60
atatataata cataatacat tagttatata tactatatat actatatata ctacacgtat     120
agtatatata tgaaactata tatatactat acgtgtagta tatatatgaa actatatata     180
tactatacgt gtagtatata tatgaaacta tatactatac gtagtatata tatatgaaac     240
tatatatact atatatactt aactataatt gtatatagtt aaaaatataa atataaaata     300
tacagttaaa tatattaata tataatagt                                       329

<210> SEQ ID NO 192
<211> LENGTH: 584
<212> TYPE: DNA
<213> ORGANISM: Homo sapiens
<220> FEATURE:
<221> NAME/KEY: misc_binding
<222> LOCATION: (1)..(584)
<223> OTHER INFORMATION: MAR of chromosome 2 genomic contig; 797844..
      798427

<400> SEQUENCE: 192
tattatttta tgttataaat agataaaaat atatactaat atatatgtac ttatatatac      60
atcaatatat aatgtattat tttatactaa cgtatattat atatactagt atataatcta     120
tattatttta tatgttataa atatataata aaatatataa atattttatg catatattaa     180
tatataatat atactaacat gctaatttat atatacttat atataattta tatagtatat     240
aatatataaa tgtatataat acataattta tatatttata tattaatagt ttatatatta     300
gtatatatac taatttttata tactaataaa taaattatat aatatataaa ttatatatta     360
tagtacataa tatatattat atagttaaat aactatgtaa ctataatata taactatata     420
tgatatacag ttatatataa tataaatttt acatacagta tataaattat atactataca     480
tttatataca tatggtatat aaattatata ctatacattt atatacatat ggtatataaa     540
ttgtatacta tataatgtgt attagtatat atactaatat atac                      584

<210> SEQ ID NO 193
<211> LENGTH: 363
<212> TYPE: DNA
<213> ORGANISM: Homo sapiens
<220> FEATURE:
<221> NAME/KEY: misc_binding
<222> LOCATION: (1)..(363)
<223> OTHER INFORMATION: MAR of chromosome 2 genomic contig; 1093824..
      1094186

<400> SEQUENCE: 193
tatacacaca catatatata cacatatata tacacatata tatatacaca tatatataca      60
catatatata cacgtatata tgtatacaca tatatatgta tatatataca catatataca     120
cacatatata cgtgtatata cgtatatacg tacatatata cgtgtatata cgtatatgcg     180
tacatatata cgtgtatata cgtatatgcg tacatatata cgtgtatata cgtatatgcg     240
tacatatata cgtgtatata cgtatatgcg tacatatata cgtgtatata cgtatatgcg     300
tacatatata cgtgtatata cgtatatgcg tacatatata cgtgtatata cgtatatgcg     360
```

```
tac                                                                363
```

<210> SEQ ID NO 194
<211> LENGTH: 545
<212> TYPE: DNA
<213> ORGANISM: Homo sapiens
<220> FEATURE:
<221> NAME/KEY: misc_binding
<222> LOCATION: (1)..(545)
<223> OTHER INFORMATION: MAR of chromosome 2 genomic contig; 3456187..
      3456731

<400> SEQUENCE: 194

```
tattataata tatatttata tattataata tatattatat tatatattta tatatttaaa    60
tatatattat attatatatt tatatattat aatatatatt atattataat atatatttat   120 attataaatat attatattat aatatatatt atattattat atattataat ataaatatata  180 ttataaatata tattatatta taattatat attatatata ttataaatata tattatatta   240 tatatatatt tatattataa tatatattat tatatattat atattataat ttatattata   300
ttacaatata tattataaat atatatatta tattataaat atatattttt atattacaat   360
atatattata aatatatatt ttatattaca atatatatta taaatatata tattatatta   420
caatatatat taaatatata tattatatta caatatatat tatattataa tatatattta   480
tatatgatat attatattta atatattata taacataata tataatatat aatatattaa   540
tataa                                                              545
```

<210> SEQ ID NO 195
<211> LENGTH: 356
<212> TYPE: DNA
<213> ORGANISM: Homo sapiens
<220> FEATURE:
<221> NAME/KEY: misc_binding
<222> LOCATION: (1)..(356)
<223> OTHER INFORMATION: MAR of chromosome 2 genomic contig; 5001567..
      5001922

<400> SEQUENCE: 195

```
tataaaatat atgttatata tataatatat attatataat atataatata tataatatat    60
aaaatatata aaatatataa tatataatat aatatataat atataatata tataaaatat   120
atataatata aaatatatat aatatataat atataataat ataatataat ataaatatata   180 atatataata tataatatat ataatatata atataaaata tataatatat ataatatata   240
atatataata tatataaatat ataatatata atatataata tataaaatata taaatatata   300 tacacacata cacacacata tatgcatata tatacatata catgtgtaca tagata        356
```

<210> SEQ ID NO 196
<211> LENGTH: 321
<212> TYPE: DNA
<213> ORGANISM: Homo sapiens
<220> FEATURE:
<221> NAME/KEY: misc_binding
<222> LOCATION: (1)..(321)
<223> OTHER INFORMATION: MAR of chromosome 2 genomic contig; 5457330..
      5457650

<400> SEQUENCE: 196

```
tatacaatat attataaaatt atatataatt tatatataat atatattata taaaattat     60 atataaattta taatatatat aaattatata taatataaat tatatataat ttatataata   120
tataaattat atattatata aattaaatat aatttatatt atatataaat tatatttaat   180
```

```
ttatataata tataaattat atttaattta tatataatat aaattatatt tttatatatt       240
atgtataatt tatatattta tacatatata cattataata tattgtatag tatatataat       300
atatagtata tataaagcat a                                                 321

<210> SEQ ID NO 197
<211> LENGTH: 361
<212> TYPE: DNA
<213> ORGANISM: Homo sapiens
<220> FEATURE:
<221> NAME/KEY: misc_binding
<222> LOCATION: (1)..(361)
<223> OTHER INFORMATION: MAR of chromosome 2 genomic contig; 8124469..
      8124829

<400> SEQUENCE: 197
tatatataat atatattata tatattatat aaattatata taatatgtaa tataaatttt       60
gtaatataaa ttatatatat aaattatata taatatatat taatatatat aatataaatt      120
aatatatata atatataatt atatataatt tatgatat ataaatat atattatata         180 taaattatat atatcataaa ttatatatca taaaattat ataatata cattatgtac        240 ataatatatg atataataa tataatatat attatatata attatatata taattata         300 taatatatat aaattataat ataatata taaaattat aatataaat atatataaat        360 t                                                                       361

<210> SEQ ID NO 198
<211> LENGTH: 418
<212> TYPE: DNA
<213> ORGANISM: Homo sapiens
<220> FEATURE:
<221> NAME/KEY: misc_binding
<222> LOCATION: (1)..(418)
<223> OTHER INFORMATION: MAR of chromosome 2 genomic contig; 11151485..
      11151902

<400> SEQUENCE: 198
atgtaactat atatatagta tatatagtat atatatacta tatagtgtgt atatatagta       60
tatatatact atatagtgtg tatatatagt atatatatag tgtatatatc gtatatacac      120
tatatactat atagtgtata tatagtatat gtagtatata tagtatatat agtatagtat      180
atatagtata tatagtgtat atatactgta tatatagtgt acatagtata ctatatagta      240
tacatatagt acactgtata gtatatatag tatagtatat atagtataca tagtatacta      300
tatatagtat agtatacata gtatactata tagtatatag agtatatata cagtatacta      360
tatagtatat agagtatata tacagtatac tatatcgtgt gtatagagta tatataca       418

<210> SEQ ID NO 199
<211> LENGTH: 394
<212> TYPE: DNA
<213> ORGANISM: Homo sapiens
<220> FEATURE:
<221> NAME/KEY: misc_binding
<222> LOCATION: (1)..(394)
<223> OTHER INFORMATION: MAR of chromosome 2 genomic contig; 13591477..
      13591870

<400> SEQUENCE: 199
ttatatatat tttatatata ttatatatat tttatatata ttatatatat attatatata       60
tattatatat aattatatat aatatatatt atatatatta tataattata tataatat      120 atattatata tattatatat ataatatata tataatatat atattttata tatgtattat      180
```

```
atatatttta tatatattat atatattata tatatatttt atatatatta tattttatat    240
atataatata acatatataa tatataatta tatattatat atatattata ttatatataa    300
tatatattat atataatata atatataatt atatatatta tatatttat atatttatat     360 aaaaattatt ttatattatt ttatatataa atat                                394
```

<210> SEQ ID NO 200
<211> LENGTH: 1194
<212> TYPE: DNA
<213> ORGANISM: Homo sapiens
<220> FEATURE:
<221> NAME/KEY: misc_binding
<222> LOCATION: (1)..(1194)
<223> OTHER INFORMATION: MAR of chromosome 2 genomic contig; 14996824..14998017

<400> SEQUENCE: 200

```
taatatttat atatacatat aaaatttata tataatatat aatatttata tatacatata     60
aaatttatat atatatataa tatttatata tacataaaa atttatatat aatatataat    120
atttatatat acatataaaa tttatatata atatataata tttatatata catataaaat   180
ttatatataa taaatatttta tatatacata taaaatttat ataatttta tatataacat   240 ataatattta tataaaat ttatatataa catatattta tatatattt atatataaca     300 tataatattt atatataata tatttatt tacaattt atatataata tataactt         360 atatatacat acataattta tatgatatat attatatata taatttat gatatataat    420 atatctaata tatattatat atattatata tattatatat aatttatata atatatatta  480
tatatataat ttatataata tatatattat atatataatt tatataatat atatattata  540
tatataattt atataatata tattatatat ataattata taatatatat tatatatata  600
atttatataa tatatattat atataattta tatataacat atttatata catatataat  660 ttatatataa tatatattta catatacata taattttt atataatata aaatatttct   720
atacacatat ataatttta tataatataa atatttcta tatacatata taattttat     780 ataatatata tttctatata catgtctaat ttttatataa tatatatttc tatatacata  840
tataattttt atataatata taatttttt atatacataa ttttataata atatatattt   900
acatatacat atataatttt tatataatat atatttat atacatatat aattttaca    960 taatatatat tatatataca tatataattt atatacaaca tataatatat acatatataa 1020
tttatataca acatataata tttatgtata catatataat gtatacacaa tatataatat 1080
ttatatatac atatataatt tatatgtaat atatacatat ataatttata tgtaatatat 1140
atacatgtat aatttatatg tagtatatat acatgtataa tttatatgta gtat        1194
```

<210> SEQ ID NO 201
<211> LENGTH: 487
<212> TYPE: DNA
<213> ORGANISM: Homo sapiens
<220> FEATURE:
<221> NAME/KEY: misc_binding
<222> LOCATION: (1)..(487)
<223> OTHER INFORMATION: MAR of chromosome 2 genomic contig; 14998429..14998915

<400> SEQUENCE: 201

```
tagtatacat ttacacatac atgtataatt atatgtaata tataatattt acatatataa     60
ttatagataa tatatattta catatacata taattatata taatatat aatgtttaca     120 tatacataca taattatata taatatatat ttaaatatac atatacaatt atatataata  180
```

```
tatatttaca tatgcatata taattataga taatatatat ttacatatac atatataatt    240
atatataata tataatgttt acatatacat ataaattat atataatata tatttaaata    300
tacatataca attatatata atatatattt acatatgcat ataaattat agataatata    360 tatttacata tacatatata attatatata atatataata tttacatata catatataat    420
gtatatataa tatataatat ttacatatac atatataatt tatatataat atatattata    480
tatatta                                                              487

<210> SEQ ID NO 202
<211> LENGTH: 421
<212> TYPE: DNA
<213> ORGANISM: Homo sapiens
<220> FEATURE:
<221> NAME/KEY: misc_binding
<222> LOCATION: (1)..(421)
<223> OTHER INFORMATION: MAR of chromosome 2 genomic contig; 16562490..
      16562910

<400> SEQUENCE: 202
tatatgaata tatatatgaa tatatacgta tatgaata tatacatgta tgtatatatg     60
aatatatgta tatatgaa tatatgta tatgaata tatgtatata tatgaatata    120
tatgtatata tgtatatata tgaatatata tgtatatatg tatatatatg aatatatatg    180
tatatatgta tatgtatata tatgaata tatgtata tatgaatata tatgaatata    240
tatgtatata tatgaatata tatgaatata tgtgtatata tatgaatata tatgtatata    300
tatgaatata tgtatatata tatgaatata tatgtatata tgtatatatg aatatatatg    360
tgtatatgaa tatatatatg aatatatatg tgtatatgaa tatatgaa tatatatgtg    420 t                                                                    421

<210> SEQ ID NO 203
<211> LENGTH: 479
<212> TYPE: DNA
<213> ORGANISM: Homo sapiens
<220> FEATURE:
<221> NAME/KEY: misc_binding
<222> LOCATION: (1)..(479)
<223> OTHER INFORMATION: MAR of chromosome 2 genomic contig; 21592301..
      21592779

<400> SEQUENCE: 203
tatatgtata cgtatataat atattata tttatacgt gtacgtatat atgtaatata     60
taatgtatat gtacacgtat ataatatata atatattata tacgtatacg tatacattat    120
atattacata tacgtatata tacgtatata aatatatgt atatattata tacgtata    180 taatatatat tatataatat ataaatata cgtatacata taatatatta tatatacata    240
ttatatatta tatatttaaa ttatatatta tatcatatat aatatatg ataaatata    300 taatatacat atattacata atatatatta tatacatata catatataat ataaatata    360 ttatatacat atacatatat aatatataat atattatata catacacata taatatatat    420
aatatattat atacatatac atatataata tataatatat tatatataca tattatata    479

<210> SEQ ID NO 204
<211> LENGTH: 870
<212> TYPE: DNA
<213> ORGANISM: Homo sapiens
<220> FEATURE:
<221> NAME/KEY: misc_binding
<222> LOCATION: (1)..(870)
```

<223> OTHER INFORMATION: MAR of chromosome 2 genomic contig; 22557584..
22558453

<400> SEQUENCE: 204

```
tataatatat aaatatacata atatgtatat tttatacaca atataaataa tatacataac      60
atatatgtat attttatata tgtatatttt atatatattt tatatatttt atatatatgt     120
atattttata tataatatat atattgtata taataatata taatatatta tattatatat     180
aatatatata atatatatat aaatatatat tatatataat atgtataata tataaatttt     240
tatatataat atgtataata tatattttat ataataataat atgtacaata tatattttat     300
ataataataat atgtacaata tatattttat ataataataat atgtacaata tatattttat     360
gtataatatg taataatatat attttatgta taatatatat tttatgtata atatatattt     420
tacgtatatt ttatatataa tataataat tttatatata atataaca ttttatatat     480
aatatataat attatatata ttatatattt tatatataat atatataaat atatatattt     540
tatatataat atattttata taaatatat ataaatatat atttatata taatatattt     600
tatatataat atattttata taaatatat aatatatttt atatattata taatatat     660
tatatattat ataataatata ttatatataa tatataaat ataatatatt atatataata     720
tataatatat aatatattat ataataatata taatatataa tatataaat attatatata     780
atatataata tgtaatatat aatatttat atataaatata taatataata tataaatttt     840
tatatataat atataatata taatatataa                                       870
```

<210> SEQ ID NO 205
<211> LENGTH: 1086
<212> TYPE: DNA
<213> ORGANISM: Homo sapiens
<220> FEATURE:
<221> NAME/KEY: misc_binding
<222> LOCATION: (1)..(1086)
<223> OTHER INFORMATION: MAR of chromosome 2 genomic contig; 30591960..
30593045

<400> SEQUENCE: 205

```
gtatatataa tatatattat attatgttat atattatgta gactatgtat taaatatatg      60
tatatattat ataaatat ataatatata tttataattt ataattataa atatatttat     120
aatatatttt tctaaatatt tatatatattat atattatatc taatgatata taataaaatat     180
atttctaata tattttatat ttataaaatat tttatatata ttatatatttt tatatatact     240
atatattata tattatatat tttatatata ctatatatta tatagtatat attttatata     300
tactatatat tatatattat atattttata tatactatat attatatatt atatatttta     360
tatatactat atactattta ttatatatttt tatatatact atatactatt tattatatat     420
tttatatata ctatatacta tttattatat attttatata tactatatat tatatatatat     480
atattttata tataatatat atttattata tatttatat attatatata ttatatatta     540
tatatttata tattataaaa tatatattat atatagaata tataatatat attatatata     600
atataatata atatatatta tataaaatat atataatata taaatataat aatatatgat     660
atatataata tatattctat atttatacat atatatttaa tattatatta atatataatt     720
atatattat c atatgtaata atagatataa tatgtaatat ataattata attatatatt     780
aatatattat attatttaat atgtatattt acacatatat taattattaa atatatatat     840
ttaatatatt aaatattatg tattaaaatat atataatata tttataaata ttttatatat     900
aatatataca tatattaaca tatatgtata tatgtatata ttatataaa cattatatat     960
```

```
attatgttac atatactata ttttatatgt tacatatact atatattata tgttacatat    1020
aatatatata acatatatta taatatgtaa catattatat ataacatata atatatagta    1080
tatata                                                                1086

<210> SEQ ID NO 206
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig; 36233909..
      36234314

<400> SEQUENCE: 206
attataaata tatattatag atattagata ttatagatat aatatatata atatatatta      60
tagatattat agatatagat ataatagata ttatagatat tatagatata atatatatta     120
tagatattat agatataata tatattatag atattataga taatatatat attatagata     180
ttatagatat aatatatatt atagatataa tatatattat agatattata gatatagata     240
ttatagatat tatatatatt atagatataa tatatattat agatattata gatatagata     300
ttatagatat aatatatatt atagatatta tagataataa tatattata gatattatag      360 atataatata tattatagat ataagatata ttatagatat tacaga                    406

<210> SEQ ID NO 207
<211> LENGTH: 797
<212> TYPE: DNA
<213> ORGANISM: Homo sapiens
<220> FEATURE:
<221> NAME/KEY: misc_binding
<222> LOCATION: (1)..(797)
<223> OTHER INFORMATION: MAR of chromosome 2 genomic contig; 36271745..
      36272541

<400> SEQUENCE: 207
atataaacat atacgtatat acacatatat acaaatacat atacacatat attatatata      60
tgtatatata ttatattata catatattat atatatatta tattatacat atacacatac     120
acacataaac atattacata catatacaaa ttatacacat atacatatat acatatatgt     180
atacacatac attatatata aatatatgta tataaaatgt acattatata tacatatata     240
ttatgtataa ataatatata aaataaacat aatatatatt tatagatatg atatatataa     300
tatatatgta tacatatata catatatgta tatataatgt acattataca tacataaaca     360
tcatatataa atgttatata taaatataa atatatataa tatataatat atactttata      420
tactatatat aatatatata atgatatata acatatacta tatatactat ataataata     480 tactatatat actgtatata atatataata taatatatac tatatatact aaatataata     540
tacataaaat aatatatact atatataata taatatatat aatatagtat atatactata    600
tataataatt acatattata tattatacat tatatatttat ataattatta tatataatta    660
tatattacat actttgtata taatgtaaat atacattaga atatataatg tatatatatg     720
tacatatata atgtatatat gtatacatta tataaactat ataaaacat tatattatat     780 aaacattata tataaac                                                    797

<210> SEQ ID NO 208
<211> LENGTH: 423
<212> TYPE: DNA
```

<213> ORGANISM: Homo sapiens
<220> FEATURE:
<221> NAME/KEY: misc_binding
<222> LOCATION: (1)..(423)
<223> OTHER INFORMATION: MAR of chromosome 2 genomic contig; 36498521..
      36498943

<400> SEQUENCE: 208

| tattatatta | tatatttaat | attatatatt | taatatatta | tatatttaat | attatatatt | 60 |
| taatatatta | tatatttaat | attatatatt | taatatatta | tatatttaat | attatatata | 120 |
| taatatatta | tatatttaat | attatatata | taatattata | tataaatat  | tatatatta  | 180 |
| atattatata | tataatatta | tatatataat | atattatata | tttagtatta | tgtatttaat | 240 |
| atattatata | tttagtatta | tgtatttaat | atattattta | tttagtatta | tatatttaat | 300 |
| atattattta | tttagtatta | tatatttaat | atattatata | tttaatatat | tatatattta | 360 |
| ttatatattg | tatatttaat | atattatata | tttattatat | attatatata | attatatatt | 420 |
| taa        |            |            |            |            |            | 423 |

<210> SEQ ID NO 209
<211> LENGTH: 304
<212> TYPE: DNA
<213> ORGANISM: Homo sapiens
<220> FEATURE:
<221> NAME/KEY: misc_binding
<222> LOCATION: (1)..(304)
<223> OTHER INFORMATION: MAR of chromosome 2 genomic contig; 37179891..
      37180194

<400> SEQUENCE: 209

| gtgtatatat | atcatatata | ttatatcata | tatatgtgta | tatatatcat | atattatatc | 60 |
| atatatatgt | gtatatatat | catatatata | tcatatatgt | gtatatatca | tatatattat | 120 |
| atatcatata | tgtgtatata | tatcatatat | tatatatcat | atatatgtgt | atatatcata | 180 |
| tatattatat | atatctcata | tgtgtatata | tatcatatat | aatatatatg | tgtatatatc | 240 |
| atatatcata | tataacatat | atatgtgtat | atatcatata | tataacatat | atcatatatg | 300 |
| tgta       |            |            |            |            |            | 304 |

<210> SEQ ID NO 210
<211> LENGTH: 693
<212> TYPE: DNA
<213> ORGANISM: Homo sapiens
<220> FEATURE:
<221> NAME/KEY: misc_binding
<222> LOCATION: (1)..(693)
<223> OTHER INFORMATION: MAR of chromosome 2 genomic contig; 38440448..
      38441140

<400> SEQUENCE: 210

| tatatattct | tttatatatt | atatataata | tatattcttt | tatatattat | atatagtata | 60 |
| tattctttta | tatattatat | atagtatata | ttctttttata | tattatatat | agtatatatt | 120 |
| cttttatata | ttatatatag | tatatattct | tttatatatt | atatatagta | tatattcttt | 180 |
| tatatattat | atatagtata | tattctttta | tatattatat | ataatatata | tattctttta | 240 |
| tatatcatat | ataatatata | ttcttttata | tattatatat | aatatatatt | cttttatata | 300 |
| ttatatatca | tgtatatata | atacaaaaa  | tatatataga | ttttatatat | agattattac | 360 |
| ataatagaat | atattatata | ttatatataa | tatatacata | atatataata | ttatatatga | 420 |
| tataatatat | atcatatata | tcatataata | tatattatat | atcatatatt | atatataata | 480 |

| atatatagat tatatataat tatatatata atatatataa ttatatatat tatctatata | 540 |
| tagataatat atataattat ataaatatata ttatatagat tatatataat tatattatat | 600 |
| acaaaatcta tatataatat atattatatt atataata tacataacta tataaaaaat | 660 |
| ataatatata atatatataa tatataatat ata | 693 |

<210> SEQ ID NO 211
<211> LENGTH: 471
<212> TYPE: DNA
<213> ORGANISM: Homo sapiens
<220> FEATURE:
<221> NAME/KEY: misc_binding
<222> LOCATION: (1)..(471)
<223> OTHER INFORMATION: MAR of chromosome 2 genomic contig; 38887582..
    38888052

<400> SEQUENCE: 211

| aacatatata ctatatatat tatatactat attatatatt atatatataa acatatatac | 60 |
| tatatataat atataaacat attatattat acatgatata gataaacata tatattatat | 120 |
| ataatataga taaaatatgt tatatataat ataatgtata gacatatatt atatatacat | 180 |
| atattctaca tatattatat atatattcta cacatattat attatatata catatattct | 240 |
| acatatatta tatatacata tattctacat attatatata tacatatatt ctacatatac | 300 |
| atatatacat atattatata tacatatatt atagatatat aatatataaa catatataat | 360 |
| attattatat ataatatata taataatatt ataataatata taataatatt atatcttata | 420 |
| tataaataat atatatattt tatatatata atattatata tatataatat a | 471 |

<210> SEQ ID NO 212
<211> LENGTH: 1221
<212> TYPE: DNA
<213> ORGANISM: Homo sapiens
<220> FEATURE:
<221> NAME/KEY: misc_binding
<222> LOCATION: (1)..(1221)
<223> OTHER INFORMATION: MAR of chromosome 2 genomic contig; 43885944..
    43887164

<400> SEQUENCE: 212

| catataaaca tatattatat gtaacatata aacatatattat atgtaacata taatatataa | 60 |
| tataaaaca tatatttat atatttatatg ttacatataa tatataatat ataaacatat | 120 |
| attatatatt atatgtaaca tataatatat aatatataaa catatatttt atataataata | 180 |
| tataaacata ttttatatat aatatataaa catattttat atataatata taaacatata | 240 |
| ttttatatat aatatataaa catattttat atataatata taaacatata ttttatataa | 300 |
| tataaaaca taataatat ataatatata aaagtatata atataaatatat ataaatata | 360 |
| aacatatata atataaatat atataaaata taaacatatg taatatataa acatatatta | 420 |
| tatataatat ataacatat attatacgta caatatataa acatatattg tacgtacaat | 480 |
| atataaacat atattatacg tacaatatat aaacatatat tatacgtaca atatataaac | 540 |
| atatattata cgtacaatat ataaacatat attatacgta caatatataa acatatatta | 600 |
| tacgtacaat atataaacat atattatacg tacaatatat aaacatatat tatacgtaca | 660 |
| atatataaac atatattata cgtacaatat ataaacatat attatacgta caataaacat | 720 |
| atattatacg tacaatatat aaacatatat tatacgtaca atatataaac atatattata | 780 |
| cgtacaatat ataaacatat attgtacgta caatatataa acatatatta tatgtataat | 840 |
| atataaacat ataatatata atatatatta tatatatgtt tattatatat gtttatatat | 900 |

```
tatatataac atatattatt atattatata tgtttatata ttatatatta tataatatat    960
atgtttatat attatatatt ataatatata tatgtttata tattatatat tatataatat   1020
atatgtttat atattatata ttatataata tatatgttta tatattatat attatataat   1080
atatatgttt atattatata tattatataa tatatatgtt tatatattat atattatata   1140
atatatatgt ttatatatta tatattatat aatatatatg tttatatatt atataaataa   1200
taaacttaca tattttatta a                                             1221
```

```
<210> SEQ ID NO 213
<211> LENGTH: 543
<212> TYPE: DNA
<213> ORGANISM: Homo sapiens
<220> FEATURE:
<221> NAME/KEY: misc_binding
<222> LOCATION: (1)..(543)
<223> OTHER INFORMATION: MAR of chromosome 2 genomic contig; 45818200..
      45818742

<400> SEQUENCE: 213
tatgtatata tacatatata tttatacatg tatatatgta tatatacata tatatttata     60
catgtatata tatacatata tatttataca tgtatatata tacatatata tttatacatg    120
tatatatata catatatatt tacatgtata tgtatatata catatatatt tacatgta      180 tgtatatata catatatatt tacatgta tgtatatata catatatatt tacatgta        240 tgtatatata catatatatt tacatgta tgtatatata catatatatt tacatgta        300 tgtatatata catatatatt tacatgta tgtatatata catatatatt tacatgta        360 tgtatatata catatatatt tacatgta tgtatatata catatatatt tacatgta        420 tgtatatata catgtatatt tacatgta tgtatatata catgtatatt tacatgta        480 tgtatatata catgtatatt tacatgta tgtatatata catgtatatt tacatgta        540 tac                                                                  543

<210> SEQ ID NO 214
<211> LENGTH: 463
<212> TYPE: DNA
<213> ORGANISM: Homo sapiens
<220> FEATURE:
<221> NAME/KEY: misc_binding
<222> LOCATION: (1)..(463)
<223> OTHER INFORMATION: MAR of chromosome 2 genomic contig; 47055478..
      47055940

<400> SEQUENCE: 214
atacatacat atatacatat atacacatat atacatataa tacacacata tttacatata     60
tacacacata tatacatata tacatatata cacatatata catgcataca catatataca    120
tatatacaca catatacaca catatataca tatatacaca tatatacaca tatacacata    180
tatacacaca tatacatata tacatatata tacatatata catatataca cacatataca    240
catatataca tatacacata tatacacata tacatatata cacatatata cacatatata    300
catatatata catatataca tatatacaca tatatacaca catatacaca tatatacata    360
tatacatatg tatacacata tatacatatg tacacacata tatacacata tacatatata    420
catacacata tatacgtata tatgtgtata tatacacata tac                      463

<210> SEQ ID NO 215
<211> LENGTH: 2482
<212> TYPE: DNA
```

<213> ORGANISM: Homo sapiens
<220> FEATURE:
<221> NAME/KEY: misc_binding
<222> LOCATION: (1)..(2482)
<223> OTHER INFORMATION: MAR of chromosome 2 genomic contig; 47492696..
      47495177

<400> SEQUENCE: 215

| | | | | | |
|---|---|---|---|---|---|
| aatatatata | aaatatatta | tattctatgt | aatatataga | atatataaaa | tatattctat | 60 |
| atattatata | gaatatatat | tttataatat | atattattta | tatattttta | tatatttata | 120 |
| ttatttatat | atttatatat | aatttatata | atttatacat | ataatttata | tataatttat | 180 |
| ataaattata | tatataattt | atatataatt | tatatataat | ttatataaat | tatatatata | 240 |
| atttatatat | aatttatatg | attttatat | ataatttata | tataatttat | ataatttta | 300 |
| tatataattt | atatataatt | tatataattt | ttatatataa | tttatataat | atatatatat | 360 |
| aatttatata | taatttatat | aatttatata | tataatttat | atataattta | tataatttat | 420 |
| atatataatt | tatatataat | ttatataatt | tatatatata | atttatatat | aatttatata | 480 |
| atttatatat | ataatttata | cataatttat | aatttatata | tataatttt | ataatttta | 540 |
| tatatataat | ttatatatat | aatttatata | atttatatat | atgatttata | taatttatat | 600 |
| ataatttta | tataatttat | atataaat | tatatatata | attttatat | aatttatata | 660 |
| tttataattt | ataatttat | ataatttata | tatttataat | ttatatattt | ataaattta | 720 |
| tatatttata | atttatatat | ttatataatt | tatatataat | tattcatata | tttatataat | 780 |
| ttacatataa | ttatttatat | attcatatat | aatttatata | tttatatata | atttatatat | 840 |
| aattattac | atatttatat | atttatatat | aatttatata | tatttatata | taatttataa | 900 |
| ataaaatata | taatatataa | tatataaat | tataatagat | aaaatatata | ctatatatta | 960 |
| tatatttttac | attatattta | atattatatg | ataatttta | tatcatatat | aatatatatg | 1020 |
| atatatataa | ttttatatca | tatataatat | atatggtata | tataatttta | tatcatatat | 1080 |
| aatatatatg | gtatatataa | ttttatatca | tatataatat | atgatatata | attttatatc | 1140 |
| atataatata | tattatatat | aatttatat | ctacatatta | tatattatat | atacaattt | 1200 |
| atatctatct | ataatatata | ttatatatac | aattttatat | ctatataata | tatattatat | 1260 |
| atacttttat | attatatata | aaatgtatat | tatatatact | tttatatttat | atataaaatg | 1320 |
| tatattatat | ataattttat | tttatatata | aaatgtatat | tatatataat | tttattttat | 1380 |
| atataaaatg | tatattatat | ataattttat | tttatatata | aaatgtatat | tatatataat | 1440 |
| ttattttat | atataaaatg | tatattatat | ataattttat | tttatataaa | aaatgtatat | 1500 |
| tatatataat | tttatattat | atataatatg | tatattatat | ataattttat | attatatata | 1560 |
| atatgtatat | tatatataat | tttatattat | ataatatg | tatattatat | ataattttat | 1620 |
| attatatata | atatgtatat | tatatataat | tttgtattat | ataataatg | tatattatat | 1680 |
| ataattttat | attatatata | atatgtatat | tatatataat | tttatattat | ataatatg | 1740 |
| tatattatat | ataattttat | attatatata | atatgtatat | tatatataat | tttatattat | 1800 |
| ataatatg | tatattatat | ataattttat | attatatata | aaatgtatat | tatatataat | 1860 |
| tttatattat | atataatatg | tatattatat | ataattttat | attatatata | atatgtatat | 1920 |
| tatatataat | tttatattat | ataaaatg | tatattatat | ataattttat | attatatata | 1980 |
| aaatgtatat | tatatatatt | atatataaaa | tgtatattat | atatatttata | tataaaatgt | 2040 |
| atattatata | tattatatat | aaaatgtata | ttatatatat | tatatataaa | atgtatatta | 2100 |

```
tgtatattat atataatgta tattatgtat attatatata atgtatatta tatataatat    2160
atattatata taatgtatat tatataaatat atattatata ttataatata taatatacat    2220
```

```
tgtatattat atataatgta tattatgtat attatatata atgtatatta tatataatat    2160
atattatata taatgtatat tatataaat  atattatata ttataatata taatatacat    2220
tatatattac atattatata taatatatta tatattatat attacatatt atatataata    2280
tattatatat tatattaaat atatatttta tatattatat attatatatt ataaaaata    2340 tatatattat atattatata aaatatatat attatatatt atatattata ttaaatatat    2400 atttatata taatatatat aatatataat atataaaata tatattatat attatatata    2460
aattatatat attatatata aa                                              2482
```

<210> SEQ ID NO 216
<211> LENGTH: 539
<212> TYPE: DNA
<213> ORGANISM: Homo sapiens
<220> FEATURE:
<221> NAME/KEY: misc_binding
<222> LOCATION: (1)..(539)
<223> OTHER INFORMATION: MAR of chromosome 2 genomic contig; 47561069..
      47561607

<400> SEQUENCE: 216

```
aacagtaata tatcactaat atataataat ataatacagt aatatatcat taatatataa     60
tatatcatta gtatataata ttaatatata ttaatatata atatatcata tacaatatta    120
atatatatta atatataata atatattatt aatgtaataat agtaatatata tatattatca    180 atatatatta ctaatatata ataatatatc gttaatatat aatagatcat taatatataa    240
tgttaatata ttatgaatag ataatatatc agtatataat attaatatat taatatatta    300
tatattattt aataatatat aatatattaa taaataatta tatattaata tagcaatata    360
ttaatatatg actgtattat attattaata tataacaata tattatatat tatataataa    420
tttattatat aatatataat aatatatatt attattatata acatattaat aatacataat    480
aacattaata atatataata atgttaatat attattatat tatatattaa tatataata    539
```

<210> SEQ ID NO 217
<211> LENGTH: 336
<212> TYPE: DNA
<213> ORGANISM: Homo sapiens
<220> FEATURE:
<221> NAME/KEY: misc_binding
<222> LOCATION: (1)..(336)
<223> OTHER INFORMATION: MAR of chromosome 2 genomic contig; 52853648..
      52853983

<400> SEQUENCE: 217

```
tatatacata aaatatatat attttatata tatacataat atatatatgt atattttatg     60
tatatatcta taatatatat aatataataa aatatacata tatattttat atatatataa    120
tatacatata aaatatacat acataaaata tacatgtata ttttatgtat atataatata    180
tatataaaat atacatgtat attttatata taatatatac atgtataatt aatatacatg    240
tatgttatat atattacatg tatattatat ataaatataca tataaatttt aaatttagtg    300
tatattacat gtatattata tataatatat gtatat                               336
```

<210> SEQ ID NO 218
<211> LENGTH: 406
<212> TYPE: DNA
<213> ORGANISM: Homo sapiens
<220> FEATURE:
<221> NAME/KEY: misc_binding
<222> LOCATION: (1)..(406)
<223> OTHER INFORMATION: MAR of chromosome 2 genomic contig; 54866263..

```
                54866668

<400> SEQUENCE: 218
tacgtatata aaaatgtata tttacatata taaaataaat attttatata cgtatataaa      60
atatatattt attttatata cgtatataaa atatttattt tatatatgta tataaaatat     120
ttattttata tacatgtata ttaaatatat atttatatat gtatataaaa atatatatta     180
tatacatgta tataaaatat atattatata tgtatataaa aatatatatg tatataaaat     240
atatatatta tatagatata taaaatatat attatataga tatataaaat atatatatta     300
tatagatata taaaatatat atattatata gatatataaa atatatatat tatatagata     360
tataaaatat atatattata tagatatata aaatatatat attata                    406

<210> SEQ ID NO 219
<211> LENGTH: 1452
<212> TYPE: DNA
<213> ORGANISM: Homo sapiens
<220> FEATURE:
<221> NAME/KEY: misc_binding
<222> LOCATION: (1)..(1452)
<223> OTHER INFORMATION: MAR of chromosome 2 genomic contig; 55113305..
      55114756

<400> SEQUENCE: 219
ataatatata atatatattg tatattatat tattatatat tatatattat taaatatata      60
tattatatta tatattatat aatatatatt atatataata atatagaata taaattata     120 tattatatta tatattatat aatatatatt atatataata atatagaata taaattata     180 tattatacta tatattatat aatatatatt atatataata atatagaata taaattata     240 tattatataa tatgtgaata atgtaatata taattatatt atttacatat tatataaat     300 ataattatat tatataatat ataattatat tatttgtata ttatatataa catatacatt     360
atattatata taatataatt atatataatt aattataaat taattatata taattatata     420
atataatata taatatacat aatatatat atataatca taatatacat aatataatat       480
atattatata taatataata tatataatat aatataatat aatgtataat ataattatat    540
attatatata atatataatg ttatataatt atattatatt atataattaa ttatatgtaa    600 ttaaatataat ataattatta tatataattt tttatataat ataatatata attatataat   660
ataatataat tatattatat tatataatat atatatatta taatataataa taattata    720 ttatataatt ataatatata ataattata atattatatt ataataataa taattatata    780
taatataata tgattatata atatatattg tatattatat attatatatt gtattatgta    840
tattatatat tatatattat gtatattata tattatgtat attatatatt atgtatatta    900
tatattatat attatattat gtaatatata ttatgtatgt tatatataat ataattatata   960 ttatatatta tgtatattat ataaaatta tattatatat tatgtatatt atataaata    1020 taaagtatat attatgtata ttatatataa tataaagtat atattatgta tattatatat   1080
aatataaagt atatattatg tatattatat ataatataaa gtatatatta tgtatattat   1140
atataatata aagtatatat tatgtatatt atatataata taagtatatat attatgtata   1200 ttatatataa tataaagtat atattatgta tattatatat aatataaagt atatattatg   1260 tatattatata ataatataaa gtatatatta tgtatattat atataaatata aagtatatat  1320 tatgtatatt atatataata taaagtatat attatgtata ttatataaaa tataaagtat   1380
atattatgta tattatatat aatataaagt atatattata tgttataaaat tatatattgt   1440
```
tatatattat at    1452

<210> SEQ ID NO 220
<211> LENGTH: 502
<212> TYPE: DNA
<213> ORGANISM: Homo sapiens
<220> FEATURE:
<221> NAME/KEY: misc_binding
<222> LOCATION: (1)..(502)
<223> OTHER INFORMATION: MAR of chromosome 2 genomic contig; 56350637..
      56351138

<400> SEQUENCE: 220
atatattata gaaatataaa tatatagata tatctatata ttatagaaat ataaatatat    60
agatatatct atatattata gaaatataaa tatatagata tatctatata ttatagaaat   120
ataaatatat agatatacct atatattata gaaatataaa tatatagata tacctatata   180
ttatagaaat ataaatatat agatatacct atatattata gaaatataaa tatatagata   240
tatctatata ttatagaaat ataaatatat agatatatct atatattata gaaatataaa   300
tatatagata tatctatata ttatagaaat ataaatatat agatatatct atatattata   360
gaaatataaa tatatagata tatctatata ttatagaaat ataaatatat agatatatac   420
aacatatatg ttacatatta tatattatat atctatatat ctatataaca ttatatatct   480
atatatctat ataacatata ta                                            502

<210> SEQ ID NO 221
<211> LENGTH: 794
<212> TYPE: DNA
<213> ORGANISM: Homo sapiens
<220> FEATURE:
<221> NAME/KEY: misc_binding
<222> LOCATION: (1)..(794)
<223> OTHER INFORMATION: MAR of chromosome 2 genomic contig; 57051633..
      57052426

<400> SEQUENCE: 221
aactatatat actatattat atagttatac tatatatact atattatata gttatataac    60
tattatataa ctgtattata tagttatata actattatat aactgtatta tatagttata   120
taactattat ataactgtat tatatagtta taaactatata ttatataact gtgttatata   180
gttatatatt ataaactat attatataac tgtattatat agttatatat tatataacta   240
tattatataa ctgtattata tagttatata ttatataact atattatata actgtattat   300
atagttatat attatataac tgtattatat agttataaaa ctatattata taactgtatt   360
atatagttat aaaactacta tataactgta ttatataatt ataaaattat actatataac   420
tgtattatat agttataaaa ctatactata taactgtatt atatagttat aaaactatac   480
tatataactg tattatatag ttataaagct atactatata actgtattat atagttatat   540
aactatacta taactgta ttatatagtt ataaaactat actatataac tgtattatat   600
agttataaaa ttatattata taactgtatt atatagttat ataactatat tatatataactg   660 tattatatag ttatataact atattatata agtgtattat atagttatat aactatatta   720
tataactgta ttatacagtt atataactat attatataac tgtattatat acttatataa   780
ctatattata taac                                                    794

<210> SEQ ID NO 222
<211> LENGTH: 300
<212> TYPE: DNA
<213> ORGANISM: Homo sapiens

```
<220> FEATURE:
<221> NAME/KEY: misc_binding
<222> LOCATION: (1)..(300)
<223> OTHER INFORMATION: MAR of chromosome 2 genomic contig; 57069272..
      57069571

<400> SEQUENCE: 222
acacatacat atatgtatat atgcacacac atatatatgt atatatacac atacatatat      60
gtatatatac atatatgtat atacgcacat acatatatgt atatatacac gtacatatat     120
gtctctatat atacacatac acatatgtat atacatatat gtgtatatat acacaatcat     180
atatgtatat acatatatac acatatacac aaacatatat gtatatacat atatgtatat     240
acatatatac acatatacac aaacatatat gtatatacat atatgtatat acatacacaa     300

<210> SEQ ID NO 223
<211> LENGTH: 370
<212> TYPE: DNA
<213> ORGANISM: Homo sapiens
<220> FEATURE:
<221> NAME/KEY: misc_binding
<222> LOCATION: (1)..(370)
<223> OTHER INFORMATION: MAR of chromosome 2 genomic contig; 57235143..
      57235512

<400> SEQUENCE: 223 tattttata taaactata tatattttat ataaattta tatatatgat catatatata        60
atcatatata taatcatata tgattatata tgatcatata tatatttata tataaatta     120 tatatactta tatataatta tatatatatt tatatatata attatgtata cttatatata     180
tttatatata taattatata tacaattta atatataatt atatataatt tatatataat     240
tatatatata aattatatat aagtatatat aattatatat atgtttatat ataattatat     300 ataaaatga tatgtataat ataaactat atataattat atataaatat atatatagat      360
tttatatata                                                          370

<210> SEQ ID NO 224
<211> LENGTH: 306
<212> TYPE: DNA
<213> ORGANISM: Homo sapiens
<220> FEATURE:
<221> NAME/KEY: misc_binding
<222> LOCATION: (1)..(306)
<223> OTHER INFORMATION: MAR of chromosome 2 genomic contig; 57693125..
      57693430

<400> SEQUENCE: 224
tacgtatata cacgtataaa tataaatata tacatgtata tacgtatata catgtataaa      60
tataaatata tatatgtata tacgtatata catgtataaa tatatatatg tatatacgta     120
tatacatgta taaatatata tatgtatata tacgtatata catgtataaa tatatatatca    180 tgtatatacg tatgttgtgt atacatacaa atctgtacat atatacatat atgttgtgtg     240
tatatataca tctatacatg tgtatgcgta tatatgtata tgtatatata gtatatataa     300
tacatg                                                              306

<210> SEQ ID NO 225
<211> LENGTH: 500
<212> TYPE: DNA
<213> ORGANISM: Homo sapiens
<220> FEATURE:
<221> NAME/KEY: misc_binding
<222> LOCATION: (1)..(500)
<223> OTHER INFORMATION: MAR of chromosome 2 genomic contig; 59810331..
```

59810830

<400> SEQUENCE: 225

```
tttattatat gtaatatata ttgtattatt atatatatta tatataatat atattgtatt        60
attatatata ttatatataa tatatattgt attattatat atattatata taatatatat       120
tgtattatta tatatattat ataaatata tattgtatat tatatatatt atatattata       180
ttattatata ttatatatat tatattatta tatattatat attatatata ttatattata       240
tattatatat tatattatat attatatatt atatattata tattatatta tatatattat       300
attatatatt atatattata ttatatatat tatattatat attatatata ttatatatta       360
tatatattat atattatata ttatatatat tatatattat ataaatata tattatatta       420 ttatataata ttatatatta tatatattat atattatata taatatatat tatattatta       480
tataatatta tatattatat                                                  500
```

<210> SEQ ID NO 226
<211> LENGTH: 565
<212> TYPE: DNA
<213> ORGANISM: Homo sapiens
<220> FEATURE:
<221> NAME/KEY: misc_binding
<222> LOCATION: (1)..(565)
<223> OTHER INFORMATION: MAR of chromosome 2 genomic contig; 59974589..
      59975153

<400> SEQUENCE: 226

```
atatatgtat aatatgtata tatgtatata ttatgtatat gttatatatg taatatatgt        60
atgtatatat tatatatcat atataatata taatgtgtat atatgtatat atgtatgtat       120
acatgtatat actatgtata tattgtatat attatatatg tatatataca tatacatata       180
taatatatac atatattata tacaatatat acatgtatat tatatacgat atacacatat       240
atattatata caatatatac atagtatata aatgtataca tacatacata tatacatatt       300
atatatgtat atatgtatac ataaatgtat atataatata tatacatata taaatgtata       360
catacgtaca tatacgtata tgtatatgca tatatgtata tatgtgcata catatatatg       420
tatatacata tatgtcacata tgtacatata cgtatatatg tacatgtata catatacgta       480 tatatgtcaca tatgtcacata tacgtatata tgtacatatg tacatatacg tatatatgta       540 catatgtcaca tatatacata tatat                                           565
```

<210> SEQ ID NO 227
<211> LENGTH: 427
<212> TYPE: DNA
<213> ORGANISM: Homo sapiens
<220> FEATURE:
<221> NAME/KEY: misc_binding
<222> LOCATION: (1)..(427)
<223> OTHER INFORMATION: MAR of chromosome 2 genomic contig; 60605573..
      60605999

<400> SEQUENCE: 227

```
tatataatgt atataatgga tatagatata gatatagata tatattttat ataatatata        60
ttatatatta tatataatat atgttatata tattatatat tttatataat atatatatta       120
tataaattat atatatataa tatataatat atatattata tatattttat ataatatata       180
tttaatatta tctattatat attttatata atatatattt tatataatat ataatatata       240
atatatattt tacataatat ataatatata atacgtatta tatataatat ataatacgta       300
ttttatataa tatataatac gtattatata taatacgtat tatatattat ataatatata       360
```

```
atacgtatta tataatatac gtaattatat tttattataa tacgtattat atattatata    420
atatata                                                              427
```

<210> SEQ ID NO 228
<211> LENGTH: 1199
<212> TYPE: DNA
<213> ORGANISM: Homo sapiens
<220> FEATURE:
<221> NAME/KEY: misc_binding
<222> LOCATION: (1)..(1199)
<223> OTHER INFORMATION: MAR of chromosome 2 genomic contig; 61229949..
      61231147

<400> SEQUENCE: 228

```
gtatacatat ataaagtgta tatataatgt atatacatat atacatatat aaagtatata     60
tataatatat acatatataa agtatatata taatatatac atatataaag tatatataat    120
atatacatat ataaagtata tataatatat acatatataa agtatatata tcatatatac    180
atatataaag tatatatata atatatacat atacatatat ataaagtata tataacatat    240
atacatatat aaagtatata taacatatat acatatataa agtatatata taatatatac    300
atatatacat atataaagta tatataacat atacatatat atacagtata tataacatat    360
atacatatat acagtatata taacatatat acatatatac agtatatata acatatatac    420
atatatacag tatatataac atatatacat atacatga agtatatata acatatatac      480
atatatacat gaagtatata taacatatat acatatatac atgaagtata taacatatat    540
atacatatat acatgaagta tatataacat atacatatat atacatatat aaagtatata    600
taacatatac atatatacat ataaaagta taacatatac atatatacat atataaagta     660
tatataatat ataacatata catatataaa gtatatataa tatataacat atacatatat    720
aaagtatata taatatataa catatacata tataaagtat atataatata tacatatata    780
catatataaa gtatatataa tatatatata catatataaa gtatatataa tatatataca    840
tatatacata tataaagtat atataatata tacatatata taaagtatat ataatatata    900
tacatatata catatataaa gtatatataa tatatataca tatatacata tataaagtat    960
atataatata tacatatata tacatatata aagtatatat aatatatata catatataca   1020
tatataaagt atatataata tatacatata tacatatata taaagtatat ataatatata   1080
tacatatata catatataaa gtatatataa tatgtataca tatatacata tataaagtat   1140
atataatatg tatacatata tacatatata aagtatatat ataatatgta tacatatat    1199
```

<210> SEQ ID NO 229
<211> LENGTH: 454
<212> TYPE: DNA
<213> ORGANISM: Homo sapiens
<220> FEATURE:
<221> NAME/KEY: misc_binding
<222> LOCATION: (1)..(454)
<223> OTHER INFORMATION: MAR of chromosome 2 genomic contig; 62181058..
      62181511

<400> SEQUENCE: 229

```
tatatatcat atattatata tgatatatat tatgtatata atacatatta tatataataa     60
atatttatta tatatgatat atattatgta taatacatat atatatata ataaatatat     120 attatattat ataataaaa tatatattat attatatata atatatattt atatataaat    180
atattatata taaatatata ttatatataa aatatttata tattatatat aaatatatat    240
```

```
tatatataaa tatttatata ttatatataa atatttatat attatatata aatatttata       300
tattatatat aaaatatatt atatatatta tatatatatt atattatata taatatattt       360
aatatataat atataaacat atattatata taatatataa acatatataa atatatttat       420
atataataga taaaaatata tataatatat ataa                                  454
```

```
<210> SEQ ID NO 230
<211> LENGTH: 658
<212> TYPE: DNA
<213> ORGANISM: Homo sapiens
<220> FEATURE:
<221> NAME/KEY: misc_binding
<222> LOCATION: (1)..(658)
<223> OTHER INFORMATION: MAR of chromosome 2 genomic contig; 62190919..
      62191576

<400> SEQUENCE: 230
tatatacaca actatatata taactatata tatacaacta tatatacaac tatatatata        60
actatatata taactatata taactatata taaactata taaactata tataactata        120 tatatataac tatatataac tatatatata actatatata actatatata actatatata       180
taactatata taactatata tataactata tatatataac tatatatact atatatataa       240
ctatatatat ataactatat atataactat atatatataa ctatatataa ctatatatat       300
ataactatat atataactat atatatataa ctatatatat aactatatat ataactatat       360
atatataact atatatatat aactatatat aactatatat atataactat atatatataact     420 atatatatat aactatatat ataactatat atatataact atatatataa ctatatatat       480
ataactatat atataactat atatataact atatatataa ctatatatat ataactatat       540
atataactat atatatataa ctatatatat aactatatat ataactatat atataactat       600
atatatataa ctatatatat aactatatat ataactatat atatataact atatatat        658
```

```
<210> SEQ ID NO 231
<211> LENGTH: 1486
<212> TYPE: DNA
<213> ORGANISM: Homo sapiens
<220> FEATURE:
<221> NAME/KEY: misc_binding
<222> LOCATION: (1)..(1486)
<223> OTHER INFORMATION: MAR of chromosome 2 genomic contig; 62384127..
      62385612

<400> SEQUENCE: 231
attatatcta atctattata tattatatct aatacatatt atatctaatc tattgtatat        60
tatatctaat atataaatata ttatatataa tatattatat attatatatt atatacaata      120
tattatatat tatataatat ataatatatt atatataata tattatatct aatatattac       180
atattatatc taatctatta tagatataat atgtaatata ttatatatta tatctaatag       240
atattagata taatatataa tatattatta atataatata ttagatataa tatataaat        300 aataatatat aatatatatt attggtaata taatatatat aattaataat atatattata       360
tataattatt atgaataata tatcatatat aatatctagt atattatata ttaataacat       420
ataaatatta tattaataat aaataacata ttaatattat attaataata taaatatac        480 taatattata ttaataatat ataatatact aatattatat taaaatata taatatacta       540 atattatatt aataatatat aatatactaa tattatatta ataatatata atatactaat      600
attatattaa taatatataa tatactaata tattaagaat atataaatata ctaatatatt     660 aagaatatat aatatactaa tattatatta ataatatata tttatattaa taatatatta     720
```

```
attattatta attaattatt aataattata taatattgat tatattaata ttatcaattt      780
aataatattg attatatatt atatattata tattatatat tatatattat atattatata      840
ttatatatta ataatatata ttagatataa taatatatat taataatata taagatataa      900
tataatatat taataatata tattagatat aatatatat attaataata tatattagat       960
ataatataat atattaataa tatatattag ataatatata atatattaat aatatatatt     1020
agatgtaata taatatatta ataatatata ttagatgtaa taatatatat taataatata     1080
tattagatgt aatataatat attaataata tatattagat gtaatataat atattaataa     1140
tatatattag atgtaatata atatattaat aatatatatt agatgtaata taatatatta     1200
ataatatata ttagatgtaa tataatatat taatatatat tagatgtaat ataatatatt     1260
aataatatat attagatata ataatatata ttaataatat attagatata atataatata     1320
ttaataatat ataagatata atataatata ttaataatat ataagatata atataatata     1380
ttaataatat ataagatata ataatatata ttaataatat atattagata tataatatat     1440
taataatata tattagatat ctaatatcta ttagatatct aataga                    1486
```

<210> SEQ ID NO 232
<211> LENGTH: 333
<212> TYPE: DNA
<213> ORGANISM: Homo sapiens
<220> FEATURE:
<221> NAME/KEY: misc_binding
<222> LOCATION: (1)..(333)
<223> OTHER INFORMATION: MAR of chromosome 2 genomic contig; 62538649..
      62538981

<400> SEQUENCE: 232

```
ttatatatat tatatatata tattttatat atatattata tatatatttt atatatatat       60
tatatatata ttttatatat atattatata tatttttat atatatatta tatatatatt       120
ttatatatat tatatatata ttttatatat attatatata tatttttat atatattata      180 tatatatttt atatatatat tatatatata ttttatatat atattatata tatatttat      240 atatatatta tatatatatt ttatatatat attatatata tatttttat atatattata      300 tatatatttt atatatatat tatatatata ttt                                   333
```

<210> SEQ ID NO 233
<211> LENGTH: 480
<212> TYPE: DNA
<213> ORGANISM: Homo sapiens
<220> FEATURE:
<221> NAME/KEY: misc_binding
<222> LOCATION: (1)..(480)
<223> OTHER INFORMATION: MAR of chromosome 2 genomic contig; 63240325..
      63240804

<400> SEQUENCE: 233

```
tatatataaa atatatattt tttaaatata aaatatatat atattttaat attaatatat       60
atatatttta atatataata tatatattat atattttata tataaaatat atatattata      120
tattttatat ataaaatata tatattatat attttatata ttaaaatata tattttatat      180 atttaatta ttaaaatata tatattatat atttaaata taaatatat atattatata        240 tttaatatata taaaatatat atatttaata tataaaatat atattttata                300
tttatatata taaaatatata tattatatat tttaatatat aaaatatata tattatatat    360
tttaatatat aaaatatata tattatatat tttaatatat aaaatatata tattatatat    420
```

```
tttaatatat ataaaatata tatattatat attttatata tattaaatat atattttata      480
```

<210> SEQ ID NO 234
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig; 63935480..
      63935781

<400> SEQUENCE: 234

```
atatatataa atatatatat aattatatat agatatatat aattatatat agatatatat       60
attctatatt ctatatatat ataatatata atatataaat tatatataga atatatatta      120 tatataaat  attatatata ttatatataa tatatatatt atatatatta tatataaat       180 atatattata tatattatat ataatttata tatattatat atagaatata tattatatat      240
agaatataga atatatataa tatatataga atacagaata tatatagaat atagaatata      300
ta                                                                     302
```

<210> SEQ ID NO 235
<211> LENGTH: 407
<212> TYPE: DNA
<213> ORGANISM: Homo sapiens
<220> FEATURE:
<221> NAME/KEY: misc_binding
<222> LOCATION: (1)..(407)
<223> OTHER INFORMATION: MAR of chromosome 2 genomic contig; 63935888..
      63936294

<400> SEQUENCE: 235

```
tataatatat taatataata tatagacagt atataaatata atatacagac agtatataat      60
atacagacag tatataatat ataatattat ataatatatt atatataata ttatataata     120
tattatatta tatatattat ataatatatt atattatata taatatatgt aatatttat      180 attatatttat acataatata ttatatataa tatattatat ataatattat atatattata    240
tataatatat ataataataa tattataata tataatatat aatagtacag tatatatat      300 atatataatt ctatatataa tatatagaat tctatctatt tataatatat atagaattct     360
atatataata tataatatac agaattctat atatatattata tatagaa                  407
```

<210> SEQ ID NO 236
<211> LENGTH: 302
<212> TYPE: DNA
<213> ORGANISM: Homo sapiens
<220> FEATURE:
<221> NAME/KEY: misc_binding
<222> LOCATION: (1)..(302)
<223> OTHER INFORMATION: MAR of chromosome 2 genomic contig; 66958350..
      66958651

<400> SEQUENCE: 236

```
tattatatat attgtatata tatgtatatt atatatattg tatatataat gtatattata       60
tatattatat atatatgtat attatatata ttgtatatat atgtatatta tatatattgt     120
atatgtgtat atgtatatat gtatgtgtat atatatacac atatacacat atatgtgtat     180
gtatatatat gtgtgtatat acgtatatat acatatatac aatttttgta tatatacata    240
tatacacata tatatgtgta tgtgtatata tatacacata tatgtgtgtg tatatacaca    300
ta                                                                    302
```

<210> SEQ ID NO 237
<211> LENGTH: 651
<212> TYPE: DNA
<213> ORGANISM: Homo sapiens
<220> FEATURE:
<221> NAME/KEY: misc_binding
<222> LOCATION: (1)..(651)
<223> OTHER INFORMATION: MAR of chromosome 2 genomic contig; 68307125..
      68307775

<400> SEQUENCE: 237
gatattatat attgtatata ttatatatgt atataatata ctattatata ttatatatgt      60
atataatttt attaatatat atattatatt atattatata ttatattata ttatattata     120
tatataatat taatattata tattattata tattatatta tattaatatt atatatatat     180
aatatatata atatatataa tagtattata tataatatat ataatagtat tatatattat     240
atatatataa tactattata tatattatat aaatagtat tatatatatt atatatataa      300
tactattata tataatatat actattatat aaatatata atactattat atatattata     360
tataatacta ttatatataa tatatataat actattatat ataatatata taatactatt    420
atatataata tatataatac tattatatat aatatatata atactattat ataataata    480 tataatacta ttatatataa tatatatatt atatataatt atattaatat ataatagtat    540
catatataat aatagtatat ataatatata atatatatat tatatatatt ataatagtat    600 ataacata taatatagta tatatattat atattatata taaaatattt a               651

<210> SEQ ID NO 238
<211> LENGTH: 367
<212> TYPE: DNA
<213> ORGANISM: Homo sapiens
<220> FEATURE:
<221> NAME/KEY: misc_binding
<222> LOCATION: (1)..(367)
<223> OTHER INFORMATION: MAR of chromosome 2 genomic contig; 68308243..
      68308609

<400> SEQUENCE: 238
atatatatat atgagtcaac catacacata tatatatata atgtttatat atataatgta      60
tatatataat gtttatatat aatgtatata tataatgttt atatatataa tgtatatata    120
taatgtttat atatataatg tatatatata atgtttatat atataatgtg tatatataat    180
gtttatatat ataatgtgta tatataatgt ttatatataa tgtgtatata taatgtttat    240
atatataatg tgtatatata atgtttatat atataatgtg tatatataat gtttatatat    300
ataatgtgta tatataat gtttatatat ataatgtgta tatataat gtttatatat          360 ataatgt                                                              367

<210> SEQ ID NO 239
<211> LENGTH: 499
<212> TYPE: DNA
<213> ORGANISM: Homo sapiens
<220> FEATURE:
<221> NAME/KEY: misc_binding
<222> LOCATION: (1)..(499)
<223> OTHER INFORMATION: MAR of chromosome 2 genomic contig; 410241..
      410739

<400> SEQUENCE: 239
ataatatgta tatatattat attatatatt atattacata ttatatatta tattacatat      60
tatatattta tatattacat attatatatt atattttata ttatatatta tatcatatat    120

```
atgttatgca ttatataata cataatatat tatatatgat ataatatata ttatatatta      180
ttatatataa tataattaat atattatgta ttatataata tatattatgt taaatatat       240 aatatatatt ataaattat ataatatatt atgtattata taatatatat tatgttataa      300
tatattatat tatatatatt atatatatat tatatatata atgtatatta tatataaatac    360 ataatatatt atatattata tattatttta taaatatat tatataatgt gatatattat      420
ataatatatt ataaacata gtatattata taatatatta taaatgtaa tatattatat      480 attatataat atattgtat                                                  499

<210> SEQ ID NO 240
<211> LENGTH: 402
<212> TYPE: DNA
<213> ORGANISM: Homo sapiens
<220> FEATURE:
<221> NAME/KEY: misc_binding
<222> LOCATION: (1)..(402)
<223> OTHER INFORMATION: MAR of chromosome 2 genomic contig; 31531..
      31932

<400> SEQUENCE: 240
cacattatat atataaacat tatatatata cacattatat atataaacat tatatatata       60
cacattatat atataaacat tatatataca cattatatat ataaacatta tatatacaca     120
ttatatatat aaacattata tatacaaatt atatatataa acattatata tacaaaattat   180 atatataaac attatatata tacattatat ataaaacat tatatatata cattatatat     240
ataaacatta tatatataca ttatatatat aaacattata tatatacatt atatatataa    300
acattatata tatacattat atatataaac gttatatata tacattatat atataaacat    360
tatatgtata cattatatat ataaacatta tatatatg tg                          402

<210> SEQ ID NO 241
<211> LENGTH: 421
<212> TYPE: DNA
<213> ORGANISM: Homo sapiens
<220> FEATURE:
<221> NAME/KEY: misc_binding
<222> LOCATION: (1)..(421)
<223> OTHER INFORMATION: MAR of chromosome 2 genomic contig; 32415..
      32835

<400> SEQUENCE: 241
ataaatattt tatatataat ataatatata tatactatat tatatgttat atatactatt       60
ataatatata taatatatat attatatatt atatatacta ttattatata tgatactatt     120
atatattaat ataattatat ataatatata tattatataa tatactatta tatattatat    180
ataatagtat attatataat atatatatta tatataatag tattatatat actattatat    240
attatatata ttatatatat ataaaatata atataatata taatatatat aatattaata   300
ttatatatat aatataatat aatataataat ataatataat atatatatta ataaaattat    360
attaatatat aatatataat agtatatttat atacatatat aatatataca atataataata  420 t                                                                    421

<210> SEQ ID NO 242
<211> LENGTH: 19
<212> TYPE: DNA
<213> ORGANISM: Artificial Sequence
<220> FEATURE:
<223> OTHER INFORMATION: Drosophila topoisomerase II binding site
<220> FEATURE:
<221> NAME/KEY: misc_feature
```

```
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 242
gtnwayattn attnatnnr                                                    19

<210> SEQ ID NO 243
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: "A-box"

<400> SEQUENCE: 243 aataaayaaa                                                              10

<210> SEQ ID NO 244
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: "T-box"

<400> SEQUENCE: 244 ttwtwttwtt                                                              10

<210> SEQ ID NO 245
<211> LENGTH: 18
<212> TYPE: DNA
<213> ORGANISM: Artificial Sequence
<220> FEATURE:
<223> OTHER INFORMATION: consensus Topoisomerase II site for vertebrates
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
```

```
<400> SEQUENCE: 245
rnynncnngy ngktnyny                                              18

<210> SEQ ID NO 246
<211> LENGTH: 15
<212> TYPE: DNA
<213> ORGANISM: Artificial Sequence
<220> FEATURE:
<223> OTHER INFORMATION: consensus Topoisomerase II site for Drosophila
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 246
gtnwayattn atnnr                                                 15
```